US007498152B1

(12) United States Patent
Patten et al.

(10) Patent No.: US 7,498,152 B1
(45) Date of Patent: Mar. 3, 2009

(54) INTERFERON-ALPHA POLYPEPTIDES AND CONJUGATES

(75) Inventors: Phillip A. Patten, Portola Valley, CA (US); Sridhar Govindarajan, Redwood City, CA (US); Sridhar Viswanathan, Menlo Park, CA (US); Torben Lauesgaard Nissen, London (GB)

(73) Assignee: Maxygen, Inc., Redwood City, CA (US)

( * ) Notice: Subject to any disclaimer, the term of this patent is extended or adjusted under 35 U.S.C. 154(b) by 313 days.

(21) Appl. No.: 11/554,557

(22) Filed: Oct. 30, 2006

Related U.S. Application Data

(60) Division of application No. 10/848,827, filed on May 19, 2004, now Pat. No. 7,314,613, which is a continuation-in-part of application No. 10/714,817, filed on Nov. 17, 2003, now abandoned.

(60) Provisional application No. 60/502,560, filed on Sep. 12, 2003, provisional application No. 60/427,612, filed on Nov. 18, 2002.

(51) Int. Cl.
C12N 15/00 (2006.01)
C12N 15/63 (2006.01)
C12P 21/00 (2006.01)
C07H 21/04 (2006.01)

(52) U.S. Cl. .................. 435/69.1; 435/320.1; 435/471; 435/325; 435/70.1; 435/71.1; 536/23.1; 536/23.52

(58) Field of Classification Search ........................ None
See application file for complete search history.

(56) References Cited

U.S. PATENT DOCUMENTS

| 4,414,150 | A | 11/1983 | Goeddel |
| 4,695,623 | A | 9/1987 | Stabinsky |
| 4,885,166 | A | 12/1989 | Meyer et al. |
| 5,382,657 | A | 1/1995 | Karasiewicz et al. |
| 5,539,063 | A | 7/1996 | Hakimi et al. |
| 5,559,213 | A | 9/1996 | Hakimi et al. |
| 5,747,646 | A | 5/1998 | Hakimi et al. |
| 5,792,834 | A | 8/1998 | Hakimi et al. |
| 5,834,594 | A | 11/1998 | Hakimi et al. |
| 5,849,860 | A | 12/1998 | Hakimi et al. |
| 5,985,262 | A | 11/1999 | Kinstler et al. |
| 6,303,344 | B1 | 10/2001 | Patten |
| 6,610,830 | B1 | 8/2003 | Goeddel et al. |
| 2004/0002474 | A1 | 1/2004 | Heinrichs et al. |
| 2004/0030101 | A1 | 2/2004 | Bailon et al. |
| 2004/0223950 | A1 | 11/2004 | Brugger et al. |

FOREIGN PATENT DOCUMENTS

| EP | 0051873 A2 | 5/1982 |
| EP | 0205404 A2 | 12/1986 |
| EP | 0422697 A1 | 4/1991 |
| EP | 0 510 356 B1 | 10/1992 |
| EP | 0 593 868 B1 | 4/1994 |
| EP | 0809996 A2 | 12/1997 |
| EP | 0911033 A2 | 4/1999 |
| KR | 20020067105 | 8/2002 |
| WO | 8302461 A1 | 7/1983 |
| WO | 9206707 A1 | 4/1992 |
| WO | 9524212 A1 | 9/1995 |
| WO | 9903887 A1 | 1/1999 |
| WO | 0042175 A1 | 7/2000 |
| WO | 0052153 A1 | 9/2000 |
| WO | 0069913 A1 | 11/2000 |
| WO | 0125438 A2 | 4/2001 |
| WO | 0187925 A2 | 11/2001 |
| WO | 0244197 A2 | 6/2002 |
| WO | 2004045648 A1 | 6/2004 |

OTHER PUBLICATIONS

Goeddel D.V., et al. The structure of eight distinct cloned human leukocyte interferon cDNAs. Nature, Mar. 5, 1981; vol. 290(5801):20-26.
Bailon P., et al. Rational design of a potent, long-lasting form of interferon: a 40 kDa branched polyethylene glycol-conjugated interferon alpha-2a for the treatment of hepatitis C. Bioconjugugate Chemistry, Mar.-Apr. 2001; vol. 12(2):195-202.
Supplementary Partial European Search Report for related application EP 03811632, dated Mar. 3, 2006.
Brideau-Andersen, A. et al. (2007) Directed evolution of gene-shuffled IFN-α molecules with activity profiles tailored for treatment of chronic viral diseases. P.N.A.S. 104(20) 8269-8274, plus Supporting Information from the P.N.A.S. website.
Allen G., Diaz M.O. (1996) Nomenclature of the human interferon proteins. J. Interferon Cytokine Res. Feb. 1996; 16(2):181-184.
Alton, K. et al. (1983) Production, characterization and biological effects of recombinant DNA derived IFN-alpha and IFN-gamma analogs. in The Biology of the Interferon System, 1983, eds. E. DeMaeyer and H. Schellekens, Elsevier Science Publications pp. 119-128.
Altrock B.W., et al. (1986) Antiviral and antitumor effects of a human interferon analog, IFN-alpha Con1, assessed in hamsters. J Interferon Res. Aug. 1986; 6(4):405-415.
Blatt L.M., et al. (1996) The biologic activity and molecular characterization of a novel synthetic interferon-alpha species, consensus interferon. J Interferon Cytokine Res. Jul. 1996; 16(7):489-499.
Chang C.C., et al. (1999) Evolution of a cytokine using DNA family shuffling. Nat Biotechnol. Aug. 1999;17(8):793-797.
Cheetham B.F., et al. (1991) Structure-function studies of human interferons-alpha: enhanced activity on human and murine cells. Antiviral Res. Jan. 1991;15(1):27-39.

(Continued)

*Primary Examiner*—Christine J Saoud
*Assistant Examiner*—Jegatheesan Seharaseyon
(74) *Attorney, Agent, or Firm*—Joanne R. Petithory; Norman J. Kruse; Maxygen, Inc.

(57) ABSTRACT

The present invention provides interferon-alpha polypeptides and conjugates, and nucleic acids encoding the polypeptides. The invention also includes compositions comprising these polypeptides, conjugates, and nucleic acids; cells containing or expressing the polypeptides, conjugates, and nucleic acids; methods of making the polypeptides, conjugates, and nucleic acids; and methods of using the polypeptides, conjugates, and nucleic acids.

21 Claims, 7 Drawing Sheets

OTHER PUBLICATIONS

Gangemi J.D., et al. (1989) Significant differences in therapeutic responses to the human interferon-alpha B/D hybrid in Rauscher or Friend murine leukemia virus infections. J Interferon Res. Jun. 1989;9(3):275-283.

Henco K., et al. (1985) Structural relationship of human interferon alpha genes and pseudogenes. J Mol Biol. Sep. 20, 1985;185(2):227-260.

Meister A., et al. (1986) Biological activities and receptor binding of two human recombinant interferons and their hybrids. J Gen Virol. Aug. 1986; 67 (Pt 8):1633-1643.

Ozes O.N., et al. (1992) A comparison of interferon-Con1 with natural recombinant interferons-alpha: antiviral, antiproliferative, and natural killer-inducing activities. J Interferon Res. Feb. 1992;12(1):55-59.

Weck P.K., et al. (1981) Antiviral activities of hybrids of two major human leukocyte interferons. Nucleic Acids Res. Nov. 25, 1981; 9(22):6153-6166.

International Search Report dated Jul. 2, 2004 for related PCT application PCT/US03/36682 filed Nov. 17, 2003.

Written Opinion dated Sep. 15, 2004 for related PCT application PCT/US03/36682 filed Nov. 17, 2003.

Fig. 2

```
                          *        20         *        40         *        60         *        80
B9X14      : CDLPQTHSLGHRRTMMLLAQMRRISLFSCLKDRHDFRFPQEEFDGNHFQKVQAIFLFYEMMQQTFNLFSTKNSSAAWDETLLEK :  84
hIFNa-14a  : .N.S.....NN...L..M.......P..........E.........Q...A...SVLH.......................... :  84

*       100         *       120         *       140         *       160
B9X14      : FYIELFQQMNDLEACVMQEVGVEETPLMNVDSILAVRKYFQRITLYLTEKKYSPCAWEVVRAEIMRSFSFSTNLQKRLRRKE : 166
hIFNa-14a  : ................I.............E................M.................................D : 166
```

Fig. 3

```
                       *       20        *       40        *       60        *       80
B9X21     : CDLPQTHSLSNRRTLMLMAQMRRISPFSCLKDRHDFGFPEEEFDGHQFQKTQAISVLHELIQQTFNLFSTKNSSAAWDETLLEKF :  85
hIFNa 1a  : ....E....D.......L...S....S...M........Q.....N....AP...........I....T..D.......D..D.. :  85
hIFNa 2b  : .........GS......L.......L.............Q...-GN....AET.P....M...I.......D..........D.. :  84
hIFNa 4b  : .........G...A.I.L...G...H.................................M..........ED.....EQS..... :  85
hIFNa 5   : ................I....G.................Q.....N....A........M...........D...T......D.. :  85
hIFNa 6   : .........GH...M..L.......L..........R..Q.....N....AE.......V...........D..V....R..D.L :  85
hIFNa 7   : .........R...A.I.L...G............E.R......................M..........ED.....EQS..... :  85
hIFNa 8b  : .........G...A.I.L..................E..Q....DK....A........M...........D....L.....DE. :  85
hIFNa 10a : .........G...A.I.LG..G..............RI.Q.....N....A........M..........ED.....EQS..... :  85
hIFNa 14a : .N.S.....N..........................E..Q.....N....A........MM........................ :  85
hIFNa 16  : .........G...A.I.L...G...H.......Y.....Q.V...N....A....AF..M...........D..........D.. :  85
hIFNa 17b : .........G...A.I.L...G...............L.Q.....N.............M..........ED.....EQS..... :  85
hIFNa 21b : .........G...A.I.L...G.................Q.....N....A........M...........D...T.EQS..... :  85

*       100        *       120        *       140        *       160
B9X21     : YIELFQQMNNLEACVIQEVGVEEIALMNVDSILAVRKYFRRITLYLTEKKYSPCAWEVVRAEIMRSFSFSTNLQKRLRRKE : 166
hIFNa 1a  : CT..Y..L.D.....M..ER.G.TP...A......K..............................L.L.....E...... : 166
hIFNa 2b  : .T..Y..L.D.......G...T.TP..KE..........Q......K.....................L.....ES..S.. : 165
hIFNa 4b  : ST..Y..L.D.............TP..............Q..........................L.............D : 166
hIFNa 5   : .T..Y..L.D....MM......DTP........T.....Q............................L.A...E...... : 166
hIFNa 6   : .T..Y..L.D.....M...W.GGTP...E..........Q............................S.R...E...... : 166
hIFNa 7   : ST..Y..L.D.............TP...E.F........Q......M..........................K.G....D : 166
hIFNa 8b  : ....D..L.D..S..M.....I.SP..YE..........Q............S...............L.I......KS.. : 166
hIFNa 10a : ST..Y..L.D.............TP...E..........Q......I.R.................L.............D : 166
hIFNa 14a : .........D.............TP...E..........Q......M.................................D : 166
hIFNa 16  : .......L.D.....T............E..........Q......MG...........................G....D : 166
hIFNa 17b : ST..Y..L............M..TP...E..........Q..........................L........I....D : 166
hIFNa 21b : ST..N..L.D.............TP..........K...Q............................L.KIF.E...... : 166
```

Fig. 4

```
                      *        20         *        40         *        60         *        80
B9X25      : CDLPQTHSLSNRRTLMLMAQMRRISPFSCLKDRHDFGFPEEEFDGHHFQKVQAIFLLYELIQQTFNLFSTKNSSAAWDETLLEK :  84
hIFNa-14a  : .N.S.....N..........................E..Q.....NQ...A...SV.H.MM....................... :  84

*       100         *       120         *       140         *       160
B9X25      : FYIELFQQMNNLEACVIQEVGVEEIALMNVDSILAVRKYFRRITLYLTEKKYSPCAWEVVRAEIMRSFSFSTNLQKRLRRKE : 166
hIFNa-14a  : ..........D.............TP...E..........Q......M.................................D : 166
```

Fig. 5

BLOSUM62 SUBSTITUTION MATRIX

|   | A | R | N | D | C | Q | E | G | H | I | L | K | M | F | P | S | T | W | Y | V | B | Z | X | * |
|---|---|---|---|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 | -2 | -1 | 0 | -4 |
| R | -1 | 5 | 0 | -2 | -3 | 1 | 0 | -2 | 0 | -3 | -2 | 2 | -1 | -3 | -2 | -1 | -1 | -3 | -2 | -3 | -1 | 0 | -1 | -4 |
| N | -2 | 0 | 6 | 1 | -3 | 0 | 0 | 0 | 1 | -3 | -3 | 0 | -2 | -3 | -2 | 1 | 0 | -4 | -2 | -3 | 3 | 0 | -1 | -4 |
| D | -2 | -2 | 1 | 6 | -3 | 0 | 2 | -1 | -1 | -3 | -4 | -1 | -3 | -3 | -1 | 0 | -1 | -4 | -3 | -3 | 4 | 1 | -1 | -4 |
| C | 0 | -3 | -3 | -3 | 9 | -3 | -4 | -3 | -3 | -1 | -1 | -3 | -1 | -2 | -3 | -1 | -1 | -2 | -2 | -1 | -3 | -3 | -2 | -4 |
| Q | -1 | 1 | 0 | 0 | -3 | 5 | 2 | -2 | 0 | -3 | -2 | 1 | 0 | -3 | -1 | 0 | -1 | -2 | -1 | -2 | 0 | 3 | -1 | -4 |
| E | -1 | 0 | 0 | 2 | -4 | 2 | 5 | -2 | 0 | -3 | -3 | 1 | -2 | -3 | -1 | 0 | -1 | -3 | -2 | -2 | 1 | 4 | -1 | -4 |
| G | 0 | -2 | 0 | -1 | -3 | -2 | -2 | 6 | -2 | -4 | -4 | -2 | -3 | -3 | -2 | 0 | -2 | -2 | -3 | -3 | -1 | -2 | -1 | -4 |
| H | -2 | 0 | 1 | -1 | -3 | 0 | 0 | -2 | 8 | -3 | -3 | -1 | -2 | -1 | -2 | -1 | -2 | -2 | 2 | -3 | 0 | 0 | -1 | -4 |
| I | -1 | -3 | -3 | -3 | -1 | -3 | -3 | -4 | -3 | 4 | 2 | -3 | 1 | 0 | -3 | -2 | -1 | -3 | -1 | 3 | -3 | -3 | -1 | -4 |
| L | -1 | -2 | -3 | -4 | -1 | -2 | -3 | -4 | -3 | 2 | 4 | -2 | 2 | 0 | -3 | -2 | -1 | -2 | -1 | 1 | -4 | -3 | -1 | -4 |
| K | -1 | 2 | 0 | -1 | -3 | 1 | 1 | -2 | -1 | -3 | -2 | 5 | -1 | -3 | -1 | 0 | -1 | -3 | -2 | -2 | 0 | 1 | -1 | -4 |
| M | -1 | -1 | -2 | -3 | -1 | 0 | -2 | -3 | -2 | 1 | 2 | -1 | 5 | 0 | -2 | -1 | -1 | -1 | -1 | 1 | -3 | -1 | -1 | -4 |
| F | -2 | -3 | -3 | -3 | -2 | -3 | -3 | -3 | -1 | 0 | 0 | -3 | 0 | 6 | -4 | -2 | -2 | 1 | 3 | -1 | -3 | -3 | -1 | -4 |
| P | -1 | -2 | -2 | -1 | -3 | -1 | -1 | -2 | -2 | -3 | -3 | -1 | -2 | -4 | 7 | -1 | -1 | -4 | -3 | -2 | -2 | -1 | -2 | -4 |
| S | 1 | -1 | 1 | 0 | -1 | 0 | 0 | 0 | -1 | -2 | -2 | 0 | -1 | -2 | -1 | 4 | 1 | -3 | -2 | -2 | 0 | 0 | 0 | -4 |
| T | 0 | -1 | 0 | -1 | -1 | -1 | -1 | -2 | -2 | -1 | -1 | -1 | -1 | -2 | -1 | 1 | 5 | -2 | -2 | 0 | -1 | -1 | 0 | -4 |
| W | -3 | -3 | -4 | -4 | -2 | -2 | -3 | -2 | -2 | -3 | -2 | -3 | -1 | 1 | -4 | -3 | -2 | 11 | 2 | -3 | -4 | -3 | -2 | -4 |
| Y | -2 | -2 | -2 | -3 | -2 | -1 | -2 | -3 | 2 | -1 | -1 | -2 | -1 | 3 | -3 | -2 | -2 | 2 | 7 | -1 | -3 | -2 | -1 | -4 |
| V | 0 | -3 | -3 | -3 | -1 | -2 | -2 | -3 | -3 | 3 | 1 | -2 | 1 | -1 | -2 | -2 | 0 | -3 | -1 | 4 | -3 | -2 | -1 | -4 |
| B | -2 | -1 | 3 | 4 | -3 | 0 | 1 | -1 | 0 | -3 | -4 | 0 | -3 | -3 | -2 | 0 | -1 | -4 | -3 | -3 | 4 | 1 | -1 | -4 |
| Z | -1 | 0 | 0 | 1 | -3 | 3 | 4 | -2 | 0 | -3 | -3 | 1 | -1 | -3 | -1 | 0 | -1 | -3 | -2 | -2 | 1 | 4 | -1 | -4 |
| X | 0 | -1 | -1 | -1 | -2 | -1 | -1 | -1 | -1 | -1 | -1 | -1 | -1 | -1 | -2 | 0 | 0 | -2 | -1 | -1 | -1 | -1 | -1 | -4 |
| * | -4 | -4 | -4 | -4 | -4 | -4 | -4 | -4 | -4 | -4 | -4 | -4 | -4 | -4 | -4 | -4 | -4 | -4 | -4 | -4 | -4 | -4 | -4 | 1 |

| C | L | K | D | R | H | D | F | R | F | P | Q | E | E | F | D | G | N | H | F | Q | K |   |   |
|---|---|---|---|---|---|---|---|---|---|---|---|---|---|---|---|---|---|---|---|---|---|---|---|
|   | L | K | D | R | H | D | F | R | F | P | Q | E | E | F | D | G | N | Q | F | Q | K | V | Q |
|   | 4 | 5 | 6 | 5 | 8 | 6 | 6 | 5 | 6 | 7 | 5 | 5 | 5 | 6 | 6 | 6 | 6 | 0 | 6 | 5 | 5 |   |   |

= 113

B.

| C | L | K | D | R | H | D | F | R | F | P | Q | E | E | F | D | G | N | H | F | Q | K |   |
|---|---|---|---|---|---|---|---|---|---|---|---|---|---|---|---|---|---|---|---|---|---|---|
|   | L | K | D | R | H | D | F | G | F | P | Q | E | E | F | G | N | Q | F | Q | K | A |
|   | 4 | 5 | 6 | 5 | 8 | 6 | 6 | 6 | −2 | 6 | 7 | 5 | 5 | 5 | 6 | −1 | 0 | 0 | −1 | −3 | 1 | −1 |

= 67

C.

| C | L | K | D | R | H | D | F | R | F | P | Q | E | E | F | D | G | N | H | F | Q | K |   |
|---|---|---|---|---|---|---|---|---|---|---|---|---|---|---|---|---|---|---|---|---|---|---|
|   | L | K | D | R | H | D | F | G | F | P | Q | E | E | F | − | G | N | Q | F | Q | K | A |
|   | 4 | 5 | 6 | 5 | 8 | 6 | 6 | 6 | −2 | 6 | 7 | 5 | 5 | 5 | 6 | −12 | 6 | 0 | 6 | 5 | 5 |   |

SEQUENCE LISTING

```
<160> NUMBER OF SEQ ID NOS: 104

<210> SEQ ID NO 1
<211> LENGTH: 166
<212> TYPE: PRT
<213> ORGANISM: Artificial Sequence
<220> FEATURE:
<223> OTHER INFORMATION: IFNalpha B9x11

<400> SEQUENCE: 1

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Lys Lys Lys Tyr Ser Pro Cys Ser Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
                165

<210> SEQ ID NO 2
<211> LENGTH: 166
<212> TYPE: PRT
<213> ORGANISM: Artificial Sequence
<220> FEATURE:
<223> OTHER INFORMATION: IFNalpha B9x12

<400> SEQUENCE: 2

Cys Asp Leu Pro Gln Thr His Ser Leu Gly His Arg Arg Thr Met Met
1               5                   10                  15
```

```
Leu Leu Ala Gln Met Arg Arg Ile Ser Leu Phe Ser Cys Leu Lys Asp
             20                  25                  30

Arg His Asp Phe Arg Phe Pro Gln Glu Glu Phe Asp Gly Asn Gln Phe
         35                  40                  45

Gln Lys Val Gln Ala Ile Phe Leu Phe Tyr Glu Met Met Gln Gln Thr
     50                  55                  60

Phe Asn Leu Phe Ser Thr Lys Asn Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Lys Lys Lys Tyr Ser Pro Cys Ser Trp Glu Val Val
        130                 135                 140

Arg Ala Glu Ile Met Arg Ser Phe Ser Phe Ser Thr Asn Leu Gln Lys
145                 150                 155                 160

Arg Leu Arg Arg Lys Glu
                165

<210> SEQ ID NO 3
<211> LENGTH: 166
<212> TYPE: PRT
<213> ORGANISM: Artificial Sequence B9x14
<220> FEATURE:
<223> OTHER INFORMATION: IFNalpha

<400> SEQUENCE: 3

Cys Asp Leu Pro Gln Thr His Ser Leu Gly His Arg Arg Thr Met Met
  1               5                  10                  15

Leu Leu Ala Gln Met Arg Arg Ile Ser Leu Phe Ser Cys Leu Lys Asp
             20                  25                  30

Arg His Asp Phe Arg Phe Pro Gln Glu Glu Phe Asp Gly Asn His Phe
         35                  40                  45

Gln Lys Val Gln Ala Ile Phe Leu Phe Tyr Glu Met Met Gln Gln Thr
     50                  55                  60

Phe Asn Leu Phe Ser Thr Lys Asn Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Phe Ser Thr Asn Leu Gln Lys
145                 150                 155                 160

Arg Leu Arg Arg Lys Glu
                165

<210> SEQ ID NO 4
<211> LENGTH: 166
<212> TYPE: PRT
<213> ORGANISM: Artificial Sequence
```

```
<220> FEATURE:
<223> OTHER INFORMATION: IFNalpha B9x15

<400> SEQUENCE: 4

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
        35                  40                  45

Gln Lys Thr Gln Ala Ile Ser Val Phe His Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Lys Lys Lys Tyr Ser Pro Cys Ser Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
                165

<210> SEQ ID NO 5
<211> LENGTH: 166
<212> TYPE: PRT
<213> ORGANISM: Artificial Sequence
<220> FEATURE:
<223> OTHER INFORMATION: IFNalpha B9x16

<400> SEQUENCE: 5

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
```

```
<210> SEQ ID NO 6
<211> LENGTH: 166
<212> TYPE: PRT
<213> ORGANISM: Artificial Sequence
<220> FEATURE:
<223> OTHER INFORMATION: IFNalpha B9x17

<400> SEQUENCE: 6

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Thr Gln Ala Ile Ser Val Phe His Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
                165

<210> SEQ ID NO 7
<211> LENGTH: 166
<212> TYPE: PRT
<213> ORGANISM: Artificial Sequence
<220> FEATURE:
<223> OTHER INFORMATION: IFNalpha B9x18

<400> SEQUENCE: 7

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
        35                  40                  45

Gln Lys Thr Gln Ala Ile Ser Val Phe His Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125
```

```
Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
                165

<210> SEQ ID NO 8
<211> LENGTH: 166
<212> TYPE: PRT
<213> ORGANISM: Artificial Sequence
<220> FEATURE:
<223> OTHER INFORMATION: IFNalpha B9x21

<400> SEQUENCE: 8

Cys Asp Leu Pro Gln Thr His Ser Leu Ser Asn Arg Arg Thr Leu Met
  1               5                  10                  15

Leu Met Ala Gln Met Arg Arg Ile Ser Pro Phe Ser Cys Leu Lys Asp
             20                  25                  30

Arg His Asp Phe Gly Phe Pro Glu Glu Glu Phe Asp Gly His Gln Phe
         35                  40                  45

Gln Lys Thr Gln Ala Ile Ser Val Leu His Glu Leu Ile Gln Gln Thr
     50                  55                  60

Phe Asn Leu Phe Ser Thr Lys Asn Ser Ser Ala Ala Trp Asp Glu Thr
 65                  70                  75                  80

Leu Leu Glu Lys Phe Tyr Ile Glu Leu Phe Gln Gln Met Asn Asn Leu
                 85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
                165

<210> SEQ ID NO 9
<211> LENGTH: 166
<212> TYPE: PRT
<213> ORGANISM: Artificial Sequence
<220> FEATURE:
<223> OTHER INFORMATION: IFNalpha B9x22

<400> SEQUENCE: 9

Cys Asp Leu Pro Gln Thr His Ser Leu Ser Asn Arg Arg Thr Leu Met
  1               5                  10                  15

Leu Met Ala Gln Met Arg Arg Ile Ser Pro Phe Ser Cys Leu Lys Asp
             20                  25                  30

Arg His Asp Phe Gly Phe Pro Glu Glu Glu Phe Asp Gly His His Phe
         35                  40                  45

Gln Lys Thr Gln Ala Ile Ser Val Leu His Glu Leu Ile Gln Gln Thr
     50                  55                  60

Phe Asn Leu Phe Ser Thr Lys Asn Ser Ser Ala Ala Trp Asp Glu Thr
 65                  70                  75                  80

Leu Leu Glu Lys Phe Tyr Ile Glu Leu Phe Gln Gln Met Asn Asn Leu
                 85                  90                  95
```

```
Glu Ala Cys Val Ile Gln Glu Val Gly Val Glu Ile Ala Leu Met
            100                 105                 110

Asn Val Asp Ser Ile Leu Ala Val Arg Lys Tyr Phe Arg Arg Ile Thr
            115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
                165

<210> SEQ ID NO 10
<211> LENGTH: 166
<212> TYPE: PRT
<213> ORGANISM: Artificial Sequence
<220> FEATURE:
<223> OTHER INFORMATION: IFNalpha B9x23

<400> SEQUENCE: 10

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Val Gln Ala Ile Phe Leu Leu Tyr Glu Leu Ile Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Ile Ala Leu Met
            100                 105                 110

Asn Val Asp Ser Ile Leu Ala Val Arg Lys Tyr Phe Arg Arg Ile Thr
            115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
                165

<210> SEQ ID NO 11
<211> LENGTH: 166
<212> TYPE: PRT
<213> ORGANISM: Artificial Sequence
<220> FEATURE:
<223> OTHER INFORMATION: IFNalpha B9x24

<400> SEQUENCE: 11

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Leu Ile Gln Gln Thr
```

```
        50                  55                  60
Phe Asn Leu Phe Ser Thr Lys Asn Ser Ser Ala Ala Trp Asp Glu Thr
 65                  70                  75                  80

Leu Leu Glu Lys Phe Tyr Ile Glu Leu Phe Gln Gln Met Asn Asn Leu
                 85                  90                  95

Glu Ala Cys Val Ile Gln Glu Val Gly Val Glu Glu Ile Ala Leu Met
                100                 105                 110

Asn Val Asp Ser Ile Leu Ala Val Arg Lys Tyr Phe Arg Arg Ile Thr
            115                 120                 125

Leu Tyr Leu Thr Lys Lys Tyr Ser Pro Cys Ser Trp Glu Val Val
        130                 135                 140

Arg Ala Glu Ile Met Arg Ser Phe Ser Phe Ser Thr Asn Leu Gln Lys
145                 150                 155                 160

Arg Leu Arg Arg Lys Glu
                165

<210> SEQ ID NO 12
<211> LENGTH: 166
<212> TYPE: PRT
<213> ORGANISM: Artificial Sequence
<220> FEATURE:
<223> OTHER INFORMATION: IFNalpha B9x25

<400> SEQUENCE: 12

Cys Asp Leu Pro Gln Thr His Ser Leu Ser Asn Arg Arg Thr Leu Met
 1               5                  10                  15

Leu Met Ala Gln Met Arg Arg Ile Ser Pro Phe Ser Cys Leu Lys Asp
                 20                  25                  30

Arg His Asp Phe Gly Phe Pro Glu Glu Glu Phe Asp Gly His His Phe
             35                  40                  45

Gln Lys Val Gln Ala Ile Phe Leu Leu Tyr Glu Leu Ile Gln Gln Thr
         50                  55                  60

Phe Asn Leu Phe Ser Thr Lys Asn Ser Ser Ala Ala Trp Asp Glu Thr
 65                  70                  75                  80

Leu Leu Glu Lys Phe Tyr Ile Glu Leu Phe Gln Gln Met Asn Asn Leu
                 85                  90                  95

Glu Ala Cys Val Ile Gln Glu Val Gly Val Glu Glu Ile Ala Leu Met
                100                 105                 110

Asn Val Asp Ser Ile Leu Ala Val Arg Lys Tyr Phe Arg Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Phe Ser Thr Asn Leu Gln Lys
145                 150                 155                 160

Arg Leu Arg Arg Lys Glu
                165

<210> SEQ ID NO 13
<211> LENGTH: 166
<212> TYPE: PRT
<213> ORGANISM: Artificial Sequence
<220> FEATURE:
<223> OTHER INFORMATION: IFNalpha B9x26

<400> SEQUENCE: 13

Cys Asp Leu Pro Gln Thr His Ser Leu Ser Asn Arg Arg Thr Leu Met
 1               5                  10                  15
```

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His His Phe
        35                  40                  45

Gln Lys Thr Gln Ala Ile Ser Val Leu His Glu Leu Ile Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Lys Lys Lys Tyr Ser Pro Cys Ser Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
            165

<210> SEQ ID NO 14
<211> LENGTH: 166
<212> TYPE: PRT
<213> ORGANISM: Artificial Sequence
<220> FEATURE:
<223> OTHER INFORMATION: IFNalpha B9x27

<400> SEQUENCE: 14

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Val Gln Ala Ile Phe Leu Leu Tyr Glu Leu Ile Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Lys Lys Lys Tyr Ser Pro Cys Ser Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
            165

<210> SEQ ID NO 15
<211> LENGTH: 166
<212> TYPE: PRT
<213> ORGANISM: Artificial Sequence
<220> FEATURE:

<223> OTHER INFORMATION: IFNalpha B9x28

<400> SEQUENCE: 15

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His His Phe
        35                  40                  45

Gln Lys Val Gln Ala Ile Phe Leu Leu Tyr Glu Leu Ile Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Lys Lys Lys Tyr Ser Pro Cys Ser Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
                165

<210> SEQ ID NO 16
<211> LENGTH: 498
<212> TYPE: DNA
<213> ORGANISM: Artificial Sequence
<220> FEATURE:
<223> OTHER INFORMATION: IFNalpha B9x11 coding sequence

<400> SEQUENCE: 16
tgtgatctgc ctcagaccca cagcctgggt cacaggagga ccatgatgct cctggcacaa      60
atgaggagaa tctctctttt ctcctgtctg aaggacagac atgacttcag atttccccag     120
gaggagtttg atggcaacca cttccagaag gttcaagcta tcttcctttt ctatgagatg     180
atgcagcaga ccttcaacct cttcagcaca aagaactcat ctgctgcttg ggatgagacc     240
ctcctagaaa aattctacat tgaacttttc agcaaatgaa tgacctggaa gcctgcgtg     300 atgcaggagg ttggagtgga agagactccc ctgatgaatg tggactccat cctggctgtg     360
aggaaatact tcaaagaat cactctttat ctgacaaaga agaagtatag cccttgttcc     420
tgggaggttg tcagagcaga aatcatgaga tctttctctt tttcaacaaa cttgcaaaaa     480
agattaagga ggaaggaa                                                  498

<210> SEQ ID NO 17
<211> LENGTH: 498
<212> TYPE: DNA
<213> ORGANISM: Artificial Sequence
<220> FEATURE:
<223> OTHER INFORMATION: IFNalpha B9x12 coding sequence

<400> SEQUENCE: 17
tgtgatctgc ctcagaccca cagcctgggt cacaggagga ccatgatgct cctggcacaa      60
atgaggagaa tctctctttt ctcctgtctg aaggacagac atgacttcag atttccccag     120

```
gaggagtttg atggcaacca gttccagaag gttcaagcta tcttcctttt ctatgagatg    180
atgcagcaga ccttcaacct cttcagcaca aagaactcat ctgctgcttg ggatgagacc    240
ctcctagaaa aattctacat tgaacttttc agcaaatga atgacctgga agcctgcgtg    300
atgcaggagg ttggagtgga agagactccc ctgatgaatg tggactccat cctggctgtg    360
aggaaatact ttcaaagaat cactctttat ctgacaaaga gaagtatag cccttgttcc    420 tgggaggttg tcagagcaga aatcatgaga tctttctctt tttcaacaaa cttgcaaaaa    480
agattaagga ggaaggaa                                                   498
```

```
<210> SEQ ID NO 18
<211> LENGTH: 498
<212> TYPE: DNA
<213> ORGANISM: Artificial Sequence
<220> FEATURE:
<223> OTHER INFORMATION: IFNalpha B9x14 coding sequence

<400> SEQUENCE: 18
tgtgatctgc ctcagaccca cagcctgggt cacaggagga ccatgatgct cctggcacaa    60
atgaggagaa tctctctttt ctcctgtctg aaggacagac atgacttcag atttccccag    120
gaggagtttg atggcaacca cttccagaag gttcaagcta tcttcctttt ctatgagatg    180
atgcagcaga ccttcaacct cttcagcaca aagaactcat ctgctgcttg ggatgagacc    240
ctcctagaaa aattctacat tgaacttttc agcaaatga atgacctgga agcctgcgtg    300
atgcaggagg ttggagtgga agagactccc ctgatgaatg tggactccat cctggctgtg    360
aggaaatact ttcaaagaat cactctttat ctgacagaga gaagtatag cccttgtgcc    420 tgggaggttg tcagagcaga aatcatgaga tctttctctt tttcaacaaa cttgcaaaaa    480
agattaagga ggaaggaa                                                   498
```

```
<210> SEQ ID NO 19
<211> LENGTH: 498
<212> TYPE: DNA
<213> ORGANISM: Artificial Sequence
<220> FEATURE:
<223> OTHER INFORMATION: IFNalpha B9x15 coding sequence

<400> SEQUENCE: 19
tgtgatctgc ctcagaccca cagcctgggt cacaggagga ccatgatgct cctggcacaa    60
atgaggagaa tctctctttt ctcctgtctg aaggacagac atgacttcag atttccccag    120
gaggagtttg atggcaacca gttccagaag actcaagcta tctctgtctt ccatgagatg    180
atgcagcaga ccttcaacct cttcagcaca aagaactcat ctgctgcttg ggatgagacc    240
ctcctagaaa aattctacat tgaacttttc agcaaatga atgacctgga agcctgcgtg    300
atgcaggagg ttggagtgga agagactccc ctgatgaatg tggactccat cctggctgtg    360
aggaaatact ttcaaagaat cactctttat ctgacaaaga gaagtatag cccttgttcc    420 tgggaggttg tcagagcaga aatcatgaga tctttctctt tttcaacaaa cttgcaaaaa    480
agattaagga ggaaggaa                                                   498
```

```
<210> SEQ ID NO 20
<211> LENGTH: 498
<212> TYPE: DNA
<213> ORGANISM: Artificial Sequence
<220> FEATURE:
<223> OTHER INFORMATION: IFNalpha B9x16 coding sequence

<400> SEQUENCE: 20
```

```
tgtgatctgc ctcagaccca cagcctgggt cacaggagga ccatgatgct cctggcacaa      60
atgaggagaa tctctctttt ctcctgtctg aaggacagac atgacttcag atttccccag     120
gaggagtttg atggcaacca gttccagaag gttcaagcta tcttcctttt ctatgagatg     180
atgcagcaga ccttcaacct cttcagcaca aagaactcat ctgctgcttg ggatgagacc     240
ctcctagaaa aattctacat tgaacttttc cagcaaatga atgacctgga agcctgcgtg     300
atgcaggagg ttggagtgga agagactccc ctgatgaatg tggactccat cctggctgtg     360
aggaaatact ttcaaagaat cactctttat ctgacagaga agaagtatag cccttgtgcc     420
tgggaggttg tcagagcaga aatcatgaga tctttctctt tttcaacaaa cttgcaaaaa     480
agattaagga ggaaggaa                                                   498
```

<210> SEQ ID NO 21
<211> LENGTH: 498
<212> TYPE: DNA
<213> ORGANISM: Artificial Sequence
<220> FEATURE:
<223> OTHER INFORMATION: IFNalpha B9x17 coding sequence

<400> SEQUENCE: 21

```
tgtgatctgc ctcagaccca cagcctgggt cacaggagga ccatgatgct cctggcacaa      60
atgaggagaa tctctctttt ctcctgtctg aaggacagac atgacttcag atttccccag     120
gaggagtttg atggcaacca cttccagaag actcaagcta tctctgtctt ccatgagatg     180
atgcagcaga ccttcaacct cttcagcaca aagaactcat ctgctgcttg ggatgagacc     240
ctcctagaaa aattctacat tgaacttttc cagcaaatga atgacctgga agcctgcgtg     300
atgcaggagg ttggagtgga agagactccc ctgatgaatg tggactccat cctggctgtg     360
aggaaatact ttcaaagaat cactctttat ctgacagaga agaagtatag cccttgtgcc     420
tgggaggttg tcagagcaga aatcatgaga tctttctctt tttcaacaaa cttgcaaaaa     480
agattaagga ggaaggaa                                                   498
```

<210> SEQ ID NO 22
<211> LENGTH: 498
<212> TYPE: DNA
<213> ORGANISM: Artificial Sequence
<220> FEATURE:
<223> OTHER INFORMATION: IFNalpha B9x18 coding sequence

<400> SEQUENCE: 22

```
tgtgatctgc ctcagaccca cagcctgggt cacaggagga ccatgatgct cctggcacaa      60
atgaggagaa tctctctttt ctcctgtctg aaggacagac atgacttcag atttccccag     120
gaggagtttg atggcaacca gttccagaag actcaagcta tctctgtctt ccatgagatg     180
atgcagcaga ccttcaacct cttcagcaca aagaactcat ctgctgcttg ggatgagacc     240
ctcctagaaa aattctacat tgaacttttc cagcaaatga atgacctgga agcctgcgtg     300
atgcaggagg ttggagtgga agagactccc ctgatgaatg tggactccat cctggctgtg     360
aggaaatact ttcaaagaat cactctttat ctgacagaga agaagtatag cccttgtgcc     420
tgggaggttg tcagagcaga aatcatgaga tctttctctt tttcaacaaa cttgcaaaaa     480
agattaagga ggaaggaa                                                   498
```

<210> SEQ ID NO 23
<211> LENGTH: 498
<212> TYPE: DNA

<210> SEQ ID NO 23
<211> LENGTH: 498
<212> TYPE: DNA
<213> ORGANISM: Artificial Sequence
<220> FEATURE:
<223> OTHER INFORMATION: IFNalpha B9x21 coding sequence

<400> SEQUENCE: 23

```
tgtgatctgc ctcagaccca cagcctgagt aacaggagga ctctgatgct catggcacaa      60
atgaggagaa tctctccttt ctcctgcctg aaggacagac atgatttcgg attccccgag     120
gaggagtttg atggccacca gttccagaag actcaagcca tctctgtcct ccatgagctg     180
atccagcaga ccttcaatct cttcagcaca aagaactcat ctgctgcttg ggatgagacc     240
ctcctagaaa aattctacat tgaacttttc agcaaatgaa taacctgga agcatgtgtg      300
atacaggagg ttggggtgga agagattgcc ctgatgaatg tggactccat cctggctgtg     360
aggaaatact tccgaagaat cactctctat ctgacagaga gaaatacag cccttgtgcc      420
tgggaggttg tcagagcaga atcatgaga tctttctctt tttcaacaaa cttgcaaaaa     480
agattaagga ggaaggaa                                                     498
```

<210> SEQ ID NO 24
<211> LENGTH: 498
<212> TYPE: DNA
<213> ORGANISM: Artificial Sequence
<220> FEATURE:
<223> OTHER INFORMATION: IFNalpha B9x22 coding sequence

<400> SEQUENCE: 24

```
tgtgatctgc ctcagaccca cagcctgagt aacaggagga ctctgatgct catggcacaa      60
atgaggagaa tctctccttt ctcctgcctg aaggacagac atgatttcgg attccccgag     120
gaggagtttg atggccacca cttccagaag actcaagcca tctctgtcct ccatgagctg     180
atccagcaga ccttcaatct cttcagcaca aagaactcat ctgctgcttg ggatgagacc     240
ctcctagaaa aattctacat tgaacttttc agcaaatgaa taacctgga agcatgtgtg      300
atacaggagg ttggggtgga agagattgcc ctgatgaatg tggactccat cctggctgtg     360
aggaaatact tccgaagaat cactctctat ctgacagaga gaaatacag cccttgtgcc      420
tgggaggttg tcagagcaga atcatgaga tctttctctt tttcaacaaa cttgcaaaaa     480
agattaagga ggaaggaa                                                     498
```

<210> SEQ ID NO 25
<211> LENGTH: 498
<212> TYPE: DNA
<213> ORGANISM: Artificial Sequence
<220> FEATURE:
<223> OTHER INFORMATION: IFNalpha B9x23 coding sequence

<400> SEQUENCE: 25

```
tgtgatctgc ctcagaccca cagcctgagt aacaggagga ctctgatgct catggcacaa      60
atgaggagaa tctctccttt ctcctgcctg aaggacagac atgatttcgg attccccgag     120
gaggagtttg atggccacca gttccagaag gttcaagcca tcttccttct ctatgagctg     180
atccagcaga ccttcaatct cttcagcaca aagaactcat ctgctgcttg ggatgagacc     240
ctcctagaaa aattctacat tgaacttttc agcaaatgaa taacctgga agcatgtgtg      300
atacaggagg ttggggtgga agagattgcc ctgatgaatg tggactccat cctggctgtg     360
aggaaatact tccgaagaat cactctctat ctgacagaga gaaatacag cccttgtgcc      420
tgggaggttg tcagagcaga atcatgaga tctttctctt tttcaacaaa cttgcaaaaa     480
agattaagga ggaaggaa                                                     498
```

<210> SEQ ID NO 26
<211> LENGTH: 498
<212> TYPE: DNA
<213> ORGANISM: Artificial Sequence
<220> FEATURE:
<223> OTHER INFORMATION: IFNalpha B9x24 coding sequence

<400> SEQUENCE: 26

```
tgtgatctgc ctcagaccca cagcctgagt aacaggagga ctctgatgct catggcacaa      60
atgaggagaa tctctccttt ctcctgcctg aaggacagac atgatttcgg attccccgag     120
gaggagtttg atggccacca gttccagaag actcaagcca tctctgtcct ccatgagctg     180
atccagcaga ccttcaatct cttcagcaca aagaactcat ctgctgcttg ggatgagacc     240
ctcctagaaa aattctacat tgaactttc cagcaaatga ataacctgga agcatgtgtg      300
atacaggagg ttggggtgga agagattgcc ctgatgaatg tggactccat cctggctgtg     360
aggaaatact tccgaagaat cactctctat ctgacaaaga gaaatacag cccttgttcc      420
tgggaggttg tcagagcaga aatcatgaga tctttctctt tttcaacaaa cttgcaaaaa     480
agattaagga ggaaggaa                                                    498
```

<210> SEQ ID NO 27
<211> LENGTH: 498
<212> TYPE: DNA
<213> ORGANISM: Artificial Sequence
<220> FEATURE:
<223> OTHER INFORMATION: IFNalpha B9x25 coding sequence

<400> SEQUENCE: 27

```
tgtgatctgc ctcagaccca cagcctgagt aacaggagga ctctgatgct catggcacaa      60
atgaggagaa tctctccttt ctcctgcctg aaggacagac atgatttcgg attccccgag     120
gaggagtttg atggccacca cttccagaag gttcaagcca tcttccttct ctatgagctg     180
atccagcaga ccttcaatct cttcagcaca aagaactcat ctgctgcttg ggatgagacc     240
ctcctagaaa aattctacat tgaactttc cagcaaatga ataacctgga agcatgtgtg      300
atacaggagg ttggggtgga agagattgcc ctgatgaatg tggactccat cctggctgtg     360
aggaaatact tccgaagaat cactctctat ctgacagaga gaaatacag cccttgtgcc      420
tgggaggttg tcagagcaga aatcatgaga tctttctctt tttcaacaaa cttgcaaaaa     480
agattaagga ggaaggaa                                                    498
```

<210> SEQ ID NO 28
<211> LENGTH: 498
<212> TYPE: DNA
<213> ORGANISM: Artificial Sequence
<220> FEATURE:
<223> OTHER INFORMATION: IFNalpha B9x26 coding sequence

<400> SEQUENCE: 28

```
tgtgatctgc ctcagaccca cagcctgagt aacaggagga ctctgatgct catggcacaa      60
atgaggagaa tctctccttt ctcctgcctg aaggacagac atgatttcgg attccccgag     120
gaggagtttg atggccacca cttccagaag actcaagcca tctctgtcct ccatgagctg     180
atccagcaga ccttcaatct cttcagcaca aagaactcat ctgctgcttg ggatgagacc     240
ctcctagaaa aattctacat tgaactttc cagcaaatga ataacctgga agcatgtgtg      300
atacaggagg ttggggtgga agagattgcc ctgatgaatg tggactccat cctggctgtg     360
```

-continued

```
aggaaatact tccgaagaat cactctctat ctgacaaaga agaaatacag cccttgttcc    420
tgggaggttg tcagagcaga aatcatgaga tctttctctt tttcaacaaa cttgcaaaaa    480
agattaagga ggaaggaa                                                   498
```

```
<210> SEQ ID NO 29
<211> LENGTH: 498
<212> TYPE: DNA
<213> ORGANISM: Artificial Sequence
<220> FEATURE:
<223> OTHER INFORMATION: IFNalpha B9x27 coding sequence

<400> SEQUENCE: 29
tgtgatctgc ctcagaccca cagcctgagt aacaggagga ctctgatgct catggcacaa     60
atgaggagaa tctctccttt ctcctgcctg aaggacagac atgatttcgg attccccgag   120
gaggagtttg atggccacca gttccagaag gttcaagcca tcttccttct ctatgagctg   180
atccagcaga ccttcaatct cttcagcaca agaactcat ctgctgcttg ggatgagacc    240
ctcctagaaa aattctacat tgaactttc cagcaaatga ataacctgga agcatgtgtg    300
atacaggagg ttgggggtgga agagattgcc ctgatgaatg tggactccat cctggctgtg   360
aggaaatact tccgaagaat cactctctat ctgacaaaga agaaatacag cccttgttcc    420
tgggaggttg tcagagcaga aatcatgaga tctttctctt tttcaacaaa cttgcaaaaa    480
agattaagga ggaaggaa                                                   498
```

```
<210> SEQ ID NO 30
<211> LENGTH: 498
<212> TYPE: DNA
<213> ORGANISM: Artificial Sequence
<220> FEATURE:
<223> OTHER INFORMATION: IFNalpha B9x28 coding sequence

<400> SEQUENCE: 30
tgtgatctgc ctcagaccca cagcctgagt aacaggagga ctctgatgct catggcacaa     60
atgaggagaa tctctccttt ctcctgcctg aaggacagac atgatttcgg attccccgag   120
gaggagtttg atggccacca cttccagaag gttcaagcca tcttccttct ctatgagctg   180
atccagcaga ccttcaatct cttcagcaca agaactcat ctgctgcttg ggatgagacc    240
ctcctagaaa aattctacat tgaactttc cagcaaatga ataacctgga agcatgtgtg    300
atacaggagg ttgggggtgga agagattgcc ctgatgaatg tggactccat cctggctgtg   360
aggaaatact tccgaagaat cactctctat ctgacaaaga agaaatacag cccttgttcc    420
tgggaggttg tcagagcaga aatcatgaga tctttctctt tttcaacaaa cttgcaaaaa    480
agattaagga ggaaggaa                                                   498
```

```
<210> SEQ ID NO 31
<211> LENGTH: 166
<212> TYPE: PRT
<213> ORGANISM: Homo sapiens
<220> FEATURE:
<223> OTHER INFORMATION: mature huIFN alpha-1a

<400> SEQUENCE: 31

Cys Asp Leu Pro Glu Thr His Ser Leu Asp Asn Arg Arg Thr Leu Met
  1               5                  10                  15

Leu Leu Ala Gln Met Ser Arg Ile Ser Pro Ser Ser Cys Leu Met Asp
             20                  25                  30

Arg His Asp Phe Gly Phe Pro Gln Glu Glu Phe Asp Gly Asn Gln Phe
```

-continued

```
                35                  40                  45

Gln Lys Ala Pro Ala Ile Ser Val Leu His Glu Leu Ile Gln Gln Ile
 50                  55                  60

Phe Asn Leu Phe Thr Thr Lys Asp Ser Ser Ala Ala Trp Asp Glu Asp
 65                  70                  75                  80

Leu Leu Asp Lys Phe Cys Thr Glu Leu Tyr Gln Gln Leu Asn Asp Leu
                 85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 32
<211> LENGTH: 165
<212> TYPE: PRT
<213> ORGANISM: Homo sapiens
<220> FEATURE:
<223> OTHER INFORMATION: mature huIFN alpha-2b

<400> SEQUENCE: 32

Cys Asp Leu Pro Gln Thr His Ser Leu Gly Ser Arg Arg Thr Leu Met
 1               5                  10                  15

Leu Leu Ala Gln Met Arg Arg Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
 50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 33
<211> LENGTH: 166
<212> TYPE: PRT
<213> ORGANISM: Homo sapiens
<220> FEATURE:
<223> OTHER INFORMATION: mature huIFN alpha-4b

<400> SEQUENCE: 33
```

```
Cys Asp Leu Pro Gln Thr His Ser Leu Gly Asn Arg Arg Ala Leu Ile
  1               5                  10                  15

Leu Leu Ala Gln Met Gly Arg Ile Ser His Phe Ser Cys Leu Lys Asp
                 20                  25                  30

Arg His Asp Phe Gly Phe Pro Glu Glu Glu Phe Asp Gly His Gln Phe
             35                  40                  45

Gln Lys Thr Gln Ala Ile Ser Val Leu His Glu Met Ile Gln Gln Thr
         50                  55                  60

Phe Asn Leu Phe Ser Thr Glu Asp Ser Ser Ala Ala Trp Glu Gln Ser
 65              70                  75                  80

Leu Leu Glu Lys Phe Ser Thr Glu Leu Tyr Gln Gln Leu Asn Asp Leu
                 85                  90                  95

Glu Ala Cys Val Ile Gln Glu Val Gly Val Glu Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Phe Ser Thr Asn Leu Gln Lys
145                 150                 155                 160

Arg Leu Arg Arg Lys Asp
                165
```

<210> SEQ ID NO 34
<211> LENGTH: 166
<212> TYPE: PRT
<213> ORGANISM: Homo sapiens
<220> FEATURE:
<223> OTHER INFORMATION: mature huIFN alpha-5

<400> SEQUENCE: 34

```
Cys Asp Leu Pro Gln Thr His Ser Leu Ser Asn Arg Arg Thr Leu Met
  1               5                  10                  15

Ile Met Ala Gln Met Gly Arg Ile Ser Pro Phe Ser Cys Leu Lys Asp
                 20                  25                  30

Arg His Asp Phe Gly Phe Pro Gln Glu Glu Phe Asp Gly Asn Gln Phe
             35                  40                  45

Gln Lys Ala Gln Ala Ile Ser Val Leu His Glu Met Ile Gln Gln Thr
         50                  55                  60

Phe Asn Leu Phe Ser Thr Lys Asp Ser Ser Ala Thr Trp Asp Glu Thr
 65              70                  75                  80

Leu Leu Asp Lys Phe Tyr Thr Glu Leu Tyr Gln Gln Leu Asn Asp Leu
                 85                  90                  95

Glu Ala Cys Met Met Gln Glu Val Gly Val Glu Asp Thr Pro Leu Met
            100                 105                 110

Asn Val Asp Ser Ile Leu Thr Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Ala Asn Leu Gln Glu
145                 150                 155                 160

Arg Leu Arg Arg Lys Glu
                165
```

<210> SEQ ID NO 35
<211> LENGTH: 166

```
<212> TYPE: PRT
<213> ORGANISM: Homo sapiens
<220> FEATURE:
<223> OTHER INFORMATION: mature huIFN alpha-6

<400> SEQUENCE: 35

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
        35                  40                  45

Gln Lys Ala Glu Ala Ile Ser Val Leu His Glu Val Ile Gln Gln Thr
    50                  55                  60

Phe Asn Leu Phe Ser Thr Lys Asp Ser Ser Val Ala Trp Asp Glu Arg
65                  70                  75                  80

Leu Leu Asp Lys Leu Tyr Thr Glu Leu Tyr Gln Gln Leu Asn Asp Leu
                85                  90                  95

Glu Ala Cys Val Met Gln Glu Val Trp Val Gly Gly Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Ser Ser Arg Asn Leu Gln Glu
145                 150                 155                 160

Arg Leu Arg Arg Lys Glu
                165

<210> SEQ ID NO 36
<211> LENGTH: 166
<212> TYPE: PRT
<213> ORGANISM: Homo sapiens
<220> FEATURE:
<223> OTHER INFORMATION: mature huIFN alpha-7a

<400> SEQUENCE: 36

Cys Asp Leu Pro Gln Thr His Ser Leu Arg Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Glu Phe Arg Phe Pro Glu Glu Glu Phe Asp Gly His Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Phe Ile Leu Ala Val Arg Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Phe Ser Phe Ser Thr Asn Leu Lys Lys
145                 150                 155                 160
```

```
Gly Leu Arg Arg Lys Asp
                165

<210> SEQ ID NO 37
<211> LENGTH: 166
<212> TYPE: PRT
<213> ORGANISM: Homo sapiens
<220> FEATURE:
<223> OTHER INFORMATION: mature huIFN alpha-8b

<400> SEQUENCE: 37

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Ile Asn Leu Gln Lys
145                 150                 155                 160

Arg Leu Lys Ser Lys Glu
                165

<210> SEQ ID NO 38
<211> LENGTH: 166
<212> TYPE: PRT
<213> ORGANISM: Homo sapiens
<220> FEATURE:
<223> OTHER INFORMATION: mature huIFN alpha-10a

<400> SEQUENCE: 38

Cys Asp Leu Pro Gln Thr His Ser Leu Gly Asn Arg Arg Ala Leu Ile
1               5                   10                  15

Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
```

```
                    115                 120                 125
Leu Tyr Leu Ile Glu Arg Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 39
<211> LENGTH: 166
<212> TYPE: PRT
<213> ORGANISM: Homo sapiens
<220> FEATURE:
<223> OTHER INFORMATION: mature huIFN alpha-14a

<400> SEQUENCE: 39

Cys Asn Leu Ser Gln Thr His Ser Leu Asn Asn Arg Arg Thr Leu Met
  1               5                  10                  15

Leu Met Ala Gln Met Arg Arg Ile Ser Pro Phe Ser Cys Leu Lys Asp
             20                  25                  30

Arg His Asp Phe Glu Phe Pro Gln Glu Glu Phe Asp Gly Asn Gln Phe
         35                  40                  45

Gln Lys Ala Gln Ala Ile Ser Val Leu His Glu Met Met Gln Gln Thr
     50                  55                  60

Phe Asn Leu Phe Ser Thr Lys Asn Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Asp
                165

<210> SEQ ID NO 40
<211> LENGTH: 166
<212> TYPE: PRT
<213> ORGANISM: Homo sapiens
<220> FEATURE:
<223> OTHER INFORMATION: mature huIFN alpha-16

<400> SEQUENCE: 40

Cys Asp Leu Pro Gln Thr His Ser Leu Gly Asn Arg Arg Ala Leu Ile
  1               5                  10                  15

Leu Leu Ala Gln Met Gly Arg Ile Ser His Phe Ser Cys Leu Lys Asp
             20                  25                  30

Arg Tyr Asp Phe Gly Phe Pro Gln Glu Val Phe Asp Gly Asn Gln Phe
         35                  40                  45

Gln Lys Ala Gln Ala Ile Ser Ala Phe His Glu Met Ile Gln Gln Thr
     50                  55                  60

Phe Asn Leu Phe Ser Thr Lys Asp Ser Ser Ala Ala Trp Asp Glu Thr
 65                  70                  75                  80
```

-continued

```
Leu Leu Asp Lys Phe Tyr Ile Glu Leu Phe Gln Gln Leu Asn Asp Leu
                85                  90                  95

Glu Ala Cys Val Thr Gln Glu Val Gly Val Glu Ile Ala Leu Met
            100                 105                 110

Asn Glu Asp Ser Ile Leu Ala Val Arg Lys Tyr Phe Gln Arg Ile Thr
            115                 120                 125

Leu Tyr Leu Met Gly Lys Lys Tyr Ser Pro Cys Ala Trp Glu Val Val
        130                 135                 140

Arg Ala Glu Ile Met Arg Ser Phe Ser Phe Ser Thr Asn Leu Gln Lys
145                 150                 155                 160

Gly Leu Arg Arg Lys Asp
                165

<210> SEQ ID NO 41
<211> LENGTH: 166
<212> TYPE: PRT
<213> ORGANISM: Homo sapiens
<220> FEATURE:
<223> OTHER INFORMATION: mature huIFN alpha-17b

<400> SEQUENCE: 41

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Leu Pro Gln Glu Glu Phe Asp Gly Asn Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asn Leu
                85                  90                  95

Glu Ala Cys Val Ile Gln Glu Val Gly Met Glu Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Phe Ser Thr Asn Leu Gln Lys
145                 150                 155                 160

Ile Leu Arg Arg Lys Asp
                165

<210> SEQ ID NO 42
<211> LENGTH: 166
<212> TYPE: PRT
<213> ORGANISM: Homo sapiens
<220> FEATURE:
<223> OTHER INFORMATION: mature huIFN alpha-21

<400> SEQUENCE: 42

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45
```

Gln Lys Ala Gln Ala Ile Ser Val Leu His Glu Met Ile Gln Gln Thr
 50                  55                  60

Phe Asn Leu Phe Ser Thr Lys Asp Ser Ser Ala Thr Trp Glu Gln Ser
 65                  70                  75                  80

Leu Leu Glu Lys Phe Ser Thr Glu Leu Asn Gln Gln Leu Asn Asp Leu
                 85                  90                  95

Glu Ala Cys Val Ile Gln Glu Val Gly Val Glu Thr Pro Leu Met
            100                 105                 110

Asn Val Asp Ser Ile Leu Ala Val Lys Lys Tyr Phe Gln Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 43
<211> LENGTH: 167
<212> TYPE: PRT
<213> ORGANISM: Artificial Sequence
<220> FEATURE:
<223> OTHER INFORMATION: IFNalpha-Con1

<400> SEQUENCE: 43

Met Cys Asp Leu Pro Gln Thr His Ser Leu Gly Asn Arg Arg Ala Leu
 1               5                  10                  15

Ile Leu Leu Ala Gln Met Arg Arg Ile Ser Pro Phe Ser Cys Leu Lys
                 20                  25                  30

Asp Arg His Asp Phe Gly Phe Pro Gln Glu Glu Phe Asp Gly Asn Gln
            35                  40                  45

Phe Gln Lys Ala Gln Ala Ile Ser Val Leu His Glu Met Ile Gln Gln
 50                  55                  60

Thr Phe Asn Leu Phe Ser Thr Lys Asp Ser Ser Ala Ala Trp Asp Glu
 65                  70                  75                  80

Ser Leu Leu Glu Lys Phe Tyr Thr Glu Leu Tyr Gln Gln Leu Asn Asp
                 85                  90                  95

Leu Glu Ala Cys Val Ile Gln Glu Val Gly Val Glu Thr Pro Leu
                100                 105                 110

Met Asn Val Asp Ser Ile Leu Ala Val Lys Lys Tyr Phe Gln Arg Ile
            115                 120                 125

Thr Leu Tyr Leu Thr Glu Lys Lys Tyr Ser Pro Cys Ala Trp Glu Val
130                 135                 140

Val Arg Ala Glu Ile Met Arg Ser Phe Ser Leu Ser Thr Asn Leu Gln
145                 150                 155                 160

Glu Arg Leu Arg Arg Lys Glu
                165

<210> SEQ ID NO 44
<211> LENGTH: 166
<212> TYPE: PRT
<213> ORGANISM: Artificial Sequence
<220> FEATURE:
<223> OTHER INFORMATION: IFNalpha B9x14C2a

<400> SEQUENCE: 44

Cys Asp Leu Pro Gln Thr His Ser Leu Gly His Arg Arg Thr Met Met

```
                1               5              10              15
Leu Leu Ala Gln Met Arg Arg Ile Ser Leu Phe Ser Cys Leu Lys Asp
                20              25              30

Arg His Asp Phe Arg Phe Pro Gln Glu Glu Phe Asp Gly Asn His Phe
                35              40              45

Gln Lys Val Gln Ala Ile Phe Leu Phe Tyr Glu Met Met Gln Gln Thr
                50              55              60

Phe Asn Leu Phe Ser Thr Lys Asn Ser Ser Ala Ala Trp Asp Glu Thr
65              70              75              80

Leu Leu Glu Lys Phe Tyr Ile Glu Leu Phe Gln Gln Met Asn Asp Leu
                85              90              95

Glu Ala Cys Val Met Gln Glu Val Gly Val Glu Glu Thr Pro Leu Met
                100             105             110

Asn Val Asp Ser Ile Leu Ala Val Arg Lys Tyr Phe Gln Arg Ile Thr
                115             120             125

Leu Tyr Leu Thr Glu Lys Lys Tyr Ser Pro Cys Ala Trp Glu Val Val
                130             135             140

Arg Ala Glu Ile Met Arg Ser Phe Ser Leu Ser Thr Asn Leu Gln Glu
145             150             155             160

Ser Leu Arg Ser Lys Glu
                165

<210> SEQ ID NO 45
<211> LENGTH: 167
<212> TYPE: PRT
<213> ORGANISM: Artificial Sequence
<220> FEATURE:
<223> OTHER INFORMATION: IFNalpha B9x14CHO1

<400> SEQUENCE: 45

Cys Asp Leu Pro Gln Thr His Ser Leu Gly His Arg Arg Thr Met Met
1               5              10              15

Leu Leu Ala Gln Met Arg Arg Ile Ser Leu Phe Ser Cys Leu Lys Asp
                20              25              30

Arg His Asp Phe Arg Phe Pro Gln Glu Glu Phe Asp Gly Asn His Phe
                35              40              45

Gln Lys Val Gln Ala Ile Phe Leu Phe Tyr Glu Met Met Gln Gln Thr
                50              55              60

Phe Asn Leu Phe Ser Thr Lys Asn Ser Ser Ala Ala Trp Asp Glu Thr
65              70              75              80

Leu Leu Glu Lys Phe Tyr Ile Glu Leu Phe Gln Gln Met Asn Asp Leu
                85              90              95

Glu Ala Cys Val Met Gln Glu Val Gly Val Glu Glu Thr Pro Leu Met
                100             105             110

Asn Val Asp Ser Ile Leu Ala Val Arg Lys Tyr Phe Gln Arg Ile Thr
                115             120             125

Leu Tyr Leu Thr Glu Lys Lys Tyr Ser Pro Cys Ala Trp Glu Val Val
                130             135             140

Arg Ala Glu Ile Met Arg Ser Phe Ser Phe Ser Thr Asn Leu Gln Lys
145             150             155             160

Arg Leu Arg Arg Lys Glu Cys
                165

<210> SEQ ID NO 46
<211> LENGTH: 166
<212> TYPE: PRT
```

```
<213> ORGANISM: Artificial Sequence
<220> FEATURE:
<223> OTHER INFORMATION: IFNalpha B9x14CHO3

<400> SEQUENCE: 46

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
                165

<210> SEQ ID NO 47
<211> LENGTH: 166
<212> TYPE: PRT
<213> ORGANISM: Artificial Sequence
<220> FEATURE:
<223> OTHER INFORMATION: IFNalpha B9x14CHO4

<400> SEQUENCE: 47

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160
```

```
Ser Leu Arg Ser Lys Glu
            165

<210> SEQ ID NO 48
<211> LENGTH: 166
<212> TYPE: PRT
<213> ORGANISM: Artificial Sequence
<220> FEATURE:
<223> OTHER INFORMATION: IFNalpha B9x14CHO5

<400> SEQUENCE: 48

Cys Asp Leu Pro Gln Thr His Ser Leu Gly His Arg Arg Thr Met Met
  1               5                  10                  15

Leu Leu Ala Gln Met Arg Arg Ile Ser Leu Phe Ser Cys Leu Lys Asp
                 20                  25                  30

Arg His Asp Phe Arg Phe Pro Gln Glu Glu Phe Asp Gly Asn His Phe
             35                  40                  45

Gln Lys Val Gln Ala Ile Phe Leu Phe Tyr Glu Met Met Gln Gln Thr
         50                  55                  60

Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Cys Leu Arg Ser Lys Glu
            165

<210> SEQ ID NO 49
<211> LENGTH: 166
<212> TYPE: PRT
<213> ORGANISM: Artificial Sequence
<220> FEATURE:
<223> OTHER INFORMATION: IFNalpha B9x14CHO6

<400> SEQUENCE: 49

Cys Asp Leu Pro Gln Thr His Ser Leu Gly His Arg Arg Thr Met Met
  1               5                  10                  15

Leu Leu Ala Gln Met Arg Arg Ile Ser Leu Phe Ser Cys Leu Lys Asp
                 20                  25                  30

Arg His Asp Phe Arg Phe Pro Gln Glu Glu Phe Asp Gly Asn His Phe
             35                  40                  45

Gln Lys Val Gln Ala Ile Phe Leu Phe Tyr Glu Met Met Gln Gln Thr
         50                  55                  60

Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125
```

Leu Tyr Leu Thr Glu Lys Lys Tyr Ser Pro Cys Ala Trp Glu Val Val
            130                 135                 140

Arg Ala Glu Ile Met Arg Ser Phe Ser Phe Ser Thr Asn Leu Gln Glu
145                 150                 155                 160

Ser Leu Arg Cys Lys Glu
            165

<210> SEQ ID NO 50
<211> LENGTH: 166
<212> TYPE: PRT
<213> ORGANISM: Artificial Sequence
<220> FEATURE:
<223> OTHER INFORMATION: IFNalpha 14Ep01

<400> SEQUENCE: 50

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
        35                  40                  45

Gln Lys Ala Gln Ala Ile Ser Val Leu His Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
            85                  90                  95

Glu Ala Cys Val Met Gln Glu Val Gly Val Glu Glu Thr Pro Leu Met
        100                 105                 110

Asn Val Asp Ser Ile Leu Ala Val Arg Lys Tyr Phe Gln Arg Ile Thr
    115                 120                 125

Leu Tyr Leu Thr Glu Lys Lys Tyr Ser Pro Cys Ala Trp Glu Val Val
            130                 135                 140

Arg Ala Glu Ile Met Arg Ser Phe Ser Leu Ser Thr Asn Leu Gln Glu
145                 150                 155                 160

Ser Leu Arg Ser Lys Glu
            165

<210> SEQ ID NO 51
<211> LENGTH: 166
<212> TYPE: PRT
<213> ORGANISM: Artificial Sequence
<220> FEATURE:
<223> OTHER INFORMATION: IFNalpha 14Ep02

<400> SEQUENCE: 51

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Ile Gln Gln Thr
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Ile Glu Leu Phe Gln Gln Leu Asn Asp Leu

```
                    85                  90                  95

Glu Ala Cys Val Thr Gln Glu Val Gly Val Glu Glu Ile Ala Leu Met
                100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 52
<211> LENGTH: 166
<212> TYPE: PRT
<213> ORGANISM: Artificial Sequence
<220> FEATURE:
<223> OTHER INFORMATION: IFNalpha 14Ep03

<400> SEQUENCE: 52

Cys Asp Leu Pro Gln Thr His Ser Leu Gly His Arg Arg Thr Met Met
  1               5                  10                  15

Leu Leu Ala Gln Met Arg Arg Ile Ser Leu Phe Ser Cys Leu Lys Asp
                 20                  25                  30

Arg His Asp Phe Arg Phe Pro Gln Glu Glu Phe Asp Gly Asn His Phe
             35                  40                  45

Gln Lys Val Gln Ala Ile Phe Leu Phe Tyr Glu Met Met Gln Gln Thr
         50                  55                  60

Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Ile Gln Glu Val Gly Val Glu Glu Thr Pro Leu Met
                100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 53
<211> LENGTH: 166
<212> TYPE: PRT
<213> ORGANISM: Artificial Sequence
<220> FEATURE:
<223> OTHER INFORMATION: IFNalpha 14Ep04

<400> SEQUENCE: 53

Cys Asp Leu Pro Gln Thr His Ser Leu Gly His Arg Arg Thr Met Met
  1               5                  10                  15

Leu Leu Ala Gln Met Arg Arg Ile Ser Leu Phe Ser Cys Leu Lys Asp
                 20                  25                  30

Arg His Asp Phe Arg Phe Pro Gln Glu Glu Phe Asp Gly Asn His Phe
             35                  40                  45
```

-continued

```
Gln Lys Val Gln Ala Ile Phe Leu Phe Tyr Glu Met Met Gln Gln Thr
         50                  55                  60

Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165
```

<210> SEQ ID NO 54
<211> LENGTH: 166
<212> TYPE: PRT
<213> ORGANISM: Artificial Sequence
<220> FEATURE:
<223> OTHER INFORMATION: IFNalpha 14Ep05

<400> SEQUENCE: 54

```
Cys Asp Leu Pro Gln Thr His Ser Leu Gly His Arg Arg Thr Met Met
  1               5                  10                  15

Leu Leu Ala Gln Met Arg Arg Ile Ser Leu Phe Ser Cys Leu Lys Asp
                 20                  25                  30

Arg His Asp Phe Arg Phe Pro Gln Glu Glu Phe Asp Gly Asn Gln Phe
             35                  40                  45

Gln Lys Ala Gln Ala Ile Ser Val Leu His Glu Met Met Gln Gln Thr
         50                  55                  60

Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Ile Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165
```

<210> SEQ ID NO 55
<211> LENGTH: 166
<212> TYPE: PRT
<213> ORGANISM: Artificial Sequence
<220> FEATURE:
<223> OTHER INFORMATION: IFNalpha 14EF

<400> SEQUENCE: 55

```
Cys Asp Leu Pro Gln Thr His Ser Leu Gly His Arg Arg Thr Met Met
  1               5                  10                  15
```

-continued

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Ile Glu Leu Phe Gln Gln Leu Asn Asp Leu
                85                  90                  95

Glu Ala Cys Val Thr Gln Glu Val Gly Val Glu Glu Ile Ala Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 56
<211> LENGTH: 166
<212> TYPE: PRT
<213> ORGANISM: Artificial Sequence
<220> FEATURE:
<223> OTHER INFORMATION: IFNalpha B9x14EP04C31

<400> SEQUENCE: 56

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Cys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 57
<211> LENGTH: 166
<212> TYPE: PRT
<213> ORGANISM: Artificial Sequence

```
<220> FEATURE:
<223> OTHER INFORMATION: IFNalpha B9x14CH04C31

<400> SEQUENCE: 57

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Cys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 58
<211> LENGTH: 166
<212> TYPE: PRT
<213> ORGANISM: Artificial Sequence
<220> FEATURE:
<223> OTHER INFORMATION: IFNalpha B9x14CH04C46

<400> SEQUENCE: 58

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Cys His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Phe Ser Thr Asn Leu Gln Glu
145                 150                 155                 160

Ser Leu Arg Ser Lys Glu
```

<210> SEQ ID NO 59
<211> LENGTH: 166
<212> TYPE: PRT
<213> ORGANISM: Artificial Sequence
<220> FEATURE:
<223> OTHER INFORMATION: IFNalpha B9x14CH04C71

<400> SEQUENCE: 59

```
Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
             20                  25                  30

Arg His Asp Phe Arg Phe Pro Gln Glu Glu Phe Asp Gly Asn His Phe
         35                  40                  45

Gln Lys Val Gln Ala Ile Phe Leu Phe Tyr Glu Met Met Gln Gln Thr
     50                  55                  60

Phe Asn Leu Phe Ser Thr Cys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165
```

<210> SEQ ID NO 60
<211> LENGTH: 166
<212> TYPE: PRT
<213> ORGANISM: Artificial Sequence
<220> FEATURE:
<223> OTHER INFORMATION: IFNalpha B9x14CH04C75

<400> SEQUENCE: 60

```
Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
             20                  25                  30

Arg His Asp Phe Arg Phe Pro Gln Glu Glu Phe Asp Gly Asn His Phe
         35                  40                  45

Gln Lys Val Gln Ala Ile Phe Leu Phe Tyr Glu Met Met Gln Gln Thr
     50                  55                  60

Phe Asn Leu Phe Ser Thr Lys Asp Ser Ser Cys Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125
```

```
Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 61
<211> LENGTH: 166
<212> TYPE: PRT
<213> ORGANISM: Artificial Sequence
<220> FEATURE:
<223> OTHER INFORMATION: IFNalpha B9x14CH04C79

<400> SEQUENCE: 61

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Cys Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 62
<211> LENGTH: 166
<212> TYPE: PRT
<213> ORGANISM: Artificial Sequence
<220> FEATURE:
<223> OTHER INFORMATION: IFNalpha B9x14CH04C107

<400> SEQUENCE: 62

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95
```

Glu Ala Cys Val Met Gln Glu Val Gly Val Cys Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 63
<211> LENGTH: 166
<212> TYPE: PRT
<213> ORGANISM: Artificial Sequence
<220> FEATURE:
<223> OTHER INFORMATION: IFNalpha B9x14CH04C122

<400> SEQUENCE: 63

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Thr Pro Leu Met
            100                 105                 110

Asn Val Asp Ser Ile Leu Ala Val Arg Cys Tyr Phe Gln Arg Ile Thr
            115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 64
<211> LENGTH: 166
<212> TYPE: PRT
<213> ORGANISM: Artificial Sequence
<220> FEATURE:
<223> OTHER INFORMATION: IFNalpha B9x14CH04C134

<400> SEQUENCE: 64

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr

-continued

```
            50                  55                  60
Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Cys Lys Tyr Ser Pro Cys Ala Trp Glu Val Val
            130                 135                 140

Arg Ala Glu Ile Met Arg Ser Phe Ser Phe Ser Thr Asn Leu Gln Glu
145                 150                 155                 160

Ser Leu Arg Ser Lys Glu
                165
```

<210> SEQ ID NO 65
<211> LENGTH: 160
<212> TYPE: PRT
<213> ORGANISM: Artificial Sequence
<220> FEATURE:
<223> OTHER INFORMATION: IFNalpha B9x14Ep04(161-166

<400> SEQUENCE: 65

```
Cys Asp Leu Pro Gln Thr His Ser Leu Gly His Arg Arg Thr Met Met
  1               5                  10                  15

Leu Leu Ala Gln Met Arg Arg Ile Ser Leu Phe Ser Cys Leu Lys Asp
                 20                  25                  30

Arg His Asp Phe Arg Phe Pro Gln Glu Glu Phe Asp Gly Asn His Phe
             35                  40                  45

Gln Lys Val Gln Ala Ile Phe Leu Phe Tyr Glu Met Met Gln Gln Thr
         50                  55                  60

Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
            130                 135                 140

Arg Ala Glu Ile Met Arg Ser Phe Ser Leu Ser Thr Asn Leu Gln Glu
145                 150                 155                 160
```

<210> SEQ ID NO 66
<211> LENGTH: 164
<212> TYPE: PRT
<213> ORGANISM: Artificial Sequence
<220> FEATURE:
<223> OTHER INFORMATION: IFNalpha B9x14Ep04(165-166

<400> SEQUENCE: 66

```
Cys Asp Leu Pro Gln Thr His Ser Leu Gly His Arg Arg Thr Met Met
  1               5                  10                  15

Leu Leu Ala Gln Met Arg Arg Ile Ser Leu Phe Ser Cys Leu Lys Asp
                 20                  25                  30
```

```
Arg His Asp Phe Arg Phe Pro Gln Glu Glu Phe Asp Gly Asn His Phe
            35                  40                  45

Gln Lys Val Gln Ala Ile Phe Leu Phe Tyr Glu Met Met Gln Gln Thr
        50                  55                  60

Phe Asn Leu Phe Ser Thr Lys Asp Ser Ser Ala Ala Trp Asp Glu Thr
 65                 70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Leu Ser Thr Asn Leu Gln Glu
145                 150                 155                 160

Ser Leu Arg Ser

<210> SEQ ID NO 67
<211> LENGTH: 159
<212> TYPE: PRT
<213> ORGANISM: Artificial Sequence
<220> FEATURE:
<223> OTHER INFORMATION: IFNalpha B9x14Ep04(1-4D44*(161-166

<400> SEQUENCE: 67

Gln Thr His Ser Leu Gly His Arg Arg Thr Met Met Leu Leu Ala Gln
 1               5                  10                  15

Met Arg Arg Ile Ser Leu Phe Ser Cys Leu Lys Asp Arg His Asp Phe
            20                  25                  30

Arg Phe Pro Gln Glu Glu Phe Gly Asn His Phe Gln Lys Val Gln Ala
        35                  40                  45

Ile Phe Leu Phe Tyr Glu Met Met Gln Gln Thr Phe Asn Leu Phe Ser
 50                 55                  60

Thr Lys Asp Ser Ser Ala Ala Trp Asp Glu Thr Leu Leu Glu Lys Phe
65                  70                  75                  80

Tyr Ile Glu Leu Phe Gln Gln Met Asn Asp Leu Glu Ala Cys Val Met
                85                  90                  95

Gln Glu Val Gly Val Glu Glu Thr Pro Leu Met Asn Val Asp Ser Ile
            100                 105                 110

Leu Ala Val Arg Lys Tyr Phe Gln Arg Ile Thr Leu Tyr Leu Thr Glu
            115                 120                 125

Lys Lys Tyr Ser Pro Cys Ala Trp Glu Val Val Arg Ala Glu Ile Met
        130                 135                 140

Arg Ser Phe Ser Leu Ser Thr Asn Leu Gln Glu Ser Leu Arg Ser
145                 150                 155

<210> SEQ ID NO 68
<211> LENGTH: 166
<212> TYPE: PRT
<213> ORGANISM: Artificial Sequence
<220> FEATURE:
<223> OTHER INFORMATION: IFNalpha B9x14CHO4NP1

<400> SEQUENCE: 68

Cys Asp Leu Pro Gln Thr His Ser Leu Gly His Arg Arg Thr Met Met
 1               5                  10                  15
```

Leu Leu Ala Gln Met Arg Arg Ile Ser Leu Phe Ser Cys Leu Lys Asp
            20                  25                  30

Arg Gln Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 69
<211> LENGTH: 166
<212> TYPE: PRT
<213> ORGANISM: Artificial Sequence
<220> FEATURE:
<223> OTHER INFORMATION: IFNalpha B9x14CHO4NP2

<400> SEQUENCE: 69

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg Gln Asp Phe Arg Phe Pro Gln Glu Glu Phe Asp Gly Asn Gln Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 70
<211> LENGTH: 166
<212> TYPE: PRT
<213> ORGANISM: Artificial Sequence
<220> FEATURE:

<223> OTHER INFORMATION: IFNalpha B9x14CHO8

<400> SEQUENCE: 70

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Arg Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 71
<211> LENGTH: 166
<212> TYPE: PRT
<213> ORGANISM: Artificial Sequence
<220> FEATURE:
<223> OTHER INFORMATION: IFNalpha B9x14CHO9

<400> SEQUENCE: 71

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Arg Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 72
<211> LENGTH: 166
<212> TYPE: PRT
<213> ORGANISM: Artificial Sequence
<220> FEATURE:
<223> OTHER INFORMATION: IFNalpha B9x14CHO10

<400> SEQUENCE: 72

```
Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Arg Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165
```

<210> SEQ ID NO 73
<211> LENGTH: 166
<212> TYPE: PRT
<213> ORGANISM: Artificial Sequence
<220> FEATURE:
<223> OTHER INFORMATION: IFNalpha B9x14CHO11

<400> SEQUENCE: 73

```
Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Arg Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
```

```
                130                 135                 140
Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 74
<211> LENGTH: 166
<212> TYPE: PRT
<213> ORGANISM: Artificial Sequence
<220> FEATURE:
<223> OTHER INFORMATION: IFNalpha B9x14CHO12

<400> SEQUENCE: 74

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
                20                  25                  30

Arg His Asp Phe Arg Phe Pro Gln Glu Glu Phe Asp Gly Asn His Phe
            35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Arg Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 75
<211> LENGTH: 166
<212> TYPE: PRT
<213> ORGANISM: Artificial Sequence
<220> FEATURE:
<223> OTHER INFORMATION: IFNalpha B9x14CHO13

<400> SEQUENCE: 75

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
                20                  25                  30

Arg His Asp Phe Arg Phe Pro Gln Glu Glu Phe Asp Gly Asn His Phe
            35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95
```

```
Glu Ala Cys Val Met Gln Glu Val Gly Val Glu Glu Thr Pro Leu Met
                100                 105                 110

Asn Val Asp Ser Ile Leu Ala Val Arg Lys Tyr Phe Gln Arg Ile Thr
            115                 120                 125

Leu Tyr Leu Thr Glu Arg Lys Tyr Ser Pro Cys Ala Trp Glu Val Val
        130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 76
<211> LENGTH: 166
<212> TYPE: PRT
<213> ORGANISM: Artificial Sequence
<220> FEATURE:
<223> OTHER INFORMATION: IFNalpha B9x14CHO14

<400> SEQUENCE: 76

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
                100                 105                 110

Asn Val Asp Ser Ile Leu Ala Val Arg Lys Tyr Phe Gln Arg Ile Thr
            115                 120                 125

Leu Tyr Leu Thr Glu Lys Arg Tyr Ser Pro Cys Ala Trp Glu Val Val
        130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 77
<211> LENGTH: 166
<212> TYPE: PRT
<213> ORGANISM: Artificial Sequence
<220> FEATURE:
<223> OTHER INFORMATION: IFNalpha B9x14CHO15

<400> SEQUENCE: 77

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn His Phe
        35                  40                  45

Gln Lys Val Gln Ala Ile Phe Leu Phe Tyr Glu Met Met Gln Gln Thr
    50                  55                  60
```

```
Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Arg Glu
                165

<210> SEQ ID NO 78
<211> LENGTH: 166
<212> TYPE: PRT
<213> ORGANISM: Artificial Sequence
<220> FEATURE:
<223> OTHER INFORMATION: IFNalpha B9x14CHO16

<400> SEQUENCE: 78

Cys Asp Leu Pro Gln Thr His Ser Leu Gly His Arg Arg Thr Met Met
  1               5                  10                  15

Leu Leu Ala Gln Met Arg Arg Ile Ser Leu Phe Ser Cys Leu Lys Asp
             20                  25                  30

Arg His Asp Phe Arg Phe Pro Gln Glu Glu Phe Asp Gly Asn His Phe
         35                  40                  45

Gln Lys Val Gln Ala Ile Phe Leu Phe Tyr Glu Met Met Gln Gln Thr
     50                  55                  60

Phe Asn Leu Phe Ser Thr Lys Asp Ser Ser Ala Ala Trp Asp Glu Thr
 65                  70                  75                  80

Leu Leu Glu Lys Phe Tyr Ile Glu Leu Phe Gln Gln Met Asn Asp Leu
                 85                  90                  95

Glu Ala Cys Val Met Gln Glu Val Gly Val Glu Glu Thr Pro Leu Met
            100                 105                 110

Asn Val Asp Ser Ile Leu Ala Val Arg Arg Tyr Phe Gln Arg Ile Thr
        115                 120                 125

Leu Tyr Leu Thr Glu Lys Arg Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 79
<211> LENGTH: 166
<212> TYPE: PRT
<213> ORGANISM: Artificial Sequence
<220> FEATURE:
<223> OTHER INFORMATION: IFNalpha B9x14CHO17

<400> SEQUENCE: 79

Cys Asp Leu Pro Gln Thr His Ser Leu Gly His Arg Arg Thr Met Met
  1               5                  10                  15

Leu Leu Ala Gln Met Arg Arg Ile Ser Leu Phe Ser Cys Leu Arg Asp
```

```
                    20                  25                  30

Arg His Asp Phe Arg Phe Pro Gln Glu Glu Phe Asp Gly Asn His Phe
            35                  40                  45

Gln Lys Val Gln Ala Ile Phe Leu Phe Tyr Glu Met Met Gln Gln Thr
     50                  55                  60

Phe Asn Leu Phe Ser Thr Lys Asp Ser Ser Ala Ala Trp Asp Glu Thr
65                   70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Thr Pro Leu Met
                100                 105                 110

Asn Val Asp Ser Ile Leu Ala Val Arg Lys Tyr Phe Gln Arg Ile Thr
                115                 120                 125

Leu Tyr Leu Thr Glu Lys Arg Tyr Ser Pro Cys Ala Trp Glu Val Val
                130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 80
<211> LENGTH: 166
<212> TYPE: PRT
<213> ORGANISM: Artificial Sequence
<220> FEATURE:
<223> OTHER INFORMATION: IFNalpha B9x14CHO18

<400> SEQUENCE: 80

Cys Asp Leu Pro Gln Thr His Ser Leu Gly His Arg Arg Thr Met Met
1                   5                   10                  15

Leu Leu Ala Gln Met Arg Arg Ile Ser Leu Phe Ser Cys Leu Arg Asp
                20                  25                  30

Arg His Asp Phe Arg Phe Pro Gln Glu Glu Phe Asp Gly Asn His Phe
            35                  40                  45

Gln Lys Val Gln Ala Ile Phe Leu Phe Tyr Glu Met Met Gln Gln Thr
     50                  55                  60

Phe Asn Leu Phe Ser Thr Lys Asp Ser Ser Ala Ala Trp Asp Glu Thr
65                   70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
                100                 105                 110

Asn Val Asp Ser Ile Leu Ala Val Arg Arg Tyr Phe Gln Arg Ile Thr
                115                 120                 125

Leu Tyr Leu Thr Glu Lys Lys Tyr Ser Pro Cys Ala Trp Glu Val Val
                130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 81
<211> LENGTH: 166
<212> TYPE: PRT
<213> ORGANISM: Artificial Sequence
<220> FEATURE:
<223> OTHER INFORMATION: IFNalpha B9x14CHO18NP2
```

<400> SEQUENCE: 81

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Arg Asp
            20                  25                  30

Arg Gln Asp Phe Arg Phe Pro Gln Glu Glu Phe Asp Gly Asn Gln Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Arg Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser Lys Glu
                165

<210> SEQ ID NO 82
<211> LENGTH: 164
<212> TYPE: PRT
<213> ORGANISM: Artificial Sequence
<220> FEATURE:
<223> OTHER INFORMATION: IFNalpha B9x14CHO18NP2(165-166

<400> SEQUENCE: 82

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Arg Asp
            20                  25                  30

Arg Gln Asp Phe Arg Phe Pro Gln Glu Glu Phe Asp Gly Asn Gln Phe
        35                  40                  45

Gln Lys Val Gln Ala Ile Phe Leu Phe Tyr Glu Met Met Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Met Gln Glu Val Gly Val Glu Glu Thr Pro Leu Met
            100                 105                 110

Asn Val Asp Ser Ile Leu Ala Val Arg Arg Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Glu
145                 150                 155                 160

Ser Leu Arg Ser

<210> SEQ ID NO 83
<211> LENGTH: 166
<212> TYPE: PRT
<213> ORGANISM: Artificial Sequence
<220> FEATURE:
<223> OTHER INFORMATION: IFNalpha B9x25CHO1

<400> SEQUENCE: 83

```
Cys Asp Leu Pro Gln Thr His Ser Leu Ser Asn Arg Arg Thr Leu Met
 1               5                  10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His His Phe
        35                  40                  45

Gln Lys Val Gln Ala Ile Phe Leu Leu Tyr Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Phe Ser Thr Asn Leu Gln Lys
145                 150                 155                 160

Arg Leu Arg Arg Lys Glu
                165
```

<210> SEQ ID NO 84
<211> LENGTH: 166
<212> TYPE: PRT
<213> ORGANISM: Artificial Sequence
<220> FEATURE:
<223> OTHER INFORMATION: IFNalpha B9x25CHO2

<400> SEQUENCE: 84

```
Cys Asp Leu Pro Gln Thr His Ser Leu Ser Asn Arg Arg Thr Leu Met
 1               5                  10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His His Phe
        35                  40                  45

Gln Lys Val Gln Ala Ile Phe Leu Leu Tyr Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
    130                 135                 140
```

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 85
<211> LENGTH: 166
<212> TYPE: PRT
<213> ORGANISM: Artificial Sequence
<220> FEATURE:
<223> OTHER INFORMATION: IFNalpha B9x25CHO3

<400> SEQUENCE: 85

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His His Phe
        35                  40                  45

Gln Lys Val Gln Ala Ile Phe Leu Leu Tyr Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Cys Leu Arg Ser Lys Glu
                165

<210> SEQ ID NO 86
<211> LENGTH: 166
<212> TYPE: PRT
<213> ORGANISM: Artificial Sequence
<220> FEATURE:
<223> OTHER INFORMATION: IFNalpha B9x25CHO4

<400> SEQUENCE: 86

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His His Phe
        35                  40                  45

Gln Lys Val Gln Ala Ile Phe Leu Leu Tyr Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Ser Leu Arg Cys Lys Glu
            165

<210> SEQ ID NO 87
<211> LENGTH: 166
<212> TYPE: PRT
<213> ORGANISM: Artificial Sequence
<220> FEATURE:
<223> OTHER INFORMATION: IFNalpha B9x25Ep01

<400> SEQUENCE: 87

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Phe Ser Thr Asn Leu Gln Lys
145                 150                 155                 160

Arg Leu Arg Arg Lys Glu
            165

<210> SEQ ID NO 88
<211> LENGTH: 166
<212> TYPE: PRT
<213> ORGANISM: Artificial Sequence
<220> FEATURE:
<223> OTHER INFORMATION: IFNalpha B9x25Ep02

<400> SEQUENCE: 88

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr

```
            65                  70                  75                  80
Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 89
<211> LENGTH: 166
<212> TYPE: PRT
<213> ORGANISM: Artificial Sequence
<220> FEATURE:
<223> OTHER INFORMATION: IFNalpha B9x25Ep03

<400> SEQUENCE: 89

Cys Asn Leu Ser Gln Thr His Ser Leu Asn Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Phe Asp Gly His Gln Phe
        35                  40                  45

Gln Lys Thr Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 90
<211> LENGTH: 166
<212> TYPE: PRT
<213> ORGANISM: Artificial Sequence
<220> FEATURE:
<223> OTHER INFORMATION: IFNalpha B9x25Ep04

<400> SEQUENCE: 90

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30
```

-continued

Arg His Asp Phe Gly Phe Pro Glu Glu Glu Phe Asp Gly His Gln Phe
        35                  40                  45

Gln Lys Thr Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Leu Ser Thr Asn Leu Gln Glu
145                 150                 155                 160

Ser Leu Arg Ser Lys Glu
            165

<210> SEQ ID NO 91
<211> LENGTH: 166
<212> TYPE: PRT
<213> ORGANISM: Artificial Sequence
<220> FEATURE:
<223> OTHER INFORMATION: IFNalpha B9x25Ep05

<400> SEQUENCE: 91

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Leu Ser Thr Asn Leu Gln Glu
145                 150                 155                 160

Ser Leu Arg Ser Lys Glu
            165

<210> SEQ ID NO 92
<211> LENGTH: 166
<212> TYPE: PRT
<213> ORGANISM: Artificial Sequence
<220> FEATURE:
<223> OTHER INFORMATION: IFNalpha B9x25Ep06

<400> SEQUENCE: 92

```
Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Ile Glu Leu Phe Gln Gln Leu Asn Asp Leu
                85                  90                  95

Glu Ala Cys Val Thr Gln Glu Val Gly Val Glu Ile Ala Leu Met
            100                 105                 110

Asn Glu Asp Ser Ile Leu Ala Val Arg Lys Tyr Phe Arg Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Ser Leu Arg Ser Lys Glu
            165

<210> SEQ ID NO 93
<211> LENGTH: 166
<212> TYPE: PRT
<213> ORGANISM: Artificial Sequence
<220> FEATURE:
<223> OTHER INFORMATION: IFNalpha B9x25Ep07

<400> SEQUENCE: 93

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Ile Ala Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Ser Leu Arg Ser Lys Glu
            165

<210> SEQ ID NO 94
```

```
<211> LENGTH: 166
<212> TYPE: PRT
<213> ORGANISM: Artificial Sequence
<220> FEATURE:
<223> OTHER INFORMATION: IFNalpha B9x25Ep08

<400> SEQUENCE: 94

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 95
<211> LENGTH: 166
<212> TYPE: PRT
<213> ORGANISM: Artificial Sequence
<220> FEATURE:
<223> OTHER INFORMATION: IFNalpha B9x25Ep10

<400> SEQUENCE: 95

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Glu Glu Glu Phe Asp Gly His His Phe
        35                  40                  45

Gln Lys Val Gln Ala Ile Phe Leu Leu Tyr Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
```

-continued

```
                 145                 150                 155                 160
Ser Leu Arg Ser Lys Glu
                165

<210> SEQ ID NO 96
<211> LENGTH: 166
<212> TYPE: PRT
<213> ORGANISM: Artificial Sequence
<220> FEATURE:
<223> OTHER INFORMATION: IFNalpha B9x25Ep11

<400> SEQUENCE: 96

Cys Asn Leu Ser Gln Thr His Ser Leu Asn Arg Arg Thr Leu Met
 1               5                  10                  15

Leu Met Ala Gln Met Arg Arg Ile Ser Pro Phe Ser Cys Leu Lys Asp
                20                  25                  30

Arg His Asp Phe Gly Phe Pro Glu Glu Glu Phe Asp Gly His His Phe
            35                  40                  45

Gln Lys Val Gln Ala Ile Phe Leu Leu Tyr Glu Leu Ile Gln Gln Thr
        50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 97
<211> LENGTH: 166
<212> TYPE: PRT
<213> ORGANISM: Artificial Sequence
<220> FEATURE:
<223> OTHER INFORMATION: IFNalpha B9x25Ep12

<400> SEQUENCE: 97

Cys Asp Leu Pro Gln Thr His Ser Leu Ser Asn Arg Arg Thr Leu Met
 1               5                  10                  15

Leu Met Ala Gln Met Arg Arg Ile Ser Pro Phe Ser Cys Leu Lys Asp
                20                  25                  30

Arg His Asp Phe Gly Phe Pro Glu Glu Glu Phe Asp Gly His His Phe
            35                  40                  45

Gln Lys Val Gln Ala Ile Phe Leu Leu Tyr Glu Leu Ile Gln Gln Thr
        50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110
```

-continued

```
Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Leu Ser Thr Asn Leu Gln Glu
145                 150                 155                 160

Ser Leu Arg Ser Lys Glu
            165

<210> SEQ ID NO 98
<211> LENGTH: 166
<212> TYPE: PRT
<213> ORGANISM: Artificial Sequence
<220> FEATURE:
<223> OTHER INFORMATION: IFNalpha B9x25Ep13

<400> SEQUENCE: 98

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Glu Glu Glu Phe Asp Gly His His Phe
        35                  40                  45

Gln Lys Val Gln Ala Ile Phe Leu Leu Tyr Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Ile Ala Leu Met
            100                 105                 110

Asn Val Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Leu Ser Thr Asn Leu Gln Glu
145                 150                 155                 160

Ser Leu Arg Ser Lys Glu
            165

<210> SEQ ID NO 99
<211> LENGTH: 166
<212> TYPE: PRT
<213> ORGANISM: Artificial Sequence
<220> FEATURE:
<223> OTHER INFORMATION: IFNalpha B9x25Ep14

<400> SEQUENCE: 99

Cys Asn Leu Ser Gln Thr His Ser Leu Asn Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His His Phe
        35                  40                  45

Gln Lys Val Gln Ala Ile Phe Leu Leu Tyr Glu Leu Ile Gln Gln Thr
    50                  55                  60

Phe Asn Leu Phe Ser Thr Lys Asp Ser Ser Ala Ala Trp Asp Glu Thr
65                  70                  75                  80
```

-continued

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 100
<211> LENGTH: 166
<212> TYPE: PRT
<213> ORGANISM: Artificial Sequence
<220> FEATURE:
<223> OTHER INFORMATION: IFNalpha B9x25Ep15

<400> SEQUENCE: 100

Cys Asp Leu Pro Gln Thr His Ser Leu Ser Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Leu Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Tyr Ile Glu Leu Phe Gln Gln Met Asn Asn Leu
                85                  90                  95

Glu Ala Cys Val Ile Gln Glu Val Gly Val Glu Glu Ile Ala Leu Met
            100                 105                 110

Asn Val Asp Ser Ile Leu Ala Val Arg Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 101
<211> LENGTH: 166
<212> TYPE: PRT
<213> ORGANISM: Artificial Sequence
<220> FEATURE:
<223> OTHER INFORMATION: IFNalpha B9x25Ep16

<400> SEQUENCE: 101

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Glu Glu Glu Phe Asp Gly His Gln Phe

```
                35                  40                  45
Gln Lys Thr Gln Ala Ile Ser Val Leu His Glu Leu Ile Gln Gln Thr
         50                  55                  60
Phe Asn Leu Phe Ser Thr Lys Asp Ser Ser Ala Ala Trp Asp Glu Thr
 65                  70                  75                  80
Leu Leu Glu Lys Phe Tyr Ile Glu Leu Phe Gln Gln Met Asn Asn Leu
                 85                  90                  95
Glu Ala Cys Val Ile Gln Glu Val Gly Val Glu Ile Ala Leu Met
            100                 105                 110
Asn Val Asp Ser Ile Leu Ala Val Arg Lys Tyr Phe Gln Arg Ile Thr
            115                 120                 125
Leu Tyr Leu Thr Glu Lys Lys Tyr Ser Pro Cys Ala Trp Glu Val Val
            130                 135                 140
Arg Ala Glu Ile Met Arg Ser Phe Ser Leu Ser Thr Asn Leu Gln Glu
145                 150                 155                 160
Ser Leu Arg Ser Lys Glu
            165
```

<210> SEQ ID NO 102
<211> LENGTH: 166
<212> TYPE: PRT
<213> ORGANISM: Artificial Sequence
<220> FEATURE:
<223> OTHER INFORMATION: IFNalpha B9x25Ep17

<400> SEQUENCE: 102

```
Cys Asn Leu Ser Gln Thr His Ser Leu Asn Asn Arg Arg Thr Leu Met
  1               5                  10                  15
Leu Met Ala Gln Met Arg Arg Ile Ser Pro Phe Ser Cys Leu Lys Asp
             20                  25                  30
Arg His Asp Phe Gly Phe Pro Glu Glu Glu Phe Asp Gly His Gln Phe
             35                  40                  45
Gln Lys Thr Gln Ala Ile Ser Val Leu His Glu Leu Ile Gln Gln Thr
         50                  55                  60
Phe Asn Leu Phe Ser Thr Lys Asp Ser Ser Ala Ala Trp Asp Glu Thr
 65                  70                  75                  80
Leu Leu Glu Lys Phe Tyr Ile Glu Leu Phe Gln Gln Met Asn Asn Leu
                 85                  90                  95
Glu Ala Cys Val Ile Gln Glu Val Gly Val Glu Ile Ala Leu Met
            100                 105                 110
Asn Val Asp Ser Ile Leu Ala Val Arg Lys Tyr Phe Gln Arg Ile Thr
            115                 120                 125
Leu Tyr Leu Thr Glu Lys Lys Tyr Ser Pro Cys Ala Trp Glu Val Val
            130                 135                 140
Arg Ala Glu Ile Met Arg Ser Phe Ser Leu Ser Thr Asn Leu Gln Glu
145                 150                 155                 160
Ser Leu Arg Ser Lys Glu
            165
```

<210> SEQ ID NO 103
<211> LENGTH: 166
<212> TYPE: PRT
<213> ORGANISM: Artificial Sequence
<220> FEATURE:
<223> OTHER INFORMATION: IFNalpha B9x25EF1

<400> SEQUENCE: 103

-continued

```
Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Met Ile Gln Gln Thr
50                  55                  60

Phe Asn Leu Phe Ser Thr Lys Asp Ser Ser Ala Ala Trp Asp Glu Thr
65                  70                  75                  80

Leu Leu Asp Lys Phe Tyr Ile Glu Leu Phe Gln Gln Leu Asn Asp Leu
                85                  90                  95

Glu Ala Cys Val Thr Gln Glu Val Gly Val Glu Glu Ile Ala Leu Met
                100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Ser Leu Arg Ser Lys Glu
                165
```

<210> SEQ ID NO 104
<211> LENGTH: 166
<212> TYPE: PRT
<213> ORGANISM: Artificial Sequence
<220> FEATURE:
<223> OTHER INFORMATION: IFNalpha B9x25EF2

<400> SEQUENCE: 104

```
Cys Asn Leu Ser Gln Thr His Ser Leu Asn Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Met Ile Gln Gln Thr
50                  55                  60

Phe Asn Leu Phe Ser Thr Lys Asp Ser Ser Ala Ala Trp Asp Glu Thr
65                  70                  75                  80

Leu Leu Asp Lys Phe Tyr Ile Glu Leu Phe Gln Gln Leu Asn Asp Leu
                85                  90                  95

Glu Ala Cys Val Thr Gln Glu Val Gly Val Glu Glu Ile Ala Leu Met
                100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Ser Leu Arg Ser Lys Glu
                165
```

INTERFERON-ALPHA POLYPEPTIDES AND CONJUGATES

CROSS-REFERENCE TO RELATED APPLICATIONS

This application is a divisional of U.S. application Ser. No. 10/848,827 filed on May 19, 2004 (now U.S. Pat. No. 7,314,613), which is a continuation-in-part of U.S. application Ser. No. 10/714,817 filed on Nov. 17, 2003 (abandoned), which claims the benefit of U.S. Provisional Application Ser. No. 60/502,560 filed on Sep. 12, 2003 and U.S. Provisional Application Ser. No. 60/427,612 filed on Nov. 18, 2002, the disclosures of each of which are incorporated by reference herein in their entirety for all purposes.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates generally to polynucleotides and polypeptides encoded therefrom, conjugates of the polypeptides, as well as vectors, cells, antibodies, and methods for using and producing the polynucleotides, polypeptides, and conjugates.

BACKGROUND OF THE INVENTION

Interferon-alphas are members of the diverse helical-bundle superfamily of cytokine genes (Sprang, S. R. et al. (1993) Curr. Opin. Struct. Biol. 3:815-827). The human interferon-alphas are encoded by a family of over 20 tandemly duplicated nonallelic genes and psuedogenes that share 85-98% sequence identity at the amino acid level (Henco, K. et al. (1985) J. Mol. Biol. 185:227-260). Genes which express active interferon-alpha proteins have been grouped into 13 families according to genetic loci. Known expressed human interferon-alpha proteins and their allelic variations are tabulated in Allen G. and Diaz M. O. (1996) J. Interferon and Cytokine Res. 16:181-184.

Interferon-alphas have been shown to inhibit various types of cellular proliferation, and are especially useful for the treatment of a variety of cellular proliferation disorders frequently associated with cancer, particularly hematologic malignancies such as leukemias. These proteins have shown antiproliferative activity against multiple myeloma, chronic lymphocytic leukemia, low-grade lymphoma, Kaposi's sarcoma, chronic myelogenous leukemia, renal-cell carcinoma, urinary bladder tumors and ovarian cancers (Bonnem, E. M. et al. (1984) J. Biol. Response Modifiers 3:580; Oldham, R. K. (1985) Hospital Practice 20:71).

Interferon-alphas are also useful against various types of viral infections (Finter, N. B. et al. (1991) Drugs 42(5):749). Interferon-alphas have activity against human papillomavirus infection, Hepatitis B, and Hepatitis C infections (Finter, N. B. et al., 1991, supra; Kashima, H. et al. (1988) Laryngoscope 98:334; Dusheiko, G. M. et al. (1986) J. Hematology 3 (Supple. 2):S199; Davis, G L et al. (1989) N. England J. Med. 321:1501). The role of interferons and interferon receptors in the pathogenesis of certain autoimmune and inflammatory diseases has also been investigated (Benoit, P. et al. (1993) J. Immunol. 150(3):707).

Although these proteins possess therapeutic value in the treatment of a number of diseases, they have not been optimized for use as pharmaceuticals. For example, dose-limiting toxicity, receptor cross-reactivity, and short serum half-lives significantly reduce the clinical utility of many of these cytokines (Dusheiko, G. (1997) Hepatology 26:112 S-121S; Vial, T. and Descotes, J. (1994) Drug Experience 10:115-150; Funke, I. et al. (1994) Ann. Hematol. 68:49-52; Schomburg, A. et al. (1993) J. Cancer Res. Clin. Oncol. 119:745-755). Diverse and severe side effect profiles which accompany interferon administration include flu-like symptoms, fatigue, hallucination, fever, hepatic enzyme elevation, and leukopenia (Pontzer, C. H. et al. (1991) Cancer Res. 51:5304; Oldham, 1985, supra).

Hepatitis C virus (HCV) is a nonhost integrated RNA virus with a very high rate of replication and is therefore associated with a large degree of genetic diversity. At least six genotypes and more than thirty subtypes of HCV RNA have been identified. HCV genotype has been shown to be a predictor of response to IFN-alpha therapy. Patients infected with HCV genotypes 2 and 3 have been found to generally respond well to interferon therapy. Patients infected with genotypes 4, 5 and 6 tend to respond less well. Patients infected with HCV genotype 1 tend to respond very poorly to interferon therapy, with about 50% of Genotype 1 patients classified as "nonresponders" towards IFN-alpha therapy. Genotype 1 is currently the most prevalent form of Hepatitis C, infecting approximately 70% of patients in the US and 50% of patients in Europe. Clearly, there is a pressing need for more effective therapies for HCV infection, particularly of the Genotype 1 variety.

There is genetic and biochemical evidence that Genotype 1 HCV (and other subtypes) actively attenuate the IFN-alpha signaling pathway by inhibiting key IFN responsive proteins such as the dsRNA-activated serine/threonine protein kinase PKR (Katze M. G., et al. (2002) Nat. Rev. Immunol. 2(9): 675-687). As a likely consequence of this genetic diversity and active inhibition of the antiviral response, HCV (particularly Genotype 1) has the ability to escape the host's immune surveillance, leading to a high rate of chronic infection. The extensive genetic heterogeneity of HCV has important diagnostic and clinical implications, potentially accounting for variations in clinical course, difficulties in vaccine development, and lack of response to therapy.

The present invention addresses the need for interferon-alpha molecules which exhibit enhanced antiviral efficacy and/or enhanced immunomodulatory efficacy compared to interferon-alphas currently in clinical use. The invention provides novel interferon-alpha polypeptides and polypeptide conjugates, nucleic acids encoding the polypeptides, and methods of using such molecules. Such molecules would be of beneficial use in a variety of applications, including, e.g., therapeutic and prophylactic treatments, particularly for viral infections and diseases and conditions associated with viral infections. The present invention fulfills these and other needs.

SUMMARY OF THE INVENTION

The present invention provides novel polypeptides, including variants and fusion polypeptides. The invention also provides conjugates comprising a polypeptide of the invention covalently linked to one or more non-polypeptide moieties.

The invention also provides nucleic acids encoding any of the polypeptides of the invention, and vectors and host cells comprising such nucleic acids. In addition, the invention provides methods of making and using such polypeptides, conjugates, and nucleic acids, and other features apparent upon further review.

In one aspect, the invention provides an isolated or recombinant polypeptide, the polypeptide comprising a sequence identified as one of SEQ ID NOs:1-15 and SEQ ID NOs:44-104 (such as one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO: 14, SEQ ID NO:15, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, and SEQ ID NO: 104).

The invention also provides isolated or recombinant polypeptides which each comprise a sequence which differs in 0-16 amino acid positions (such as in 0, 1, 2, 3, 4, 5, 6, 7, 8, 9, 10, 11, 12, 13, 14, 15, or 16 amino acid positions), e.g. in 0-14 amino acid positions, in 0-12 amino acid positions, in 0-10 amino acid positions, in 0-8 amino acid positions, in 0-6 amino acid positions, in 0-5 amino acid positions, in 0-4 amino acid positions, in 0-3 amino acid positions, in 0-2 amino acid positions, or in 0-1 amino acid position, from one of SEQ ID NOs:1-15 and SEQ ID NOs:44-104, such as, for example, one of SEQ ID NOs:1-15, 47, or 53 (for example, SEQ ID NO:1, SEQ ID NO:3, SEQ ID NO:8, SEQ ID NO:12, SEQ ID NO:47, or SEQ ID NO:53). In some instances, the polypeptide exhibits an interferon-alpha activity (such as, e.g., antiviral activity, $T_H1$ differentiation activity, and/or antiproliferative activity). In some instances, the polypeptide sequence comprises a substitution at one or more of positions 47, 51, 52, 53, 54, 55, 56, 57, 58, 60, 61, 64, 69, 71, 72, 75, 76, 77, 78, 79, 80, 83, 84, 85, 86, 87, 90, 93, 133, 140, 154, 160, 161, and 162, relative to one of SEQ ID NOs: 1-15, 47, or 53, such as, for example, one of SEQ ID NO:1, SEQ ID NO:3, SEQ ID NO:8, SEQ ID NO:12, SEQ ID NO:47, or SEQ ID NO:53. In some instances, the polypeptide sequence comprises one or more of: His or Gln at position 47; Val, Ala or Thr at position 51; Gln, Pro or Glu at position 52; Ala or Thr at position 53; Phe, Ser, or Pro at position 55; Leu, Val or Ala at position 56; Phe or Leu at position 57; Tyr or His at position 58; Met, Leu or Val at position 60; Met or Ile at position 61; Thr or Ile at position 64; Ser or Thr at position 69; Lys or Glu at position 71; Asn or Asp at position 72; Ala or Val at position 75; Ala or Thr at position 76; Trp or Leu at position 77; Asp or Glu at position 78; Glu or Gln at position 79; Thr, Asp, Ser, or Arg at position 80; Glu or Asp at position 83; Lys or Glu at position 84; Phe or Leu at position 85; Tyr, Cys or Ser at position 86; Ile or Thr at position 87; Phe, Tyr, Asp or Asn at position 90; Met or Leu at position 93; Lys or Glu at position 133; Ser or Ala at position 140; Phe or Leu at position 154; Lys or Glu at position 160; Arg or Ser at position 161; and Arg or Ser at position 162; the position numbering relative to that of SEQ ID NO:1. In some instances, the polypeptide sequence comprises one or more of His47, Val51, Phe55, Leu56, Tyr58, Lys133, and Ser140, the position numbering relative to that of SEQ ID NO:1. Some such polypeptides include SEQ ID NOs:1-15 and SEQ ID NOs:44-104. The invention also provides fusion proteins and conjugates comprising any of these polypeptides, nucleic acids encoding such polypeptides, and methods of making such polypeptides.

Some polypeptides of the invention comprise one or more substitution, including but not limited to a substitution selected from: D2C, L3C, P4C, Q5C, T6C, H7C, S8C, L9C, G10C, R12C, R13C, M16C, A19C, Q20C, R22C, R23C, I24C, S25C, L26C, F27C, S28C, L30C, K31C, R33C, H34C, D35C, R37C, Q40C, E41C, E42C, D44C, N46C, H47C, Q49C, K50C, V51C, Q52C, E59C, Q62C, Q63C, N66C, S69C, T70C, K71C, N72C, S74C, A75C, D78C, E79C, T80C, L81C, E83C, K84C, I87C, F90C, Q91C, N94C, D95C, E97C, A98C, V100C, M101C, Q102C, E103C, V104C, G105C, E107C, E108C, T109C, P110C, L111C, M112C, N113C, V114C, D115C, L118C, R121C, K122C, Q125C, R126C, T128C, L129C, T132C, K133C, K134C, K135C, Y136C, S137C, P138C, A146C, M149C, R150C, S153C, F154C, N157C, Q159C, K160C, R161C, L162C, R163C, R164C, K165C and E166C (or equivalent position relative to SEQ ID NO:1), and combinations thereof.

Some polypeptides of the invention comprise one or more substitution, including but not limited to a substitution selected from: D2K, L3K, P4K, Q5K, T6K, H7K, S8K, L9K, G10K, R12K, R13K, M16K, A19K, Q20K, R22K, R23K, I24K, S25K, L26K, F27K, S28K, L30K, R33K, H34K, D35K, R37K, Q40K, E41K, E42K, D44K, N46K, H47K, Q49K, V51K, Q52K, E59K, Q62K, Q63K, N66K, S69K, T70K, N72K, S74K, A75K, D78K, E79K, T80K, L81K, E83K, I87K, F90K, Q91K, N94K, D95K, E97K, A98K, V100K, M101K, Q102K, E103K, V104K, G105K, E107K, E108K, T109K, P110K, L111K, M112K, N113K, V114K, D115K, L118K, R121K, Q125K, R126K, T128K, L129K, T132K, Y136K, S137K, P138K, A146K, M149K, R150K, S153K, F154K, N157K, Q159K, R161K, L162K, R163K, R164K, and E166K (or equivalent position relative to SEQ ID NO:1), and combinations thereof.

Some polypeptides of the invention comprise one or more substitution of an amino acid residue for a different amino acid residue, or one or more deletion of an amino acid residue, which removes one or more lysines, e.g., K31, K50, K71, K84, K122, K133, K134, K135, K160, and/or K165 (relative to SEQ ID NO: 1) from any polypeptide of the invention such as, for example, any one of SEQ ID NOs:1-15 and SEQ ID NOs:44-104 (such as, e.g., SEQ ID NO:1, SEQ ID NO:3, SEQ ID NO:8, SEQ ID NO:12, SEQ ID NO:47 or SEQ ID NO:53). The one or more lysine residue(s) to be removed may be substituted with any other amino acid, may be substituted with an Arg (R) or Gln (Q), or may be deleted.

Some polypeptides of the invention comprise one or more substitution of an amino acid residue for a different amino acid residue, or one or more deletion of an amino acid residue, which removes one or more histidines, e.g., H7, H11, H34, and/or H47 (relative to SEQ ID NO:1) from any polypeptide of the invention such as, for example, one of SEQ ID NOs:1-15 and SEQ ID NOs:44-104 (such as, e.g., SEQ ID NO:1, SEQ ID NO:3, SEQ ID NO:8, SEQ ID NO:12, SEQ ID NO:47, or SEQ ID NO:53). The one or more histidine residue (s) to be removed may be substituted with any other amino acid, may be substituted with an Arg (R) or Gln (Q), or may be deleted.

Some polypeptides of the invention comprise one or more substitution, including but not limited to substitutions selected from: D2N+P4S/T, L3N+Q5S/T, P4Q, P4Q+T6S, Q5N+H7S/T, T6N, T6N+S8T, H7N+L9S/T, S8N+G10S/T, L9N+H11S/T, G10N+R12S/T, R12N, R12N+T14S, R13N+M15S/T, M16N+L18S/T, A19N+M21S/T, Q20N+R22S/T, R22N+I24S/T, R23N, R23N+S25T, I24N+L26S/T, S25N+F27S/T, L26N, L26N+S28T, S28N+L30S/T, L30N+D32S/T, K31N+R33S/T, R33N+D35S/T, H34N+F36S/T, D35N+R37S/T, R37N+P39S/T, Q40N+E42S/T, E41N+F43S/T, E42N+D44S/T, D44N+N46S/T, F48S/T, H47N+Q49S/T, Q49N+V51S/T, K50N+Q52S/T, V51N+A53S/T, Q52N+I54S/T, E59N+M61S/T, Q62N, Q62N+T64S, Q63N+F65S/T, F68S/T, S69N+K71S/T, T70N+N72S/T, K71N, K71N+S73T, S74T, S74N+A76S/T, A75N+W77S/T, D78N, D78N+T80S, E79N+L81S/T, T80N+L82S/T, L81N+E83S/T, E83N+F85S/T, K84N+Y86S/T, I87N+L89S/T, F90N+Q92S/T, Q91N+M93S/T, L96S/T, D95N+E97S/T, E97N+C99S/T, A98N+V100S/T, V100N+Q102S/T, M101N+E103S/T, Q102N+V104S/T, E103N+G105S/T, V104N+V106S/T, G105N+E107S/T, E107, E107N+T109S, E108N+P110S/T, L111N+N113S/T, M112N+V114S/T, N113N+D115S/T, V114N, V114N+S116T, D115N+I117S/T, L118N+V120S/T, R121N+Y123S/T, K122N+F124S/T, Q125N+I127S/T, R126N, R126N+T128S, T128N+Y130S/T, L129N+L131S/T, T132N+K134S/T, K133N+K135S/T, K134N+Y136S/T, K135N, K135N+S137T, Y136N+P138S/T, P138N, P138N+S140T, A146N+I148S/T, M149N, M149N+S151T, R150N+F152S/T, S153N, S153N+S155T, F154N+F156S/T, Q159S/T, K160N+L162S/T, R161N+R163S/T, L162N+R164S/T, R163N+K165S/T and R164N+E166S/T (or equivalent positions relative to SEQ ID NO:1), and combinations thereof.

The invention also provides fusion proteins and conjugates comprising any of the above polypeptides, nucleic acids encoding such polypeptides, and methods of making and using such polypeptides.

In another aspect, the invention provides isolated or recombinant polypeptides which each comprise a sequence having at least about 90% amino acid sequence identity to one of SEQ ID NOs: 1-15 and SEQ ID NOs:44-104, such as, for example, one of SEQ ID NOs: 1-15, 47, and 53 (such as, for example, SEQ ID NO:1, SEQ ID NO: 3, SEQ ID NO:8, SEQ ID NO:12, SEQ ID NO:47, or SEQ ID NO:53). Some such polypeptides exhibit an interferon-alpha activity (such as, e.g., antiviral activity, $T_H1$ differentiation activity, and/or antiproliferative activity). In some instances, the sequence has at least about 91%, 92%, 93%, 94%, 95%, 96%, 97%, 98% or 99% identity to one of SEQ ID NOs:1-15 and SEQ ID NOs 44-104 (such as, e.g., SEQ ID NO:1, SEQ ID NO:3, SEQ ID NO:8, SEQ ID NO:12, SEQ ID NO:47, or SEQ ID NO:53). In some instances, the polypeptide sequence comprises a substitution at one or more of positions 47, 51, 52, 53, 54, 55, 56, 57, 58, 60, 61, 64, 69, 71, 72, 75, 76, 77, 78, 79, 80, 83, 84, 85, 86, 87, 90, 93, 133, 140, 154, 160, 161, and 162, relative to, e.g., one of SEQ ID NOs:1-15. In some instances, the polypeptide sequence comprises one or more of: His or Gln at position 47; Val, Ala or Thr at position 51; Gln, Pro or Glu at position 52; Ala or Thr at position 53; Phe, Ser, or Pro at position 55; Leu, Val or Ala at position 56; Phe or Leu at position 57; Tyr or His at position 58; Met, Leu or Val at position 60; Met or Ile at position 61; Thr or Ile at position 64; Ser or Thr at position 69; Lys or Glu at position 71; Asn or Asp at position 72; Ala or Val at position 75; Ala or Thr at position 76; Trp or Leu at position 77; Asp or Glu at position 78; Glu or Gln at position 79; Thr, Asp, Ser, or Arg at position 80; Glu or Asp at position 83; Lys or Glu at position 84; Phe or Leu at position 85; Tyr, Cys or Ser at position 86; Ile or Thr at position 87; Phe, Tyr, Asp or Asn at position 90; Met or Leu at position 93; Lys or Glu at position 133; Ser or Ala at position 140; Phe or Leu at position 154; Lys or Glu at position 160; Arg or Ser at position 161; and Arg or Ser at position 162 (the position numbering relative to that of SEQ ID NO:1). In some instances, the polypeptide sequence comprises one or more of His47, Val51, Phe55, Leu56, Tyr58, Lys133, and Ser140, the position numbering relative to that of SEQ ID NO:1. Some such polypeptides comprise a sequence selected from SEQ ID NOs:1-15 and SEQ ID NOs:44-104. The invention also provides fusion proteins and conjugates comprising any of the above polypeptides, nucleic acids encoding such polypeptides, and methods of making such polypeptides.

In another aspect, the invention provides isolated or recombinant polypeptides which are variants of a parent polypeptide, each variant comprising a variant sequence which differs from the parent polypeptide sequence in least one amino acid position relative to the parent polypeptide sequence, wherein the parent polypeptide sequence is one of SEQ ID NOs:1-15 and SEQ ID NOs:44-104, such as, for example, one of SEQ ID NOs:1-15, 47, and 53, e.g., SEQ ID NO:1, SEQ ID NO:3, SEQ ID NO:8, SEQ ID NO:12, SEQ ID NO:47, or SEQ ID NO:53. In some instances, the variant exhibits an interferon-alpha activity (such as, antiviral activity, $T_H1$ differentiation activity, and/or antiproliferative activity). In some instances, the variant sequence differs from the parent polypeptide sequence in 1-16 amino acid positions (such as in 1, 2, 3, 4, 5, 6, 7, 8, 9, 10, 11, 12, 13, 14, 15, or 16 amino acid positions), e.g. in 1-14 amino acid positions, in 1-12 amino acid positions, in 1-10 amino acid positions, in 1-8 amino acid positions, in 1-6 amino acid positions, in 1-5 amino acid positions, in 1-4 amino acid positions, in 1-3 amino acid positions, or in 1-2 amino acid positions. In some instances, the variant sequence comprises a substitution at one or more of positions 47, 51, 52, 53, 54, 55, 56, 57, 58, 60, 61, 64, 69, 71, 72, 75, 76, 77, 78, 79, 80, 83, 84, 85, 86, 87, 90, 93, 133, 140, 154, 160, 161, and 162, relative to one of SEQ ID NOs:1-15. In some instances, the variant sequence comprises one or more of: His or Gln at position 47; Val, Ala or Thr at position 51; Gln, Pro or Glu at position 52; Ala or Thr at position 53; Phe, Ser, or Pro at position 55; Leu, Val or Ala at position 56; Phe or Leu at position 57; Tyr or His at position 58; Met, Leu or Val at position 60; Met or Ile at position 61; Thr or Ile at position 64; Ser or Thr at position 69; Lys or Glu at position 71; Asn or Asp at position 72; Ala or Val at position 75; Ala or Thr at position 76; Trp or Leu at position 77; Asp or Glu at position 78; Glu or Gln at position 79; Thr, Asp, Ser, or Arg at position 80; Glu or Asp at position 83; Lys or Glu at position 84; Phe or Leu at position 85; Tyr, Cys or Ser at position 86; Ile or Thr at position 87; Phe, Tyr, Asp or Asn at position 90; Met or Leu at position 93; Lys or Glu at position 133; Ser or Ala at position 140; Phe or Leu at position 154; Lys or Glu at position 160; Arg or Ser at position 161; and Arg or Ser at position 162; the position numbering relative to that of SEQ ID NO:1. In some instances, the variant sequence comprises one or more of His47, Val51, Phe55, Leu56, Tyr58, Lys133, and Ser140, the position numbering relative to that of SEQ ID NO:1. Some such variants comprise a sequence selected from SEQ ID NOs:1-15 and SEQ ID NOs:44-104. The invention also provides fusion proteins and conjugates comprising any of these variants, nucleic acids encoding any of these variants, and methods of making such variants.

In another aspect, the invention provides isolated or recombinant polypeptides which are variants of a parent interferon-alpha polypeptide, each variant comprising a variant sequence which differs from the parent interferon-alpha polypeptide sequence in least one amino acid position, wherein the variant sequence comprises one or more of His47, Val51, Phe55, Leu56, Tyr58, Lys133, and Ser140, the position numbering relative to that of SEQ ID NO:1. In some instances the parent interferon-alpha polypeptide sequence is a sequence of a naturally-occurring human interferon-alpha, such as one of SEQ ID NO:31-SEQ ID NO:42 or SEQ ID NO:32+R23K, or a non-naturally occurring (i.e., synthetic) interferon-alpha, such as SEQ ID NO:43. In some instances, the variant sequence differs from the parent interferon-alpha polypeptide sequence in 1-16 amino acid positions (such as in 1, 2, 3, 4, 5, 6, 7, 8, 9, 10, 11, 12, 13, 14, 15, or 16 amino acid positions), e.g. in 1-14 amino acid positions, in 1-12 amino acid positions, in 1-10 amino acid positions, in 1-8 amino acid positions, in 1-6 amino acid positions, in 1-5 amino acid positions, in 1-4 amino acid positions, in 1-3 amino acid positions, or in 1-2 amino acid positions. In some instances, the variant exhibits an interferon-alpha activity (such as, e.g., antiviral activity, $T_H1$ differentiation activity, and/or antiproliferative activity). The invention also provides fusion proteins and conjugates comprising any of these variants, nucleic acids encoding any of these variants, and methods of making such variants.

The invention also provides conjugates comprising a polypeptide of the invention, such as any of the polypeptides of the invention (including variants) described above, and at least one non-polypeptide moiety attached to an attachment group of the polypeptide, wherein the conjugate exhibits an interferon-alpha activity. In some instances, the non-polypeptide moiety is a polymer (such as, e.g., PEG or mPEG), or a sugar moiety. The at least one non-polypeptide moiety may be attached to a cysteine, to a lysine, to the N-terminal amino group of the polypeptide, to an in vivo glycosylation site of the polypeptide. The invention also provides methods of making and using such conjugates.

The invention also provides isolated or recombinant nucleic acids encoding any of the polypeptides (including variants) of the invention. The invention also provides vectors and host cells comprising such nucleic acids, and methods of making polypeptides of the invention, comprising culturing host cells comprising such nucleic acids.

In another aspect, the invention provides a method of inhibiting viral replication in virus-infected cells, the method comprising contacting the virus-infected cells with a polypeptide or a conjugate of the invention. The invention also provides a method of reducing the number of copies of a virus in virus-infected cells, comprising contacting the virus-infected cells with a polypeptide or a conjugate of the invention.

In another aspect, the invention provides a method for reducing the level of a virus in the serum of a patient infected with the virus, comprising administering to the patient the polypeptide or a conjugate of the invention in an amount effective to reduce the level of the virus in the serum compared to the level present prior to the start of treatment.

These and other objects and features of the invention will become more fully apparent when the following detailed description is read in conjunction with the accompanying figures.

BRIEF DESCRIPTION OF THE FIGURES

FIG. 2 shows an alignment of the sequence of a polypeptide of the invention (SEQ ID NO:1) with the following human interferon-alpha polypeptide sequences: huIFN-alpha 1a (SEQ ID NO:31), huIFN-alpha 2b (SEQ ID NO:32), huIFN-alpha 4b (SEQ ID NO:33), huIFN-alpha 5 (SEQ ID NO:34), huIFN-alpha 6 (SEQ ID NO:35), huIFN-alpha 7 (SEQ ID NO:36), huIFN-alpha 8b (SEQ ID NO:37), huIFN-alpha 10a (SEQ ID NO:38), huIFN-alpha 14a (SEQ ID NO:39), huIFN-alpha 16 (SEQ ID NO:40), huIFN-alpha 17b (SEQ ID NO:41) and huIFN-alpha 21b (SEQ ID NO:42). The naming conventions for the huIFN-alpha sequences are according to Allen G. and Diaz M. O. (1996) J. Interferon and Cytokine Res. 16:181-184. The arrows indicate residues His47, Val51, Phe55, Leu56, Tyr58, Lys133, and Ser140 of SEQ ID NO:1, which are not present in any of SEQ ID NOs:31-SEQ ID NO:42. Amino acid residue positions in SEQ ID NOs:31-42 which are identical to SEQ ID NO:1 are indicated with a period (.), and gaps in the sequence are indicated with a dash (-).

FIG. 3 shows an alignment of the sequence of a polypeptide of the invention (SEQ ID NO:3) with huIFN-alpha 14a (SEQ ID NO:39) (LeIF H; Goeddel et al. (1981) Nature 290:20-26) using the following parameters: BLOSUM62 matrix, gap open penalty 11, gap extension penalty 1. Amino acid positions in SEQ ID NO:39 which are identical to SEQ ID NO:3 are indicated with a period (.).

FIG. 4 shows an alignment of the sequence of a polypeptide of the invention (SEQ ID NO:8) with human interferon-alpha polypeptide sequences SEQ ID NO:31-SEQ ID NO:42. Amino acid residue positions in SEQ ID NOs:31-42 which are identical to SEQ ID NO:8 are indicated with a period (.), and gaps in the sequence are indicated with a dash (-).

FIG. 5 shows an alignment of the sequence of a polypeptide of the invention (SEQ ID NO:12) with huIFN-alpha 14a (SEQ ID NO:39) (LeIF H; Goeddel et al. (1981) Nature 290:20-26) using the following parameters: BLOSUM62 matrix, gap open penalty 11, gap extension penalty 1. Amino acid positions in SEQ ID NO:39 which are identical to SEQ ID NO:12 are indicated with a period (.).

FIG. 6 shows the BLOSUM62 substitution matrix.

FIGS. 7A, 7B and 7C show examples of calculations of alignment scores used to determine optimal sequence alignments, using the following parameters: BLOSUM62 matrix, gap open penalty=11, and gap extension penalty=1.

DETAILED DESCRIPTION OF THE INVENTION

Definitions

Figure 1:
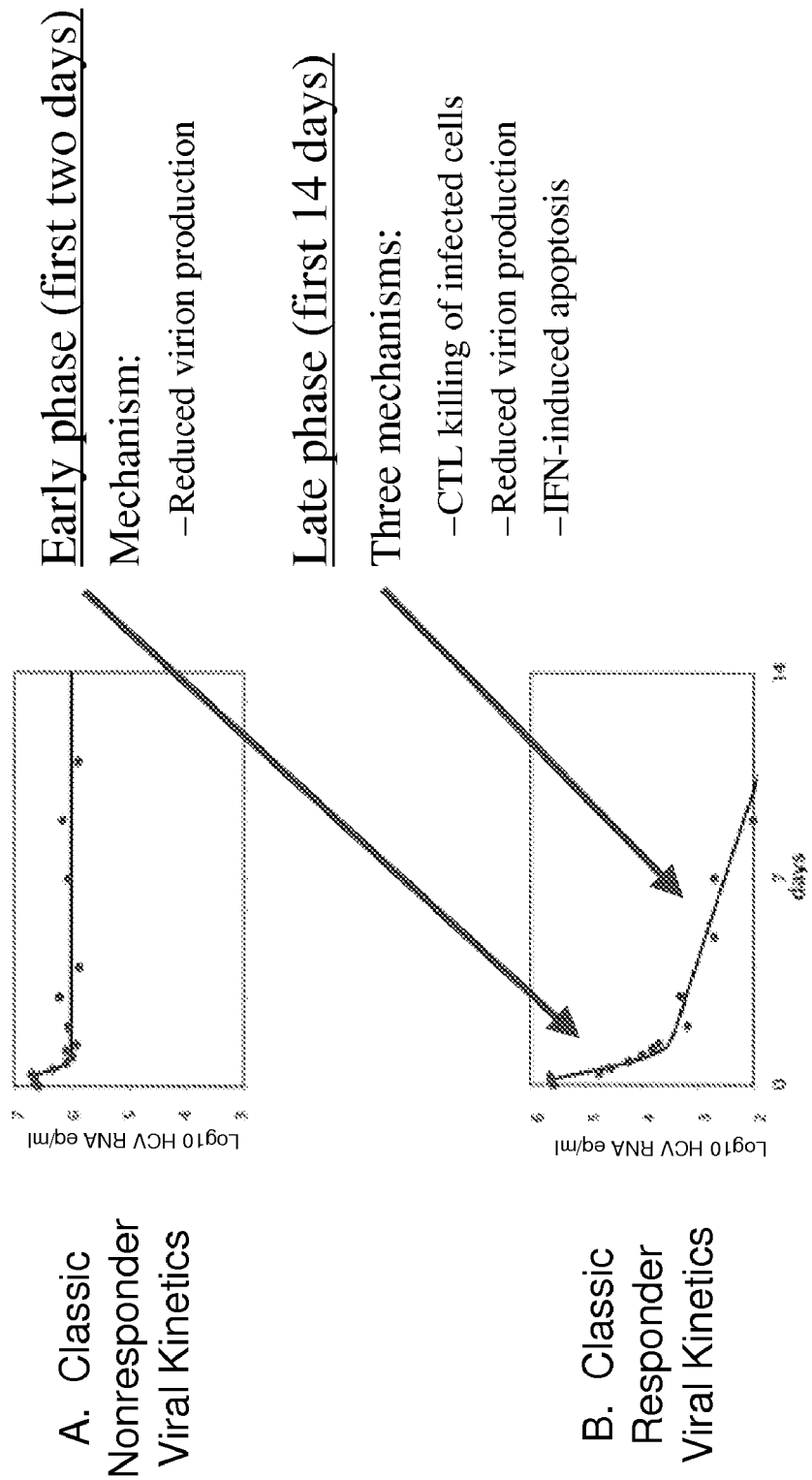
FIGS. 1A and 1B show biphasic timecourses for viral clearance from HCV-infected cells following IFN-alpha treatment (A. Nonresponder kinetics; B. Responder kinetics).

Unless otherwise defined herein or in the remainder of the specification, all technical and scientific terms used herein have the same meaning as commonly understood by those of ordinary skill in the art to which the invention belongs.

A "polypeptide sequence" (e.g., a protein, polypeptide, peptide, etc.) is a polymer of amino acids comprising naturally occurring amino acids or artificial amino acid analogues, or a character string representing an amino acid polymer, depending on context. Given the degeneracy of the genetic code, one or more nucleic acids, or the complementary nucleic acids thereof, that encode a specific polypeptide sequence can be determined from the polypeptide sequence.

A "polynucleotide sequence" (e.g., a nucleic acid, polynucleotide, oligonucleotide, etc.) is a polymer of nucleotides comprising nucleotides A, C, T, U, G, or other naturally occurring nucleotides or artificial nucleotide analogues, or a character string representing a nucleic acid, depending on context. Either the given nucleic acid or the complementary nucleic acid can be determined from any specified polynucleotide sequence.

Numbering of a given amino acid polymer or nucleic acid polymer "corresponds to" or is "relative to" the numbering of a selected amino acid polymer or nucleic acid polymer when the position of any given polymer component (e.g., amino acid, nucleotide, also referred to generically as a "residue") is designated by reference to the same or an equivalent position in the selected amino acid or nucleic acid polymer, rather than by the actual numerical position of the component in the given polymer. Thus, for example, the numbering of a given amino acid position in a given polypeptide sequence corresponds to the same or equivalent amino acid position in a selected polypeptide sequence used as a reference sequence.

Figure 2:
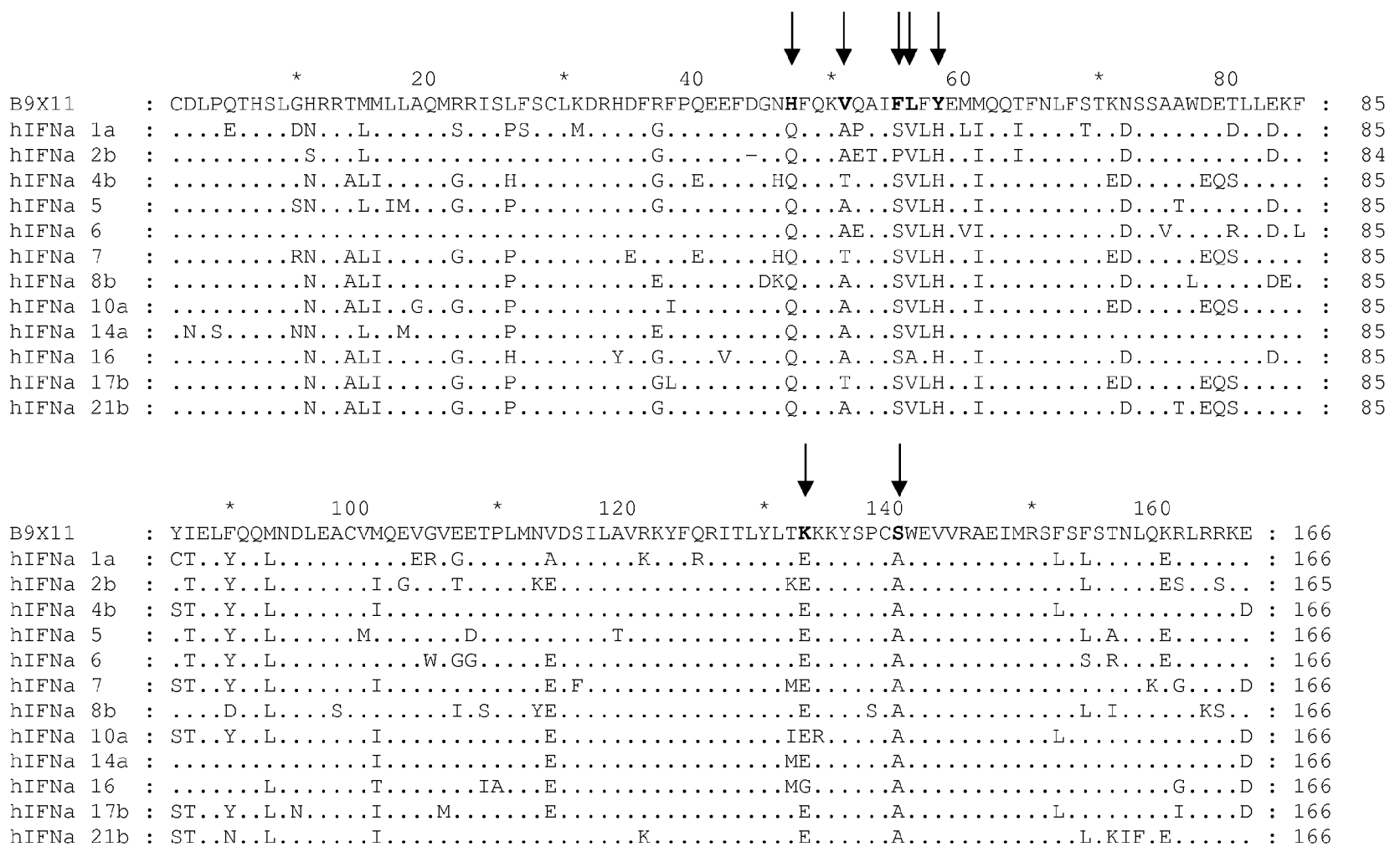

An "equivalent position" (for example, an "equivalent amino acid position" or "equivalent residue position") is defined herein as a position (such as, an amino acid position or a residue position) of a test polypeptide sequence which aligns with a corresponding position of a reference polypeptide sequence, using an alignment algorithm as described herein. The equivalent amino acid position of the test polypeptide sequence need not have the same numerical position number as the corresponding position of the test polypeptide. As an example, FIG. 2 shows the sequence of a polypeptide of the invention (SEQ ID NO:1) aligned with various known human interferon-alpha polypeptide sequences. In this example, amino acid position number 47 of SEQ ID NO:1 is considered to be an equivalent amino acid position to (i.e. is "equivalent to") that of amino acid position number 46 of SEQ ID NO:32 (huIFN-alpha 2b), since amino acid number 47 of SEQ ID NO:1 aligns with amino acid number 46 of SEQ ID NO:32. In other words, amino acid position 47 of SEQ ID NO:1 corresponds to amino acid position 46 of SEQ ID NO:32. Likewise, residue H47 in SEQ ID NO:1 is understood to correspond to residue Q47 in SEQ ID NO:5, so that for example the substitution H47C relative to SEQ ID NO:1 is understood to correspond to the substitution Q47C in, e.g., SEQ ID NO:5 (and so on).

Two polypeptide sequences are "optimally aligned" when they are aligned using defined parameters, i.e., a defined amino acid substitution matrix, gap existence penalty (also termed gap open penalty), and gap extension penalty, so as to arrive at the highest similarity score possible for that pair of sequences. The BLOSUM62 matrix (Henikoff and Henikoff (1992) Proc. Natl. Acad. Sci. USA 89(22):10915-10919) is often used as a default scoring substitution matrix in polypeptide sequence alignment algorithms (such as BLASTP). The gap existence penalty is imposed for the introduction of a single amino acid gap in one of the aligned sequences, and the gap extension penalty is imposed for each residue position in the gap. Unless otherwise stated, alignment parameters employed herein are: BLOSUM62 scoring matrix, gap existence penalty=11, and gap extension penalty=1. The alignment score is defined by the amino acid positions of each sequence at which the alignment begins and ends (e.g. the alignment window), and optionally by the insertion of a gap or multiple gaps into one or both sequences, so as to arrive at the highest possible similarity score, as described in more detail below in the section entitled "Percent Sequence Identity".

The terminology used for identifying amino acid positions and amino acid substitutions is illustrated as follows: H47 indicates position number 47 occupied by a histidine (His) residue in a reference amino acid sequence, e.g. SEQ ID NO:1. H47Q indicates that the histidine residue of position 47 has been substituted with a glutamine (Gln) residue. Alternative substitutions are indicated with a "/", e.g., H47S/T means an amino acid sequence in which the histidine residue in position 47 is substituted with a serine or a threonine residue. Multiple substitutions may be indicated with a "+", e.g. H47Q+V51S/T means an amino acid sequence which comprises a substitution of the histidine residue at position 47 with an glutamine residue and a substitution of the valine residue at position 51 with a serine or a threonine residue. Deletions are indicated by an asterix. For example, H47* indicates that the histidine residue in position 47 has been deleted. Deletions of two or more continuous amino acids may be indicated as follows, e.g., R161*-E166* indicates the deletion of residues R161-E166 inclusive (that is, residues 161, 162, 163, 164, 164, and 166 are deleted). Insertions are indicated the following way: Insertion of an additional serine residue after the histidine residue located at position 47 is indicated as H47HS. Combined substitutions and insertions are indicated in the following way: Substitution of the histidine residue at position 47 with a serine residue and insertion of an alanine residue after the position 47 amino acid residue is indicated as H47SA.

Unless otherwise indicated, the position numbering of amino acid residues recited herein is relative to the amino acid sequence SEQ ID NO:1. It is to be understood that while the examples and modifications to the parent polypeptide are generally provided herein relative to the sequence SEQ ID NO:1 (or relative to another specified sequence), the examples pertain to other polypeptides of the invention, and the modifications described herein may be made in equivalent amino acid positions of any of the other polypeptides described herein. Thus, as an example, the substitution H47C relative to SEQ ID NO:1 is understood to correspond to the substitution Q47C in SEQ ID NO:5, and so on.

The term "exhibiting (or exhibits, or having, or has) an interferon-alpha activity" is intended to indicate that the polypeptide or conjugate of the invention has at least one activity exhibited by a reference interferon-alpha polypeptide (such as, for example, a human interferon-alpha polypeptide, e.g., huIFN-alpha 2b identified herein as SEQ ID NO:32, huIFN-alpha 2a identified herein as SEQ ID NO:32+R23K, hIFN-alpha 8b identified herein as SEQ ID NO:37, or any other human interferon alpha polypeptide known in the art, such as, for example, those shown in FIGS. 2 and 4 herein and/or listed in Allen G. and Diaz M. O. (1996), supra). Such activity includes the ability to signal through an interferon-alpha receptor, as evidenced by, for example, one or more of: inhibition of viral replication in virus-infected cells ("antiviral activity"); enhancement of differentiation of naïve T-cells to a $T_H1$ phenotype and/or suppression of differentiation of naïve T-cells to a $T_H2$ phenotype ("$T_H1$ differentiation activity"); or inhibition of cell proliferation ("antiproliferative activity"). The one or more interferon-alpha activity is assayed using assays known in the art and/or described in the Examples.

A polypeptide or a conjugate exhibiting an interferon-alpha activity is considered to have such activity when it displays a measurable activity, e.g., a measurable antiviral activity, antiproliferative activity, or $T_H1$ differentiation activity (e.g., as determined by assays known in the art and/or described in the Examples). One of skill in the art recognizes that what constitutes a measurable activity depends in part on the nature of the assay being undertaken, but as a general guideline a measurable activity is one in which the assay signal generated in the presence of the test compound (e.g., a polypeptide of the invention) is quantifiably different than the assay signal generated in the absence of the test compound. It is to be understood that the polypeptide or conjugate of the invention need not exhibit all of the known activities of a particular reference interferon-alpha, or exhibit such activities to the same extent as the reference interferon-alpha. In some instances the activity exhibited by a polypeptide or conjugate of the invention (as evidenced, e.g., by an $EC_{50}$, specific activity, or other value related to activity) may be about equal to, be less than, or be greater than that of the particular activity exhibited by the reference interferon-alpha.

A "variant" is a polypeptide comprising a sequence which differs in one or more amino acid position(s) from that of a parent polypeptide sequence. For example, a variant may comprise a sequence which differs from the parent polypeptides sequence in up to 10% of the total number of residues of the parent polypeptide sequence, such as in up to 8% of the residues, e.g., in up to 5%, 4%, 3% 2% or 1% of the total number of residue of the parent polypeptide sequence. For example, a variant of SEQ ID NO:1 may comprise a sequence which differs from SEQ ID NO:1 in 1-16 amino acid positions (such as in 1, 2, 3, 4, 5, 6, 7, 8, 9, 10, 11, 12, 13, 14, 15, or 16 amino acid positions), e.g. in 1-15 amino acid positions, in 1-14 amino acid positions, in 1-13 amino acid positions, in 1-12 amino acid positions, in 1-11 amino acid positions, in 1-10 amino acid positions, in 1-9 amino acid positions, in 1-8 amino acid positions, in 1-7 amino acid positions, in 1-6 amino acid positions, in 1-5 amino acid positions, in 1-4 amino acid positions, in 1-3 amino acid positions, or in 1-2 amino acid positions.

The term "parent polypeptide" or "parent interferon-alpha" is intended to indicate the polypeptide sequence to be modified in accordance with the present invention. The parent polypeptide sequence may be that of a naturally occurring IFN-alpha (such as a mammalian IFN-alpha, e.g., a primate IFN-alpha, such as a human IFN-alpha, such as a huIFN-alpha polypeptide identified herein as SEQ ID NOs:31-42, SEQ ID NO:32+R23K, or other huIFN-alpha sequence described herein and/or in Allen G. and Diaz M. O. (1996), supra). The parent polypeptide sequence may be that of a non-naturally occurring (i.e., "synthetic") interferon-alpha, such as IFN-alpha Con1 (SEQ ID NO:43). In some instances, the parent polypeptide to be modified may itself be a polypeptide of the invention, such as, e.g. any one of SEQ ID NOs: 1-15 and SEQ ID NOs:44-104.

"Naturally occurring" as applied to an object refers to the fact that the object can be found in nature as distinct from being artificially produced by man. For example, a polypeptide or polynucleotide sequence that is present in an organism (including viruses, bacteria, protozoa, insects, plants or mammalian tissue) that can be isolated from a source in nature and which has not been intentionally modified by man in the laboratory is naturally occurring. "Non-naturally occurring" (also termed "synthetic" or "artificial") as applied to an object means that the object is not naturally-occurring—i.e., the object cannot be found in nature as distinct from being artificially produced by man.

A "fragment" or "subsequence" is any portion of an entire sequence, up to but not including the entire sequence. Thus, a fragment or subsequence refers to a sequence of amino acids or nucleic acids that comprises a part of a longer sequence of amino acids (e.g., polypeptide) or nucleic acids (e.g., polynucleotide).

One type of fragment contemplated by the present invention is a fragment in which amino acid residues are removed from the N-terminus or the C-terminus of the parent polypeptide (or both); such a polypeptide is considered to be "N-terminally truncated" or "C-terminally truncated", respectively. It is known that deletion of at least the first four amino acids from the N-terminus does not significantly affect interferon-alpha activity (Lydon, N. B. et al. (1985) Biochemistry 24: 4131-41). Furthermore, variants retaining interferon-alpha activity have been described wherein between 7 and 11 amino acids have been deleted from the C-terminus (Cheetham B. F. et al. (1991) Antiviral Res. 15(1):27-39; Chang N. T. et al. (1983) Arch. Biochem Biophys. 221(2): 585-589; Franke A. E. et al. (1982) DNA 1(3):223-230).

A "receptor" e.g., an "interferon-alpha receptor" (also known as a "Type I interferon receptor") is a receptor which is activated in cells by an interferon-alpha, e.g., binds an interferon-alpha and initiates intracellular signaling, such as a type I interferon receptor comprising receptor subunits IFNAR-2 and IFNAR-1 (Domanski et al. (1998) J. Biol. Chem. 273(6):3144-3147; Mogensen et al., (1999) Journal of Interferon and Cytokine Research, 19:1069-1098). In the context of this invention, receptor is also meant to include truncated forms of a full-length receptor molecule, such as for example a receptor molecule which lacks a membrane-binding portion, such as a soluble form of a receptor molecule (also known as a "soluble receptor") which comprises an extracelluar binding domain, which binds an interferon-alpha, but may not necessarily bind to a membrane and/or initiate intracellular signaling.

A "specific binding affinity" between two molecules, e.g., a ligand and a receptor, means a preferential binding of one molecule for another in a mixture of molecules. The binding of the molecules is typically considered specific if the binding affinity is about $1 \times 10^4 M^{-1}$ to about $1 \times 10^9 M^{-1}$ or greater (i.e., $K_D$ of about $10^4$ to $10^{-9}$ M or less). Binding affinity of a ligand and a receptor may be measured by standard techniques known to those of skill in the art. Non-limiting examples of well-known techniques for measuring binding affinities include Biacore® technology (Biacore AB, Sweden), isothermal titration microcalorimetry (MicroCal LLC, Northampton, Mass. USA), ELISA, and FACS. For example, FACS or other sorting methods may be used to select for populations of molecules (such as for example, cell surface-displayed ligands) which specifically bind to the associated binding pair member (such as a receptor, e.g., a soluble receptor). Ligand-receptor complexes may be detected and sorted e.g., by fluorescence (e.g., by reacting the complex with a fluorescent antibody that recognizes the complex). Molecules of interest which bind an associated binding pair member (e.g., receptor) are pooled and re-sorted in the presence of lower concentrations of receptor. By performing multiple rounds sorting in the presence of decreasing concentrations of receptor (an exemplary concentration range being on the order of $10^{-6}$ M down to $10^{-9}$ M, i.e., 1 micromolar (μM) down to 1 nanomolar (nM), or less, depending on the nature of the ligand-receptor interaction), populations of the molecule of interest exhibiting specific binding affinity for the receptor may be isolated.

A polypeptide, nucleic acid, or other component is "isolated" when it is partially or completely separated from components with which it is normally associated (other peptides, polypeptides, proteins (including complexes, e.g., polymerases and ribosomes which may accompany a native sequence), nucleic acids, cells, synthetic reagents, cellular contaminants, cellular components, etc.), e.g., such as from other components with which it is normally associated in the cell from which it was originally derived. A polypeptide, nucleic acid, or other component is isolated when it is partially or completely recovered or separated from other components of its natural environment such that it is the predominant species present in a composition, mixture, or collection of components (i.e., on a molar basis it is more abundant than any other individual species in the composition). In some instances, the preparation consists of more than about 60%, 70% or 75%, typically more than about 80%, or preferably more than about 90% of the isolated species.

A "substantially pure" or "isolated" nucleic acid (e.g., RNA or DNA), polypeptide, protein, or composition also means where the object species (e.g., nucleic acid or polypeptide) comprises at least about 50, 60, or 70 percent by weight (on a molar basis) of all macromolecular species present. A substantially pure or isolated composition can also comprise at least about 80, 90, or 95 percent by weight of all macromolecular species present in the composition. An isolated object species can also be purified to essential homogeneity (contaminant species cannot be detected in the composition by conventional detection methods) wherein the composition consists essentially of derivatives of a single macromolecular species. The term "purified" generally denotes that a nucleic acid, polypeptide, or protein gives rise to essentially one band in an electrophoretic gel. It typically means that the nucleic acid, polypeptide, or protein is at least about 50% pure, 60% pure, 70% pure, 75% pure, more preferably at least about 85% pure, and most preferably at least about 99% pure.

The term "isolated nucleic acid" may refer to a nucleic acid (e.g., DNA or RNA) that is not immediately contiguous with both of the coding sequences with which it is immediately contiguous (i.e., one at the 5' and one at the 3' end) in the naturally occurring genome of the organism from which the nucleic acid of the invention is derived. Thus, this term includes, e.g., a cDNA or a genomic DNA fragment produced by polymerase chain reaction (PCR) or restriction endonuclease treatment, whether such cDNA or genomic DNA fragment is incorporated into a vector, integrated into the genome of the same or a different species than the organism, including, e.g., a virus, from which it was originally derived, linked to an additional coding sequence to form a hybrid gene encoding a chimeric polypeptide, or independent of any other DNA sequences. The DNA may be double-stranded or single-stranded, sense or antisense.

A "recombinant polynucleotide" or a "recombinant polypeptide" is a non-naturally occurring polynucleotide or polypeptide which may include nucleic acid or amino acid sequences, respectively, from more than one source nucleic acid or polypeptide, which source nucleic acid or polypeptide can be a naturally occurring nucleic acid or polypeptide, or can itself have been subjected to mutagenesis or other type of modification. A nucleic acid or polypeptide may be deemed "recombinant" when it is synthetic or artificial or engineered, or derived from a synthetic or artificial or engineered polypeptide or nucleic acid. A recombinant nucleic acid (e.g., DNA or RNA) can be made by the combination (e.g., artificial combination) of at least two segments of sequence that are not typically included together, not typically associated with one another, or are otherwise typically separated from one another. A recombinant nucleic acid can comprise a nucleic acid molecule formed by the joining together or combination of nucleic acid segments from different sources and/or artificially synthesized. A "recombinant polypeptide" often refers to a polypeptide that results from a cloned or recombinant nucleic acid. The source polynucleotides or polypeptides from which the different nucleic acid or amino acid sequences are derived are sometimes homologous (i.e., have, or encode a polypeptide that encodes, the same or a similar structure and/or function), and are often from different isolates, serotypes, strains, species, of organism or from different disease states, for example.

The term "recombinant" when used with reference, e.g., to a cell, polynucleotide, vector, protein, or polypeptide typically indicates that the cell, polynucleotide, or vector has been modified by the introduction of a heterologous (or foreign) nucleic acid or the alteration of a native nucleic acid, or that the protein or polypeptide has been modified by the introduction of a heterologous amino acid, or that the cell is derived from a cell so modified. Recombinant cells express nucleic acid sequences that are not found in the native (non-recombinant) form of the cell or express native nucleic acid sequences that would otherwise be abnormally expressed, under-expressed, or not expressed at all. The term "recombinant" when used with reference to a cell indicates that the cell replicates a heterologous nucleic acid, or expresses a polypeptide encoded by a heterologous nucleic acid. Recombinant cells can contain coding sequences that are not found within the native (non-recombinant) form of the cell. Recombinant cells can also contain coding sequences found in the native form of the cell wherein the coding sequences are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, recombination, and related techniques.

The term "recombinantly produced" refers to an artificial combination usually accomplished by either chemical synthesis means, recursive sequence recombination of nucleic acid segments or other diversity generation methods (such as, e.g., shuffling) of nucleotides, or manipulation of isolated segments of nucleic acids, e.g., by genetic engineering techniques known to those of ordinary skill in the art. "Recombinantly expressed" typically refers to techniques for the production of a recombinant nucleic acid in vitro and transfer of the recombinant nucleic acid into cells in vivo, in vitro, or ex vivo where it may be expressed or propagated.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

An "immunogen" refers to a substance capable of provoking an immune response, and includes, e.g., antigens, autoantigens that play a role in induction of autoimmune diseases, and tumor-associated antigens expressed on cancer cells. An immune response generally refers to the development of a cellular or antibody-mediated response to an agent, such as an antigen or fragment thereof or nucleic acid encoding such agent. In some instances, such a response comprises a production of at least one or a combination of CTLs, B cells, or various classes of T cells that are directed specifically to antigen-presenting cells expressing the antigen of interest.

An "antigen" refers to a substance that is capable of eliciting the formation of antibodies in a host or generating a specific population of lymphocytes reactive with that substance. Antigens are typically macromolecules (e.g., proteins and polysaccharides) that are foreign to the host.

An "adjuvant" refers to a substance that enhances an antigen's immune-stimulating properties or the pharmacological effect(s) of a drug. An adjuvant may non-specifically enhance the immune response to an antigen. "Freund's Complete Adjuvant," for example, is an emulsion of oil and water containing an immunogen, an emulsifying agent and mycobacteria. Another example, "Freund's incomplete adjuvant," is the same, but without mycobacteria.

A vector is a component or composition for facilitating cell transduction or transfection by a selected nucleic acid, or expression of the nucleic acid in the cell. Vectors include, e.g., plasmids, cosmids, viruses, YACs, bacteria, poly-lysine, etc. An "texpression vector" is a nucleic acid construct or sequence, generated recombinantly or synthetically, with a series of specific nucleic acid elements that permit transcription of a particular nucleic acid in a host cell. The expression vector can be part of a plasmid, virus, or nucleic acid fragment. The expression vector typically includes a nucleic acid to be transcribed operably linked to a promoter. The nucleic acid to be transcribed is typically under the direction or control of the promoter.

"Substantially the entire length of a polynucleotide sequence" or "substantially the entire length of a polypeptide sequence" refers to at least 50%, generally at least about 60%, 70%, or 75%, usually at least about 80%, or typically at least about 85%, 90%, 91%, 92%, 93%, 94%, 95%, 96%, 97%, 98%, 99% or more of a length of a polynucleotide sequence or polypeptide sequence.

The term "immunoassay" includes an assay that uses an antibody or immunogen to bind or specifically bind an antigen. The immunoassay is typically characterized by the use of specific binding properties of a particular antibody to isolate, target, and/or quantify the antigen.

The term "subject" as used herein includes, but is not limited to, an organism; a mammal, including, e.g., a human, non-human primate (e.g., baboon, orangutan, monkey), mouse, pig, cow, goat, cat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

The term "pharmaceutical composition" means a composition suitable for pharmaceutical use in a subject, including an animal or human. A pharmaceutical composition generally comprises an effective amount of an active agent and a carrier, including, e.g., a pharmaceutically acceptable carrier.

The term "effective amount" means a dosage or amount sufficient to produce a desired result. The desired result may comprise an objective or subjective improvement in the recipient of the dosage or amount.

A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such as a nucleic acid, vector, gene, polypeptide, protein, substance, or composition thereof that, when administered to a subject who does not display signs or symptoms of pathology, disease or disorder, or who displays only early signs or symptoms of pathology, disease, or disorder, diminishes, prevents, or decreases the risk of the subject developing a pathology, disease, or disorder. A "prophylactically useful" agent or compound (e.g., nucleic acid or polypeptide) refers to an agent or compound that is useful in diminishing, preventing, treating, or decreasing development of pathology, disease or disorder.

A "therapeutic treatment" is a treatment administered to a subject who displays symptoms or signs of pathology, disease, or disorder, in which treatment is administered to the subject for the purpose of diminishing or eliminating those signs or symptoms of pathology, disease, or disorder. A "therapeutic activity" is an activity of an agent, such as a nucleic acid, vector, gene, polypeptide, protein, substance, or composition thereof, that eliminates or diminishes signs or symptoms of pathology, disease or disorder, when administered to a subject suffering from such signs or symptoms. A "therapeutically useful" agent or compound (e.g., nucleic acid or polypeptide) indicates that an agent or compound is useful in diminishing, treating, or eliminating such signs or symptoms of a pathology, disease or disorder.

The term "gene" broadly refers to any segment of DNA associated with a biological function. Genes include coding sequences and/or regulatory sequences required for their expression. Genes also include non-expressed DNA nucleic acid segments that, e.g., form recognition sequences for other proteins (e.g., promoter, enhancer, or other regulatory regions). Genes can be obtained from a variety of sources, including cloning from a source of interest or synthesizing from known or predicted sequence information, and may include sequences designed to have desired parameters.

Generally, the nomenclature used hereafter and the laboratory procedures in cell culture, molecular genetics, molecular biology, nucleic acid chemistry, and protein chemistry described below are those well known and commonly employed by those of ordinary skill in the art. Standard techniques, such as described in Sambrook et al., Molecular Cloning—A Laboratory Manual (2nd Ed.), Vols. 1-3, Cold Spring Harbor Laboratory, Cold Spring Harbor, N.Y., 1989 (hereinafter "Sambrook") and Current Protocols in Molecular Biology, F. M. Ausubel et al., eds., Current Protocols, a joint venture between Greene Publishing Associates, Inc. and John Wiley & Sons, Inc. (1994, supplemented through 1999) (hereinafter "Ausubel"), are used for recombinant nucleic acid methods, nucleic acid synthesis, cell culture methods, and transgene incorporation, e.g., electroporation, injection, gene gun, impressing through the skin, and lipofection. Generally, oligonucleotide synthesis and purification steps are performed according to specifications. The techniques and procedures are generally performed according to conventional methods in the art and various general references which are provided throughout this document. The procedures therein are believed to be well known to those of ordinary skill in the art and are provided for the convenience of the reader.

As used herein, an "antibody" refers to a protein comprising one or more polypeptides substantially or partially encoded by immunoglobulin genes or fragments of immunoglobulin genes. The term antibody is used to mean whole antibodies and binding fragments thereof. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 KDa) and one "heavy" chain (about 50-70 KDa). The N-terminus of each chain defines a variable region of about 100 to 110 or more amino acids primarily responsible for antigen recognition. The terms variable light chain (VL) and variable heavy chain (VH) refer to these light and heavy chains, respectively.

Antibodies also include single-armed composite monoclonal antibodies, single chain antibodies, including single chain Fv (sFv) antibodies in which a variable heavy and a variable light chain are joined together (directly or through a peptide linker) to form a continuous polypeptide, as well as diabodies, tribodies, and tetrabodies (Pack et al. (1995) J Mol Biol 246:28; Biotechnol 11:1271; and Biochemistry 31:1579). The antibodies are, e.g., polyclonal, monoclonal, chimeric, humanized, single chain, Fab fragments, fragments produced by an Fab expression library, or the like.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

An "antigen-binding fragment" of an antibody is a peptide or polypeptide fragment of the antibody that binds an antigen. An antigen-binding site is formed by those amino acids of the antibody that contribute to, are involved in, or affect the binding of the antigen. See Scott, T. A. and Mercer, E. I., Concise Encyclopedia: Biochemistry and Molecular Biology (de Gruyter, 3d ed. 1997), and Watson, J. D. et al., Recombinant DNA (2d ed. 1992) [hereinafter "Watson, Recombinant DNA"], each of which is incorporated herein by reference in its entirety for all purposes.

The term "screening" describes, in general, a process that identifies optimal molecules of the present invention, such as, e.g., polypeptides of the invention, and related fusion polypeptides including the same, and nucleic acids encoding all such molecules. Several properties of these respective molecules can be used in selection and screening, for example: an ability of a respective molecule to bind a ligand or to a receptor, to inhibit cell proliferation, to inhibit viral replication in virus-infected cells, to induce or inhibit cellular cytokine production, to alter an immune response, e.g., induce or inhibit a desired immune response, in a test system or an in vitro, ex vivo or in vivo application. In the case of antigens, several properties of the antigen can be used in selection and screening including antigen expression, folding, stability, immunogenicity and presence of epitopes from several related antigens.

"Selection" is a form of screening in which identification and physical separation are achieved simultaneously by, e.g., expression of a selection marker, which, in some genetic circumstances, allows cells expressing the marker to survive while other cells die (or vice versa). Screening markers include, for example, luciferase, beta-galactosidase and green fluorescent protein, and the like. Selection markers include drug and toxin resistance genes, and the like. Another mode of selection involves physical sorting based on a detectable event, such as binding of a ligand to a receptor, reaction of a substrate with an enzyme, or any other physical process which can generate a detectable signal either directly (e.g., by utilizing a chromogenic substrate or ligand) or indirectly (e.g., by reacting with a chromogenic secondary antibody). Selection by physical sorting can by accomplished by a variety of methods, such as by FACS in whole cell or microdroplet formats.

An "exogenous" nucleic acid," "exogenous DNA segment," "heterologous sequence," or "heterologous nucleic acid," as used herein, is one that originates from a source foreign to the particular host cell, or, if from the same source, is modified from its original form. Thus, a heterologous gene in a host cell includes a gene that is endogenous to the particular host cell, but has been modified. Modification of a heterologous sequence in the applications described herein typically occurs through the use of recursive sequence recombination. The terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res 19:5081; Ohtsuka et al. (1985) J Biol Chem 260: 2605-2608; Cassol et al. (1992); Rossolini et al. (1994) Mol Cell Probes 8:91-98). The term nucleic acid is used interchangeably with gene, cDNA, and mRNA encoded by a gene.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample. A nucleic acid is "operably linked" when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

The term "cytokine" includes, for example, interleukins, interferons, chemokines, hematopoietic growth factors, tumor necrosis factors and transforming growth factors. In general these are low molecular weight proteins that regulate maturation, activation, proliferation, and differentiation of cells of the immune system.

In the present description and claims, any reference to "a" component, e.g. in the context of a non-polypeptide moiety, an amino acid residue, a substitution, a buffer, a cation, etc., is Molecules and Methods of the Invention Molecules of the invention (e.g., polypeptides of the invention, conjugates of the invention, and nucleic acids encoding said polypeptides) are useful for the treatment of diseases and conditions which are responsive to treatment by interferon-alpha, particularly diseases and conditions associated with viral infection, such as, for example, infection by HCV.

Patients with chronic HCV infection have viral loads typically in the range of 104-10$^7$ copies of HCV RNA/ml of serum prior to treatment. Upon treatment with IFN-alpha, viral load in these patients characteristically undergoes two distinct log-linear phases of decline (FIG. 1B; Neumann A. U., et al. (1998) Science 282:103-107). The initial rapid drop in viral load that occurs within the first two days of IFN-alpha therapy is believed to be due to interferon-alpha mediated reduction in virus production in the infected liver cells and concomitant protection of naïve cells against infection. The rate of viral production reaches a new steady state at about two days, at which time a second less rapid log-linear phase of viral clearance is observed. This second phase of viral clearance is generally believed to be due in part to T-cell mediated killing of infected liver cells (Neumann, et al., supra). IFN-alpha is believed to play a key role in this biological response through the stimulation of antigen specific T cells to differentiate into $T_H1$ cells. Furthermore, the mode of action of Ribavirin is believed to be due to augmentation of the $T_H1$ response, and is thought to be the mechanistic basis of its efficacy in combination therapy with IFN-alpha. HCV-infected patients who are non-responsive to interferon-alpha therapies currently in use (generally termed "non-responders") exhibit much shallower viral load clearance profiles (FIG. 1A).

Although the present invention is not intended to be limited by a particular theory of underlying mechanism, it is proposed that antiviral activity in surrogate assay systems (such as those described in more detail herein) may be predictive of interferon-alpha efficacy, for example in the first phase of viral clearance. An exemplary antiviral assay, described in the Examples section, monitors the effectiveness of IFN-alpha in protecting against the cytopathic effect of Encephalomyocarditis Virus (EMCV) in HuH7 human liver-derived cells, as a surrogate system for effectiveness against HCV in human liver cells. Example 2 shows antiviral activities of representative polypeptides of the invention in the EMCV/HuH7 antiviral activity assay. Preliminary experiments (data not shown) indicates that polypeptides of the invention exhibit antiviral activity in other virus/cell systems, including EMCV in WISH human amniotic tissue-derived cells, EMCV in HeLa human cervical carcinoma cells, Vesicular Stomatitis Virus (VSV) in HuH7 cells, Vaccinia Virus (VV) in HeLa cells, Yellow Fever Virus (YFV) in HepG2 human hepatocarcinoma cells, as well as Human Immunodeficiency Virus (HIV) in human primary CD4+ T-cells. This suggests that polypeptides of the invention exhibit antiviral activity against a broad spectrum of viruses and cell types.

Other surrogate assay system for HCV replication in infected hepatocytes include HCV replicon systems, as described, for example, by Lohmann V., et al., (1999) Science 285(5424):285-3; Randall G. and Rice C. M. (2001) Curr Opin Infect Dis 14(6):743-7; and Bartenschlager, R. (2002) Nature Reviews/Drug Discovery 1:911. An example of a useful in vivo system for monitoring HCV antiviral efficacy is a chimeric human liver SCID mouse, as described by Mercer, et al. (2001) Nature Medicine 7(8):927-933.

It is furthermore proposed, without being limited by theory, that enhancement of $T_H1$ differentiation and/or suppression of $T_H2$ differentiation by IFN-alpha may be a contributing factor to interferon-alpha efficacy, for example, in the second phase of viral clearance. According to this theory, evolved IFN-alphas with increased potency in these biological activities (i.e., enhancement of $T_H1$ differentiation and/or suppression of $T_H2$ differentiation) would be predicted to have increased efficacy relative to, for example, currently approved therapeutic interferon-alpha molecules administered at the same dosage. An exemplary assay, described in the Examples section herein, monitors the enhancement of $T_H1$ differentiation and/or suppression of $T_H2$ differentiation by IFN-alpha on naïve $T_H0$ cells, by measuring production of cytokines associated with the $T_H1$-phenotype (e.g., IFN-gamma) and/or the $T_H2$-phenotype (e.g., IL-5, IL4) via ELISA or via intracellular staining and FACS sorting.

The therapeutic efficacy of IFN-alpha molecules tends to be diminished in part due to dose-limiting toxicities, e.g. thrombocytopenia and neutropenia. Although the present invention is not intended to be limited by a particular theory of underlying mechanism, it is proposed that such toxicity may be associated with anti-proliferative effects of IFN-alpha on platelet and neutrophil precursors, and that antiproliferative activity in surrogate assay systems (such as those described herein) may be predictive of the relative toxicity of an interferon-alpha molecule. Thus, dose-limiting toxicities associated with IFN-alpha therapy may be diminished in IFN-alpha molecules that exhibit reduced antiproliferative activity relative to, for example, currently approved therapeutic interferon-alpha molecules, such as ROFERON®-A (Interferon alfa-2a, recombinant; Hoffmann-La Roche Inc.), INTRON® A (Interferon alfa-2b, recombinant; Schering Corporation), and INFERGEN® (interferon alfacon-1; InterMune, Inc.). An exemplary antiproliferative activity assay, described in the Examples section herein, monitors the effect of IFN-alpha on the proliferation of human Daudi lymphoid cells. Alternatively, or in addition, dose-limiting toxicities may be reduced as a result of administering more therapeutically active molecules, which would permit dosing in lower concentrations or at lower frequency than currently approved molecules.

It is an object of the invention to provide novel interferon-alpha polypeptides, and nucleic acids which encode the polypeptides. Polypeptides of the invention are useful for the treatment of diseases and disorders which are responsive to treatment by interferon-alpha, particularly diseases associated with viral infection, such as, for example, infection by HCV. Some polypeptides of the invention exhibit an interferon-alpha activity, such as, for example, antiviral activity, antiproliferative activity, and/or $T_H1$ differentiation activity. Some polypeptides of the invention exhibit one or more of the following properties: increased or decreased antiviral activity compared to a reference IFN-alpha polypeptide; increased or decreased $T_H1$ differentiation activity compared to a reference IFN-alpha polypeptide; increased or decreased antiproliferative activity compared to a reference IFN-alpha polypeptide. The reference IFN-alpha polypeptide may comprise a sequence of a non-naturally occurring interferon-alpha, such as IFN-alpha Con1 (SEQ ID NO:43), or may comprise a sequence of a naturally-occurring (i.e., wild-type) interferon-alpha polypeptide. Examples of sequences of naturally occurring interferon-alpha polypeptides include sequences of human IFN-alpha polypeptides, such as, for example, huIFN-alpha 2b (SEQ ID NO:32), huIFN-alpha 2a (SEQ ID NO:32 with position 23=Lys), huIFN-alpha 2c (SEQ ID NO:32 with position 34=Arg), huIFN-alpha 8b (SEQ ID NO:33), huIFN-alpha 8a (SEQ ID NO:33 with positions 98=Val, 99=Leu, 100=Cys, and 101=Asp), huIFN-alpha 8c (SEQ ID NO:33 with position 161=Asp and amino acids at positions 162-166 deleted), huIFN-alpha 14a (SEQ ID NO:39), huIFN-alpha 14c (SEQ ID NO:39 with position 152=Leu), or a sequence of any other naturally occurring human interferon alpha polypeptide, such as those shown in FIGS. 2 and 4 herein (SEQ ID NOs:31-42) and/or listed in Allen G. and Diaz M. O. (1996), supra.

In another aspect, the invention provides interferon-alpha polypeptides which exhibit enhanced efficacy in clearing a virus from virus-infected cells, compared to a reference interferon-alpha molecule, such as one currently employed as a therapeutic (such as, for example, ROFERON-A, INTRON A, or INFERGEN). Exemplary viruses include, but are not limited to, viruses of the Flaviviridae family, such as, for example, Hepatitis C Virus, Yellow Fever Virus, West Nile Virus, Japanese Encephalitis Virus, Dengue Virus, and Bovine Viral Diarrhea Virus; viruses of the Hepadnaviridae family, such as, for example, Hepatitis B Virus; viruses of the Picornaviridae family, such as, for example, Encephalomyocarditis Virus, Human Rhinovirus, and Hepatitis A Virus; viruses of the Retroviridae family, such as, for example, Human Immunodeficiency Virus, Simian Immunodeficiency Virus, Human T-Lymphotropic Virus, and Rous Sarcoma Virus; viruses of the Coronaviridae family, such as, for example, SARS coronavirus; viruses of the Rhabdoviridae family, such as, for example, Rabies Virus and Vesicular Stomatitis Virus, viruses of the Paramyxoviridae family, such as, for example, Respiratory Syncytial Virus and Parainfluenza Virus, viruses of the Papillomaviridae family, such as, for example, Human Papillomavirus, and viruses of the Herpesviridae family, such as, for example, Herpes Simplex Virus. Such enhanced efficacy may arise from enhanced antiviral activity, enhanced $T_H1$-differentiation activity, or both, relative to the reference molecule. For example, some interferon-alpha polypeptides of the invention may be particularly useful in clearing viruses or viral strains that show poor response to treatment with interferon-alpha molecules currently in use, such as, for example, Genotype 1 of HCV.

Some polypeptides of the invention exhibit an increased ratio of (antiviral activity/antiproliferative activity) compared to the reference IFN-alpha molecule, and/or an increased ratio of ($T_H1$ differentiation activity/antiproliferative activity) compared to the reference IFN-alpha molecule. Polypeptides exhibiting such properties may be particularly effective in treatment of viral infections, such as, for example, infection by a virus listed above. Some such polypeptides may, for example, provide enhanced therapeutic efficacy over currently-approved interferon-alpha molecules in the treatment of HCV, in one or both phases of the biphasic viral clearance profile, and/or may exhibit reduced toxicity. Some such polypeptides may provide enhanced therapeutic efficacy over currently-approved interferon-alpha molecules in the treatment of Genotype 1 HCV.

It is another object of the invention to provide conjugates, such conjugates comprising one or more non-polypeptide moiety linked to a polypeptide of the invention, which conjugate exhibits an interferon-alpha activity (such as one or more of the activities listed above), and which optionally exhibits other desirable properties, such as increased serum half-life and/or functional in vivo half-life, and/or decreased antigenicity, compared to the non-conjugated polypeptide. Some such conjugates may exhibit enhanced efficacy in clearing a virus from cells infected with the virus, compared to a reference interferon-alpha molecule, such as an interferon-alpha conjugate currently employed as a therapeutic (such as, for example, PEGASYS® (Peginterferon alfa-2a; Hoffmann-La Roche, Inc.) or PEG-INTRON® (peginterferon alfa-2b; Schering Corporation). Exemplary viruses include, but are not limited to, viruses of the Flaviviridae family, such as, for example, Hepatitis C Virus, Yellow Fever Virus, West Nile Virus, Japanese Encephalitis Virus, Dengue Virus, and Bovine Viral Diarrhea Virus; viruses of the Hepadnaviridae family, such as, for example, Hepatitis B Virus; viruses of the Picornaviridae family, such as, for example, Encephalomyocarditis Virus, Human Rhinovirus, and Hepatitis A Virus; viruses of the Retroviridae family, such as, for example, Human Immunodeficiency Virus, Simian Immunodeficiency Virus, Human T-Lymphotropic Virus, and Rous Sarcoma Virus; viruses of the Coronaviridae family, such as, for example, SARS coronavirus; viruses of the Rhabdoviridae family, such as, for example, Rabies Virus and Vesicular Stomatitis Virus, viruses of the Paramyxoviridae family, such as, for example, Respiratory Syncytial Virus and Parainfluenza Virus, viruses of the Papillomaviridae family, such as, for example, Human Papillomavirus, and viruses of the Herpesviridae family, such as, for example, Herpes Simplex Virus. Such enhanced efficacy may arise from enhanced antiviral activity, enhanced $T_H1$-differentiation activity, or both, relative to the reference molecule. For example, some interferon-alpha conjugates of the invention may be particularly useful in clearing viruses or viral strains that show poor response to treatment with interferon-alpha molecules currently in use, such as, for example, Genotype 1 of HCV.

Some conjugates of the invention exhibit an increased ratio of (antiviral activity/antiproliferative activity) compared to the reference IFN-alpha molecule, and/or an increased ratio of ($T_H1$ differentiation activity/antiproliferative activity) compared to the reference IFN-alpha molecule. Conjugates exhibiting such properties may be particularly effective in treatment of viral infections, such as infection by a virus listed above, such as, for example, HCV. Some such conjugates may, for example, provide enhanced therapeutic efficacy over currently-approved interferon-alpha molecules in the treatment of HCV, in one or both phases of the biphasic viral clearance profile, and/or may exhibit reduced toxicity. Some such conjugates may provide enhanced therapeutic efficacy over currently-approved interferon-alpha molecules in the treatment of Genotype 1 HCV.

It is another object of the invention to provide a method of inhibiting viral replication in virus-infected cells, the method comprising administering to the virus-infected cells a polypeptide or conjugate of the invention in an amount effective to inhibit viral replication in said cells. The invention also provides a method of reducing the number of copies of a virus in virus-infected cells, comprising administering to the virus-infected cells a polypeptide or conjugate of the invention in an amount effective to reduce the number of copies of the virus in said cells. The virus may, for example, be a virus of the Flaviviridae family, such as, for example, Hepatitis C Virus, Yellow Fever Virus, West Nile Virus, Japanese Encephalitis Virus, Dengue Virus, or Bovine Viral Diarrhea Virus; a virus of the Hepadnaviridae family, such as, for example, Hepatitis B Virus; a virus of the Picornaviridae family, such as, for example, Encephalomyocarditis Virus, Human Rhinovirus, or Hepatitis A Virus; a virus of the Retroviridae family, such as, for example, Human Immunodeficiency Virus, Simian Immunodeficiency Virus, Human T-Lymphotropic Virus, or Rous Sarcoma Virus; a virus of the Coronaviridae family, such as, for example, SARS coronavirus; a virus of the Rhabdoviridae family, such as, for example, Rabies Virus or Vesicular Stomatitis Virus, a virus of the Paramyxoviridae family, such as, for example, Respiratory Syncytial Virus or Parainfluenza Virus, a virus of the Papillomaviridae family, such as, for example, Human Papillomavirus, or a virus of the Herpesviridae family, such as, for example, Herpes Simplex Virus. The virus may for example be an RNA virus, such as HCV, a DNA virus, such as HBV, or a retrovirus, such as HIV. The cells may be in culture or otherwise isolated from a mammal (i.e., in vitro or ex vivo), or may be in vivo, e.g., in a mammal (e.g. such as a SCID mouse model as described by Mercer, et al. (2001) Nature Medicine. 7(8): 927-933), in a primate, or in man.

The invention also provides a method of enhancing $T_H1$ differentiation of $T_H0$ cells, comprising administering to a population comprising $T_H0$ cells a polypeptide or conjugate of the invention in an amount effective to increase the production of a cytokine associated with the $T_H1$-phenotype (e.g., IFN-gamma) and/or decrease the production of a cytokine associated with the $T_H2$-phenotype (e.g., IL-4 or IL-5) in said population. The population may be in culture or otherwise isolated from a mammal (i.e., in vitro or ex vivo), or may be in vivo, e.g., in a mammal, in a primate, or in man.

The invention also provides a method of inhibiting proliferation of a cell population, comprising contacting the cell population with a polypeptide or conjugate of the invention in an amount effective to decrease proliferation of the cell population. The cell population may be in culture or otherwise isolated from a mammal (i.e., in vitro or ex vivo), or may be in vivo, e.g., in a mammal, a primate, or man.

These and other objects of the invention are discussed in more detail below.

Polypeptides of the Invention

The invention provides novel interferon-alpha polypeptides, collectively referred to herein as "polypeptides of the invention". The term "polypeptide(s) of the invention" is intended throughout to include variants of the polypeptide sequences disclosed herein. Also included in this invention are fusion proteins comprising polypeptides of the invention, and conjugates comprising polypeptides of the invention.

Fragments of various interferon-alpha coding sequences were recursively recombined to form libraries comprising recombinant polynucleotides, from which some polypeptides of the invention were discovered. Methods for obtaining libraries of recombinant polynucleotides and/or for obtaining diversity in nucleic acids used as the substrates for recursive sequence recombination are also described infra.

Exemplary polypeptides of the invention include polypeptides comprising sequences identified herein as SEQ ID NOs: 1-15, such as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14 and SEQ ID NO:15, encoded by nucleic acids identified herein as SEQ ID NOs:16-30, such as SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29 and SEQ ID NO:30. Polypeptides of the invention also include those comprising sequences identified herein as SEQ ID NOs:44-104, such as SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, and SEQ ID NO:104. Some such polypeptides further comprise an additional amino acid, such as a methionine, added to the N-terminus. The invention also provides fusion proteins and conjugates comprising these polypeptides, and isolated or recombinant nucleic acids encoding these polypeptides.

The invention also includes polypeptides comprising sequences which differ in 0-16 amino acid positions (such as in 0, 1, 2, 3, 4, 5, 6, 7, 8, 9, 10, 11, 12, 13, 14, 15, or 16 amino acid positions), e.g. in 0-16 positions, 0-15 positions, 0-14 positions, 0-13 positions, 0-12 positions, 0-11 positions, 0-10 positions, 0-9 positions, 0-8 positions, 0-7 positions, 0-6 positions, 0-5 positions, 0-4 positions, 0-3 positions, 0-2 positions, or 0-1 positions, from any one of SEQ ID NOs:1-15 and SEQ ID NOs:44-104, such as, one of SEQ ID NOs:1-15, 47, and 53 (for example, SEQ ID NO:1, SEQ ID NO:3, SEQ ID NO:8, SEQ ID NO:12, SEQ ID NO:47, or SEQ ID NO:53). In some instances, the polypeptide exhibits an interferon-alpha activity (e.g., antiviral activity, $T_H1$ differentiation activity, and/or antiproliferative activity). Some such polypeptides further comprise an additional amino acid, such as a methionine, added to the N-terminus. The invention also provides fusion proteins and conjugates comprising these polypeptides, and isolated or recombinant nucleic acids encoding these polypeptides.

In some instances, the sequence of the polypeptide of the invention comprises a substitution of an amino acid for a different amino acid at one or more positions, including, but not limited to, positions 47, 51, 52, 53, 54, 55, 56, 57, 58, 60, 61, 64, 69, 71, 72, 75, 76, 77, 78, 79, 80, 83, 84, 85, 86, 87, 90, 93, 133, 140, 154, 160, 161, and 162, relative to any one of SEQ ID NOs:1-15, 47, and 53, such as, for example, SEQ ID NO:1, SEQ ID NO:3, SEQ ID NO:8, SEQ ID NO:12, SEQ ID NO:47, or SEQ ID NO:53. In some instances, the polypeptide sequence comprises one or more of: His or Gln at position 47; Val, Ala or Thr at position 51; Gln, Pro or Glu at position 52; Ala or Thr at position 53; Phe, Ser, or Pro at position 55; Leu, Val or Ala at position 56; Phe or Leu at position 57; Tyr or His at position 58; Met, Leu or Val at position 60; Met or Ile at position 61; Thr or Ile at position 64; Ser or Thr at position 69; Lys or Glu at position 71; Asn or Asp at position 72; Ala or Val at position 75; Ala or Thr at position 76; Trp or Leu at position 77; Asp or Glu at position 78; Glu or Gln at position 79; Thr, Asp, Ser, or Arg at position 80; Glu or Asp at position 83; Lys or Glu at position 84; Phe or Leu at position 85; Tyr, Cys or Ser at position 86; Ile or Thr at position 87; Phe, Tyr, Asp or Asn at position 90; Met or Leu at position 93; Lys or Glu at position 133; Ser or Ala at position 140; Phe or Leu at position 154; Lys or Glu at position 160; Arg or Ser at position 161; and Arg or Ser at position 162; the position numbering relative to that of SEQ ID NO:1. The invention also provides fusion proteins and conjugates comprising these polypeptides, and isolated or recombinant nucleic acids encoding these polypeptides.

Some polypeptides of the invention comprise a substitution at a position which in a parent molecule is predicted to contain an amino acid residue that is exposed to the surface of the molecule, e.g., that is calculated to have at least 25%, such as at least 50% of its side chain exposed to the surface. Some such polypeptides of the invention comprise a substitution of an amino acid for a different amino acid at one or more positions including, but not limited to, the following positions which contain amino acid residues having more than 25% fractional Accessible Surface Area (ASA): positions 2, 3, 4, 5, 6, 7, 8, 9, 10, 12, 13, 16, 19, 20, 22, 23, 24, 25, 26, 27, 28, 30, 31, 33, 34, 35, 37, 40, 41, 42, 44, 46, 47, 49, 50, 51, 52, 59, 62, 63, 66, 69, 70, 71, 72, 74, 75, 78, 79, 80, 81, 83, 84, 87, 90, 91, 94, 95, 97, 98, 100, 101, 102, 103, 104, 105, 107, 108, 109, 110, 111, 112, 113, 114, 115, 118, 121, 122, 125, 126, 128, 129, 132, 133, 134, 135, 136, 137, 138, 139, 146, 149, 150, 153, 154, 157, 159, 160, 161, 162, 163, 164, 165, and 166, relative to any one of SEQ ID NOs:1-15, 47, and 53 (for example, SEQ ID NO:1, SEQ ID NO:3, SEQ ID NO:8, SEQ ID NO:12, SEQ ID NO:47, or SEQ ID NO:53). Some such polypeptides of the invention comprise a substitution of an amino acid for a different amino acid at one or more positions including, but not limited to, the following positions which contain amino acid residues having more than 50% fractional ASA: 2, 3, 4, 5, 6, 7, 8, 9, 12, 13, 16, 19, 25, 27, 28, 31, 33, 34, 35, 37, 41, 44, 46, 47, 49, 50, 66, 71, 75, 78, 79, 80, 83, 84, 87, 90, 91, 94, 95, 101, 102, 103, 105, 107, 108, 109, 110, 111, 114, 115, 118, 121, 122, 125, 126, 129, 132, 133, 135, 138, 150, 160, 162, 163, 164, 165, and 166, relative to any one of SEQ ID NOs:1-15, 47, and 53 (for example, SEQ ID NO:1, SEQ ID NO:3, SEQ ID NO:8, SEQ ID NO:12, SEQ ID NO:47, or SEQ ID NO:53).

Some polypeptides of the invention comprise one or more of the following substitutions which introduce a cysteine residue into a position which has more than 25% fractional ASA: D2C, L3C, P4C, Q5C, T6C, H7C, S8C, L9C, G10C, R12C, R13C, M16C, A19C, Q20C, R22C, R23C, I24C, S25C, L26C, F27C, S28C, L30C, K31C, R33C, H34C, D35C, R37C, Q40C, E41C, E42C, D44C, N46C, H47C, Q49C, K50C, V51C, Q52C, E59C, Q62C, Q63C, N66C, S69C, T70C, K71C, N72C, S74C, A75C, D78C, E79C, T80C, L81C, E83C, K84C, I87C, F90C, Q91C, N94C, D95C, E97C, A98C, V100C, M101C, Q102C, E103C, V104C, G105C, E107C, E108C, T109C, P110C, L111C, M112C, N113C, V114C, D115C, L118C, R121C, K122C, Q125C, R126C, T128C, L129C, T132C, K133C, K134C, K135C, Y136C, S137C, P138C, A146C, M149C, R150C, S153C, F154C, N157C, Q159C, K160C, R161C, L162C, R163C, R164C, K165C and E166C (or equivalent position relative to SEQ ID NO: 1), and combinations thereof.

Some polypeptides of the invention comprise one or more of the following substitutions which introduce a lysine residue into a position which has more than 25% fractional ASA: D2K, L3K, P4K, Q5K, T6K, H7K, S8K, L9K, G10K, R12K, R13K, M16K, A19K, Q20K, R22K, R23K, I24K, S25K, L26K, F27K, S28K, L30K, R33K, H34K, D35K, R37K, Q40K, E41K, E42K, D44K, N46K, H47K, Q49K, V51K, Q52K, E59K, Q62K, Q63K, N66K, S69K, T70K, N72K, S74K, A75K, D78K, E79K, T80K, L81K, E83K, I87K, F90K, Q91K, N94K, D95K, E97K, A98K, V100K, M101K, Q102K, E103K, V104K, G105K, E107K, E108K, T109K, P110K, L111K, M112K, N113K, V114K, D115K, L118K, R121K, Q125K, R126K, T128K, L129K, T132K, Y136K, S137K, P138K, A146K, M149K, R150K, S153K, F154K, N157K, Q159K, R161K, L162K, R163K, R164K, and E166K (or equivalent position relative to SEQ ID NO: 1), and combinations thereof.

Some polypeptides of the invention comprise a substitution of an amino acid residue for a different amino acid residue, or a deletion of an amino acid residue, which removes one or more lysines, e.g., K31, K50, K71, K84, K122, K133, K134, K135, K160, and/or K165 (relative to SEQ ID NO:1) from any polypeptide of the invention, such as one of SEQ ID NOs:1-15 and SEQ ID NOs:44-104, such as, for example, one of SEQ ID NOs:1-15, 47, and 53 (for example, SEQ ID NO:1, SEQ ID NO:3, SEQ ID NO:8, SEQ ID NO:12, SEQ ID NO:47, or SEQ ID NO:53). The one or more lysine residue(s) to be removed may be substituted with any other amino acid, may be substituted with an Arg (R) or Gln (Q), or may be deleted. Some such polypeptides comprise the substitutions K31R+K122R; K31R+K133R; K122R+K133R; or K31R+K122R+K133R. Other exemplary substitutions include K71E; K84E; K133E/G; and K160E.

Some polypeptides of the invention comprise a substitution or a deletion which removes one or more histidines, e.g., H7, H11, H34, and/or H47 (relative to SEQ ID NO:1) from any polypeptide of the invention, such as one of SEQ ID NOs:1-15 and SEQ ID NOs:44-104, such as, for example, one of SEQ ID NOs:1-15, 47, and 53 (for example, SEQ ID NO:1, SEQ ID NO:3, SEQ ID NO:8, SEQ ID NO:12, SEQ ID NO:47, or SEQ ID NO:53). The one or more histidine residue(s) to be removed may be substituted with any other amino acid, may be substituted with an Arg (R) or Gln (Q), or may be deleted. Some such polypeptides comprise the substitutions H34Q; H47Q; or H34Q+H47Q.

Some polypeptides of the invention comprise a substitution of an amino acid for a different amino acid, a deletion of an amino acid, or an insertion of an amino acid, which removes or otherwise disrupts the spatial arrangement of the N-linked glycosylation site N72 S73 S74 (relative to SEQ ID NO:1). Removal of this site may be accomplished in a number of ways, for example by deletion of N72 or substitution of N72 for a different amino acid, substitution of Ser73 with Pro, substitution of Ser74 for an amino acid other than Ser, Thr, or Cys, or insertion of an amino acid residue other than Ser, Thr, or Cys between positions 73 and 74. For example, some such polypeptides comprise the substitution N72D.

Some polypeptides of the invention comprise one or more amino acid substitution, deletion or insertion which removes one or more basic residues or one or more pairs of basic residues (such as, Arg-Arg, Arg-Lys, Lys-Arg, Lys-Lys) in order to, for example, minimize the presence of potential protease-sensitive sites, or in some instances to remove sites potentially reactive towards amine-reactive conjugation (e.g. PEGylation) reagents. For example, removal of dibasic sequences near the C-terminus may be accomplished by removal of one or more of Lys160, Arg161, Arg163, Arg164, and Lys165 (relative to SEQ ID NO:1). The one or more Lys or Arg to be removed may for example be deleted, or substituted with any amino acid other than Lys or Arg. Some such polypeptides of the invention comprise a substitution of one or more of Lys160, Arg161, and Arg164 for an amino acid other than Lys or Arg, such as, for example, one or more of the substitutions Lys160Glu; Arg161Ser/Cys; and Arg164Ser/Cys. Some such polypeptides alternatively or in addition comprise a deletion of one or more of Lys 160, Arg161, Arg163, Arg164, and Lys165, which may be via individual deletions (e.g., K165*) or in groups of more than one, including via C-terminal truncation (e.g., K165*-E166*).

Other modifications contemplated for polypeptides of the invention include those described below and in the section entitled “INTERFERON-ALPHA CONJUGATES”.

It is to be understood that while the examples and modifications to the parent polypeptide are generally provided herein relative to the sequence SEQ ID NO:1 (or relative to some other specified sequence), the disclosed modifications may also be made in equivalent amino acid positions of any of the other polypeptides of the invention (including SEQ ID NOs:2-15 and SEQ ID NOs:44-104 and variants thereof) described herein. Thus, as an example, the substitution H47C relative to SEQ ID NO:1 is understood to correspond to Q47C in SEQ ID NO:5, and so on.

The following tables provide sequences of some interferon-alpha polypeptides of the invention. For clarity, the sequences are shown relative to SEQ ID NO:3 (Table 1) or SEQ ID NO:12 (Table 2). Some such polypeptides exhibit an interferon-alpha activity, such as antiviral activity, $T_H1$ differentiation activity, and/or antiproliferative activity.

TABLE 1

| Polypeptide Sequence (relative to SEQ ID NO:3) | Clone name(s) | SEQ ID |
|---|---|---|
| SEQ ID NO:3 + E133K, A140S | B9x11 | SEQ ID NO:1 |
| SEQ ID NO:3 + H47Q, E133K, A140S | B9x12 | SEQ ID NO:2 |
| SEQ ID NO:3 | B9x14, B9x14CHO2 | SEQ ID NO:3 |
| SEQ ID NO:3 + H47Q, V51T, F55S, L56V, Y58H, E133K, A140S | B9x15 | SEQ ID NO:4 |
| SEQ ID NO:3 + H47Q | B9x16 | SEQ ID NO:5 |
| SEQ ID NO:3 + V51T, F55S, L56V, Y58H | B9x17 | SEQ ID NO:6 |
| SEQ ID NO:3 + H47Q, V51T, F55S, L56V, Y58H | B9x18 | SEQ ID NO:7 |
| SEQ ID NO:3 + F154L, K160E, R161S, R164S | B9x14C2a | SEQ ID NO:44 |
| SEQ ID NO:3 + E166EC | B9x14CHO1 | SEQ ID NO:45 |
| SEQ ID NO:3 + N72D | B9x14CHO3 | SEQ ID NO:46 |
| SEQ ID NO:3 + N72D, K160E, R161S, R164S | B9x14CHO4, B9x14EC4 | SEQ ID NO:47 |
| SEQ ID NO:3 + N72D, K160E, R161C, R164S | B9x14CHO5, B9x14EC5 | SEQ ID NO:48 |
| SEQ ID NO:3 + N72D, K160E, R161S, R164C | B9x14CHO6, B9x14EC3 | SEQ ID NO:49 |
| SEQ ID NO:3 + H47Q, V51A, F55S, L56V, F57L, Y58H, N72D, F154L, K160E, R161S, R164S | 14Ep01 | SEQ ID NO:50 |
| SEQ ID NO:3 + M61I, N72D, E83D, M93L, M101T, T109I, P110A, V114E, F154L, K160E, R161S, R164S | 14Ep02 | SEQ ID NO:51 |
| SEQ ID NO:3 + N72D, M101I, F154L, K160E, R161S, R164S | 14Ep03 | SEQ ID NO:52 |
| SEQ ID NO:3 + N72D, F154L, K160E, R161S, R164S | 14Ep04 | SEQ ID NO:53 |
| SEQ ID NO:3 + H47Q, V51A, F55S, L56V, F57L, Y58H, N72D, M101I, F154L, K160E, R161S, R164S | 14Ep05 | SEQ ID NO:54 |
| SEQ ID NO:3 + H47Q, V51A, F55S, L56V, F57L, Y58H, M61I, N72D, E83D, M93L, M101T, T109I, P110A, V114E, F154L, K160E, R161S, R164S | 14EF | SEQ ID NO:55 |
| SEQ ID NO:3 + K31C, N72D, F154L, K160E, R161S, R164S | B9x14Ep04C31 | SEQ ID NO:56 |
| SEQ ID NO:3 + K31C, N72D, K160E, R161S, R164S | B9x14CHO4C31 | SEQ ID NO:57 |
| SEQ ID NO:3 + N46C, N72D, K160E, R161S, R164S | B9x14CHO4C46 | SEQ ID NO:58 |
| SEQ ID NO:3 + K71C, N72D, K160E, R161S, R164S | B9x14CHO4C71 | SEQ ID NO:59 |
| SEQ ID NO:3 + N72D, A75C, K160E, R161S, R164S | B9x14CHO4C75 | SEQ ID NO:60 |
| SEQ ID NO:3 + N72D, E79C, K160E, R161S, R164S | B9x14 CHO4C79 | SEQ ID NO:61 |
| SEQ ID NO:3 + N72D, E107C, K160E, R161S, R164S | B9x14CHO4C107 | SEQ ID NO:62 |
| SEQ ID NO:3 + N72D, K122C, K160E, R161S, R164S | B9x14 CHO4C122 | SEQ ID NO:63 |
| SEQ ID NO:3 + N72D, K134C, K160E, R161S, R164S | B9x14CHO4C134 | SEQ ID NO:64 |
| SEQ ID NO:3 + N72D, F154L, K160E, R161*-E166* | B9x14Ep04 Δ161-166 | SEQ ID NO:65 |
| SEQ ID NO:3 + N72D, F154L, K160E, R161S, R164S, K165*-E166* | B9x14Ep04 Δ165-166 | SEQ ID NO:66 |
| SEQ ID NO:3 + | B9x14Ep04Δ1-4 | SEQ ID NO:67 |

TABLE 1-continued

| Polypeptide Sequence (relative to SEQ ID NO:3) | Clone name(s) | SEQ ID |
|---|---|---|
| C1*-P4*, D44*, N72D, F154L, K160E, R161S, R164S, K165*-E166* | D44*Δ165-166 | |
| SEQ ID NO:3 + H34Q, N72D, K160E, R161S, R164S | B9x14CHO4NP1 | SEQ ID NO:68 |
| SEQ ID NO:3 + H34Q, H47Q, N72D, K160E, R161S, R164S | B9x14 CHO4NP2 | SEQ ID NO:69 |
| SEQ ID NO:3 + K31R, N72D, K160E, R161S, R164S | B9x14CHO8 | SEQ ID NO:70 |
| SEQ ID NO:3 + K50R, N72D, K160E, R161S, R164S | B9x14CHO9 | SEQ ID NO:71 |
| SEQ ID NO:3 + K71R, N72D, K160E, R161S, R164S | B9x14CHO10 | SEQ ID NO:72 |
| SEQ ID NO:3 + N72D, K84R, K160E, R161S, R164S | B9x14CHO11 | SEQ ID NO:73 |
| SEQ ID NO:3 + N72D, K122R, K160E, R161S, R164S | B9x14CHO12 | SEQ ID NO:74 |
| SEQ ID NO:3 + N72D, K134R, K160E, R161S, R164S | B9x14CHO13 | SEQ ID NO:75 |
| SEQ ID NO:3 + N72D, K135R, K160E, R161S, R164S | B9x14CHO14 | SEQ ID NO:76 |
| SEQ ID NO:3 + N72D, K160E, R161S, R164S, K165R | B9x14CHO15 | SEQ ID NO:77 |
| SEQ ID NO:3 + N72D, K122R, K135R, K160E, R161S, R164S | B9x14CHO16 | SEQ ID NO:78 |
| SEQ ID NO:3 + K31R, N72D, K135R, K160E, R161S, R164S | B9x14CHO17 | SEQ ID NO:79 |
| SEQ ID NO:3 + K31R, N72D, K122R, K160E, R161S, R164S | B9x14CHO18 | SEQ ID NO:80 |
| SEQ ID NO:3 + K31R, H34Q, H47Q, N72D, K122R, K160E, R161S, R164S | B9x14CHO18NP2 | SEQ ID NO:81 |
| SEQ ID NO:3 + K31R, H34Q, H47Q, N72D, K122R, K160E, R161S, R164S, K165*-E166* | B9x14CHO18NP2 Δ165-166 | SEQ ID NO:82 |

TABLE 2

| Polypeptide Sequence (relative to SEQ ID NO:12) | Clone name(s) | SEQ ID |
|---|---|---|
| SEQ ID NO:12 + H47Q, V51T, F55S, L56V, Y58H | B9X21 | SEQ ID NO:8 |
| SEQ ID NO:12 + V51T, F55S, L56V, Y58H | B9X22 | SEQ ID NO:9 |
| SEQ ID NO:12 + H47Q | B9X23 | SEQ ID NO:10 |
| SEQ ID NO:12 + H47Q, V51T, F55S, L56V, Y58H, E133K, A140S | B9X24 | SEQ ID NO:11 |
| SEQ ID NO:12 | B9X25 | SEQ ID NO:12 |
| SEQ ID NO:12 + V51T, F55S, L56V, Y58H, E133K, A140S | B9X26 | SEQ ID NO:13 |
| SEQ ID NO:12 + H47Q, E133K, A140S | B9X27 | SEQ ID NO:14 |
| SEQ ID NO:12 + E133K, A140S | B9X28 | SEQ ID NO:15 |
| SEQ ID NO:12 + N72D | B9x25CHO1 | SEQ ID NO:83 |
| SEQ ID NO:12 + N72D, F154L, K160E, R161S, R164S | B9x25CHO2, 25Ep09, B9x25EC1 | SEQ ID NO:84 |
| SEQ ID NO:12 + N72D, F154L, K160E, R161C, R164S | B9x25CHO3, B9x25EC2 | SEQ ID NO:85 |
| SEQ ID NO:12 + N72D, F154L, K160E, R161S, R164C | B9x25CHO4, B9x25EC3 | SEQ ID NO:86 |
| SEQ ID NO:12 + H47Q, V51T, F55S, L56V, Y58H, N72D | 25Ep01 | SEQ ID NO:87 |
| SEQ ID NO:12 + L17I, R22G, H47Q, V51T, F55S, L56V, Y58H, N72D, F154L, K160E, R161S, R164S | 25Ep02 | SEQ ID NO:88 |
| SEQ ID NO:12 + D2N, P4S, S10N, H47Q, V51T, F55S, L56V, Y58H, N72D, F154L, K160E, R161S, R164S | 25Ep03 | SEQ ID NO:89 |
| SEQ ID NO:12 + H47Q, V51T, F55S, L56V, Y58H, L60M, N72D, F154L, K160E, R161S, R164S | 25Ep04 | SEQ ID NO:90 |

TABLE 2-continued

| Polypeptide Sequence (relative to SEQ ID NO:12) | Clone name(s) | SEQ ID |
|---|---|---|
| SEQ ID NO:12 + H47Q, V51T, F55S, L56V, Y58H, N72D, N95D, F154L, K160E, R161S, R164S | 25Ep05 | SEQ ID NO:91 |
| SEQ ID NO:12 + H47Q, V51T, F55S, L56V, Y58H, N72D, E83D, M93L, N95D, I101T, V114E, F154L, K160E, R161S, R164S | 25Ep06 | SEQ ID NO:92 |
| SEQ ID NO:12 + H47Q, V51T, F55S, L56V, Y58H, N72D, R125Q, F154L, K160E, R161S, R164S | 25Ep07 | SEQ ID NO:93 |
| SEQ ID NO:12 + H47Q, V51T, F55S, L56V, Y58H, N72D, F154L, K160E, R161S, R164S | 25Ep08 | SEQ ID NO:94 |
| SEQ ID NO:12 + L17I, R22G, N72D, F154L, K160E, R161S, R164S, | 25Ep10 | SEQ ID NO:95 |
| SEQ ID NO:12 + D2N, P4S, S10N, N72D, F154L, K160E, R161S, R164S | 25Ep11 | SEQ ID NO:96 |
| SEQ ID NO:12 + N72D, R125Q, F154L, K160E, R161S, R164S | 25Ep12 | SEQ ID NO:97 |
| SEQ ID NO:12 + L17I, R22G, N72D, R125Q, F154L, K160E, R161S, R164S | 25Ep13 | SEQ ID NO:98 |
| SEQ ID NO:12 + D2N, P4S, S10N, N72D, R125Q, F154L, K160E, R161S, R164S | 25Ep14 | SEQ ID NO:99 |
| SEQ ID NO:12 + H47Q, V51T, F55S, L56V, Y58H, N72D, F154L, K160E, R161S, R164S | 25Ep15 | SEQ ID NO:100 |
| SEQ ID NO:12 + L17I, R22G, H47Q, V51T, F55S, L56V, Y58H, N72D, R125Q, F154L, K160E, R161S, R164S | 25Ep16 | SEQ ID NO:101 |
| SEQ ID NO:12 + D2N, P4S, S10N, H47Q, V51T, F55S, L56V, Y58H, N72D, R125Q, F154L, K160E, R161S, R164S | 25Ep17 | SEQ ID NO:102 |
| SEQ ID NO:12 + L17I, R22G, H47Q, V51T, F55S, L56V, Y58H, L60M, N72D, E83D, M93L, N95D, I101T, V114E, R125Q, F154L, K160E, R161S, R164S | 25EF1 | SEQ ID NO:103 |
| SEQ ID NO:12 + D2N, P4S, S10N, H47Q, V51T, F55S, L56V, Y58H, L60M, N72D, E83D, M93L, N95D, I101T, V114E, R125Q, F154L, K160E, R161S, R164S | 25EF2 | SEQ ID NO:104 |

Variants

In another aspect, the invention provides an isolated or recombinant polypeptide which is a variant of a parent interferon-alpha polypeptide, the variant comprising a sequence which differs from the parent polypeptide sequence in least one amino acid position, wherein the variant sequence comprises one or more of His at position 47, Val at position 51, Phe at position 55, Leu at position 56, Tyr at position 58, Lys at position 133, and at position Ser140, the position numbering relative to that of SEQ ID NO:1. In some instances the parent interferon-alpha polypeptide sequence is a sequence of a naturally-occurring human interferon-alpha (such as, for example, huIFN-alpha 2b (SEQ ID NO:32), huIFN-alpha 2a (SEQ ID NO:32 with position 23=Lys), huIFN-alpha 2c (SEQ ID NO:32 with position 34=Arg), huIFN-alpha 8b (SEQ ID NO:33), huIFN-alpha 8a (SEQ ID NO:33 with positions 98=Val, 99=Leu, 100=Cys, and 101=Asp), huIFN-alpha 8c (SEQ ID NO:33 with position 161=Asp and amino acids at positions 162-166 deleted), huIFN-alpha 14a (SEQ ID NO:39), huIFN-alpha 14c (SEQ ID NO:39 with position 152=Leu), or a sequence of any other naturally occurring human interferon alpha polypeptide, such as those shown in FIGS. 2 and 4 herein (SEQ ID NOs:31-42) and/or listed in Allen G. and Diaz M. O. (1996), supra). In some instances the parent interferon-alpha polypeptide sequence is a sequence of a non-naturally occurring (i.e., synthetic) interferon-alpha, such as IFN-alphaCon1 (SEQ ID NO:43) In some instances, the parent polypeptide to be modified may itself be a polypeptide of the invention, such as, e.g. any one of SEQ ID NOs: 1-15 and SEQ ID NOs:44-104. In some instances, the variant sequence differs from the parent polypeptide sequence in 1-16 amino acid positions (such as in 1, 2, 3, 4, 5, 6, 7, 8, 9, 10, 11, 12, 13, 14, 15, or 16 amino acid positions), e.g. in 1-14 amino acid positions, in 1-12 amino acid positions, in 1-10 amino acid positions, in 1-8 amino acid positions, in 1-6 amino acid positions, in 1-5 amino acid positions, in 1-4 amino acid positions, in 1-3 amino acid positions, or in 1-2 amino acid positions. Some such variants exhibit an interferon-alpha activity. The invention also provides fusion proteins and conjugates comprising these variants, and isolated or recombinant nucleic acids encoding these variants.

Sequence Variations

As noted above, polypeptides of the present invention include polypeptides comprising sequences which differ from any one of SEQ ID NOs:1-15 and SEQ ID NOs:44-104, such as one of SEQ ID NOs:1-15, 47, and 53 (for example, SEQ ID NO:1, SEQ ID NO:3, SEQ ID NO:8, SEQ ID NO:12, SEQ ID NO:47, or SEQ ID NO:53), in 0-16 amino acid positions (such as in 0, 1, 2, 3, 4, 5, 6, 7, 8, 9, 10, 11, 12, 13, 14, 15, or 16 amino acid positions), e.g. in 0-16 positions, 0-15 positions, 0-14 positions, 0-13 positions, 0-12 positions, 0-11 positions, 0-10 positions, 0-9 positions, 0-8 positions, 0-7 positions, 0-6 positions, 0-5 positions, 0-4 positions, 0-3 positions, 0-2 positions, or 0-1 positions. Some such polypeptides exhibit an interferon-alpha activity.

For example, some such polypeptides of the invention comprise a sequence having a length of about 150 amino acids, such as about 151, 152, 153, 154, 155, 156, 157, 158, 159, 160, 161, 162, 163, 164, or 165 amino acids, corresponding to a deletion of between 1 and 16 amino acids relative to a parent polypeptide sequence (such as, for example, one of SEQ ID NOs:1-15). In some instances, between 1 and 11, e.g., between 1 and 10, such as between 1 and 7, e.g. between 1 and 5, such as between 1 and 3 amino acids are deleted from the C-terminus, i.e. the polypeptide is C-terminally truncated compared to the parent polypeptide sequence (such as, for example, one of SEQ ID NOs:1-15, 47, or 53) by 1-11 amino acid residues (e.g. by 1, 2, 3, 4, 5, 6, 7, 8, 9, 10, or 11 amino acid residues), such as by 1-10, 1-7, e.g., by 1-5 or by 1-3 amino acid residues. Alternatively, or in addition, some such polypeptides are N-terminally truncated compared to the parent polypeptide sequence (such as, one of SEQ ID NOs:1-15, 47, or 53) by 1-4 amino acid residues (e.g. by 1, 2, 3, or 4 amino acid residues), e.g., 1-4, 1-3, 1-2 or 1 amino acid residue(s) are removed from the N-terminus. Some such polypeptides further comprise a methionine at the N-terminus. Some such polypeptides exhibit an interferon-alpha activity.

As another example, some such polypeptides of the invention comprise a sequence containing between 0 and 16 amino acid substitutions relative to one of SEQ ID NOs:1-15, 47, or 53 (e.g. 0, 1, 2, 3, 4, 5, 6, 7, 8, 9, 10, 11, 12, 13, 14, 15, or 16 amino acid substitutions), such as 0-14 or 0-12 or 0-10 or 0-8 or 0-6 or 0-5 or 0-4 or 0-3 or 0-2 or 0-1 amino acid substitutions. In some instances, one or more of the amino acid substitutions are made according to, for example, a substitution group (such as, a conservative substitution group), such as one set forth below. Some such polypeptides exhibit an interferon-alpha activity.

Some polypeptides of the invention comprise a sequence comprising between 0 and 16 amino acid substitutions relative to one of SEQ ID NOs:1-15 and SEQ ID NOs:44-104 (for example, SEQ ID NO:1, SEQ ID NO:3, SEQ ID NO:8, SEQ ID NO:12, SEQ ID NO:47, or SEQ ID NO:53), e.g. 0, 1, 2, 3, 4, 5, 6, 7, 8, 9, 10, 11, 12, 13, 14, 15, or 16 amino acid substitutions, such as 0-14 or 0-12 or 0-10 or 0-8 or 0-6 or 0-5 or 0-4 or 0-3 or 0-2 or 0-1 amino acid substitutions, where at least one of said substitution(s) introduces an amino acid residue comprising an attachment group for a non-polypeptide moiety. Examples include introduction of one or more N-glycosylation site(s), or introduction of one or more cysteine residue(s) or lysine residue(s), as described above and in the section entitled "INTERFERON-ALPHA CONJUGATES". Some such polypeptides exhibit an interferon-alpha activity.

Some polypeptides of the invention comprise a sequence containing between 0 and 16 amino acid substitutions or deletions or insertions relative to one of SEQ ID NOs:1-15 and SEQ ID NOs:44-104 (for example, SEQ ID NO:1, SEQ ID NO:3, SEQ ID NO:8, SEQ ID NO:12, SEQ ID NO:47, or SEQ ID NO:53), such as 0-14 or 0-12 or 0-10 or 0-8 or 0-6 or 0-5 or 0-4 or 0-3 or 0-2 or 0-1 amino acid substitutions deletions or insertions (or a combination thereof), where at least one of said substitution or deletion removes an amino acid residue from a parent polypeptide sequence which comprises an attachment group for a non-polypeptide moiety or, in the case of an amino acid insertion, disrupts the spatial arrangement of residues required for such attachment group (e.g., an insertion of an amino acid to disrupt an N-glycosylation N-X-S/T motif). Examples include removal from the parent polypeptide sequence of an N-glycosylation site, or removal of a lysine, histidine, or cysteine residue, as described above and in the section entitled "INTERFERON-ALPHA CONJUGATES". Some such polypeptides exhibit an interferon-alpha activity.

As a non-limiting example, a polypeptide of the invention may have the sequence SEQ ID NO:3 or a sequence which differs from SEQ ID NO:3 in a total of up to 16 positions (which may be a combination of amino acid substitutions, deletions, and/or insertions, including those described above). In some instances, none, some, or all of the substitutions are substitutions according to a substitution group defined below.

Amino acid substitutions in accordance with the invention may include, but are not limited to, one or more conservative amino acid substitutions. Conservative substitution tables providing functionally similar amino acids are well known in the art. One example is provided in the table below (Table 3), which sets forth six exemplary groups that contain amino acids which may be considered "conservative substitutions" for one another.

TABLE 3

Conservative Substitution Groups

| 1 | Alanine (A) | Glycine (G) | Serine (S) | Threonine (T) |
|---|---|---|---|---|
| 2 | Aspartic acid (D) | Glutamic acid (E) | | |
| 3 | Asparagine (N) | Glutamine (Q) | | |
| 4 | Arginine (R) | Lysine (K) | Histidine (H) | |
| 5 | Isoleucine (I) | Leucine (L) | Methionine (M) | Valine (V) |
| 6 | Phenylalanine (F) | Tyrosine (Y) | Tryptophan (W) | |

Other substitution groups of amino acids can be envisioned. For example, amino acids can be grouped by similar function or chemical structure or composition (e.g., acidic, basic, aliphatic, aromatic, sulfur-containing). For example, an Aliphatic grouping may comprise: Glycine (G), Alanine (A), Valine (V), Leucine (L), Isoleucine (I). Other groups containing amino acids that are considered conservative substitutions for one another include: Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also Creighton (1984) Proteins, W.H. Freeman and Company, for additional groupings of amino acids. Listing of a polypeptide sequence herein, in conjunction with the above substitution groups, provides an express listing of all conservatively substituted polypeptide sequences.

Percent Sequence Identity

In one aspect, the invention provides an isolated or recombinant polypeptides each comprising a sequence having at least 90% sequence identity (e.g., at least about 91%, at least about 92%, at least about 93%, at least about 94%, at least about 95%, at least about 96%, at least about 97%, at least about 98%, or at least about 99% amino acid sequence identity) to any one of SEQ ID NOs:1-15 and SEQ ID NOs:44-104, such as, for example, to one of SEQ ID NOs:1-15, 47, and 53 (for example, SEQ ID NO:1, SEQ ID NO:3, SEQ ID NO:8, SEQ ID NO:12, SEQ ID NO:47, or SEQ ID NO:53). In some instances the polypeptide exhibits an interferon-alpha activity. In some instances, the polypeptide sequence differs at one or more amino acid positions, e.g., in up to 16 positions (such as, 1-16 positions, 1-15 positions, 1-14 positions, 1-13 positions, 1-12 positions, 1-11 positions, 1-10 positions, 1-9 positions, 1-8 positions, 1-7 positions, 1-6 positions, 1-5 positions, 1-4 positions, 1-3 positions, or 1-2 positions) from any one of SEQ ID NO:1-15 and 44-104, such as, for example, SEQ ID NO:1, SEQ ID NO:3, SEQ ID NO:8, SEQ ID NO:12, SEQ ID NO:47, or SEQ ID NO:53. As an example, some positions which may be substituted for another amino acid in accordance with the invention include, but are not limited to, one or more of positions 47, 51, 52, 53, 54, 55, 56, 57, 58, 60, 61, 64, 69, 71, 72, 75, 76, 77, 78, 79, 80, 83, 84, 85, 86, 87, 90, 93, 133, 140, 154, 160, 161, and 162, relative to one of SEQ ID NOs:1-15 and 44-104. In some instances, the sequence comprises one or more of: His or Gln at position 47; Val, Ala or Thr at position 51; Gln, Pro or Glu at position 52; Ala or Thr at position 53; Phe, Ser, or Pro at position 55; Leu, Val or Ala at position 56; Phe or Leu at position 57; Tyr or His at position 58; Met, Leu or Val at position 60; Met or Ile at position 61; Thr or Ile at position 64; Ser or Thr at position 69; Lys or Glu at position 71; Asn or Asp at position 72; Ala or Val at position 75; Ala or Thr at position 76; Trp or Leu at position 77; Asp or Glu at position 78; Glu or Gln at position 79; Thr, Asp, Ser, or Arg at position 80; Glu or Asp at position 83; Lys or Glu at position 84; Phe or Leu at position 85; Tyr, Cys or Ser at position 86; Ile or Thr at position 87; Phe, Tyr, Asp or Asn at position 90; Met or Leu at position 93; Lys or Glu at position 133; Ser or Ala at position 140; Phe or Leu at position 154; Lys or Glu at position 160; Arg or Ser at position 161; and Arg or Ser at position 162; the position numbering relative to that of SEQ ID NO:1. Other substitutions contemplated in sequences of the invention are described above and in the section entitled "INTERFERON-ALPHA CONJUGATES". The invention also provides fusion proteins comprising such polypeptides, conjugates comprising such polypeptides, and isolated or recombinant nucleic acids encoding such polypeptides.

In another aspect, the present invention provides nucleic acids having at least about 60%, 70%, 75%, 80%, 85%, 90%, 91%, 92%, 93%, 94%, 95%, 96%, 97%, 98%, 99% or more percent sequence identity to one or more of SEQ ID NOS: 16-30. Some such nucleic acids encode polypeptides exhibiting an interferon-alpha activity as described herein.

The degree to which a sequence (polypeptide or nucleic acid) is similar to another provides an indication of similar structural and functional properties for the two sequences. Accordingly, in the context of the present invention, sequences which have a similar sequence to any given exemplar sequence are a feature of the present invention. In particular, sequences that have percent sequence identities as defined below are a feature of the invention.

A variety of methods of determining sequence relationships can be used, including manual alignment and computer assisted sequence alignment and analysis. A variety of computer programs for performing sequence alignments are available, or an alignment can be prepared manually by one of skill, as described below.

As noted above, the sequences of the nucleic acids and polypeptides employed in the subject invention need not be identical, but can be substantially identical to the corresponding sequence of a polypeptide of the invention or nucleic acid of the invention. For example, polypeptides of the invention can be subject to various changes, such as one or more amino acid insertions, deletions, and/or substitutions, either conservative or non-conservative, including where, e.g., such changes might provide for certain advantages in their use, such as, in their therapeutic or prophylactic use or administration or diagnostic application. The nucleic acids of the invention can also be subject to various changes, such as one or more substitutions of one or more nucleic acids in one or more codons such that a particular codon encodes the same or a different amino acid, resulting in either a silent variation (as defined herein) or non-silent variation, or one or more deletions of one or more nucleic acids (or codons) in the sequence. The nucleic acids can also be modified to include one or more codons that provide for optimum expression in an expression system (e.g., bacterial or mammalian), while, if desired, said one or more codons still encode the same amino acid(s). Such nucleic acid changes might provide for certain advantages in their therapeutic or prophylactic use or administration, or diagnostic application. The nucleic acids and polypeptides can be modified in a number of ways so long as they comprise a sequence substantially identical (as defined below) to a sequence in a respective nucleic acid or polypeptide of the invention.

The term "identical" or "identity," in the context of two or more nucleic acid or polypeptide sequences, refers to two or more sequences that are the same or have a specified percentage of amino acid residues or nucleotides that are the same, when compared and aligned for maximum similarity, as determined using the sequence comparison algorithm described below or by visual inspection.

The "percent sequence identity" ("% identity") of a subject sequence to a reference (i.e. query) sequence means that the subject sequence is identical (i.e., on an amino acid-by-amino acid basis for a polypeptide sequence, or a nucleotide-by-nucleotide basis for a polynucleotide sequence) by a specified percentage to the query sequence over a comparison length.

The percent sequence identity of a subject sequence to a query sequence is calculated as follows. First, the optimal alignment of the two sequences is determined using a sequence comparison algorithm with specific alignment parameters. This determination of the optimal alignment may be performed using a computer, or may be manually calculated, as described below. Then, the two optimally aligned sequences are compared over the comparison length, and the number of positions in the optimal alignment at which identical residues occur in both sequences are determined, which provides the number of matched positions. The number of matched positions is then divided by the total number of positions of the comparison length (which, unless otherwise specified, is the length of the query sequence), and then the result is multiplied by 100, to yield the percent sequence identity of the subject sequence to the query sequence.

With regard to polypeptide sequences, typically one sequence is regarded as a "query sequence" (for example, a polypeptide sequence of the invention) to which one or more other sequences, i.e., "subject sequence(s)" (for example, sequences present in a sequence database) are compared. The sequence comparison algorithm uses the designated alignment parameters to determine the optimal alignment between the query sequence and the subject sequence(s). When comparing a query sequence against a sequence database, such as, e.g., GENBANK® (Genetic Sequence Data Bank; U.S. Department of Health and Human Services) or GENESEQ® (Thomson Derwent; also available as DGENE® on STN), usually only the query sequence and the alignment parameters are input into the computer; optimal alignments between the input query sequence and each subject sequence present in the database are returned, generally for up to a desired number of subject sequences.

Two polypeptide sequences are "optimally aligned" when they are aligned using defined parameters, i.e., a defined amino acid substitution matrix, gap existence penalty (also termed gap open penalty), and gap extension penalty, so as to arrive at the highest similarity score possible for that pair of sequences. The BLOSUM62 matrix (Henikoff and Henikoff (1992) Proc. Natl. Acad. Sci. USA 89(22):10915-10919) is often used as a default scoring substitution matrix in polypeptide sequence alignment algorithms (such as BLASTP, described below). The gap existence penalty is imposed for the introduction of a single amino acid gap in one of the aligned sequences, and the gap extension penalty is imposed for each residue position in the gap. Unless otherwise stated, alignment parameters employed herein are: BLOSUM62 scoring matrix, gap existence penalty=11, and gap extension penalty=1. The alignment score is defined by the amino acid positions of each sequence at which the alignment begins and ends (e.g. the alignment window), and optionally by the insertion of a gap or multiple gaps into one or both sequences, so as to arrive at the highest possible similarity score.

While optimal alignment between two or more sequences can be determined manually (as described below), the process is facilitated by the use of a computer-implemented alignment algorithm such as BLAST® (National Library of Medicine), e.g., BLASTP for polypeptide sequences and BLASTN for nucleic acid sequences, described in Altschul et al. (1997) Nucleic Acids Res. 25:3389-3402, and made available to the public through various sources, such as the National Center for Biotechnology Information (NCBI) Website. When using a computerized BLAST interface, if the option exists to use a "low complexity filter", this option should be turned off (i.e., no filter).

FIG. 3 shows an alignment of a polypeptide of the invention (B9x14, SEQ ID NO:3) with human IFN-alpha 14a (also known as LeIF H, Goeddel et al. (1981) Nature 290:20-26; SEQ ID NO:39), which was the most closely-related sequence retrieved in a BLASTP search of query sequence SEQ ID NO:3 against the GENBANK and GENESEQ databases using the BLOSUM62 matrix, gap open penalty 11, gap extension penalty 1. These two sequences differ in 18 amino acid positions over a length of 166 amino acids (i.e., SEQ ID NO:39 differs from SEQ ID NO:3 in 18 amino acid positions); furthermore, SEQ ID NO:39 is 89% identical to SEQ ID NO:3, since ((166−18)/166)×100=89.

FIG. 5 shows an alignment of another polypeptide of the invention (B9x25, SEQ ID NO:12) with human IFN-alpha 14a (SEQ ID NO:39) which was the most closely-related sequence retrieved in a BLASTP search of query sequence SEQ ID NO:12 against the GENBANK and GENESEQ databases using the parameters specified above. SEQ ID NO:39 differs from SEQ ID NO:12 in 20 amino acid positions over a length of 166 amino acids; furthermore, SEQ ID NO:39 is 88% identical to SEQ ID NO:3, since ((166−20)/166)×100=88.

The optimal alignment between two polypeptide sequences can also be determined by a manual calculation of the BLASTP algorithm (i.e., without aid of a computer) using the same alignment parameters specified above (matrix=BLOSUM62, gap open penalty=11, and gap extension penalty=1). To begin, the two sequences are initially aligned by visual inspection. An initial alignment score is then calculated as follows: for each individual position of the alignment (i.e., for each pair of aligned residues), a numerical value is assigned according to the BLOSUM62 matrix (FIG. 6). The sum of the values assigned to each pair of residues in the alignment is the initial alignment score. If the two sequences being aligned are highly similar, often this initial alignment provides the highest possible alignment score. The alignment with the highest possible alignment score is the optimal alignment based on the alignment parameters employed. FIG. 7A shows an example calculation of an alignment score for two sequences, a "query" sequence, identified herein as residues 29-50 of SEQ ID NO:3 (upper), and a "subject" sequence, identified herein as residues 30-52 of SEQ ID NO:5 (lower). The sequences were aligned by visual inspection, and the numerical value assigned by the BLOSUM62 matrix for each aligned pair of amino acids is shown beneath each position in the alignment (to aid in visualization, each identical pair of amino acids in the alignment is shown in boldface). In this example, this initial alignment provided the highest possible alignment score (the sum of the values shown beneath each aligned position); any other alignment of these two sequences, with or without gaps, would result in a lower alignment score.

In some instances, a higher alignment score might be obtained by introducing one or more gaps into the alignment. Whenever a gap is introduced into an alignment, a gap open penalty is assigned, and in addition a gap extension penalty is assessed for each residue position within that gap. Therefore, using the alignment parameters described above (including gap open penalty=11 and gap extension penalty=1), a gap of one residue in the alignment would correspond to a value of −(11+(1×1))=−12 assigned to the gap; a gap of three residues would correspond to a value of −(11+(3×1))=−14 assigned to the gap, and so on. This calculation is repeated for each new gap introduced into the alignment. FIGS. 7B and 7C show an example which demonstrates how introduction of a gap into an alignment can result in a higher alignment score, despite the gap penalty. FIG. 7B shows an initial alignment of residues 29-50 of SEQ ID NO:3 (upper, query) and residues 30-50 of SEQ ID NO:32 (lower, subject) made by visual inspection, which results in an initial alignment score of 67. FIG. 7C shows the effect of a one-residue gap in SEQ ID NO:32 on the alignment score; despite the gap penalty of −12, the overall alignment score of the two sequences increases to 88. In this example, the alignment shown in FIG. 7C provides the highest possible alignment score, and is thus the optimal alignment of these two sequences; any other alignment of these two sequences (with or without gaps) would result in a lower alignment score.

It is to be understood that the examples of sequence alignment calculations described above, which use relatively short sequences, are provided for illustrative purposes only; in practice, the alignment parameters employed (BLOSUM62 matrix, gap open penalty=11, and gap extension penalty=1) are generally intended for polypeptide sequences 85 amino acids in length or longer. The NCBI website provides the following alignment parameters for sequences of other lengths (which are suitable for computer-aided as well as manual alignment calculation, using the same procedure as described above). For sequences of 50-85 amino acids in length, optimal parameters are BLOSUM80 matrix (Henikoff and Henikoff, supra), gap open penalty=10, and gap extension penalty=1. For sequences of 35-50 amino acids in length, optimal parameters are PAM70 matrix (Dayhoff, M. O., Schwartz, R. M. & Orcutt, B. C. (1978) "A model of evolutionary change in proteins." In Atlas of Protein Sequence and Structure, vol. 5, suppl. 3, M. O. Dayhoff (ed.), pp. 345-352, Natl. Biomed. Res. Found., Washington, D.C.), gap open penalty=10, and gap extension penalty=1. For sequences of less than 35 amino acids in length, optimal parameters are PAM30 matrix (Dayhoff, M. O., supra), gap open penalty=9, and gap extension penalty=1.

Once the sequences are optimally aligned, the percent identity of the subject sequence relative to the query sequence is calculated by counting the number of positions in the optimal alignment which contain identical residue pairs, divide that by the number of residues in the comparison length (which, unless otherwise specified, is the number of residues in the query sequence), and multiplying the resulting number by 100. Referring back to the examples shown in FIG. 7, in each example the sequence designated as the query sequence is 22 amino acids in length. Referring to the alignment of FIG. 7A, 20 pairs of aligned amino acid residues (shown in boldface) are identical in the optimal alignment of the query sequence (upper) with the subject sequence (lower). Thus, this particular subject sequence has (20/22)×100=91.1% identity to the query sequence; in other words, the subject sequence in the alignment of FIG. 7A has at least 91% amino acid sequence identity to the query sequence. In the alignment shown in FIG. 7C, 18 pairs of amino acid residues (shown in boldface) in the optimal alignment are identical; thus this particular subject sequence has (18/22)×100=81.8% identity to the query sequence; in other words, the subject sequence in the alignment of FIG. 7C has at least 81% amino acid sequence identity to the query sequence.

As applied to polypeptides, the term "substantial identity" (or "substantially identical") typically means that when two amino acid sequences (i.e. a query sequence and a subject sequence) are optimally aligned using the BLASTP algorithm (manually or via computer) using appropriate parameters described above, the subject sequence has at least about 60%, 70%, 75%, 80%, 85%, 90%, 91%, 92%, 93%, 94%, 95%, 96%, 97%, 98%, 99%, or more percent amino acid sequence identity to the query sequence. In some instances, the substantial identity exists over a comparison length of at least about 100 amino acid residues, such as, at least about 110, 120, 125, 130, 135, 140, 145, 150, 155, 156, 157, 158, 159, 160, 161, 162, 163, 164, 165, or 166 amino acid residues.

Similarly, as applied in the context of two nucleic acid sequences, the term substantial identity (or substantially identical) means that when two nucleic acid sequences (i.e. a query and a subject sequence) are optimally aligned using the BLASTN algorithm (manually or via computer) using appropriate parameters described below, the subject sequence has at least about 60%, 70%, 75%, 80%, 85%, 90%, 91%, 92%, 93%, 94%, 95%, 96%, 97%, 98%, 99%, or more percent nucleic acid sequence identity to the query sequence. Parameters used for nucleic acid sequence alignments are: match reward 1, mismatch penalty −3, gap existence penalty 5, gap extension penalty 2 (substitution matrices are not used in the BLASTN algorithm). In some instances, the substantial identity exists over a comparison length of at least about 300 nucleotide residues, such as at least about 330, 360, 375, 390, 405, 420, 435, 450, 465, 480, 483, 486, 489, 492, 495, or 498 nucleotides.

Additional Aspects

Any polypeptide of the invention may be present as part of a larger polypeptide sequence, e.g. a fusion protein, such as occurs upon the addition of one or more domains or subsequences for stabilization or detection or purification of the polypeptide. A polypeptide purification subsequence may include, e.g., an epitope tag, a FLAG tag, a polyhistidine sequence, a GST fusion, or any other detection/purification subsequence or "tag" known in the art. These additional domains or subsequences either have little or no effect on the activity of the polypeptide of the invention, or can be removed by post synthesis processing steps such as by treatment with a protease, inclusion of an intein, or the like.

Any polypeptide of the invention may also comprise one or more modified amino acid. The modified amino acid may be, e.g., a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent. The presence of modified amino acids may be advantageous in, for example, (a) increasing polypeptide serum half-life and/or functional in vivo half-life, (b) reducing polypeptide antigenicity, (c) increasing polypeptide storage stability, or (d) increasing bioavailability, e.g. increasing the $AUC_{sc}$. Amino acid(s) are modified, for example, co-translationally or post-translationally during recombinant production (e.g., N-linked glycosylation at N-X-S/T motifs during expression in mammalian cells) or modified by synthetic means. This aspect is described in more detail in the section herein entitled "INTERFERON-ALPHA CONJUGATES".

The invention also provides a composition comprising at least one polypeptide of the invention, and an excipient or carrier. In one aspect, the composition comprises an isolated or recombinant polypeptide comprising an amino acid sequence which differs in 0-16 amino acid positions (such as in 0, 1, 2, 3, 4, 5, 6, 7, 8, 9, 10, 11, 12, 13, 14, 15, or 16 amino acid positions), from one of SEQ ID NOs:1-15 and SEQ ID NOs:44-104 (such as, for example, one of SEQ ID NO:1, SEQ ID NO:3, SEQ ID NO:8, SEQ ID NO:12, SEQ ID NO:47, or SEQ ID NO:53), plus a carrier or excipient. The composition may be a composition comprising a pharmaceutically acceptable excipient or carrier. Exemplary compositions and excipients and carriers are described below.

Making Polypeptides

Recombinant methods for producing and isolating polypeptides of the invention are described herein. In addition to recombinant production, the polypeptides may be produced by direct peptide synthesis using solid-phase techniques (see, e.g., Stewart et al. (1969) Solid-Phase Peptide Synthesis, WH Freeman Co, San Francisco; Merrifield J. (1963) J Am Chem Soc 85:2149-2154). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. For example, subsequences may be chemically synthesized separately and combined using chemical methods to provide full-length polypeptides or fragments thereof. Alternatively, such sequences may be ordered from any number of companies which specialize in production of polypeptides. Most commonly, polypeptides of the invention may be produced by expressing coding nucleic acids and recovering polypeptides, e.g., as described below.

Methods for producing the polypeptides of the invention are also included. One such method comprises introducing into a population of cells any nucleic acid of the invention described herein, which is operatively linked to a regulatory sequence effective to produce the encoded polypeptide, culturing the cells in a culture medium to express the polypeptide, and isolating the polypeptide from the cells or from the culture medium. An amount of nucleic acid sufficient to facilitate uptake by the cells (transfection) and/or expression of the polypeptide is utilized. The nucleic acid is introduced into such cells by any delivery method described herein, including, e.g., injection, gene gun, passive uptake, etc. The nucleic acid may be part of a vector, such as a recombinant expression vector, including a DNA plasmid vector, or any vector described herein. The nucleic acid or vector comprising a nucleic acid of the invention may be prepared and formulated as described herein, above. Such a nucleic acid or expression vector may be introduced into a population of cells of a mammal in vivo, or selected cells of the mammal (e.g., tumor cells) may be removed from the mammal and the nucleic acid expression vector introduced ex vivo into the population of such cells in an amount sufficient such that uptake and expression of the encoded polypeptide results. Or, a nucleic acid or vector comprising a nucleic acid of the invention is produced using cultured cells in vitro. In one aspect, the method of producing a polypeptide of the invention comprises introducing into a population of cells a recombinant expression vector comprising any nucleic acid of the invention described herein in an amount and formula such that uptake of the vector and expression of the encoded polypeptide will result; administering the expression vector into a mammal by any introduction/delivery format described herein; and isolating the polypeptide from the mammal or from a byproduct of the mammal.

Antibodies

In another aspect of the invention, a polypeptide of the invention (or an antigenic fragment thereof) is used to produce antibodies which have, e.g., diagnostic, therapeutic, or prophylactic uses, e.g., related to the activity, distribution, and expression of polypeptides and fragments thereof. Antibodies to polypeptides of the invention may be generated by methods well known in the art. Such antibodies may include, but are not limited to, polyclonal, monoclonal, chimeric, humanized, single chain, Fab fragments and fragments produced by a Fab expression library. Antibodies, e.g., those that block receptor binding, are especially preferred for therapeutic and/or prophylactic use.

Polypeptides for antibody induction do not require biological activity; however, the polypeptides or peptides should be antigenic. Peptides used to induce specific antibodies may have an amino acid sequence consisting of at least about 10 amino acids, preferably at least about 15 or 20 amino acids or at least about 25 or 30 amino acids. Short stretches of a polypeptide may be fused with another protein, such as keyhole limpet hemocyanin, and antibody produced against the chimeric molecule.

Methods of producing polyclonal and monoclonal antibodies are known to those of skill in the art, and many antibodies are available. See, e.g., Current Protocols in Immunology, John Colligan et al., eds., Vols. I-IV (John Wiley & Sons, Inc., NY, 1991 and 2001 Supplement); and Harlow and Lane (1989) Antibodies: A Laboratory Manual Cold Spring Harbor Press, NY; Stites et al. (eds.) Basic and Clinical Immunology (4th ed.) Lange Medical Publications, Los Altos, Calif., and references cited therein; and Goding (1986) Monoclonal Antibodies: Principles and Practice (2d ed.) Academic Press, New York, N.Y.; and Kohler and Milstein (1975) Nature 256:495-497. Other suitable techniques for antibody preparation include selection of libraries of recombinant antibodies in phage or similar vectors. See, Huse et al. (1989) Science 246:1275-1281; and Ward et al. (1989) Nature 341: 544-546. Specific monoclonal and polyclonal antibodies and antisera will usually bind with a $K_D$ of at least about 0.1 µM, preferably at least about 0.01 µM or better, and most typically and preferably, 0.001 µM or better.

Detailed methods for preparation of chimeric (humanized) antibodies can be found in U.S. Pat. No. 5,482,856. Additional details on humanization and other antibody production and engineering techniques can be found in Borrebaeck (ed.) (1995) Antibody Engineering, $2^{nd}$ Edition Freeman and Company, NY (Borrebaeck); McCafferty et al. (1996) Antibody Engineering, A Practical Approach IRL at Oxford Press, Oxford, England (McCafferty), and Paul (1995) Antibody Engineering Protocols Humana Press, Towata, N.J. (Paul).

In one aspect, this invention provides for fully humanized antibodies against the polypeptides of the invention or fragments thereof. Humanized antibodies are especially desirable in applications where the antibodies are used as therapeutics and/or prophylactics in vivo in human patients. Human antibodies consist of characteristically human immunoglobulin sequences. The human antibodies of this invention can be produced in using a wide variety of methods (see, e.g., Larrick et al., U.S. Pat. No. 5,001,065, and Borrebaeck McCafferty and Paul, supra, for a review). In one aspect, the human antibodies of the present invention are produced initially in trioma cells. Genes encoding the antibodies are then cloned and expressed in other cells, such as nonhuman mammalian cells. The general approach for producing human antibodies by trioma technology is described by Ostberg et al. (1983), Hybridoma 2:361-367, Ostberg, U.S. Pat. No. 4,634,664, and Engelman et al., U.S. Pat. No. 4,634,666. The antibody-producing cell lines obtained by this method are called triomas because they are descended from three cells—two human and one mouse. Triomas have been found to produce antibody more stably than ordinary hybridomas made from human cells.

Other uses contemplated for polypeptides of the invention are provided throughout the specification.

Interferon-Alpha Conjugates

In another aspect, the invention relates to a conjugate comprising a polypeptide exhibiting an interferon-alpha activity which comprises an amino acid sequence of any one of SEQ ID NOs:1-15 and SEQ ID NOs:44-104, and at least one non-polypeptide moiety attached to the polypeptide, such as e.g., 1-6, 1-5, 1-4, 1-3, e.g. 1 or 2 non-polypeptide moieties attached to the polypeptide. It will be understood that the conjugate also exhibits an interferon-alpha activity (such as, antiviral activity, $T_H1$ differentiation activity, and/or antiproliferative activity).

In another aspect, the invention relates to a conjugate comprising a polypeptide exhibiting an interferon-alpha activity, which polypeptide comprises an amino acid sequence that differs from the amino acid sequence of any one of SEQ ID NOs:1-15 and SEQ ID NOs:44-104 (such as, one of SEQ ID NOs:1-15, 47, or 53), in at least one amino acid residue selected from an introduced or removed amino acid residue comprising an attachment group for a non-polypeptide moiety. Examples of amino acid residues to be introduced and/or removed according to this aspect are described in further detail in the following sections. It will be understood that the conjugate itself also exhibits an interferon-alpha activity.

In another aspect the conjugate comprises an amino acid sequence which differs from the amino acid sequence of any of SEQ ID NOs:1-15 and SEQ ID NOs:44-104 (such as, one of SEQ ID NOs:1-15, 47, or 53) in 0-16 amino acid positions (such as in 0, 1, 2, 3, 4, 5, 6, 7, 8, 9, 10, 11, 12, 13, 14, 15, or 16 amino acid positions), e.g. in 0-14 amino acid positions, in 0-12 amino acid positions, in 0-10 amino acid positions, in 0-8 amino acid positions, in 0-6 amino acid positions, in 0-5 amino acid positions, in 0-4 amino acid positions, in 0-3 amino acid positions, in 0-2 amino acid positions, or in 0-1 amino acid positions. In one aspect of the invention, the amino acid residue comprising an attachment group for the non-polypeptide moiety is introduced (e.g., by substitution of an amino acid residue for a different residue which comprises an attachment group for the non-polypeptide moiety, or by insertion of an additional amino acid residue which comprises an attachment group for the non-polypeptide moiety).

The term "conjugate" (or interchangeably "polypeptide conjugate" or "conjugated polypeptide") is intended to indicate a heterogeneous (in the sense of composite) molecule formed by the covalent attachment of one or more polypeptides of the invention to one or more non-polypeptide moieties. The term "covalent attachment" means that the polypeptide and the non-polypeptide moiety are either directly covalently joined to one another, or else are indirectly covalently joined to one another through an intervening moiety or moieties, such as a bridge, spacer, or linkage moiety or moieties. Preferably, a conjugated polypeptide is soluble at relevant concentrations and conditions, i.e. soluble in physiological fluids such as blood. Examples of conjugated polypeptides of the invention include glycosylated and/or PEGylated polypeptides. The term "non-conjugated polypeptide" may be used to refer to the polypeptide part of the conjugated polypeptide.

The term "non-polypeptide moiety" is intended to mean a molecule that is capable of conjugating to an attachment group of the polypeptide. Preferred examples of non-polypeptide moieties include polymer molecules, sugar moieties, lipophilic compounds, or organic derivatizing agents, in particular polymer molecules or sugar moieties. It will be understood that the non-polypeptide moiety is linked to the polypeptide through an attachment group of the polypeptide. Except where the number of non-polypeptide moieties, such as polymer molecule(s), attached to the polypeptide is expressly indicated, every reference to "a non-polypeptide moiety" attached to the polypeptide or otherwise used in the present invention shall be a reference to one or more non-polypeptide moieties attached to the polypeptide.

The term "polymer molecule" is defined as a molecule formed by covalent linkage of two or more monomers, wherein none of the monomers is an amino acid residue. The term "polymer" may be used interchangeably with the term "polymer molecule".

The term "sugar moiety" is intended to indicate a carbohydrate molecule attached by in vivo or in vitro glycosylation, such as N- or O-glycosylation.

An "N-glycosylation site" has the sequence N-X-S/T/C, wherein X is any amino acid residue except proline, N is asparagine and S/T/C is either serine, threonine or cysteine, preferably serine or threonine, and most preferably threonine.

An "O-glycosylation site" comprises the OH-group of a serine or threonine residue.

The term "attachment group" is intended to indicate an amino acid residue group capable of coupling to the relevant non-polypeptide moiety such as a polymer molecule or a sugar moiety. Non-limiting examples of useful attachment groups and some corresponding non-polypeptide moieties are provided in Table 4 below.

TABLE 4

Useful attachment groups and examples of corresponding non-polypeptide moieties

| Attachment group | Amino acid | Examples of non-polypeptide moiety | Conjugation method/activated PEG | Reference |
|---|---|---|---|---|
| —NH$_2$ | N-terminus, Lys | Polymer, e.g. PEG | mPEG-SPA<br>mPEG2-NHS<br>mPEG2-butryALD | Nektar Inc. 2003 Catalog |
| —COOH | C-terminus, Asp, Glu | Polymer, e.g. PEG<br>Sugar moiety | mPEG-Hz<br>In vitro coupling | Nektar Inc. 2003 Catalog |
| —SH | Cys | Polymer, e.g. PEG, Sugar moiety | mPEG-VS<br>mPEG2-MAL<br>In vitro coupling | Nektar Inc. 2003 Catalog;<br>Delgado et al,<br>Critical Reviews in Therapeutic Drug Carrier Systems 9(3,4):249-304 (1992) |
| —OH | Ser, Thr, OH—, Lys | Sugar moiety | In vivo O-linked glycosylation | |
| —CONH$_2$ | Asn as part of an N-glycosylation site | Sugar moiety | In vivo glycosylation | |
| Aromatic residue | Phe, Tyr, Trp | Sugar moiety | In vitro coupling | |
| —CONH$_2$ | Gln | Sugar moiety | In vitro coupling | Yan and Wold, Biochemistry, 1984, Jul 31; 23(16): 3759-65 |
| Aldehyde Ketone | Oxidized carbohydrate | Polymer, e.g. PEG, PEG-hydrazide | PEGylation | Andresz et al., 1978, Makromol. Chem. 179:301; WO 92/16555, WO 00/23114 |
| Guanidino | Arg | Sugar moiety | In vitro coupling | Lundblad and Noyes, Chemical Reagents for Protein |

TABLE 4-continued

Useful attachment groups and examples of corresponding non-polypeptide moieties

| Attachment group | Amino acid | Examples of non-polypeptide moiety | Conjugation method/activated PEG | Reference |
| --- | --- | --- | --- | --- |
| Imidazole ring | His | Sugar moiety | In vitro coupling | Modification, CRC Press Inc. Boca Raton, Fl As for guanidine |

For in vivo N-glycosylation, the term "attachment group" is used in an unconventional way to indicate the amino acid residues constituting an N-glycosylation site (with the sequence N-X-S/T/C, wherein X is any amino acid residue except proline, N is asparagine and S/T/C is either serine, threonine or cysteine, preferably serine or threonine, and most preferably threonine). Although the asparagine residue of the N-glycosylation site is the one to which the sugar moiety is attached during glycosylation, such attachment cannot be achieved unless the other amino acid residues of the N-glycosylation site is present. Accordingly, when the non-polypeptide moiety is a sugar moiety and the conjugation is to be achieved by N-glycosylation, the term "amino acid residue comprising an attachment group for the non-polypeptide moiety" as used in connection with alterations of the amino acid sequence of the polypeptide of the invention is to be understood as one, two or all of the amino acid residues constituting an N-glycosylation site is/are to be altered in such a manner that either a functional N-glycosylation site is introduced into the amino acid sequence, removed from said sequence or a functional N-glycosylation site is retained in the amino acid sequence (e.g. by substituting a serine residue, which already constitutes part of an N-glycosylation site, with a threonine residue and vice versa).

The term "introduce" (i.e., an "introduced" amino acid residue, "introduction" of an amino acid residue) is primarily intended to mean substitution of an existing amino acid residue for another amino acid residue, but may also mean insertion of an additional amino acid residue.

The term "remove" (i.e., a "removed" amino acid residue, "removal" of an amino acid residue) is primarily intended to mean substitution of the amino acid residue to be removed for another amino acid residue, but may also mean deletion (without substitution) of the amino acid residue to be removed.

The term "amino acid residue comprising an attachment group for the non-polypeptide moiety" is intended to indicate that the amino acid residue is one to which the non-polypeptide moiety binds (in the case of an introduced amino acid residue) or would have bound (in the case of a removed amino acid residue).

The term "functional in vivo half-life" is used in its normal meaning, i.e. the time at which 50% of the biological activity of the polypeptide is still present in the body/target organ, or the time at which the activity of the polypeptide is 50% of the initial value. The functional in vivo half-life may be determined in an experimental animal, such as rat, mice, rabbit, dog or monkey. Preferably, the functional in vivo half half-life is determined in a non-human primate, such as a monkey. Furthermore, the functional in vivo half-life may be determined for a sample that has been administered intravenously or subcutaneously.

As an alternative to determining functional in vivo half-life, "serum half-life" may be determined, i.e. the time at which 50% of the polypeptide circulates in the plasma or bloodstream prior to being cleared. Determination of serum half-life is often more simple than determining the functional in vivo half-life and the magnitude of serum half-life is usually a good indication of the magnitude of functional in vivo half-life. Alternatively terms to serum half-life include "plasma half-life", "circulating half-life", "serum clearance", "plasma clearance" and "clearance half-life". The serum half-life may be determined as described above in connection with determination of functional in vivo half-life.

The term "serum" is used in its normal meaning, i.e. as blood plasma without fibrinogen and other clotting factors.

The term "increased" as used about the functional in vivo half-life or serum half-life is used to indicate that the relevant half-life of the conjugate of the invention is statistically significantly increased relative to that of a reference molecule, such as a wild-type interferon-alpha, e.g., a human interferon-alpha, such as one of SEQ ID NO:31-SEQ ID NO:42 (or other huIFN-alpha sequences as described herein and/or in Allen G. and Diaz M. O. (1996), supra), or the corresponding non-conjugated polypeptide. Thus, interesting conjugates of the invention include those which have an increased functional in vivo half-life or an increased serum half-life as compared to a reference molecule mentioned above.

The term "$AUC_{sc}$" or "Area Under the Curve when administered subcutaneously" is used in its normal meaning, i.e. as the area under the interferon-alpha-activity-in-serum vs. time curve, where the conjugated molecule has been administered subcutaneously to an experimental animal. Once the experimental interferon-alpha activity time points have been determined, the $AUC_{sc}$ may conveniently be calculated by a computer program, such as GraphPad Prism 3.01.

The term "increased" as used about the $AUC_{sc}$ is used to indicate that the Area Under the Curve for a conjugate of the invention, when administered subcutaneously, is statistically significantly increased relative to that of a reference molecule, such as wild-type interferon-alpha, e.g., a human interferon-alpha, such as one of SEQ ID NO:31-SEQ ID NO:42 (or other huIFN-alpha sequences as described herein and/or in Allen G. and Diaz M. O. (1996), supra), or the corresponding non-conjugated polypeptide, when determined under comparable conditions. Evidently, the same amount of interferon-alpha activity should be administered for the conjugate of the invention and the reference molecule. Consequently, in order to make direct comparisons between different interferon-alpha molecules, the $AUC_{sc}$ values should typically be normalized, i.e. be expressed as $AUC_{sc}$/dose administered.

The term "$T_{max,sc}$" is used about the time point in the interferon-alpha-activity-in-serum vs. time curve where the highest interferon-alpha activity in serum is observed.

It will be understood that while the examples and modifications to the parent polypeptide are generally provided herein in regards to the sequence SEQ ID NO:1, the disclosed modifications may also be made in equivalent amino acid positions of any of the other polypeptides of the invention (including SEQ ID NOs:2-15 and 44-104 and variants thereof) described above.

By removing and/or introducing amino acid residues comprising an attachment group for the non-polypeptide moiety it is possible to specifically adapt the polypeptide so as to make the molecule more susceptible to conjugation to the non-polypeptide moiety of choice, to optimize the conjugation pattern (e.g. to ensure an optimal distribution of non-polypeptide moieties on the surface of the interferon-alpha molecule and thereby, e.g., effectively shield epitopes and other surface parts of the polypeptide without significantly impairing the function thereof). For instance, by introduction of attachment groups, the interferon-alpha polypeptide is altered in the content of the specific amino acid residues to which the relevant non-polypeptide moiety binds, whereby a more efficient, specific and/or extensive conjugation is achieved. By removal of one or more attachment groups it is possible to avoid conjugation to the non-polypeptide moiety in parts of the polypeptide in which such conjugation is disadvantageous, e.g. to an amino acid residue located at or near a functional site of the polypeptide (since conjugation at such a site may result in inactivation or reduced interferon-alpha activity of the resulting conjugate due to impaired receptor recognition). Further, it may be advantageous to remove an attachment group located close to another attachment group.

It will be understood that the amino acid residue comprising an attachment group for a non-polypeptide moiety, whether it be removed or introduced, is selected on the basis of the nature of the non-polypeptide moiety and, in some instances, on the basis of the conjugation method to be used. For instance, when the non-polypeptide moiety is a polymer molecule, such as a polyethylene glycol or polyalkylene oxide derived molecule, amino acid residues capable of functioning as an attachment group may be selected from the group consisting of cysteine, lysine (and/or the N-terminal amino group of the polypeptide), aspartic acid, glutamic acid, histidine and arginine. When the non-polypeptide moiety is a sugar moiety, the attachment group is an in vivo or in vitro N- or O-glycosylation site, preferably an N-glycosylation site.

In some instances, when an attachment group for a non-polypeptide moiety is to be introduced into or removed from the interferon-alpha polypeptide, the position of the interferon-alpha polypeptide to be modified may be conveniently selected as follows:

The position to be modified may be located at the surface of the interferon-alpha polypeptide, such as a position occupied by an amino acid residue which has more than 25% of its side chain exposed to the solvent, such as more than 50% of its side chain exposed to the solvent. Such positions have been identified on the basis of an analysis of a 3D structure of the human interferon-alpha 2a molecule as described in the "Materials and Methods" section herein.

Alternatively or additionally, the position to be modified may be identified on the basis of an analysis of an interferon-alpha protein sequence family (such as shown in the alignments depicted in FIGS. 2 and 4). For the purposes of the following example, SEQ ID NO:1 as shown in the top line of the alignment of FIG. 2 may be considered the parent interferon-alpha to be modified, and the human interferon-alpha sequences in the rest of the alignment are considered the other members of the family. For example, the position to be modified in the parent sequence may be one which, in one or more members of the family other than the parent interferon-alpha, is (a) occupied by an amino acid residue comprising the relevant attachment group (when such amino acid residue is to be introduced into the parent sequence) or (b) which in the parent interferon-alpha, but not in one or more other members of the family, is occupied by an amino acid residue comprising the relevant attachment group (when such amino acid residue is to be removed from the parent sequence).

In order to determine an optimal distribution of attachment groups, the distance between amino acid residues located at the surface of the interferon-alpha molecule was calculated on the basis of a 3D structure of an interferon-alpha polypeptide. More specifically, the distance between the CB's of the amino acid residues comprising such attachment groups, or the distance between the functional group (NZ for lysine, CG for aspartic acid, CD for glutamic acid, SG for cysteine) of one and the CB of another amino acid residue comprising an attachment group were determined. In case of glycine, CA was used instead of CB. In the interferon-α polypeptide part of a conjugate of the invention, any of said distances may be more than 8 Å, such as more than 10 Å in order to avoid or reduce heterogeneous conjugation and to provide a uniform distribution of attachment groups, e.g. with the aim of epitope shielding.

Furthermore, in the interferon-alpha polypeptide part of a conjugate of the invention, in some instances attachment groups located at or near the receptor binding sites of interferon-alpha are removed, such as by substitution of the amino acid residue comprising such group. In some instances, amino acid residues comprising an attachment group for a non-polypeptide moiety, such as cysteine or lysine, are often not introduced at or near the receptor binding site of the interferon alpha molecule.

Another approach for modifying an interferon-alpha polypeptide is to shield and thereby modify or destroy or otherwise inactivate an epitope present in the parent interferon-alpha, by conjugation to a non-polypeptide moiety. Epitopes of interferon-alpha polypeptides may be identified by use of methods known in the art, also known as epitope mapping, see e.g. Romagnoli et al., *J. Biol Chem.,* 1999, 380(5):553-9, DeLisser H M, *Methods Mol Biol,* 1999, 96:11-20, Van de Water et al., *Clin Immunol Immunopathol,* 1997, 85(3):229-35, Saint-Remy J M, *Toxicology,* 1997, 119 (1):77-81, and Lane D P and Stephen C W, *Curr Opin Immunol,* 1993, 5(2):268-71. One method is to establish a phage display library expressing random oligopeptides of, e.g., 9 amino acid residues. IgG1 antibodies from specific antisera towards human interferon-alpha are purified by immunoprecipitation and the reactive phages are identified by immunoblotting. By sequencing the DNA of the purified reactive phages, the sequence of the oligopeptide can be determined followed by localization of the sequence on the 3D-structure of the interferon-alpha. Alternatively, epitopes can be identified according to the method described in U.S. Pat. No. 5,041,376. The thereby identified region on the structure constitutes an epitope that then can be selected as a target region for introduction of an attachment group for the non-polypeptide moiety. Preferably, at least one epitope, such as two, three or four epitopes of interferon-alpha are shielded by a non-polypeptide moiety according to the present invention. Accordingly, in one aspect, the conjugate of the invention has at least one shielded epitope as compared to a wild type human interferon-alpha, including any commercially available interferon-alpha. This may be done by introduction of an attachment group for a non-polypeptide moiety into a position located in the vicinity of (i.e. within 4 amino acid residues in the primary sequence or within about 10 Å in the tertiary sequence) of a given epitope. The 10 Å distance is measured between CB's (CA's in case of glycine). Such specific introductions are described in the following sections.

In case of removal of an attachment group, the relevant amino acid residue comprising such group and occupying a position as defined above may be substituted with a different amino acid residue that does not comprise an attachment group for the non-polypeptide moiety in question, or may be deleted. Removal of an N-glycosylation group, may also be accomplished by insertion or removal of an amino acid reside within the motif N-X-S/T/C.

In case of introduction of an attachment group, an amino acid residue comprising such group is introduced into the position, such as by substitution of the amino acid residue occupying such position.

The exact number of attachment groups available for conjugation and present in the interferon-alpha polypeptide is dependent on the effect desired to be achieved by conjugation. The effect to be obtained is, e.g., dependent on the nature and degree of conjugation (e.g. the identity of the non-polypeptide moiety, the number of non-polypeptide moieties desirable or possible to conjugate to the polypeptide, where they should be conjugated or where conjugation should be avoided, etc.). For instance, if reduced immunogenicity is desired, the number (and location of) attachment groups should be sufficient to shield most or all epitopes. This is normally obtained when a greater proportion of the interferon-alpha polypeptide is shielded. Effective shielding of epitopes is normally achieved when the total number of attachment groups available for conjugation is in the range of 1-6 attachment groups, e.g., 1-5, such as in the range of 1-3, such as 1, 2, or 3 attachment groups.

Functional in vivo half-life is i.a. dependent on the molecular weight of the conjugate, and the number of attachment groups needed for providing increased half-life thus depends on the molecular weight of the non-polypeptide moiety in question. Some such conjugates comprise 1-6, e.g., 1-5, such as 1-3, e.g. 1, 2, or 3 non-polypeptide moieties each having a MW of about 2-40 kDa, such as about 2 kDa, about 5 kDa, about 12 kDa, about 15 kDa, about 20 kDa, about 30 kDa, or about 40 kDa.

In the conjugate of the invention, some, most, or substantially all conjugatable attachment groups are occupied by the relevant non-polypeptide moiety.

The conjugate of the invention may exhibit one or more of the following improved properties:

For example, the conjugate may exhibit a reduced immunogenicity as compared to a human interferon-alpha (such as any of the polypeptides defined herein as SEQ ID NO:31-42, SEQ ID NO:32+R23K, or any other huIFN-alpha described herein and/or in Allen G. and Diaz M. O. (1996), supra) or as compared to the corresponding non-conjugated polypeptide, e.g. a reduction of at least 10%, such as a reduction of at least of 25%, such as a reduction of at least of 50%, e.g. a reduction of at least 75% compared to the non-conjugated polypeptide or compared to a human interferon-alpha.

In another aspect the conjugate may exhibit a reduced reaction or no reaction with neutralizing antibodies from patients treated with a human interferon-alpha (such as any of the polypeptides defined herein as SEQ ID NO:31-42, SEQ ID NO:32+R23K, or any other huIFN-alpha described herein and/or in Allen G. and Diaz M. O. (1996), supra) or as compared to the corresponding non-conjugated polypeptide, e.g. a reduction of neutralisation of at least 10%, such as at least of 25%, such as of at least 50%, e.g., at least 75%.

In another aspect of the invention the conjugate may exhibit an increased functional in vivo half-life and/or increased serum half-life as compared to a reference molecule such as a human interferon-alpha (e.g. any of the polypeptides defined herein as SEQ ID NO:31-42, SEQ ID NO:32+R23K, or any other huIFN-alpha described herein and/or in Allen G. and Diaz M. O. (1996), supra) or as compared to the corresponding non-conjugated polypeptide. Particular preferred conjugates are such conjugates where the ratio between the functional in vivo half-life (or serum half-life) of said conjugate and the functional in vivo half-life (or serum half-life) of said reference molecule is at least 1.25, such as at least 1.50, such as at least 1.75, such as at least 2, such as at least 3, such as at least 4, such as at least 5, such as at least 6, such as at least 7, such as at least 8. As mentioned above, the half-life is conveniently determined in an experimental animal, such as rat or monkey, and may be based on intravenously or subcutaneously administration.

In a further aspect the conjugate may exhibit an increased bioavailability as compared to a reference molecule such as a human interferon-alpha (e.g. any of the polypeptides defined herein as SEQ ID NO:31-42, SEQ ID NO:32+R23K, or any other huIFN-alpha described herein and/or in Allen G. and Diaz M. O. (1996), supra) or the corresponding non-conjugated polypeptide. For example, the conjugate may exhibit an increased $AUC_{sc}$ as compared to a reference molecule such as a human interferon-alpha or the corresponding non-conjugated polypeptide. Thus, exemplary conjugates are such conjugates where the ratio between the $AUC_{sc}$ of said conjugate and the $AUC_{sc}$ of said reference molecule is at least 1.25, such as at least 1.5, such as at least 2, such as at least 3, such as at least 4, such as at least 5 or at least 6, such as at least 7, such as at least 8, such as at least 9 or at least 10, such as at least 12, such as at least 14, e.g. at least 16, at least 18 or at least 20 when administered subcutaneously, in particular when administered subcutaneously in an experimental animal such as rat or monkey. Analogously, some conjugates of the invention are such conjugates wherein the ratio between $T_{max}$ for said conjugate and $T_{max}$ for said reference molecule, such as a human interferon-alpha or the corresponding non-conjugated polypeptide, is at least 1.2, such as at least 1.4, e.g. at least 1.6, such as at least 1.8, such as at least 2, e.g. at least 2.5, such as at least 3, such as at least 4, e.g. at least 5, such as at least 6, such as at least 7, e.g. at least 8, such as at least 9, such as at least 10, when administered subcutaneously, in particular when administered subcutaneously in an experimental animal such as rat or monkey.

In some instances, the magnitude of the antiviral activity of a conjugate of the invention may be reduced (e.g. by at least about 75%, at least about 50%, at least about 25%, at least about 10%) or increased (e.g. by at least about 10%) or is about equal (e.g. within about +/−10% or about +/−5%) to that of a human interferon-alpha (e.g. any of the polypeptides identified herein as SEQ ID NO:31-42, SEQ ID NO:32+R23K, or any other huIFN-alpha described herein and/or in Allen G. and Diaz M. O. (1996), supra) or to that of the corresponding non-conjugated polypeptide. In some instances the degree of antiviral activity as compared to antiproliferative activity of a conjugate of the invention may vary, and thus be higher, lower or about equal to that of a human interferon-alpha or to that of the corresponding non-conjugated polypeptide.

Conjugate of the Invention where the Non-Polypeptide Moiety Binds to a Cysteine Residue In another aspect, the invention relates to a conjugate exhibiting an interferon-alpha activity and comprising at least one non-polypeptide moiety conjugated to at least one cysteine residue of an interferon-alpha, the amino acid sequence of which differs in 0-16 amino acid positions from that of a parent interferon-alpha polypeptide, such as an interferon-alpha polypeptide comprising the amino acid sequence of any of SEQ ID NOs:1-15 and 44-104 (such as, one of SEQ ID NO:1, SEQ ID NO:3, SEQ ID NO:8, SEQ ID NO:12, SEQ ID NO:47 or SEQ ID NO:53), in that at least one cysteine residue has been introduced, such as by substitution or insertion, into a position that is occupied in the parent interferon-alpha by an amino acid residue that is exposed to the surface of the molecule, preferably one that has at least 25%, such as at least 50% of its side chain exposed to the surface. Typically, the conjugate comprises an amino acid sequence which differs from the amino acid sequence of any one of, e.g., SEQ ID NOs:1-15, 47 or 53, in 1-16 amino acid positions (such as in 1, 2, 3, 4, 5, 6, 7, 8, 9, 10, 11, 12, 13, 14, 15, or 16 amino acid positions), e.g. in 1-14 amino acid positions, in 1-12 amino acid positions, in 1-10 amino acid positions, in 1-8 amino acid positions, in 1-6 amino acid positions, in 1-5 amino acid positions, in 1-4 amino acid positions, in 1-3 amino acid positions or in 1-2 amino acid positions.

Some conjugates of the invention comprise a polypeptide sequence comprising one or more of the following substitutions, relative to SEQ ID NO:1, which introduces a cysteine residue into a position which is predicted to be exposed at the surface of the molecule with more than a 25% fractional ASA: D2C, L3C, P4C, Q5C, T6C, H7C, S8C, L9C, G10C, R12C, R13C, M16C, A19C, Q20C, R22C, R23C, I24C, S25C, L26C, F27C, S28C, L30C, K31C, R33C, H34C, D35C, R37C, Q40C, E41C, E42C, D44C, N46C, H47C, Q49C, K50C, V51C, Q52C, E59C, Q62C, Q63C, N66C, S69C, T70C, K71C, N72C, S74C, A75C, D78C, E79C, T80C, L81C, E83C, K84C, I87C, F90C, Q91C, N94C, D95C, E97C, A98C, V100C, M101C, Q102C, E103C, V104C, G105C, E107C, E108C, T109C, P110C, L111C, M112C, N113C, V114C, D115C, L118C, R121C, K122C, Q125C, R126C, T128C, L129C, T132C, K133C, K134C, K135C, Y136C, S137C, P138C, A146C, M149C, R150C, S153C, F154C, N157C, Q159C, K160C, R161C, L162C, R163C, R164C, K165C and E166C, said amino acid residue positions relative to SEQ ID NO:1. In some instances, among the above-mentioned positions, one or more of the amino acid residues at positions 47, 51 and 133 are not substituted with cysteine.

For example, some such conjugates of the invention comprise a polypeptide sequence comprising one or more of the following substitutions, relative to SEQ ID NO:1, which introduces a cysteine residue into a position which is predicted to be exposed at the surface of the molecule with more than a 50% fractional ASA: D2C, L3C, P4C, Q5C, T6C, H7C, S8C, L9C, R12C, R13C, M16C, A19C, S25C, F27C, S28C, K31C, R33C, H34C, D35C, R37C, E41C, D44C, N46C, H47C, Q49C, K50C, N66C, K71C, A75C, D78C, E79C, T80C, E83C, K84C, I87C, F90C, Q91C, N94C, D95C, M101C, Q102C, E103C, G105C, E107C, E108C, T109C, P110C, L111C, V114C, D115C, L118C, R121C, K122C, Q125C, R126C, L129C, T132C, K133C, K135C, P138C, R150C, K160C, L162C, R163C, R164C, K165C and E166C, said amino acid residue positions relative to SEQ ID NO:1. In some instances, one or both of the amino acid residues at positions 47 and 133 are not are not substituted with cysteine.

As indicated above, in some instances it may be preferable to introduce cysteine residues outside of potential receptor binding sites of interferon-alpha, i.e., outside of about positions 29-40, 79-96, and 124-141, position numbering relative to SEQ ID NO:1. Thus, in some instances the one or more cysteine substitutions are selected from the group consisting of D2C, L3C, P4C, Q5C, T6C, H7C, S8C, L9C, G10C, R12C, R13C, M16C, A19C, Q20C, R22C, R23C, I24C, S25C, L26C, F27C, S28C, E41C, E42C, D44C, N46C, H47C, Q49C, K50C, V51C, Q52C, E59C, Q62C, Q63C, N66C, S69C, T70C, K71C, N72C, S74C, A75C, E97C, A98C, V100C, M101C, Q102C, E103C, V104C, G105C, E107C, E108C, T109C, P110C, L111C, M112C, N113C, V114C, D115C, L118C, R121C, K122C, A146C, M149C, R150C, S153C, F154C, N157C, Q159C, K160C, R161C, L162C, R163C, R164C, K165C and E166C (positions which are predicted to be exposed at the surface of the molecule with more than a 25% fractional ASA and are not part of the putative receptor binding sites), relative to SEQ ID NO:1. In some instances, one or both of positions 47 and 51 are not substituted with cysteine.

In other aspects the cysteine substitution is selected from the group consisting of: D2C, L3C, P4C, Q5C, T6C, H7C, S8C, L9C, R12C, R13C, M16C, A19C, S25C, F27C, S28C, E41C, D44C, N46C, H47C, Q49C, K50C, N66C, K71C, A75C, M101C, Q102C, E103C, G105C, E107C, E108C, T109C, P110C, L111C, V114C, D115C, L118C, R121C, K122C, R150C, K160C, L162C, R163C, R164C, K165C and E166C (positions which are predicted to be exposed at the surface of the molecule with more than a 50% fractional ASA and are not part of the putative receptor binding sites), relative to SEQ ID NO:1. In some instances, position 47 is not substituted with a cysteine.

Some such conjugates of the invention comprise a polypeptide sequence containing one or more of the substitutions S25C, S28C, L30C, K31C, N46C, K71C, S74C, A75C, E79C, E107C, E108C, T132C, K133C, P138C, and K135C, relative to SEQ ID NO:1.

In another aspect, the one or more cysteine residue is introduced at or near the C-terminus either by substitution (for example, Q159C, K160C, R161C, L162C, R163C, R164C, K165C or E166C, relative to SEQ ID NO: 1) or by insertion (for example, E166EC, also referred to herein as 167C). It will be understood that cysteine residues may also be introduced, either by substitution or by insertion, in C-terminally truncated fragments of the interferon-alpha molecules described herein.

In some instances, only a single cysteine residue is introduced in order to avoid formation of disulfide bridges between two or more introduced cysteine residues.

In interferon alphas, disulfide bonds are formed between cysteines at positions 1/99 and 29/139. The disulfide bond 29/139 is essential for biological activity, while the 1/99 bond can be reduced without significantly affecting biological activity (Beilharz M. W. et al. (1986) J. Interferon Res. 6(6): 677-685). Thus, in another aspect of the invention one of C1 or C99 is removed, preferably by substitution, e.g. C1S or C99S, thereby leaving the other cysteine residue available for conjugation to a non-polypeptide moiety.

Non-polypeptide moieties contemplated in this aspect of the invention include polymer molecules, such as any of the molecules mentioned in the section entitled "Conjugation to a polymer molecule", such as PEG or mPEG. The conjugation between the cysteine-containing polypeptide and the polymer molecule may be achieved in any suitable manner, e.g. as described in the section entitled "Conjugation to a polymer molecule", e.g. in using a one step method or in the stepwise manner referred to in said section. An exemplary method for PEGylating the interferon-alpha polypeptide is to covalently attach PEG to cysteine residues using cysteine-reactive PEGs. A number of highly specific, cysteine-reactive PEGs with different groups (e.g. orthopyridyl-disulfide (OPSS), maleimide (MAL) and vinylsulfone (VS)) and different size linear or branched PEGs (e.g., 2-40 kDa, such as 2 kDa, 5 kDa, 12 kDa, 15 kDa, 20 kDa, 30 kDa, or 40 kDa) are commercially available, e.g. from Nektar Therapeutics Inc., Huntsville, Ala., USA, or SunBio, Anyang City, South Korea.

It is to be understood that while the examples of modifications to the parent polypeptide are generally provided herein relative to the sequence SEQ ID NO:1 (or relative to some other specified sequence), the disclosed modifications may also be made in equivalent amino acid positions of any of the other polypeptides of the invention (including SEQ ID NOs: 2-15 and SEQ ID NOs:44-104 and variants thereof) described herein. Thus, as an example, the substitution H47C relative to SEQ ID NO:1 is understood to correspond to Q47C in SEQ ID NO:5, and so on.

Conjugate of the Invention where the Non-Polypeptide Moiety Binds to a Lysine Residue In another aspect, the invention relates to a conjugate exhibiting an interferon-alpha activity and comprising at least one non-polypeptide moiety conjugated to at least one lysine residue, and/or to the N-terminal amino group, of an interferon-alpha polypeptide comprising a sequence selected from SEQ ID NOs:1-15 and 44-104, or comprising a sequence which differs from any of SEQ ID NOs:1-15 and 44-104 (such as, one of SEQ ID NO:1, SEQ ID NO:3, SEQ ID NO:8, SEQ ID NO:12, SEQ ID NO:47 or SEQ ID NO:53), in 0-16 amino acid positions (such as in 0, 1, 2, 3, 4, 5, 6, 7, 8, 9, 10, 11, 12, 13, 14, 15, or 16 amino acid positions), e.g. in 0-14 amino acid positions, in 0-12 amino acid positions, in 0-10 amino acid positions, in 0-8 amino acid positions, in 0-6 amino acid positions, in 0-5 amino acid positions, in 0-4 amino acid positions, in 0-3 amino acid positions, in 0-2 amino acid positions or in 0-1 amino acid position. Some conjugates according to this aspect comprise at least one removed lysine residue and/or at least one removed histidine residue, and/or at least one introduced lysine residue.

Some conjugates of the invention comprise a polypeptide sequence comprising a substitution of an amino acid residue for a different amino acid residue, or a deletion of an amino acid residue, which removes one or more lysines, e.g., K31, K50, K71, K84, K122, K133, K134, K135, K160, and/or K165 (relative to SEQ ID NO:1) from any polypeptide of the invention such as, for example, one of SEQ ID NO:1, SEQ ID NO:3, SEQ ID NO:8, SEQ ID NO:12, SEQ ID NO:47 or SEQ ID NO:53. The one or more lysine residue(s) to be removed may be substituted with any other amino acid, may be substituted with an Arg (R) or Gln (Q), or may be deleted. Some such conjugates comprise the substitutions K31R+K122R; K31R+K133R; K122R+K133R; or K31R+K122R+K133R. Other exemplary substitutions include K71E; K84E; K133E/G; and K160E.

In instances where amine-reactive conjugation chemistries are employed, it may be advantageous to avoid or to minimize the potential for conjugation to histidine residues. Therefore, some conjugates of the invention comprise a polypeptide sequence comprising a substitution or a deletion which removes one or more histidines, e.g., H7, H11, H34, and/or H47 (relative to SEQ ID NO:1) from any polypeptide sequence of the invention such as, for example, one of SEQ ID NO:1, SEQ ID NO:3, SEQ ID NO:8, SEQ ID NO:12, SEQ ID NO:47 or SEQ ID NO:53. The one or more histidine residue(s) to be removed may be substituted with any other amino acid, may be substituted with an Arg (R) or Gln (Q), or may be deleted. Some such conjugates comprise the substitutions H34Q; H47Q; or H34Q+H47Q.

Alternatively, or in addition, some conjugates of the invention comprise a polypeptide sequence comprising a modification which introduces a lysine into a position that is occupied in the parent sequence (e.g., one of SEQ ID NOs:1-15, 47, or 53) by an amino acid residue that is exposed to the surface of the molecule, e.g., one that has at least 25%, such as at least 50% of its side chain exposed to the surface. Some such conjugates comprise a polypeptide sequence comprising one or more of the following substitutions, relative to SEQ ID NO:1, which introduces a lysine residue into a position which is predicted to be exposed at the surface of the molecule with more than a 25% fractional ASA: D2K, L3K, P4K, Q5K, T6K, H7K, S8K, L9K, G10K, R12K, R13K, M16K, A19K, Q20K, R22K, R23K, I24K, S25K, L26K, F27K, S28K, L30K, R33K, H34K, D35K, R37K, Q40K, E41K, E42K, D44K, N46K, H47K, Q49K, V51K, Q52K, E59K, Q62K, Q63K, N66K, S69K, T70K, N72K, S74K, A75K, D78K, E79K, T80K, L81K, E83K, I87K, F90K, Q91K, N94K, D95K, E97K, A98K, V100K, M101K, Q102K, E103K, V104K, G105K, E107K, E108K, T109K, P110K, L111K, M112K, N113K, V114K, D115K, L118K, R121K, Q125K, R126K, T128K, L129K, T132K, Y136K, S137K, P138K, A146K, M149K, R150K, S153K, F154K, N157K, Q159K, R161K, L162K, R163K, R164K, and E166K, said amino acid residue positions relative to SEQ ID NO:1. In some instances, among the above-mentioned positions, one or more of the amino acid residues at positions 47, 51, 52, and 154 are not substituted with lysine.

Some such conjugates of the invention comprise a polypeptide sequence comprising one or more of the following substitutions, relative to SEQ ID NO:1, which introduces a lysine residue into a position which is predicted to be exposed at the surface of the molecule with more than a 50% fractional ASA: D2K, L3K, P4K, Q5K, T6K, H7K, S8K, L9K, R12K, R13K, M16K, A19K, S25K, F27K, S28K, R33K, H34K, D35K, R37K, E41K, D44K, N46K, H47K, Q49K, N66K, A75K, D78K, E79K, T80K, E83K, I87K, F90K, Q91K, N94K, D95K, M101K, Q102K, E103K, G105K, E107K, E108K, T109K, P110K, L111K, V114K, D115K, L118K, R121K, Q125K, R126K, L129K, T132K, P138K, R150K, L162K, R163K, R164K and E166K, said amino acid residue positions relative to SEQ ID NO:1. In some instances, among the above-mentioned positions, positions 47 is not substituted with lysine.

As indicated above, in some instances it may be preferable to introduce lysine residues outside of potential receptor binding sites of interferon-alpha, i.e., outside of about positions 29-40, 79-96, and 124-141, position numbering relative to SEQ ID NO:1. Thus, in some instances the one or more lysine substitutions are selected from the group consisting of D2K, L3K, P4K, Q5K, T6K, H7K, S8K, L9K, G10K, R12K, R13K, M16K, A19K, Q20K, R22K, R23K, I24K, S25K, L26K, F27K, S28K, E41K, E42K, D44K, N46K, H47K, Q49K, V51K, Q52K, E59K, Q62K, Q63K, N66K, S69K, T70K, N72K, S74K, A75K, E97K, A98K, V100K, M101K, Q102K, E103K, V104K, G105K, E107K, E108K, T109K, P110K, L111K, M112K, N113K, V114K, D115K, L118K, R121K, A146K, M149K, R150K, S153K, F154K, N157K, Q159K, R161K, L162K, R163K, R164K, and E166K (residues having more than 25% of the side chain exposed to the surface and not forming part of the putative receptor binding sites), relative to SEQ ID NO:1. In some instances, one or more of positions 47, 51, and 154 are not substituted with lysine.

In some instances the one or more lysine substitutions are selected from the group consisting of: D2K, L3K, P4K, Q5K, T6K, H7K, S8K, L9K, R12K, R13K, M16K, A19K, S25K, F27K, S28K, E41K, D44K, N46K, H47K, Q49K, N66K, A75K, M101K, Q102K, E103K, G105K, E107K, E108K, T109K, P110K, L111K, V114K, D115K, L118K, R121K, R150K, L162K, R163K, R164K and E166K (residues having more than 50% of the side chain exposed to the surface an not forming part of the putative receptor binding sites), relative to SEQ ID NO:1. In some instances, position 47 is not substituted with a lysine.

Non-polypeptide moieties contemplated for this aspect of the invention include polymer molecules, such as any of the molecules mentioned in the section entitled "Conjugation to a polymer molecule", such as PEG or mPEG. The conjugation between the lysine-containing polypeptide and the polymer molecule may be achieved in any suitable manner, e.g. as described in the section entitled "Conjugation to a polymer molecule", e.g. in using a one step method or in the stepwise manner referred to in said section. An exemplary method for PEGylating the interferon-alpha polypeptide is to covalently attach PEG to lysine residues using lysine-reactive PEGs. A number of highly specific, lysine-reactive PEGs (such as for example, succinimidyl propionate (SPA), succinimidyl butanoate (SBA), N-hydroxylsuccinimide (NHS), and aldehyde (e.g., ButyrALD)) and different size linear or branched PEGs (e.g., 2-40 kDa, such as 2 kDa, 5 kDa, 12 kDa, 15 kDa, 20 kDa, 30 kDa, or 40 kDa,) are commercially available, e.g. from Nektar Therapeutics Inc., Huntsville, Ala., USA, or SunBio, Anyang City, South Korea.

It is to be understood that while the examples of modifications to the parent polypeptide are generally provided herein relative to the sequence SEQ ID NO:1 (or relative to some other specified sequence), the disclosed modifications may also be made in equivalent amino acid positions of any of the other polypeptides of the invention (including SEQ ID NOs: 2-15 and SEQ ID NOs:44-104 and variants thereof) described herein. Thus, as an example, the substitution H47K relative to SEQ ID NO:1 is understood to correspond to Q47K in SEQ ID NO:5, and so on.

Conjugate of the Invention where the Non-Polypeptide Moiety is a Sugar Moiety

In another aspect, the invention relates to a conjugate exhibiting interferon-alpha activity and comprising at least one sugar moiety conjugated to an interferon-alpha polypeptide, the amino acid sequence of which differs from that of a parent interferon-alpha polypeptide, such as any one of SEQ ID NOs:1-15 and SEQ ID NOs:44-104 (such as one of SEQ ID NO:1, SEQ ID NO:3, SEQ ID NO:8, SEQ ID NO:12, SEQ ID NO:47 or SEQ ID NO:53), 1-16 amino acid positions, in that at least one glycosylation site, preferably an in vivo N-glycosylation site, has been introduced, preferably by substitution, into a position that in the parent interferon-alpha polypeptide is occupied by an amino acid residue that is exposed to the surface of the molecule, e.g. one that has at least 25%, such as at least 50% of its side chain exposed to the surface. Typically, the conjugate comprises an amino acid sequence which differs from the amino acid sequence of any of, for example, SEQ ID NOs:1-15, 47, or 53, in 1-16 amino acid positions (such as in 1, 2, 3, 4, 5, 6, 7, 8, 9, 10, 11, 12, 13, 14, 15, or 16 amino acid positions), e.g. in 1-14 amino acid positions, in 1-12 amino acid positions, in 1-10 amino acid positions, in 1-8 amino acid positions, in 1-6 amino acid positions, in 1-5 amino acid positions, in 1-4 amino acid positions, in 1-3 amino acid positions or in 1-2 amino acid positions.

The N-glycosylation site is introduced in such a way that the N-residue (Asn) of said site is located in the designated position. Analogously, an O-glycosylation site is introduced so that the S (Ser) or T (Thr) residue making up such site is located in said position. It should be understood that when the term "at least 25% (or 50%) of its side chain exposed to the surface" is used in connection with introduction of an in vivo N-glycosylation site this term refers to the surface accessibility of the amino acid side chain in the position where the sugar moiety is actually attached. In many cases it will be necessary to introduce a serine or a threonine residue in position +2 relative to the asparagine residue to which the sugar moiety is actually attached and these positions, where the serine or threonine residues are introduced, are allowed to be buried, i.e. to have less than 25% (or 50%) of their side chains exposed to the surface of the molecule.

Some conjugates of the invention comprise a polypeptide sequence comprising one or more of the following substitutions, relative to SEQ ID NO:1, which introduces an N-glycosylation site into a position which is predicted to be exposed at the surface of the molecule with more than a 25% fractional ASA: D2N+P4S/T, L3N+Q5S/T, P4Q, P4Q+T6S, Q5N+H7S/T, T6N, T6N+S8T, H7N+L9S/T, S8N+G10S/T, L9N+H11S/T, G10N+R12S/T, R12N, R12N+T14S, R13N+ M15S/T, M16N+L18S/T, A19N+M21S/T, Q20N+R22S/T, R22N+I24S/T, R23N, R23N+S25T, I24N+L26S/T, S25N+ F27S/T, L26N, L26N+S28T, S28N+L30S/T, L30N+D32S/T, K31N+R33S/T, R33N+D35S/T, H34N+F36S/T, D35N+ R37S/T, R37N+P39S/T, Q40N+E42S/T, E41N+F43S/T, E42N+D44S/T, D44N+N46S/T, F48S/T, H47N+Q49S/T, Q49N+V51S/T, K50N+Q52S/T, V51N+A53S/T, Q52N+ I54S/T, E59N+M61S/T, Q62N, Q62N+T64S, Q63N+F65S/ T, F68S/T, S69N+K71S/T, T70N+N72S/T, K71N, K71N+ S73T, S74T, S74N+A76S/T, A75N+W77S/T, D78N, D78N+ T80S, E79N+L81S/T, T80N+L82S/T, L81N+E83S/T, E83N+F85S/T, K84N+Y86S/T, I87N+L89S/T, F90N+ Q92S/T, Q91N+M93S/T, L96S/T, D95N+E97S/T, E97N+ C99S/T, A98N+V100S/T, V100N+Q102S/T, M101N+ E103S/T, Q102N+V104S/T, E103N+G105S/T, V104N+ V106S/T, G105N+E107S/T, E107, E107N+T109S, E108N+ P110S/T, L111N+N113S/T, M112N+V114S/T, N113N+ D115S/T, V114N, V114N+S116T, D115N+I117S/T, L118N+V120S/T, R121N+Y123S/T, K122N+F124S/T, Q125N+I127S/T, R126N, R126N+T128S, T128N+Y130S/ T, L129N+L131S/T, T132N+K134S/T, K133N+K135S/T, K134N+Y136S/T, K135N, K135N+S137T, Y136N+P138S/ T, P138N, P138N+S140T, A146N+I148S/T, M149N, M149N+S151T, R150N+F152S/T, S153N, S153N+S155T, F154N+F156S/T, Q159S/T, K160N+L162S/T, R161N+ R163S/T, L162N+R164S/T, R163N+K165S/T and R164N+ E166S/T, relative to SEQ ID NO:1. In some instances, among the above-mentioned positions, the amino acid residues at one or more of positions 47, 51, 133 and 140 are not modified as shown above. S/T indicates a substitution to a serine or threonine residue, preferably a threonine residue.

Some conjugates of the invention comprise a polypeptide sequence comprising one or more of the following substitutions, relative to SEQ ID NO:1, which introduces an N-glycosylation site into a position which is predicted to be exposed at the surface of the molecule with more than a 50% fractional ASA: D2N+P4S/T, L3N+Q5S/T, P4Q, P4Q+T6S, Q5N+H7S/T, T6N, T6N+S8T, H7N+L9S/T, S8N+G10S/T, L9N+H11S/T, R12N, R12N+T14S, R13N+M15S/T, M16N+ L18S/T, A19N+M21S/T, S25N+F27S/T, S28N+L30S/T, R33N+D35S/T, H34N+F36S/T, D35N+R37S/T, R37N+ P39S/T, E41N+F43S/T, D44N+N46S/T, F48S/T, H47N+ Q49S/T, Q49N+V51S/T, K50N+Q52S/T, F68S/T, K71N, K71N+S73T, A75N+W77S/T, D78N, D78N+T80S, E79N+ L81S/T, T80N+L82S/T, E83N+F85S/T, K84N+Y86S/T, I87N+L89S/T, F90N+Q92S/T, Q91N+M93S/T, L96S/T, D95N+E97S/T, M101N+E103S/T, Q102N+V104S/T, E103N+G105S/T, G105N+E107S/T, E107, E107N+T109S, E108N+P110S/T, L111N+N113S/T, V114N, V114N+

S116T, D115N+I17S/T, L118N+V120S/T, R121N+Y123S/T, K122N+F124S/T, Q125N+I127S/T, R126N, R126N+T128S, L129N+L131S/T, T132N+K134S/T, K133N+K135S/T, K135N, K135N+S137T, P138N, P138N+S140T, R150N+F152S/T, K160N+L162S/T, L162N+R164S/T, R163N+K165S/T and R164N+E166S/T, relative to SEQ ID NO:1. In some instances, among the above-mentioned positions, the amino acid residues at one or more of positions 47, 51, 133 and 140 are not modified as described above. S/T indicates a substitution to a serine or threonine residue, preferably a threonine residue.

In some instances it may be preferable to introduce N-glycosylation site(s) outside of potential receptor binding sites of interferon-alpha, i.e., outside of about positions 29-40, 79-96, and 124-141, position numbering relative to SEQ ID NO:1. Thus, the substitution(s) leading to introduction of one or more N-glycosylation site may include one or more of D2N+P4S/T, L3N+Q5S/T, P4Q, P4Q+T6S, Q5N+H7S/T, T6N, T6N+S8T, H7N+L9S/T, S8N+G10S/T, L9N+H11S/T, G10N+R12S/T, R12N, R12N+T14S, R13N+M15S/T, M16N+L18S/T, A19N+M21S/T, Q20N+R22S/T, R22N+I24S/T, R23N, R23N+S25T, I24N+L26S/T, S25N+F27S/T, L26N, L26N+S28T, S28N+L30S/T, E41N+F43S/T, E42N+D44S/T, D44N+N46S/T, F48S/T, H47N+Q49S/T, Q49N+V51S/T, K50N+Q52S/T, V51N+A53S/T, Q52N+I54S/T, E59N+M61S/T, Q62N, Q62N+T64S, Q63N+F65S/T, F68S/T, S69N+K71S/T, T70N+N72S/T, K71N, K71N+S73T, S74T, S74N+A76S/T, A75N+W77S/T, E97N+C99S/T, A98N+V100S/T, V100N+Q102S/T, M101N+E103S/T, Q102N+V104S/T, E103N+G105S/T, V104N+V106S/T, G105N+E107S/T, E107, E107N+T109S, E108N+P110S/T, L111N+N113S/T, M112N+V114S/T, N113N+D115S/T, V114N, V114N+S116T, D115N+I117S/T, L118N+V120S/T, R121N+Y123S/T, K122N+F124S/T, A146N+I148S/T, M149N, M149N+S151T, R150N+F152S/T, S153N, S153N+S155T, F154N+F156S/T, Q159S/T, K160N+L162S/T, R161N+R163S/T, L162N+R164S/T, R163N+K165S/T and R164N+E166S/T (residues having more than 25% of the side chain exposed to the surface an not forming part of the putative binding sites). In some instances, among the above-mentioned positions, the amino acid residues at one or both of positions 47 and 51 are not modified as shown above. S/T indicates a substitution to a serine or threonine residue, preferably a threonine residue.

In some instances the substitution(s) are selected from the group consisting of: D2N+P4S/T, L3N+Q5S/T, P4Q, P4Q+T6S, Q5N+H7S/T, T6N, T6N+S8T, H7N+L9S/T, S8N+G10S/T, L9N+H11S/T, R12N, R12N+T14S, R13N+M15S/T, M16N+L18S/T, A19N+M21S/T, S25N+F27S/T, S28N+L30S/T, E41N+F43S/T, D44N+N46S/T, F48S/T, H47N+Q49S/T, Q49N+V51S/T, K50N+Q52S/T, F68S/T, K71N, K71N+S73T, A75N+W77S/T, M101N+E103S/T, Q102N+V104S/T, E103N+G105S/T, G105N+E107S/T, E107, E107N+T109S, E108N+P110S/T, L111N+N113S/T, V114N, V114N+S116T, D115N+I117S/T, L118N+V120S/T, R121N+Y123S/T, K122N+F124S/T, R150N+F152S/T, K160N+L162S/T, L162N+R164S/T, R163N+K165S/T and R164N+E166S/T (residues having more than 50% of the side chain exposed to the surface an not forming part of the putative binding sites). In some instances, among the above-mentioned positions, the amino acid residues at one or both of positions 47 and 51 are not modified as shown above. S/T indicates a substitution to a serine or threonine residue, preferably a threonine residue.

In order to obtain efficient utilization of the introduced N-glycosylation site it is desirable to select any of the above-mentioned substitutions within about the 125 N-terminal amino acid residues, such as within about the 100 N-terminal amino acid residues, e.g. within the 75 N-terminal amino acid residues or within the 50 N-terminal amino acid residues.

When the interferon-alpha polypeptide part of a conjugate of the invention is glycosylated, it may contain a single introduced in vivo glycosylation site, such as a single introduced in vivo N-glycosylation site. However, in order to obtain efficient shielding of epitopes present on the surface of the parent polypeptide it may be desirable that the polypeptide comprises more than one in vivo glycosylation site, such as 2-5 in vivo glycosylation sites, e.g. 2, 3, 4, or 5 in vivo glycosylation sites.

It is to be understood that while the examples of modifications to the parent polypeptide are generally provided herein relative to the sequence SEQ ID NO:1 (or relative to some other specified sequence), the disclosed modifications may also be made in equivalent amino acid positions of any of the other polypeptides of the invention (including SEQ ID NOs: 2-15 and SEQ ID NOs:44-104 and variants thereof) described herein. Thus, as an example, the substitution H47N+Q49S/T relative to SEQ ID NO:1 is understood to correspond to Q47N+Q49S/T in SEQ ID NO:5, and so on.

Non-Polypeptide Moiety of the Conjugate of the Invention

As indicated above, the non-polypeptide moiety of the conjugate of the invention is generally selected from the group consisting of a polymer molecule, a lipophilic compound, a sugar moiety (e.g., by way of in vivo N-glycosylation) and an organic derivatizing agent. All of these agents may confer desirable properties to the polypeptide part of the conjugate, such as reduced immunogenicity, increased functional in vivo half-life, increased serum half-life, increased bioavailability and/or increased $AUC_{sc}$. The polypeptide part of the conjugate is often conjugated to only one type of non-polypeptide moiety, but may also be conjugated to two or more different types of non-polypeptide moieties, e.g. to a polymer molecule and a sugar moiety, etc. The conjugation to two or more different non-polypeptide moieties may be done simultaneously or sequentially. The choice of non-polypeptide moiety/moieties, depends especially on the effect desired to be achieved by the conjugation. For instance, sugar moieties have been found particularly useful for reducing immunogenicity, whereas polymer molecules such as PEG are of particular use for increasing functional in vivo half-life and/or serum half-life. Using a combination of a polymer molecule and a sugar moiety may enhance the reduction in immunogenicity and the increase in functional in vivo or serum half-life.

In the following sections "Conjugation to a lipophilic compound", "Conjugation to a polymer molecule", "Conjugation to a sugar moiety" and "Conjugation to an organic derivatizing agent" conjugation to specific types of non-polypeptide moieties is described.

Conjugation to a Lipophilic Compound

For conjugation to a lipophilic compound the following polypeptide groups may function as attachment groups: the N-terminus or C-terminus of the polypeptide, the hydroxy groups of the amino acid residues Ser, Thr or Tyr, the ε-amino group of Lys, the SH group of Cys or the carboxyl group of Asp and Glu. The polypeptide and the lipophilic compound may be conjugated to each other either directly or by use of a linker. The lipophilic compound may be a natural compound such as a saturated or unsaturated fatty acid, a fatty acid diketone, a terpene, a prostaglandin, a vitamin, a carotenoid or steroid, or a synthetic compound such as a carbon acid, an alcohol, an amine and sulphonic acid with one or more alkyl, aryl, alkenyl or other multiple unsaturated compounds. The conjugation between the polypeptide and the lipophilic compound, optionally through a linker may be done according to methods known in the art, e.g. as described by Bodanszky in Peptide Synthesis, John Wiley, New York, 1976 and in WO 96/12505.

Conjugation to a Polymer Molecule

The polymer molecule to be coupled to the polypeptide may be any suitable polymer molecule, such as a natural or synthetic homo-polymer or heteropolymer, typically with a molecular weight in the range of about 300-100,000 Da, such as about 1000-50,000 Da, e.g. in the range of about 1000-40,000 Da. More particularly, the polymer molecule, such as PEG, in particular mPEG, will typically have a molecular weight of about 2, 5, 10, 12, 15, 20, 30, 40 or 50 kDa, in particular a molecular weight of about 5 kDa, about 10 kDa, about 12 kDa, about 15 kDa, about 20 kDa, about 30 kDa or about 40 kDa. The PEG molecule may be branched (e.g., mPEG2), or may be unbranched (i.e., linear).

When used about polymer molecules herein, the word "about" indicates an approximate average molecular weight and reflects the fact that there will normally be a certain molecular weight distribution in a given polymer preparation.

Examples of homo-polymers include a polyol (i.e. poly-OH), a polyamine (i.e. poly-$NH_2$) and a polycarboxylic acid (i.e. poly-COOH). A hetero-polymer is a polymer which comprises one or more different coupling groups, such as a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs (PEG2), poly-vinyl alcohol (PVA), poly-carboxylate, poly-(vinylpyrolidone), polyethylene-co-maleic acid anhydride, polystyrene-co-malic acid anhydride, dextran including carboxymethyl-dextran, or any other biopolymer suitable for reducing immunogenicity and/or increasing functional in vivo half-life and/or serum half-life. Generally, polyalkylene glycol-derived polymers are biocompatible, non-toxic, non-antigenic, non-immunogenic, have various water solubility properties, and are easily excreted from living organisms.

PEG is the preferred polymer molecule to be used, since it has only few reactive groups capable of cross-linking compared to e.g. polysaccharides such as dextran. In particular, monofunctional PEG, e.g. monomethoxypolyethylene glycol (mPEG), is of interest since its coupling chemistry is relatively simple (only one reactive group is available for conjugating with attachment groups on the polypeptide). Consequently, the risk of cross-linking is eliminated, the resulting polypeptide conjugates are more homogeneous and the reaction of the polymer molecules with the polypeptide is easier to control.

To effect covalent attachment of the polymer molecule(s) to the polypeptide, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl propionate (SPA), succinimidyl butanoate (SBA), succinimidyl carboxymethylate (SCM), benzotriazole carbonate (BTC), N-hydroxysuccinimide (NHS), aldehyde, nitrophenylcarbonate (NPC), and tresylate (TRES)). Suitably activated polymer molecules are commercially available, e.g. from Nektar Therapeutics, Inc., Huntsville, Ala., USA; PolyMASC Pharmaceuticals plc, UK; or SunBio Corporation, Anyang City, South Korea. Alternatively, the polymer molecules can be activated by conventional methods known in the art, e.g. as disclosed in WO 90/13540. Specific examples of activated linear or branched polymer molecules suitable for use in the present invention are described in the Nektar Therapeutics, Inc. 2003 Catalog ("Nektar Molecule Engineering: Polyethylene Glycol and Derivatives for Advanced Pegylation, Catalog 2003"), incorporated by reference herein. Specific examples of activated PEG polymers include the following linear PEGs: NHS-PEG, SPA-PEG, SSPA-PEG, SBA-PEG, SS-PEG, SSA-PEG, SC-PEG, SG-PEG, SCM-PEG, NOR-PEG, BTC-PEG, EPOX-PEG, NCO-PEG, NPC-PEG, CDI-PEG, ALD-PEG, TRES-PEG, VS-PEG, OPSS-PEG, IODO-PEG, and MAL-PEG, and branched PEGs, such as PEG2-NHS, PEG2-MAL, and those disclosed in U.S. Pat. No. 5,932,462 and U.S. Pat. No. 5,643,575, both of which are incorporated herein by reference. Furthermore, the following publications, incorporated herein by reference, disclose useful polymer molecules and/or PEGylation chemistries: U.S. Pat. No. 5,824,778, U.S. Pat. No. 5,476,653, WO 97/32607, EP 229,108, EP 402,378, U.S. Pat. No. 4,902,502, U.S. Pat. No. 5,281,698, U.S. Pat. No. 5,122,614, U.S. Pat. No. 5,219,564, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. No. 5,473,034, U.S. Pat. No. 5,516,673, EP 605 963, U.S. Pat. No. 5,382,657, EP 510 356, EP 400 472, EP 183 503 and EP 154 316.

The conjugation of the polypeptide and the activated polymer molecules is conducted by use of any conventional method, e.g. as described in the following references (which also describe suitable methods for activation of polymer molecules): Harris and Zalipsky, eds., Poly(ethylene glycol) Chemistry and Biological Applications, AZC, Washington; R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.

For PEGylation of cysteine residues the polypeptide is usually treated with a reducing agent, such as dithiothreitol (DDT) prior to PEGylation. The reducing agent is subsequently removed by any conventional method, such as by desalting. Conjugation of PEG to a cysteine residue typically takes place in a suitable buffer at pH 6-9 at temperatures varying from 4° C. to 25° C. for periods up to about 16 hours. Examples of activated PEG polymers for coupling to cysteine residues include the following linear and branched PEGs: vinylsulfone-PEG (PEG-VS), such as vinylsulfone-mPEG (mPEG-VS); orthopyridyl-disulfide-PEG (PEG-OPSS), such as orthopyridyl-disulfide-mPEG (mPEG-OPSS); and maleimide-PEG (PEG-MAL), such as maleimide-mPEG (mPEG-MAL) and branched maleimide-mPEG2 (mPEG2-MAL).

Pegylation of lysines often employs PEG-N-hydroxylsuccinimide (e.g., mPEG-NHS or mPEG2-NHS), or esters such as PEG succinimidyl propionate (e.g., mPEG-SPA) or PEG succinimidyl butanoate (e.g., mPEG-SBA). One or more PEGs can be attached to a protein within 30 minutes at pH 8-9.5 at room temperature if about equimolar amounts of PEG and protein are mixed. A molar ratio of PEG to protein amino groups of 1-5 to 1 will usually suffice. Increasing pH increases the rate of reaction, while lowering pH reduces the rate of reaction. These highly reactive active esters can couple at physiological pH, but less reactive derivatives typically require higher pH. Low temperatures may also be employed if a labile protein is being used. Under low temperature conditions, a longer reaction time may be used.

N-terminal PEGylation is facilitated by the difference between the pKa values of the α-amino group of the N-terminal amino acid (~7.6 to 8.0) and the ε-amino group of lysine (~10). PEGylation of the N-terminal amino group often employs PEG-aldehydes (such as mPEG-propionaldehyde or mPEG-butylaldehyde), which are more selective for amines and thus are less likely to react with the imidazole group of histidine; in addition, PEG reagents used for lysine conjugation (such as mPEG-SPA or mPEG-SBA) may also be used for conjugation of the N-terminal amine. Conjugation of a PEG-aldehyde to the N-terminal amino group typically takes place in a suitable buffer (such as, 100 mM sodium acetate or 100 mM sodium bisphosphate buffer with 20 mM sodium cyanoborohydride) at pH ~5.0 overnight at temperatures varying from about 4° C. to 25° C. Useful N-terminal PEGylation methods and chemistries are also described in U.S. Pat. No. 5,985,265 and U.S. Pat. No. 6,077,939, both incorporated herein by reference.

Typically, linear PEG or mPEG polymers will have a molecular weight of about 5 kDa, about 10 kDa, about 12 kDa, about 15 kDa, about 20 kDa, or about 30 kDa. Branched PEG (PEG2 or mPEG2) polymers will typically have a molecular weight of about 10 kDa, about 20 kDa, or about 40 kDa. In some instances, the higher-molecular weight branched PEG2 reagents, such as 20 kDa or 40 kDa PEG2, including e.g. mPEG2-NHS for lysine PEGylation, mPEG2-MAL for cysteine PEGylation, or MPEG2-aldehyde for N-terminal PEGylation (all available from Nektar Therapeutics, Inc, Huntsville Ala.), may be used. The branched structure of the PEG2 compound results in a relatively large molecular volume, so fewer attached molecules (or, one attached molecule) may impart the desired characteristics of the PEGylated molecule.

The skilled person will be aware that the activation method and/or conjugation chemistry to be used depends on the attachment group(s) of the interferon-alpha polypeptide as well as the functional groups of the polymer (e.g., being amino, hydroxyl, carboxyl, aldehyde or sulfhydryl). The PEGylation may be directed towards conjugation to all available attachment groups on the polypeptide (i.e. such attachment groups that are exposed at the surface of the polypeptide) or may be directed towards specific attachment groups, e.g. cysteine residues, lysine residues, or the N-terminal amino group. Furthermore, the conjugation may be achieved in one step or in a stepwise manner (e.g. as described in WO 99/55377).

In some instances, the polymer conjugation is performed under conditions aiming at reacting as many of the available polymer attachment groups as possible with polymer molecules. This is achieved by means of a suitable molar excess of the polymer in relation to the polypeptide. Typical molar ratios of activated polymer molecules to polypeptide are up to about 1000-1, such as up to about 200-1 or up to about 100-1. In some cases, the ratio may be somewhat lower, however, such as up to about 50-1, 10-1 or 5-1. Also equimolar ratios may be used.

It is also contemplated according to the invention to couple the polymer molecules to the polypeptide through a linker. Suitable linkers are well known to the skilled person. A preferred example is cyanuric chloride (Abuchowski et al., (1977), J. Biol. Chem., 252, 3578-3581; U.S. Pat. No. 4,179,337; Shafer et al., (1986), J. Polym. Sci. Polym. Chem. Ed., 24, 375-378).

Subsequent to the conjugation residual activated polymer molecules are blocked according to methods known in the art, e.g. by addition of primary amine to the reaction mixture, and the resulting inactivated polymer molecules removed by a suitable method.

Covalent in vitro coupling of a sugar moiety to amino acid residues of interferon-alpha may be used to modify or increase the number or profile of sugar substituents. Depending on the coupling mode used, the carbohydrate(s) may be attached to a) arginine and histidine (Lundblad and Noyes, Chemical Reagents for Protein Modification, CRC Press Inc. Boca Raton, Fla.), b) free carboxyl groups (e.g. of the C-terminal amino acid residue, asparagine or glutamine), c) free sulfhydryl groups such as that of cysteine, d) free hydroxyl groups such as those of serine, threonine, tyrosine or hydroxyproline, e) aromatic residues such as those of phenylalanine or tryptophan or f) the amide group of glutamine. These amino acid residues constitute examples of attachment groups for a sugar moiety, which may be introduced and/or removed in the interferon-alpha polypeptide. Suitable methods of in vitro coupling are described in WO 87/05330 and in Aplin et al., CRC Crit Rev. Biochem., pp. 259-306, 1981. The in vitro coupling of sugar moieties or PEG to protein- and peptide-bound Gln-residues can also be carried out by transglutaminases (TGases), e.g. as described by Sato et al., 1996 Biochemistry 35, 13072-13080 or in EP 725145.

Coupling to a Sugar Moiety

In order to achieve in vivo glycosylation of an interferon-alpha polypeptide that has been modified by introduction of one or more glycosylation sites (see the section "Conjugates of the invention wherein the non-polypeptide moiety is a sugar moiety"), the nucleotide sequence encoding the polypeptide part of the conjugate is inserted in a glycosylating, eukaryotic expression host. The expression host cell may be selected from fungal (filamentous fungal or yeast), insect, mammalian animal cells, from transgenic plant cells or from transgenic animals. Furthermore, the glycosylation may be achieved in the human body when using a nucleotide sequence encoding the polypeptide part of a conjugate of the invention or a polypeptide of the invention in gene therapy. In one aspect the host cell is a mammalian cell, such as a CHO cell, a COS cell, a BHK or HEK cell, e.g. HEK293, or an insect cell, such as an SF9 cell, or a yeast cell, e.g. *Saccharomyces cerevisiae, Pichia pastoris* or any other suitable glycosylating host, e.g. as described further below. Optionally, sugar moieties attached to the interferon-α polypeptide by in vivo glycosylation are further modified by use of glycosyltransferases, e.g. using the GlycoAdvance™ technology marketed by Neose, Horsham, Pa., USA. Thereby, it is possible to, e.g., increase the sialyation of the glycosylated interferon-alpha polypeptide following expression and in vivo glycosylation by CHO cells.

Coupling to an Organic Derivatizing Agent

Covalent modification of the interferon-alpha polypeptide may be performed by reacting (an) attachment group(s) of the polypeptide with an organic derivatizing agent. Suitable derivatizing agents and methods are well known in the art. For example, cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(4-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are derivatized by reaction with diethylpyrocarbonate at pH 5.5-7.0 because this agent is relatively specific for the histidyl side chain. Para-bromophenacyl bromide is also useful; the reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate. Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group. Carboxyl side groups (aspartyl or glutamyl or C-terminal amino acid residue) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Blocking of a Functional Site

Since excessive polymer conjugation may lead to a loss of activity of the interferon-α polypeptide to which the polymer is conjugated, it may be advantageous to remove attachment groups located at the functional site or to block the functional site prior to conjugation. These latter strategies constitute further aspects of the invention (the first strategy being exemplified further above, e.g. by removal of lysine residues which may be located close to a functional site). More specifically, according to the second strategy the conjugation between the interferon-alpha polypeptide and the non-polypeptide moiety is conducted under conditions where the functional site of the polypeptide is blocked by a helper molecule capable of binding to the functional site of the polypeptide. Preferably, the helper molecule is one which specifically recognizes a functional site of the polypeptide, such as a receptor, in particular the type I interferon receptor. Alternatively, the helper molecule may be an antibody, in particular a monoclonal antibody recognizing the interferon-alpha polypeptide. In particular, the helper molecule may be a neutralizing monoclonal antibody.

The polypeptide is allowed to interact with the helper molecule before effecting conjugation. This ensures that the functional site of the polypeptide is shielded or protected and consequently unavailable for derivatization by the non-polypeptide moiety such as a polymer. Following its elution from the helper molecule, the conjugate between the non-polypeptide moiety and the polypeptide can be recovered with at least a partially preserved functional site.

The subsequent conjugation of the polypeptide having a blocked functional site to a polymer, a lipophilic compound, an organic derivatizing agent or any other compound is conducted in the normal way, e.g. as described in the sections above entitled "Conjugation to . . . ".

Irrespective of the nature of the helper molecule to be used to shield the functional site of the polypeptide from conjugation, it is desirable that the helper molecule is free from or comprises only a few attachment groups for the non-polypeptide moiety of choice in parts of the molecule where the conjugation to such groups would hamper the desorption of the conjugated polypeptide from the helper molecule. Hereby, selective conjugation to attachment groups present in non-shielded parts of the polypeptide can be obtained and it is possible to reuse the helper molecule for repeated cycles of conjugation. For instance, if the non-polypeptide moiety is a polymer molecule such as PEG, which has the epsilon amino group of a lysine or N-terminal amino acid residue as an attachment group, it is desirable that the helper molecule is substantially free from conjugatable epsilon amino groups, preferably free from any epsilon amino groups. Accordingly, in some instances the helper molecule is a protein or peptide capable of binding to the functional site of the polypeptide, which protein or peptide is free from any conjugatable attachment groups for the non-polypeptide moiety of choice.

In a further aspect the helper molecule is first covalently linked to a solid phase such as column packing materials, for instance Sephadex or agarose beads, or a surface, e.g. reaction vessel. Subsequently, the polypeptide is loaded onto the column material carrying the helper molecule and conjugation carried out according to methods known in the art, e.g. as described in the sections above entitled "Conjugation to . . . ". This procedure allows the polypeptide conjugate to be separated from the helper molecule by elution. The polypeptide conjugate is eluted by conventional techniques under physico-chemical conditions that do not lead to a substantive degradation of the polypeptide conjugate. The fluid phase containing the polypeptide conjugate is separated from the solid phase to which the helper molecule remains covalently linked. The separation can be achieved in other ways: For instance, the helper molecule may be derivatized with a second molecule (e.g. biotin) that can be recognized by a specific binder (e.g. streptavidin). The specific binder may be linked to a solid phase thereby allowing the separation of the polypeptide conjugate from the helper molecule-second molecule complex through passage over a second helper-solid phase column which will retain, upon subsequent elution, the helper molecule-second molecule complex, but not the polypeptide conjugate. The polypeptide conjugate may be released from the helper molecule in any appropriate fashion. De-protection may be achieved by providing conditions in which the helper molecule dissociates from the functional site of the interferon-α to which it is bound. For instance, a complex between an antibody to which a polymer is conjugated and an anti-idiotypic antibody can be dissociated by adjusting the pH to an acid or alkaline pH.

Conjugation of a Tagged Interferon-Alpha Polypeptide

In another aspect the interferon-alpha polypeptide is expressed as a fusion protein with a tag, i.e. an amino acid sequence or peptide made up of typically 1-30, such as 1-20 or 1-15 or 1-10 or 1-5 amino acid residues, e.g. added to the N-terminus or to the C-terminus of the polypeptide. Besides allowing for fast and easy purification, the tag is a convenient tool for achieving conjugation between the tagged polypeptide and the non-polypeptide moiety. In particular, the tag may be used for achieving conjugation in microtiter plates or other carriers, such as paramagnetic beads, to which the tagged polypeptide can be immobilised via the tag. The conjugation to the tagged polypeptide in, e.g., microtiter plates has the advantage that the tagged polypeptide can be immobilised in the microtiter plates directly from the culture broth (in principle without any purification) and subjected to conjugation. Thereby, the total number of process steps (from expression to conjugation) can be reduced. Furthermore, the tag may function as a spacer molecule ensuring an improved accessibility to the immobilised polypeptide to be conjugated. The conjugation using a tagged polypeptide may be to any of the non-polypeptide moieties disclosed herein, e.g. to a polymer molecule such as PEG.

The identity of the specific tag to be used is not critical as long as the tag is capable of being expressed with the polypeptide and is capable of being immobilised on a suitable surface or carrier material. A number of suitable tags are commercially available, e.g. from Unizyme Laboratories, Denmark. Antibodies against such tags are commercially available, e.g. from ADI, Aves Lab and Research Diagnostics.

Polynucleotides of the Invention

The invention provides isolated or recombinant nucleic acids (also referred to herein as polynucleotides), collectively referred to as "nucleic acids (or polynucleotides) of the invention", which encode polypeptides of the invention. The polynucleotides of the invention are useful in a variety of applications. As discussed above, the polynucleotides are useful in producing polypeptides of the invention. In addition, polynucleotides of the invention can be incorporated into expression vectors useful for gene therapy, DNA vaccination, and immunotherapy, as described in more detail below.

In one aspect, the invention provides isolated or recombinant nucleic acids that each comprise a polynucleotide sequence selected from: (a) a polynucleotide sequence selected from SEQ ID NOS:16-30, or a complementary polynucleotide sequence thereof; (b) a polynucleotide sequence which encodes a polypeptide selected from SEQ ID NOS:1-15 and 44-104, or a complementary polynucleotide sequence thereof.

The invention also provides isolated or recombinant nucleic acids that each comprise a polynucleotide sequence which encodes a polypeptide comprising a sequence which differs in 0-16 amino acid positions (such as in 0, 1, 2, 3, 4, 5, 6, 7, 8, 9, 10, 11, 12, 13, 14, 15, or 16 amino acid positions), e.g. in 0-16 positions, 0-15 positions, 0-14 positions, 0-13 positions, 0-12 positions, 0-11 positions, 0-10 positions, 0-9 positions, 0-8 positions, 0-7 positions, 0-6 positions, 0-5 positions, 0-4 positions, 0-3 positions, 0-2 positions, or 0-1 positions, from any one of SEQ ID NOs:1-15 and SEQ ID NOs: 44-104 (such as one of SEQ ID NO:1, SEQ ID NO:3, SEQ ID NO:8, SEQ ID NO:12, SEQ ID NO:47 or SEQ ID NO:53). In some instances the encoded polypeptide exhibits an interferon-alpha activity.

The invention also provides isolated or recombinant nucleic acids that each comprise a polynucleotide sequence which encodes a polypeptide comprising a sequence having at least about 90%, 91%, 92%, 93%, 94%, 95%, 96%, 97%, 98%, or 99% or more amino acid sequence identity to any one of SEQ ID NOs:1-15 and SEQ ID NOs:44-104 (such as one of SEQ ID NO:1, SEQ ID NO:3, SEQ ID NO:8, SEQ ID NO:12, SEQ ID NO:47 or SEQ ID NO:53). In some instances the encoded polypeptide exhibits an interferon-alpha activity.

The invention also provides isolated or recombinant nucleic acids that each comprise a polynucleotide sequence which encodes a polypeptide which is a variant of a parent interferon-alpha polypeptide, the encoded variant comprising a sequence which differs from the parent interferon-alpha polypeptide sequence in least one amino acid position, wherein the variant sequence comprises one or more of His at position 47, Val at position 51, Phe at position 55, Leu at position 56, Tyr at position 58, Lys at position 133, and at position Ser140, the position numbering relative to that of SEQ ID NO:1. In some instances the parent interferon-alpha polypeptide sequence is a sequence of a naturally-occurring human interferon-alpha (such as any one of SEQ ID NO:31-SEQ ID NO:42, or SEQ ID NO:32+R23K, or other huIFN-alpha sequence as described herein and/or in Allen G. and Diaz M. O. (1996), supra), or is a sequence of a non-naturally occurring (i.e., synthetic) interferon-alpha, such as IFN-alpha Con1 (SEQ ID NO:43). In some instances, the variant sequence differs from the parent polypeptide sequence in 1-16 amino acid positions (such as in 1, 2, 3, 4, 5, 6, 7, 8, 9, 10, 11, 12, 13, 14, 15, or 16 amino acid positions), e.g. in 1-10 amino acid positions, in 1-5 amino acid positions, or in 1-3 amino acid positions. In some instances, the variant exhibits an interferon-alpha activity.

In another aspect, the invention provides isolated or recombinant nucleic acids that each comprise a polynucleotide sequence which hybridizes under highly stringent conditions over substantially the entire length of one of SEQ ID NOs: 16-30, which polynucleotide sequence encodes a polypeptide exhibiting an interferon alpha activity.

Additional Aspects

Any of the nucleic acids of the invention (which includes those described above) may encode a fusion protein comprising at least one additional amino acid sequence, such as, for example, a secretion/localization sequence, a sequence useful for solubilization or immobilization (e.g., for cell surface display) of the polypeptide, a sequence useful for detection and/or purification of the polypeptide (e.g., a polypeptide purification subsequence, such as an epitope tag, a polyhistidine sequence, and the like). In another aspect, the invention provides cells comprising one or more of the nucleic acids of the invention. Such cells may express one or more polypeptides encoded by the nucleic acids of the invention.

The invention also provides vectors comprising any of the nucleic acids of the invention. Such vectors may comprise a plasmid, a cosmid, a phage, a virus, or a fragment of a virus. Such vectors may comprise an expression vector, and, if desired, the nucleic acid is operably linked to a promoter, including those discussed herein and below. Furthermore, in another aspect, the invention provides compositions comprising an excipient or carrier and at least one of any of the nucleic acids of the invention, or vectors, cells, or host comprising such nucleic acids. Such composition may be pharmaceutical compositions, and the excipient or carrier may be a pharmaceutically acceptable excipient or carrier.

The invention also includes compositions comprising two or more nucleic acids of the invention, or fragments thereof (e.g., as substrates for recombination). The composition can comprise a library of recombinant nucleic acids, where the library contains at least 2, at least 3, at least 5, at least 10, at least 20, at least 50, or at least 100 or more nucleic acids described above. The nucleic acids are optionally cloned into expression vectors, providing expression libraries.

The nucleic acids of the invention and fragments thereof, as well as vectors comprising such polynucleotides, may be employed for therapeutic or prophylactic uses in combination with a suitable carrier, such as a pharmaceutical carrier. Such compositions comprise a therapeutically and/or prophylactically effective amount of the compound, and a pharmaceutically acceptable carrier or excipient. Such a carrier or excipient includes, but is not limited to, saline, buffered saline, dextrose, water, glycerol, ethanol, and combinations thereof.

The formulation should suit the mode of administration. Methods of administering nucleic acids, polypeptides, and proteins are well known in the art, and are further discussed below.

The invention also includes compositions produced by digesting one or more of any of the nucleic acids of the invention with a restriction endonuclease, an RNAse, or a DNAse (e.g., as is performed in certain of the recombination formats noted above); and compositions produced by fragmenting or shearing one or more nucleic acids of the invention by mechanical means (e.g., sonication, vortexing, and the like), which can also be used to provide substrates for recombination in the methods described herein. The invention also provides compositions produced by cleaving at least one of any of the nucleic acids of the invention. The cleaving may comprise mechanical, chemical, or enzymatic cleavage, and the enzymatic cleavage may comprise cleavage with a restriction endonuclease, an RNAse, or a DNAse.

Also included in the invention are compositions produced by a process comprising incubating one or more of the fragmented nucleic acids of the invention in the presence of ribonucleotide or deoxyribonucleotide triphosphates and a nucleic acid polymerase. This resulting composition forms a recombination mixture for many of the recombination formats noted above. The nucleic acid polymerase may be an RNA polymerase, a DNA polymerase, or an RNA-directed DNA polymerase (e.g., a "reverse transcriptase"); the polymerase can be, e.g., a thermostable DNA polymerase (e.g., VENT, TAQ, or the like).

Similarly, compositions comprising sets of oligonucleotides corresponding to more than one nucleic acids of the invention are useful as recombination substrates and are a feature of the invention. For convenience, these fragmented, sheared, or oligonucleotide synthesized mixtures are referred to as fragmented nucleic acid sets.

The invention also provides an isolated or recombinant nucleic acid encoding a polypeptide that exhibits an interferon-alpha activity, produced by mutating or recombining at least one nucleic acid of the invention.

Making Polynucleotides

Polynucleotides, oligonucleotides, and nucleic acid fragments of the invention can be prepared by standard solid-phase methods, according to known synthetic methods. Typically, fragments of up to about 100 bases are individually synthesized, then joined (e.g., by enzymatic or chemical ligation methods, or polymerase mediated recombination methods) to form essentially any desired continuous sequence. For example, the polynucleotides and oligonucleotides of the invention can be prepared by chemical synthesis using, e.g., classical phosphoramidite method described by, e.g., Beaucage et al. (1981) Tetrahedron Letters 22:1859-69, or the method described by Matthes et al. (1984) EMBO J 3:801-05, e.g., as is typically practiced in automated synthetic methods. According to the phosphoramidite method, oligonucleotides are synthesized, e.g., in an automatic DNA synthesizer, purified, annealed, ligated and cloned into appropriate vectors.

In addition, essentially any polynucleotide can be custom ordered from any of a variety of commercial sources, such as Operon Technologies Inc. (Alameda, Calif.) and many others. Similarly, peptides and antibodies can be custom ordered from any of a variety of sources, e.g., Celtek Peptides (Nashville, Tenn.); Washington Biotechnology, Inc. (Baltimore Md.); Global Peptide Services (Ft. Collin Colo.), and many others.

Certain polynucleotides of the invention may also be obtained by screening cDNA libraries (e.g., libraries generated by recombining homologous nucleic acids as in typical recursive sequence recombination methods) using oligonucleotide probes that can hybridize to or PCR-amplify polynucleotides which encode interferon-alpha polypeptides and fragments of those polypeptides. Procedures for screening and isolating cDNA clones are well-known to those of skill in the art. Such techniques are described in, e.g., Berger and Kimmel, Guide to Molecular Cloning Techniques, Methods in Enzymol. Vol. 152, Acad. Press, Inc., San Diego, Calif. ("Berger"); Sambrook, supra, and Current Protocols in Molecular Biology, Ausubel, supra. Some polynucleotides of the invention can be obtained by altering a naturally occurring sequence, e.g., by mutagenesis, recursive sequence recombination (e.g., shuffling), or oligonucleotide recombination. In other cases, such polynucleotides can be made in silico or through oligonucleotide recombination methods as described in the references cited herein.

As described in more detail herein, the polynucleotides of the invention include polynucleotides that encode polypeptides of the invention, polynucleotide sequences complementary to these polynucleotide sequences, and polynucleotides that hybridize under at least stringent conditions to the sequences defined herein. A coding sequence refers to a polynucleotide sequence encoding a particular polypeptide or domain, region, or fragment of said polypeptide. A coding sequence may encode (code for) a polypeptide of the invention exhibiting an interferon alpha activity as described above. The polynucleotides of the invention may be in the form of RNA or in the form of DNA, and include mRNA, cRNA, synthetic RNA and DNA, and cDNA. The polynucleotides may be double-stranded or single-stranded, and if single-stranded, can be the coding strand or the non-coding (anti-sense, complementary) strand. The polynucleotides of the invention include the coding sequence of a polypeptide of the invention (i) in isolation, (ii) in combination with one or more additional coding sequences, so as to encode, e.g., a fusion protein, a pre-protein, a prepro-protein, or the like, (iii) in combination with non-coding sequences, such as introns, control elements, such as a promoter (e.g., naturally occurring or recombinant or shuffled promoter), a terminator element, or 5' and/or 3' untranslated regions effective for expression of the coding sequence in a suitable host, and/or (iv) in a vector, cell, or host environment in which the coding sequence is a heterologous gene.

Polynucleotides of the invention can also be found in combination with typical compositional formulations of nucleic acids, including in the presence of carriers, buffers, adjuvants, excipients, and the like, as are known to those of ordinary skill in the art. Polynucleotide fragments typically comprise at least about 200 nucleotide bases, such as at least about 250, 300, 350, 400, 450, 460, 470, or more bases. The nucleotide fragments of polynucleotides of the invention may hybridize under highly stringent conditions to a polynucleotide sequence described herein and/or encode amino acid sequences having at least one of the properties of polypeptides of the invention described herein.

Modified Coding Sequences

As will be understood by those of ordinary skill in the art, it can be advantageous to modify a coding sequence to enhance its expression in a particular host. The genetic code is redundant with 64 possible codons, but most organisms preferentially use a subset of these codons. The codons that are utilized most often in a species are considered optimal codons, and those not utilized very often are classified as rare or low-usage codons (see, e.g., Zhang, S. P. et al. (1991) Gene 105:61-72). Codons can be substituted to reflect the preferred codon usage of the host, a process sometimes termed "codon optimization" or "controlling for species codon bias."

Modified coding sequence containing codons preferred by a particular prokaryotic or eukaryotic host (see, e.g., Murray, E. et al. (1989) Nuc Acids Res 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for S. cerevisiae and mammals are UAA and UGA respectively. The preferred stop codon for monocotyledonous plants is UGA, whereas insects and E. coli prefer to use UAA as the stop codon (Dalphin, M. E. et al. (1996) Nucl. Acids Res. 24:216-218).

The polynucleotide sequences of the present invention can be engineered in order to alter a coding sequence of the invention for a variety of reasons, including but not limited to, alterations which modify the cloning, processing and/or expression of the gene product. For example, alterations may be introduced using techniques which are well known in the art, e.g., site-directed mutagenesis, to insert new restriction sites, to alter glycosylation patterns, to introduce or remove attachment groups (e.g., for pegylation or other conjugation), to change codon preference, to introduce splice sites, etc.

Silent Variations

Because of the degeneracy of the genetic code, a large number of functionally identical nucleic acids encode any given polypeptide. For instance, inspection of the codon table below (Table 5) shows that codons AGA, AGG, CGA, CGC, CGG, and CGU all encode the amino acid arginine. Thus, at every position in a nucleic acid sequence where an arginine is specified by a codon, the codon can be altered to any of the corresponding codons described above without altering the encoded polypeptide. Such nucleic acid variations are "silent variations". It is to be understood that U in an RNA sequence corresponds to T in a DNA sequence.

TABLE 5

Codon Table

| Amino acid | | | Codon(s) | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It will thus be appreciated by those skilled in the art that due to the degeneracy of the genetic code, a multitude of nucleic acids sequences encoding polypeptides of the invention may be produced, some of which may bear minimal sequence identity to the nucleic acid sequences explicitly disclosed herein. One of ordinary skill in the art will recognize that each codon in a nucleic acid (except AUG and UGC, which are ordinarily the only codon for methionine and tryptophan, respectively) can be modified by standard techniques to encode a functionally identical polypeptide. Accordingly, each silent variation of a nucleic acid which encodes a polypeptide is implicit in any described sequence. The invention also provides each and every possible variation of a nucleic acid sequence encoding a polypeptide of the invention that can be made by selecting combinations based on possible codon choices. These combinations are made in accordance with the standard triplet (codon) genetic code (e.g., as set forth in Table 5), as applied to the nucleic acid sequence encoding a polypeptide of the invention. All such variations of every nucleic acid herein are specifically provided and described by consideration of the sequence in combination with the genetic code. One of skill is fully able to generate any silent substitution of the sequences listed herein.

Using Polynucleotides

The polynucleotides of the invention have a variety of uses in, for example, recombinant production (i.e., expression) of the polypeptides of the invention typically through expression of a plasmid expression vector comprising a sequence encoding the polypeptide or fragment thereof; as therapeutics; as prophylactics; as diagnostic tools; as immunogens; as adjuvants; as diagnostic probes for the presence of complementary or partially complementary nucleic acids (including for detection of a wild-type interferon-alpha nucleic acid), as substrates for further reactions, e.g., recursive sequence recombination reactions or mutation reactions to produce new and/or improved variants, and the like.

Vectors, Promoters, and Expression Systems

The present invention also includes recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), and the like, into which a nucleic acid sequence of the invention has been inserted, in a forward or reverse orientation. In some instances, the construct further comprises regulatory sequences, including, for example, a promoter, operably linked to the nucleic acid sequence. Large numbers of suitable vectors and promoters are known to those of skill in the art, and are commercially available.

General texts that describe molecular biological techniques useful herein, including the use of vectors, promoters and many other relevant topics, include Berger, supra; Sambrook (1989), supra, and Ausubel, supra. Examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, all supra, as well as Mullis et al. (1987) U.S. Pat. No. 4,683,202; PCR Protocols: A Guide to Methods and Applications (Innis et al., eds.) Academic Press Inc. San Diego, Calif. (1990) ("Innis"); Arnheim & Levinson (Oct. 1, 1990) C&EN 36-47; The Journal Of NIH Research (1991) 3:81-94; (Kwoh et al. (1989) Proc Natl Acad Sci USA 86:1173-1177; Guatelli et al. (1990) Proc Natl Acad Sci USA 87:1874-1878; Lomeli et al. (1989) J Clin Chem 35:1826-1831; Landegren et al. (1988) Science 241:1077-1080; Van Brunt (1990) Biotechnology 8:291-294; Wu and Wallace (1989) Gene 4:560-569; Barringer et al. (1990) Gene 89:117-122, and Sooknanan and Malek (1995) Biotechnology 13:563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) Nature 369:684-685 and the references therein, in which PCR amplicons of up to 40 kilobases (kb) are generated. One of skill will appreciate that essentially any RNA can be converted into a double stranded DNA suitable for restriction digestion, PCR expansion and sequencing using reverse transcriptase and a polymerase. See Ausubel, Sambrook and Berger, all supra.

The present invention also provides host cells that are transduced with vectors of the invention, and the production of polypeptides of the invention by recombinant techniques. Host cells are genetically engineered (e.g., transduced, transformed or transfected) with the vectors of this invention, which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants, or amplifying genes. The culture conditions, such as temperature, pH, and the like, are those previously used with the host cell selected for expression, and will be apparent to those skilled in the art and in the references cited herein, including, e.g., Freshney (1994) Culture of Animal Cells, a Manual of Basic Technique, third edition, Wiley-Liss, New York and the references cited therein.

The polypeptides of the invention can also be produced in non-animal cells such as plants, yeast, fungi, bacteria and the like. In addition to Sambrook, Berger and Ausubel, details regarding cell culture are found in, e.g., Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg N.Y.); Atlas & Parks (eds.) The Handbook of Microbiological Media (1993) CRC Press, Boca Raton, Fla.

The polynucleotides of the present invention and fragments thereof may be included in any one of a variety of expression vectors for expressing a polypeptide. Such vectors include chromosomal, nonchromosomal and synthetic DNA sequences, e.g., derivatives of SV40, bacterial plasmids, phage DNA, baculovirus, yeast plasmids, vectors derived from combinations of plasmids and phage DNA, viral DNA such as vaccinia, adenovirus, fowl pox virus, pseudorabies, adeno-associated virus, retroviruses and many others. Any vector that transduces genetic material into a cell, and, if replication is desired, which is replicable and viable in the relevant host can be used.

The nucleic acid sequence in the expression vector is operatively linked to an appropriate transcription control sequence (promoter) to direct mRNA synthesis. Examples of such promoters include: LTR or SV40 promoter, $E.$ $coli$ lac or trp promoter, phage lambda $P_L$ promoter, CMV promoter, and other promoters known to control expression of genes in prokaryotic or eukaryotic cells or their viruses. The expression vector also contains a ribosome binding site for translation initiation, and a transcription terminator. The vector optionally includes appropriate sequences for amplifying expression, e.g., an enhancer. In addition, the expression vectors optionally comprise one or more selectable marker genes to provide a phenotypic trait for selection of transformed host cells, such as dihydrofolate reductase or neomycin resistance for eukaryotic cell culture, or such as tetracycline or ampicillin resistance in $E.$ $coli$.

The vector containing the appropriate DNA sequence encoding a polypeptide of the invention, as well as an appropriate promoter or control sequence, may be employed to transform an appropriate host to permit the host to express the polypeptide. Examples of appropriate expression hosts include: bacterial cells, such as $E.$ $coli,$ $Streptomyces,$ and $Salmonella$ $typhimurium$; fungal cells, such as $Saccharomyces$ $cerevisiae,$ $Pichia$ $pastoris,$ and $Neurospora$ $crassa$; insect cells such as $Drosophila$ and $Spodoptera$ $frugiperda$; mammalian cells such as CHO, COS, BHK, HEK 293 or Bowes melanoma; plant cells, etc. It is understood that not all cells or cell lines need to be capable of producing fully functional polypeptides of the invention or fragments thereof; for example, antigenic fragments of the polypeptide may be produced in a bacterial or other expression system. The invention is not limited by the host cells employed.

In bacterial systems, a number of expression vectors may be selected depending upon the use intended for the polypeptide or fragment thereof. For example, when large quantities of a polypeptide or fragments thereof are needed for the induction of antibodies, vectors which direct high level expression of fusion proteins that are readily purified may be desirable. Such vectors include, but are not limited to, multifunctional $E.$ $coli$ cloning and expression vectors such as BLUESCRIPT (Stratagene), in which the nucleotide coding sequence may be ligated into the vector in-frame with sequences for the amino-terminal Met and the subsequent 7 residues of beta-galactosidase so that a hybrid protein is produced; pIN vectors (Van Heeke & Schuster (1989) J Biol Chem 264:5503-5509); pET vectors (Novagen, Madison Wis.); and the like.

Similarly, in the yeast $Saccharomyces$ $cerevisiae$ a number of vectors containing constitutive or inducible promoters such as alpha factor, alcohol oxidase and PGH may be used for production of the polypeptides of the invention. For reviews, see Ausubel, supra, Berger, supra, and Grant et al. (1987) Methods in Enzymology 153:516-544.

In mammalian host cells, a number of expression systems, such as viral-based systems, may be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome results in a viable virus capable of expressing a polypeptide of the invention in infected host cells (Logan and Shenk (1984) Proc Natl Acad Sci USA 81:3655-3659). In addition, transcription enhancers, such as the rous sarcoma virus (RSV) enhancer, are used to increase expression in mammalian host cells. Host cells, media, expression systems, and methods of production include those known for cloning and expression of various mammalian interferon-alphas (e.g., human interferon-alphas).

Additional Expression Elements

Specific initiation signals can aid in efficient translation of a polynucleotide coding sequence of the invention and/or fragments thereof. These signals can include, e.g., the ATG initiation codon and adjacent sequences. In cases where an coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous nucleic acid transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression can enhanced by the inclusion of enhancers appropriate to the cell system in use (see, e.g., Scharf D. et al. (1994) Results Probl Cell Differ 20:125-62; and Bittner et al. (1987) Methods in Enzymol 153:516-544).

Secretion/Localization Sequences

Polynucleotides encoding polypeptides of the invention can also be fused, for example, in-frame to nucleic acid encoding a secretion/localization sequence, to target polypeptide expression to a desired cellular compartment, membrane, or organelle, or to direct polypeptide secretion to the periplasmic space or into the cell culture media. Such sequences are known to those of skill, and include secretion leader or signal peptides, organelle targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

Expression Hosts

In a further aspect, the present invention relates to host cells containing any of the above-described nucleic acids, vectors, or other constructs of the invention. The host cell can be a eukaryotic cell, such as a mammalian cell, a yeast cell, or a plant cell, or the host cell can be a prokaryotic cell, such as a bacterial cell. Introduction of the construct into the host cell can be effected by calcium phosphate transfection, DEAE-Dextran mediated transfection, electroporation, gene or vaccine gun, injection, or other common techniques (see, e.g., Davis, L., Dibner, M., and Battey, I. (1986) Basic Methods in Molecular Biology) for in vivo, ex vivo or in vitro methods.

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "pre" or a "prepro" form of the protein may also be important for correct insertion, folding and/or function. Different host cells such as E. coli, Bacillus sp., yeast or mammalian cells such as CHO, HeLa, BHK, MDCK, HEK 293, W138, etc. have specific cellular machinery and characteristic mechanisms for such post-translational activities and may be chosen to ensure the correct modification and processing of the introduced foreign protein.

Stable expression can be used for long-term, high-yield production of recombinant proteins. For example, cell lines which stably express a polypeptide of the invention are transduced using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. For example, resistant clumps of stably transformed cells can be proliferated using tissue culture techniques appropriate to the cell type.

Host cells transformed with a nucleotide sequence encoding a polypeptide of the invention are optionally cultured under conditions suitable for the expression and recovery of the encoded protein from cell culture. The polypeptide produced by a recombinant cell may be secreted, membrane-bound, or contained intracellularly, depending on the sequence and/or the vector used. As will be understood by those of skill in the art, expression vectors containing polynucleotides encoding polypeptides of the invention can be designed with signal sequences which direct secretion of the mature polypeptides through a prokaryotic or eukaryotic cell membrane.

Additional Sequences

The polynucleotides of the present invention optionally comprise a coding sequence fused in-frame to a marker sequence which, e.g., facilitates purification and/or detection of the encoded polypeptide. Such purification subsequences include, but are not limited to, metal chelating peptides such as histidine-tryptophan modules that allow purification on immobilized metals, a sequence which binds glutathione (e.g., GST), a hemagglutinin (HA) tag (corresponding to an epitope derived from the influenza hemagglutinin protein; Wilson, I. et al. (1984) Cell 37:767), maltose binding protein sequences, the FLAG epitope utilized in the FLAGS extension/affinity purification system, and the like. The inclusion of a protease-cleavable polypeptide linker sequence between the purification domain and the polypeptide sequence is useful to facilitate purification.

For example, one expression vector possible to use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography, as described in Porath et al. (1992) Protein Expression and Purification 3:263-281) while the enterokinase cleavage site provides a method for separating the desired polypeptide from the polyhistidine region. pGEX vectors (Promega; Madison, Wis.) are optionally used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

An additional construction in the compositions and methods described herein provides for proteins, and their encoding nucleic acids, comprising polypeptides of the invention (or one or more fragments thereof), e.g., as described herein, fused to an Ig molecule, e.g., human IgG Fc ("fragment crystallizable," or fragment complement binding) hinge, CH2 domain and CH3 domain (and nucleotide sequences encoding them). Fc is the portion of the antibody responsible for binding to antibody receptors on cells and the C1q component of complement. These fusion proteins or fragments thereof and their encoding nucleic acids are optionally useful as prophylactic and/or therapeutic drugs or as diagnostic tools (see also, e.g., Challita-Eid, P. et al. (1998) J Immunol 160: 3419-3426; Sturmhoefel, K. et al. (1999) Cancer Res 59:4964-4972).

Polypeptide Production and Recovery

Following transduction of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Eukaryotic or microbial cells employed in expression of the proteins can be disrupted by any convenient method, including freeze-thaw cycling, sonication, mechanical disruption, or use of cell lysing agents, or other methods, which are well know to those skilled in the art.

As noted, many references are available for the culture and production of many cells, including cells of bacterial, plant, animal (especially mammalian) and archebacterial origin.

See, e.g., Sambrook, Ausubel, and Berger (all supra), as well as Freshney (1994) Culture of Animal Cells, a Manual of Basic Technique, third edition, Wiley-Liss, New York and the references cited therein; Doyle and Griffiths (1997) Mammalian Cell Culture: Essential Techniques John Wiley and Sons, NY; Humason (1979) Animal Tissue Techniques, fourth edition W.H. Freeman and Company; and Ricciardelli et al. (1989) In vitro Cell Dev Biol 25:1016-1024. For plant cell culture and regeneration see, e.g., Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg New York) and Plant Molecular Biology (1993) R. R. D. Croy (ed.) Bios Scientific Publishers, Oxford, U.K. ISBN 0 12 198370 6. Cell culture media in general are set forth in Atlas and Parks (eds.) The Handbook of Microbiological Media (1993) CRC Press, Boca Raton, Fla. Additional information for cell culture is found in available commercial literature such as the Life Science Research Cell Culture Catalogue from Sigma-Aldrich, Inc (St Louis, Mo.) ("Sigma-LSRCCC") and, e.g., the Plant Culture Catalogue and supplement also from Sigma-Aldrich, Inc (St Louis, Mo.) ("Sigma-PCCS").

Polypeptides of the invention can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein or fragments thereof. Finally, high performance liquid chromatography (HPLC) can be employed in the final purification steps. In addition to the references noted, supra, a variety of purification methods are well known in the art, including, e.g., those set forth in Sandana (1997) Bioseparation of Proteins, Academic Press, Inc.; Bollag et al. (1996) Protein Methods, $2^{nd}$ Edition Wiley-Liss, NY; Walker (1996) The Protein Protocols Handbook Humana Press, NJ; Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice $3^{rd}$ Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ.

In Vitro Expression Systems

Cell-free transcription/translation systems can also be employed to produce polypeptides of the invention using polynucleotides of the present invention. Several such systems are commercially available. A general guide to in vitro transcription and translation protocols is found in Tymms (1995) In vitro Transcription and Translation Protocols: Methods in Molecular Biology Volume 37, Garland Publishing, NY.

In Vivo Uses and Applications

Polynucleotides that encode a polypeptide of the invention, or complements of the polynucleotides (including e.g., antisense or ribozyme molecules), are optionally administered to a cell to accomplish a therapeutically useful process or to express a therapeutically useful product. These in vivo applications, including gene therapy, include a multitude of techniques by which gene expression may be altered in cells. Such methods include, for instance, the introduction of genes for expression of, e.g., therapeutically and/or prophylactically useful polypeptides, such as the polypeptides of the present invention.

In Vivo Polypeptide Expression

Polynucleotides encoding polypeptides of the invention are particularly useful for in vivo therapeutic applications, using techniques well known to those skilled in the art. For example, cultured cells are engineered ex vivo with at least one polynucleotide (DNA or RNA) of the invention and/or other polynucleotide sequences encoding, e.g., at least one of an antigen, cytokine, other co-stimulatory molecule, adjuvant, etc., and the like, with the engineered cells then being returned to the patient. Cells may also be engineered in vivo for expression of one or more polypeptides in vivo. including polypeptides and/or antigenic peptides of the invention.

A number of viral vectors suitable for organismal in vivo transduction and expression are known. Such vectors include retroviral vectors (see, e.g., Miller, Curr Top Microbiol Immunol (1992) 158:1-24; Salmons and Gunzburg (1993) Human Gene Therapy 4:129-141; Miller et al. (1994) Methods in Enzymology 217:581-599) and adeno-associated vectors (reviewed in Carter (1992) Curr Opinion Biotech 3:533-539; Muzycka (1992) Curr Top Microbiol Immunol. 158: 97-129). Other viral vectors that are used include adenoviral vectors, herpes viral vectors and Sindbis viral vectors, as generally described in, e.g., Jolly (1994) Cancer Gene Therapy 1:51-64; Latchman (1994) Molec Biotechnol 2:179-195; and Johanning et al. (1995) Nucl Acids Res 23:1495-1501.

In one aspect, a pox virus vector can be used. The pox viral vector is transfected with a polynucleotide sequence encoding a polypeptide of the invention, and is useful in prophylactic, therapeutic and diagnostic applications where enhancement of an immune response, such as e.g., increased or improved T cell proliferation is desired. See viral vectors discussed in, e.g., Berencsi et al., J Infect Dis (2001)183(8): 1171-9; Rosenwirth et al., Vaccine 2001 Feb. 8; 19(13-14): 1661-70; Kittlesen et al., J Immunol (2000) 164(8):4204-11; Brown et al. Gene Ther 2000 7(19):1680-9; Kanesa-thasan et al., Vaccine (2000) 19(4-5):483-91; Sten (2000) Drug 60(2): 249-71. Compositions comprising such vectors and an acceptable excipient are also a feature of the invention.

Gene therapy and genetic vaccines provide methods for combating chronic infectious diseases (e.g., HIV infection, viral hepatitis), as well as non-infectious diseases including cancer and some forms of congenital defects such as enzyme deficiencies, and such methods can be employed with polynucleotides of the invention, including, e.g., vectors and cells comprising such polynucleotides. Several approaches for introducing nucleic acids and vectors into cells in vivo, ex vivo and in vitro have been used and can be employed with polynucleotides of the invention, and vectors comprising such polynucleotides. These approaches include liposome based gene delivery (Debs and Zhu (1993) WO 93/24640 and U.S. Pat. No. 5,641,662; Mannino and Gould-Fogerite (1988) BioTechniques 6(7):682-691; Rose, U.S. Pat. No. 5,279,833; Brigham (1991) WO 91/06309; and Felgner et al. (1987) Proc Natl Acad Sci USA 84:7413-7414; Brigham et al. (1989) Am J Med Sci 298:278-281; Nabel et al. (1990) Science 249: 1285-1288; Hazinski et al. (1991) Am J Resp Cell Molec Biol 4:206-209; and Wang and Huang (1987) Proc Natl Acad Sci USA 84:7851-7855); adenoviral vector mediated gene delivery, e.g., to treat cancer (see, e.g., Chen et al. (1994) Proc Natl Acad Sci USA 91:3054-3057; Tong et al. (1996) Gynecol Oncol 61:175-179; Clayman et al. (1995) Cancer Res. 5:1-6; O'Malley et al. (1995) Cancer Res 55:1080-1085; Hwang et al. (1995) Am J Respir Cell Mol Biol 13:7-16; Haddada et al. (1995) Curr Top Microbiol Immunol. 1995 (Pt. 3):297-306; Addison et al. (1995) Proc Natl Acad Sci USA 92:8522-8526; Colak et al. (1995) Brain Res 691:76-82; Crystal (1995) Science 270:404-410; Elshami et al. (1996) Human Gene Ther 7:141-148; Vincent et al. (1996) J Neurosurg 85:648-654), and many others. Replication-defective retroviral vectors harboring therapeutic polynucleotide sequence as part of the retroviral genome have also been used, particularly with regard to simple MuLV vectors. See, e.g., Miller et al. (1990) Mol Cell Biol 10:4239 (1990); Kolberg (1992) J NIH Res 4:43, and Cornetta et al. (1991) Hum Gene Ther 2:215). Nucleic acid transport coupled to ligand-specific, cation-based transport systems (Wu and Wu (1988) J Biol Chem, 263:14621-14624) has also been used. Naked DNA expression vectors have also been described (Nabel et al. (1990), supra); Wolff et al. (1990) Science, 247:1465-1468). In general, these approaches can be adapted to the invention by incorporating nucleic acids encoding the polypeptides of the invention into the appropriate vectors.

General texts which describe gene therapy protocols, which can be adapted to the present invention by introducing the nucleic acids of the invention into patients, include, e.g., Robbins (1996) Gene Therapy Protocols, Humana Press, NJ, and Joyner (1993) Gene Targeting: A Practical Approach, IRL Press, Oxford, England.

Antisense Technology

In addition to expression of the nucleic acids of the invention as gene replacement nucleic acids, the nucleic acids are also useful for sense and anti-sense suppression of expression, e.g., to down-regulate expression of a nucleic acid of the invention, once, or when, expression of the nucleic acid is no-longer desired in the cell. Similarly, the nucleic acids of the invention, or subsequences or anti-sense sequences thereof, can also be used to block expression of naturally occurring homologous nucleic acids. A variety of sense and anti-sense technologies are known in the art, e.g., as set forth in Lichtenstein and Nellen (1997) Antisense Technology: A Practical Approach IRL Press at Oxford University, Oxford, England, and in Agrawal (1996) Antisense Therapeutics Humana Press, NJ, and the references cited therein.

Use as Probes

Also contemplated are uses of polynucleotides, also referred to herein as oligonucleotides, typically having at least 12 bases, preferably at least 15, more preferably at least 20, at least 30, or at least 50 or more bases, which hybridize under highly stringent conditions to a polynucleotide of the invention, or fragments thereof. The polynucleotides may be used as probes, primers, sense and antisense agents, and the like, according to methods as noted supra.

Nucleic Acid Hybridization

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology—Hybridization with Nucleic Acid Probes, part I, chapter 2, "Overview of principles of hybridization and the strategy of nucleic acid probe assays," (Elsevier, N.Y.) (hereinafter "Tjissen"), as well as in Ausubel, supra, Hames and Higgins (1995) Gene Probes 1, IRL Press at Oxford University Press, Oxford, England (Hames and Higgins 1) and Hames and Higgins (1995) Gene Probes 2, IRL Press at Oxford University Press, Oxford, England (Hames and Higgins 2) provide details on the synthesis, labeling, detection and quantification of DNA and RNA, including oligonucleotides.

An indication that two nucleic acid sequences are substantially identical is that the two molecules hybridize to each other under at least stringent conditions. The phrase "hybridizing specifically to," refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

"Stringent hybridization wash conditions" and "stringent hybridization conditions" in the context of nucleic acid hybridization experiments, such as Southern and northern hybridizations, are sequence dependent, and are different under different environmental parameters. An extensive guide to hybridization of nucleic acids is found in Tijssen (1993), supra, and in Hames and Higgins 1 and Hames and Higgins 2, supra.

For purposes of the present invention, generally, "highly stringent" hybridization and wash conditions are selected to be about 5° C. or less lower than the thermal melting point ($T_m$) for the specific sequence at a defined ionic strength and pH (as noted below, highly stringent conditions can also be referred to in comparative terms). The $T_m$ is the temperature (under defined ionic strength and pH) at which 50% of the test sequence hybridizes to a perfectly matched probe. In other words, the $T_m$ indicates the temperature at which the nucleic acid duplex is 50% denatured under the given conditions and its represents a direct measure of the stability of the nucleic acid hybrid. Thus, the $T_m$ corresponds to the temperature corresponding to the midpoint in transition from helix to random coil; it depends on length, nucleotide composition, and ionic strength for long stretches of nucleotides. Typically, under "stringent conditions," a probe will hybridize to its target subsequence, but to no other sequences. "Very stringent conditions" are selected to be equal to the $T_m$ for a particular probe.

After hybridization, unhybridized nucleic acid material can be removed by a series of washes, the stringency of which can be adjusted depending upon the desired results. Low stringency washing conditions (e.g., using higher salt and lower temperature) increase sensitivity, but can product non-specific hybridization signals and high background signals. Higher stringency conditions (e.g., using lower salt and higher temperature that is closer to the hybridization temperature) lowers the background signal, typically with only the specific signal remaining. See, Rapley, R. and Walker, J. M. eds., Molecular Biomethods Handbook (Humana Press, Inc. 1998) (hereinafter "Rapley and Walker"), which is incorporated herein by reference in its entirety for all purposes.

The $T_m$ of a DNA-DNA duplex can be estimated using equation (1):

$$T_m(°C.) = 81.5°C. + 16.6(\log_{10} M) + 0.41(\% \, G+C) - 0.72(\% \, f) - 500/n,$$

where M is the molarity of the monovalent cations (usually Na+), (% G+C) is the percentage of guanosine (G) and cystosine (C) nucleotides, (% f) is the percentage of formalize and n is the number of nucleotide bases (i.e., length) of the hybrid. See, Rapley and Walker, supra.

The $T_m$ of an RNA-DNA duplex can be estimated using equation (2):

$$T_m(°C.)=79.8°C.+18.5(\log_{10}M)+0.58(\%\ G+C)-11.8(\%\ G+C)^2-0.56(\%\ f)-820/n,$$

where M is the molarity of the monovalent cations (usually Na+), (% G+C) is the percentage of guanosine (G) and cystosine (C) nucleotides, (% f) is the percentage of formamide and n is the number of nucleotide bases (i.e., length) of the hybrid. Id. Equations 1 and 2 above are typically accurate only for hybrid duplexes longer than about 100-200 nucleotides. Id.

The Tm of nucleic acid sequences shorter than 50 nucleotides can be calculated as follows:

$$T_m(°C.)=4(G+C)+2(A+T), \text{ where A (adenine), C, T (thymine), and G are the numbers of the corresponding nucleotides.}$$

An example of stringent hybridization conditions for hybridization of complementary nucleic acids which have more than 100 complementary residues on a filter in a Southern or northern blot is 50% formalin (or formamide) with 1 mg of heparin at 42° C., with the hybridization being carried out overnight. An example of stringent wash conditions is a 0.2×SSC wash at 65° C. for 15 minutes (see Sambrook, supra, for a description of SSC buffer). Often, the high stringency wash is preceded by a low stringency wash to remove background probe signal. An example low stringency wash is 2×SSC at 40° C. for 15 minutes. An example of highly stringent wash conditions is 0.15M NaCl at 72° C. for about 15 minutes. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na$^+$ ion, typically about 0.01 to 1.0 M Na$^+$ ion concentration (or other salts) at pH 7.0 to 8.3, and the temperature is typically at least about 30° C. Stringent conditions can also be achieved with the addition of destabilizing agents such as formamide.

In general, a signal to noise ratio of 2× or 2.5×-5× (or higher) than that observed for an unrelated probe in the particular hybridization assay indicates detection of a specific hybridization. Detection of at least stringent hybridization between two sequences in the context of the present invention indicates relatively strong structural similarity or homology to, e.g., the nucleic acids of the present invention provided in the sequence listings herein.

As noted, "highly stringent" conditions are selected to be about 5° C. or less lower than the thermal melting point ($T_m$) for the specific sequence at a defined ionic strength and pH. Target sequences that are closely related or identical to the nucleotide sequence of interest (e.g., "probe") can be identified under highly stringency conditions. Lower stringency conditions are appropriate for sequences that are less complementary. See, e.g., Rapley and Walker; Sambrook, all supra.

Comparative hybridization can be used to identify nucleic acids of the invention, and this comparative hybridization method is a preferred method of distinguishing nucleic acids of the invention. Detection of highly stringent hybridization between two nucleotide sequences in the context of the present invention indicates relatively strong structural similarity/homology to, e.g., the nucleic acids provided in the sequence listing herein. Highly stringent hybridization between two nucleotide sequences demonstrates a degree of similarity or homology of structure, nucleotide base composition, arrangement or order that is greater than that detected by stringent hybridization conditions. In particular, detection of highly stringent hybridization in the context of the present invention indicates strong structural similarity or structural homology (e.g., nucleotide structure, base composition, arrangement or order) to, e.g., the nucleic acids provided in the sequence listings herein. For example, it is desirable to identify test nucleic acids which hybridize to the exemplar nucleic acids herein under stringent conditions.

Thus, one measure of stringent hybridization is the ability to hybridize to one of the listed nucleic acids of the invention (e.g., nucleic acid sequences SEQ ID NOS:16-30, and complementary polynucleotide sequences thereof) under highly stringent conditions (or very stringent conditions, or ultra-high stringency hybridization conditions, or ultra-ultra high stringency hybridization conditions). Stringent hybridization (including, e.g., highly stringent, ultra-high stringency, or ultra-ultra high stringency hybridization conditions) and wash conditions can easily be determined empirically for any test nucleic acid.

For example, in determining highly stringent hybridization and wash conditions, the hybridization and wash conditions are gradually increased (e.g., by increasing temperature, decreasing salt concentration, increasing detergent concentration and/or increasing the concentration of organic solvents, such as formalin, in the hybridization or wash), until a selected set of criteria are met. For example, the hybridization and wash conditions are gradually increased until a probe comprising one or more nucleic acid sequences selected from SEQ ID NOS:16-30, and complementary polynucleotide sequences thereof, binds to a perfectly matched complementary target (again, a nucleic acid comprising one or more nucleic acid sequences selected from SEQ ID NOS: 16-30, and complementary polynucleotide sequences thereof), with a signal to noise ratio that is at least 2.5×, and optionally 5× or more as high as that observed for hybridization of the probe to an unmatched target. In this case, the unmatched target is a nucleic acid corresponding to, e.g., a known interferon-alpha nucleic acid sequence (e.g., an interferon-alpha nucleic acid sequence present in a public database such as GenBank or GENESEQ at the time of filing of the subject application).

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 2.5×-10×, typically 5×-10× as high as that observed for hybridization to any of the unmatched target nucleic acids such as, e.g., a known interferon-alpha nucleic acid sequence as set forth above. For some such nucleic acids, the stringent conditions are selected such that a perfectly complementary oligonucleotide to the coding oligonucleotide hybridizes to the coding oligonucleotide with at least about a 5× higher signal to noise ratio than for hybridization of the perfectly complementary oligonucleotide to a control nucleic acid corresponding to a known interferon-alpha sequence as set forth above.

Ultra high-stringency hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids, such as, e.g., a known interferon-alpha nucleic acid sequence as set forth above. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids, such as, e.g., a known interferon-alpha nucleic acid sequence as set forth above. A target nucleic acid which hybridizes to a probe under such conditions, with a signal to noise ratio of at least ½ that of the perfectly matched complementary target nucleic acid is said to bind to the probe under ultra-ultra-high stringency conditions.

Target nucleic acids which hybridize to the nucleic acids represented by SEQ ID NOS:16-30 under high, ultra-high and ultra-ultra high stringency conditions are a feature of the invention. Examples of such nucleic acids include those with one or a few silent or conservative nucleic acid substitutions as compared to a given nucleic acid sequence.

Substrates and Formats for Sequence Recombination

The polynucleotides of the invention and fragments thereof are optionally used as substrates for any of a variety of recombination and recursive sequence recombination reactions, in addition to their use in standard cloning methods as set forth in, e.g., Ausubel, Berger and Sambrook, e.g., to produce additional polynucleotides that encode polypeptides having desired properties. A variety of such reactions are known, including those developed by the inventors and their co-workers.

A variety of diversity generating protocols for generating and identifying molecules having one of more of the properties described herein are available and described in the art. The procedures can be used separately, and/or in combination to produce one or more variants of a nucleic acid or set of nucleic acids, as well variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics. While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties, or that encode proteins with or which confer desirable properties. Following diversification by one or more of the methods herein, or otherwise available to one of skill, any nucleic acids that are produced can be selected for a desired activity or property, e.g., altered binding affinity for an interferon-alpha receptor, altered antiviral or antiproliferative activity, altered capacities to induce $T_H1$ differentiation, altered abilities to induce or inhibit cytokine production. This can include identifying any activity that can be detected, for example, in an automated or automatable format, by any of the assays in the art and the assays of the invention discussed here and in the Example section below. A variety of related (or even unrelated) properties can be evaluated, in serial or in parallel, at the discretion of the practitioner.

Descriptions of a variety of diversity generating procedures for generating modified nucleic acid sequences that encode polypeptides as described herein are found in the following publications and the references cited therein: Soong, N. et al. (2000) "Molecular breeding of viruses" Nat Genet 25(4):436-439; Stemmer, et al. (1999) "Molecular breeding of viruses for targeting and other clinical properties" Tumor Targeting 4:1-4; Ness et al. (1999) "DNA Shuffling of subgenomic sequences of subtilisin" Nature Biotechnology 17:893-896; Chang et al. (1999) "Evolution of a cytokine using DNA family shuffling" Nature Biotechnology 17:793-797; Minshull and Stemmer (1999) "Protein evolution by molecular breeding" Current Opinion in Chemical Biology 3:284-290; Christians et al. (1999) "Directed evolution of thymidine kinase for AZT phosphorylation using DNA family shuffling" Nature Biotechnology 17:259-264; Crameri et al. (1998) "DNA shuffling of a family of genes from diverse species accelerates directed evolution" Nature 391:288-291; Crameri et al. (1997) "Molecular evolution of an arsenate detoxification pathway by DNA shuffling," Nature Biotechnology 15:436-438; Zhang et al. (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Crameri et al. (1996) "Improved green fluorescent protein by molecular evolution using DNA shuffling" Nature Biotechnology 14:315-319; Gates et al. (1996) "Affinity selective isolation of ligands from peptide libraries through display on a lac repressor 'headpiece dimer'" Journal of Molecular Biology 255:373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al., (1995) "Single-step assembly of a gene and entire plasmid form large numbers of oligodeoxy-ribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

The term "shuffling" is used herein to indicate recombination between non-identical sequences, in some instances shuffling may include crossover via homologous recombination or via non-homologous recombination, such as via cre/lox and/or flp/frt systems. Shuffling can be carried out by employing a variety of different formats, including for example, in vitro and in vivo shuffling formats, in silico shuffling formats, shuffling formats that utilize either double-stranded or single-stranded templates, primer based shuffling formats, nucleic acid fragmentation-based shuffling formats, and oligonucleotide-mediated shuffling formats, all of which are based on recombination events between non-identical sequences and are described in more detail or referenced herein below, as well as other similar recombination-based formats.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100: 468-500; and Zoller & Smith (1987) "Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787 (1985); Nakamaye & Eckstein (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999).

Additional suitable methods include point mismatch repair (Kramer et al. (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh & Henikoff (1986) "Use of oligonucleotides to generate large deletions" Nucl. Acids Res. 14: 5115), restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundström et al. (1985) "Oligonucleotide-directed mutagenesis by microscale 'shotgun' gene synthesis" Nucl. Acids Res. 13: 3305-3316), double-strand break repair (Mandecki (1986) "Oligonucleotide-directed double-strand break repair in plasmids of *Escherichia coli*: a method for site-specific mutagenesis" Proc. Natl. Acad. Sci. USA, 83:7177-7181; and Arnold (1993) "Protein engineering for unusual environments" Current Opinion in Biotechnology 4:450-455). Additional details on many of the above methods can be found in Methods in Enzymology Volume 154, which also describes useful controls for trouble-shooting problems with various mutagenesis methods.

Additional details regarding various diversity generating methods can be found in the following U.S. patents, PCT publications and applications, and EPO publications: U.S. Pat. No. 5,605,793 to Stemmer (Feb. 25, 1997), "Methods for In vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" PCT/US00/26708 by Welch et al., "Use of Codon-Varied Oligonucleotide Synthesis for Synthetic Shuffling;" and PCT/US01/06775 "Single-Stranded Nucleic Acid Template-Mediated Recombination and Nucleic Acid Fragment Isolation" by Affholter.

Several different general classes of sequence modification methods, such as mutation, recombination, etc. are applicable to the present invention and set forth, e.g., in the references above and below. The following exemplify some of the different types of preferred formats for diversity generation in the context of the present invention, including, e.g., certain recombination based diversity generation formats.

Nucleic acids can be recombined in vitro by any of a variety of techniques discussed in the references above, including e.g., DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction. This process and many process variants is described in several of the references above, e.g., in Stemmer (1994) Proc. Natl. Acad. Sci. USA 91:10747-10751.

Similarly, nucleic acids can be recursively recombined in vivo, e.g., by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references noted above.

Whole genome recombination methods can also be used in which whole genomes of cells or other organisms are recombined, optionally including spiking of the genomic recombination mixtures with desired library components (e.g., genes corresponding to the pathways of the present invention). These methods have many applications, including those in which the identity of a target gene is not known. Details on such methods are found, e.g., in WO 98/31837 by del Cardayre et al. "Evolution of Whole Cells and Organisms by Recursive Sequence Recombination;" and in, e.g., PCT/US99/15972 by del Cardayre et al., also entitled "Evolution of Whole Cells and Organisms by Recursive Sequence Recombination."

Synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Details regarding such approaches are found in the references noted above, including, e.g., WO 00/42561 by Crameri et al., "Olgonucleotide Mediated Nucleic Acid Recombination;" PCT/US00/26708 by Welch et al., "Use of Codon-Varied Oligonucleotide Synthesis for Synthetic Shuffling;" WO 00/42560 by Selifonov et al., "Methods for Making Character Strings, Polynucleotides and Polypeptides Having Desired Characteristics;" and WO 00/42559 by Selifonov and Stemmer "Methods of Populating Data Structures for Use in Evolutionary Simulations."

In silico methods of recombination can be effected in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis/gene reassembly techniques. This approach can generate random, partially random or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (e.g., based on crossover site selection) as well as designed, pseudo-random or random recombination methods are described in WO 00/42560 by Selifonov et al., "Methods for Making Character Strings, Polynucleotides and Polypeptides Having Desired Characteristics" and WO 00/42559 by Selifonov and Stemmer "Methods of Populating Data Structures for Use in Evolutionary Simulations." Extensive details regarding in silico recombination methods are found in these applications. This methodology is generally applicable to the present invention in providing for recombination of the molecules in silico and/or the generation of corresponding nucleic acids or proteins.

Many methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. In one method employing a single-stranded template, the fragment population derived from the genomic library(ies) is annealed with partial, or, often approximately full length ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (e.g., if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. Additional details regarding this approach are found, e.g., in "Single-Stranded Nucleic Acid Template-Mediated Recombination and Nucleic Acid Fragment Isolation" by Affholter, PCT/US01/06775.

In another approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library enriched sequences which hybridize to the probe. A library produced in this manner provides a desirable substrate for further diversification using any of the procedures described herein.

Any of the preceding general recombination formats can be practiced in a reiterative fashion (e.g., one or more cycles of mutation/recombination or other diversity generation methods, optionally followed by one or more selection methods) to generate a more diverse set of recombinant nucleic acids.

Mutagenesis employing polynucleotide chain termination methods have also been proposed (see e.g., U.S. Pat. No. 5,965,408, "Method of DNA reassembly by interrupting synthesis" to Short, and the references above), and can be applied to the present invention. In this approach, double stranded DNAs corresponding to one or more genes sharing regions of sequence similarity are combined and denatured, in the presence or absence of primers specific for the gene. The single stranded polynucleotides are then annealed and incubated in the presence of a polymerase and a chain terminating reagent (e.g., ultraviolet, gamma or X-ray irradiation; ethidium bromide or other intercalators; DNA binding proteins, such as single strand binding proteins, transcription activating factors, or histones; polycyclic aromatic hydrocarbons; trivalent chromium or a trivalent chromium salt; or abbreviated polymerization mediated by rapid thermocycling; and the like), resulting in the production of partial duplex molecules. The partial duplex molecules, e.g., containing partially extended chains, are then denatured and reannealed in subsequent rounds of replication or partial replication resulting in polynucleotides which share varying degrees of sequence similarity and which are diversified with respect to the starting population of DNA molecules. Optionally, the products, or partial pools of the products, can be amplified at one or more stages in the process. Polynucleotides produced by a chain termination method, such as described above, are suitable substrates for any other described recombination format.

Diversity also can be generated in nucleic acids or populations of nucleic acids using a recombinational procedure termed "incremental truncation for the creation of hybrid enzymes" ("ITCHY") described in Ostermeier et al. (1999) "A combinatorial approach to hybrid enzymes independent of DNA homology" Nature Biotech 17:1205. This approach can be used to generate an initial a library of variants which can optionally serve as a substrate for one or more in vitro or in vivo recombination methods. See, also, Ostermeier et al. (1999) "Combinatorial Protein Engineering by Incremental Truncation," Proc. Natl. Acad. Sci. USA, 96: 3562-67; Ostermeier et al. (1999), "Incremental Truncation as a Strategy in the Engineering of Novel Biocatalysts," Biological and Medicinal Chemistry, 7: 2139-44.

Mutational methods which result in the alteration of individual nucleotides or groups of contiguous or non-contiguous nucleotides can be favorably employed to introduce nucleotide diversity. Many mutagenesis methods are found in the above-cited references; additional details regarding mutagenesis methods can be found in following, which can also be applied to the present invention. For example, error-prone PCR can be used to generate nucleic acid variants. Using this technique, PCR is performed under conditions where the copying fidelity of the DNA polymerase is low, such that a high rate of point mutations is obtained along the entire length of the PCR product. Examples of such techniques are found in the references above and, e.g., in Leung et al. (1989) Technique 1:11-15 and Caldwell et al. (1992) PCR Methods Applic. 2:28-33. Similarly, assembly PCR can be used, in a process which involves the assembly of a PCR product from a mixture of small DNA fragments. A large number of different PCR reactions can occur in parallel in the same reaction mixture, with the products of one reaction priming the products of another reaction.

Oligonucleotide directed mutagenesis can be used to introduce site-specific mutations in a nucleic acid sequence of interest. Examples of such techniques are found in the references above and, e.g., in Reidhaar-Olson et al. (1988) Science, 241:53-57. Similarly, cassette mutagenesis can be used in a process that replaces a small region of a double stranded DNA molecule with a synthetic oligonucleotide cassette that differs from the native sequence. The oligonucleotide can contain, e.g., completely and/or partially randomized native sequence(s).

Recursive ensemble mutagenesis is a process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are found in Arkin & Youvan (1992) Proc. Natl. Acad. Sci. USA 89:7811-7815. Exponential ensemble mutagenesis can be used for generating combinatorial libraries with a high percentage of unique and functional mutants. Small groups of residues in a sequence of interest are randomized in parallel to identify, at each altered position, amino acids which lead to functional proteins. Examples of such procedures are in Delegrave & Youvan (1993) Biotechnology Research 11:1548-1552.

In vivo mutagenesis can be used to generate random mutations in any cloned DNA of interest by propagating the DNA, e.g., in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA. Such procedures are described in the references noted above.

Other procedures for introducing diversity into a genome, e.g. a bacterial, fungal, animal or plant genome can be used in conjunction with the above described and/or referenced methods. For example, in addition to the methods above, techniques have been proposed which produce nucleic acid multimers suitable for transformation into a variety of species (see, e.g., Schellenberger U.S. Pat. No. 5,756,316 and the references above). Transformation of a suitable host with such multimers, consisting of genes that are divergent with respect to one another, (e.g., derived from natural diversity or through application of site directed mutagenesis, error prone PCR, passage through mutagenic bacterial strains, and the like), provides a source of nucleic acid diversity for DNA diversification, e.g., by an in vivo recombination process as indicated above.

Alternatively, a multiplicity of monomeric polynucleotides sharing regions of partial sequence similarity can be transformed into a host species and recombined in vivo by the host cell. Subsequent rounds of cell division can be used to generate libraries, members of which, include a single, homogenous population, or pool of monomeric polynucleotides.

Alternatively, the monomeric nucleic acid can be recovered by standard techniques, e.g., PCR and/or cloning, and recombined in any of the recombination formats, including recursive recombination formats, described above.

Methods for generating multispecies expression libraries have been described (in addition to the reference noted above, see, e.g., Peterson et al. (1998) U.S. Pat. No. 5,783,431 "METHODS FOR GENERATING AND SCREENING NOVEL METABOLIC PATHWAYS," and Thompson, et al. (1998) U.S. Pat. No. 5,824,485 METHODS FOR GENERATING AND SCREENING NOVEL METABOLIC PATHWAYS) and their use to identify protein activities of interest has been proposed (In addition to the references noted above, see Short (1999) U.S. Pat. No. 5,958,672 "PROTEIN ACTIVITY SCREENING OF CLONES HAVING DNA FROM UNCULTIVATED MICROORGANISMS"). Multispecies expression libraries include, in general, libraries comprising cDNA or genomic sequences from a plurality of species or strains, operably linked to appropriate regulatory sequences, in an expression cassette. The cDNA and/or genomic sequences are optionally randomly ligated to further enhance diversity. The vector can be a shuttle vector suitable for transformation and expression in more than one species of host organism, e.g., bacterial species, eukaryotic cells. In some cases, the library is biased by preselecting sequences which encode a protein of interest, or which hybridize to a nucleic acid of interest. Any such libraries can be provided as substrates for any of the methods herein described.

The above-described procedures have been largely directed to increasing nucleic acid and/or encoded protein diversity. However, in many cases, not all of the diversity is useful, e.g., functional, and contributes merely to increasing the background of variants that must be screened or selected to identify the few favorable variants. In some applications, it is desirable to preselect or prescreen libraries (e.g., an amplified library, a genomic library, a cDNA library, a normalized library, etc.) or other substrate nucleic acids prior to diversification, e.g., by recombination-based mutagenesis procedures, or to otherwise bias the substrates towards nucleic acids that encode functional products. For example, in the case of antibody engineering, it is possible to bias the diversity generating process toward antibodies with functional antigen binding sites by taking advantage of in vivo recombination events prior to manipulation by any of the described methods. For example, recombined CDRs derived from B cell cDNA libraries can be amplified and assembled into framework regions (e.g., Jirholt et al. (1998) "Exploiting sequence space: shuffling in vivo formed complementarity determining regions into a master framework" Gene 215: 471) prior to diversifying according to any of the methods described herein.

Libraries can be biased towards nucleic acids which encode proteins with desirable enzyme activities. For example, after identifying a clone from a library which exhibits a specified activity, the clone can be mutagenized using any known method for introducing DNA alterations. A library comprising the mutagenized homologues is then screened for a desired activity, which can be the same as or different from the initially specified activity. An example of such a procedure is proposed in Short (1999) U.S. Pat. No. 5,939,250 for "PRODUCTION OF ENZYMES HAVING DESIRED ACTIVITIES BY MUTAGENESIS." Desired activities can be identified by any method known in the art. For example, WO 99/10539 proposes that gene libraries can be screened by combining extracts from the gene library with components obtained from metabolically rich cells and identifying combinations which exhibit the desired activity. It has also been proposed (e.g., WO 98/58085) that clones with desired activities can be identified by inserting bioactive substrates into samples of the library, and detecting bioactive fluorescence corresponding to the product of a desired activity as described herein using a fluorescent analyzer, e.g., a flow cytometry device, a CCD, a fluorometer, or a spectrophotometer.

Libraries can also be biased towards nucleic acids which have specified characteristics, e.g., hybridization to a selected nucleic acid probe. For example, application WO 99/10539 proposes that polynucleotides encoding a desired activity (e.g., an enzymatic activity, for example: a lipase, an esterase, a protease, a glycosidase, a glycosyl transferase, a phosphatase, a kinase, an oxygenase, a peroxidase, a hydrolase, a hydratase, a nitrilase, a transaminase, an amidase or an acylase) can be identified from among genomic DNA sequences in the following manner. Single stranded DNA molecules from a population of genomic DNA are hybridized to a ligand-conjugated probe. The genomic DNA can be derived from either a cultivated or uncultivated microorganism, or from an environmental sample. Alternatively, the genomic DNA can be derived from a multicellular organism, or a tissue derived therefrom. Second strand synthesis can be conducted directly from the hybridization probe used in the capture, with or without prior release from the capture medium or by a wide variety of other strategies known in the art. Alternatively, the isolated single-stranded genomic DNA population can be fragmented without further cloning and used directly in, e.g., a recombination-based approach, that employs a single-stranded template, as described above.

"Non-Stochastic" methods of generating nucleic acids and polypeptides are alleged in Short "Non-Stochastic Generation of Genetic Vaccines and Enzymes" WO 00/46344. These methods, including proposed non-stochastic polynucleotide reassembly and site-saturation mutagenesis methods can be applied to the present invention as well. Random or semi-random mutagenesis using doped or degenerate oligonucleotides is also described in, e.g., Arkin and Youvan (1992) "Optimizing nucleotide mixtures to encode specific subsets of amino acids for semi-random mutagenesis" *Biotechnology* 10:297-300; Reidhaar-Olson et al. (1991) "Random mutagenesis of protein sequences using oligonucleotide cassettes" *Methods Enzymol.* 208:564-86; Lim and Sauer (1991) "The role of internal packing interactions in determining the structure and stability of a protein" *J. Mol. Biol.* 219:359-76; Breyer and Sauer (1989) "Mutational analysis of the fine specificity of binding of monoclonal antibody 51F to lambda repressor" *J. Biol. Chem.* 264:13355-60); and "Walk-Through Mutagenesis" (Crea, R; U.S. Pat. Nos. 5,830,650 and 5,798,208, and EP Patent 0527809 B1.

It will readily be appreciated that any of the above described techniques suitable for enriching a library prior to diversification can also be used to screen the products, or libraries of products, produced by the diversity generating methods.

Kits for mutagenesis, library construction and other diversity generation methods are also commercially available. For example, kits are available from, e.g., Stratagene (e.g., QuickChange™ site-directed mutagenesis kit; and Chameleon™ double-stranded, site-directed mutagenesis kit), Bio/Can Scientific, Bio-Rad (e.g., using the Kunkel method described above), Boehringer Mannheim Corp., Clonetech Laboratories, DNA Technologies, Epicentre Technologies (e.g., 5 prime 3 prime kit); Genpak Inc, Lemargo Inc, Life Technologies (Gibco BRL), New England Biolabs, Pharmacia Biotech, Promega Corp., Quantum Biotechnologies, Amersham International plc (e.g., using the Eckstein method above), and Anglian Biotechnology Ltd (e.g., using the Carter/Winter method above).

The above references provide many mutational formats, including recombination, recursive recombination, recursive mutation and combinations or recombination with other forms of mutagenesis, as well as many modifications of these formats. Regardless of the diversity generation format that is used, the nucleic acids of the invention can be recombined (with each other, or with related (or even unrelated) sequences) to produce a diverse set of recombinant nucleic acids, including, e.g., sets of homologous nucleic acids, as well as corresponding polypeptides.

A recombinant nucleic acid produced by recombining one or more polynucleotide sequences of the invention with one or more additional nucleic acids using any of the above-described formats alone or in combination also forms a part of the invention. The one or more additional nucleic acids may include another polynucleotide of the invention; optionally, alternatively, or in addition, the one or more additional nucleic acid can include, e.g., a nucleic acid encoding a naturally-occurring interferon-alpha or a subsequence thereof, or any homologous interferon-alpha or subsequence thereof (e.g., as found in GenBank or other available literature), or, e.g., any other homologous or non-homologous nucleic acid or fragments thereof (certain recombination formats noted above, notably those performed synthetically or in silico, do not require homology for recombination).

Therapeutic Uses

Various interferon-alpha polypeptides and interferon-alpha conjugates have been approved or are in clinical development for treatment of a variety of diseases or conditions such as Chronic Hepatitis C, Chronic Hepatitis B, Hairy Cell Leukemia, Malignant Melanoma, Follicular Lymphoma, Condylomata Acuminata, AIDS-related Kaposi's Sarcoma, Non-Hodgkin's Lymphoma, Chronic Melogenous Leukemia, Basal Cell Carcinoma, Multiple Myeloma, carcinoid tumors, bladder cancer, Crohn's disease, Cutaneous T Cell Lymphoma, Renal Cell Carcinoma, Multiple Sclerosis, and AIDS. Accordingly, the present invention contemplates the use of a composition comprising one or more polypeptide or conjugate of the invention (i.e., a "composition of the invention") to treat a disease or condition which is responsive to an interferon-alpha polypeptide and/or an interferon-alpha conjugate, such as a condition described above, or any other disease or condition which is responsive to a polypeptide or a conjugate of the invention.

Treatment of Viral Infections and Conditions Associated with Viral Infection

In one aspect, the invention provides a method for treating a subject infected with a virus, comprising administering to the subject a composition of the invention in an amount effective to decrease the level of the virus in the subject and/or to ameliorate a symptom or condition associated with the viral infection. Exemplary viral infections contemplated for treatment methods of the invention include, but are not limited to, infection by a virus of the Flaviviridae family, such as, for example, Hepatitis C Virus, Yellow Fever Virus, West Nile Virus, Japanese Encephalitis Virus, Dengue Virus, and Bovine Viral Diarrhea Virus; infection by a virus of the Hepadnaviridae family, such as, for example, Hepatitis B Virus; infection by a virus of the Picornaviridae family, such as, for example, Encephalomyocarditis Virus, Human Rhinovirus, and Hepatitis A Virus; infection by a virus of the Retroviridae family, such as, for example, Human Immunodeficiency Virus, Simian Immunodeficiency Virus, Human T-Lymphotropic Virus, and Rous Sarcoma Virus; infection by a virus of the Coronaviridae family, such as, for example, SARS coronavirus; infection by a virus of the Rhabdoviridae family, such as, for example, Rabies Virus and Vesicular Stomatitis Virus; infection by a virus of the Paramyxoviridae family, such as, for example, Respiratory Syncytial Virus and Parainfluenza Virus; infection by a virus of the Papillomaviridae family, such as, for example, Human Papillomavirus; and infection by a virus of the Herpesviridae family, such as, for example, Herpes Simplex Virus.

The following provides non-limiting examples for treatment of exemplary viral infections and diseases and conditions associated with such infections, using polypeptides and conjugates of the invention, including suggested dosing schedules for polypeptides and conjugates of the invention and approaches to monitoring the efficacy of such treatments. The dosing schedules of polypeptides or conjugates of the invention for the treatment of other viral infections and diseases and conditions associated with viral infections, and approaches to monitoring the efficacy of such treatments, is ascertainable by one skilled in the art.

Hepatitis C Virus

In one aspect the invention provides a method of treating a patient infected with Hepatitis C Virus (HCV), comprising administering to the patient an effective amount of a composition of the invention comprising one or more polypeptide or conjugate of the invention. The invention also provides a composition for use in treating a patient infected with HCV, comprising one or more polypeptide or conjugate of the invention and a pharmaceutically acceptable carrier or excipient. A patient diagnosed as infected with HCV includes a patient exhibiting HCV RNA in the blood and/or exhibiting anti-HCV antibody in the serum.

A composition comprising a polypeptide of the invention will generally be administered at a dose and frequency similar to what is employed in HCV therapeutic regimens using clinically-approved interferon-alpha polypeptides, such as, e.g. ROFERON®-A (Interferon alfa-2a, recombinant; Hoffmann-La Roche Inc.), INTRON® A (Interferon alfa-2b, recombinant; Schering Corporation), and INFERGEN® (interferon alfacon-1; InterMune, Inc.). Exemplary recommended dosing schedules of ROFERON or INTRON A for the treatment of chronic HCV is 3 million IU (approximately 15 micrograms (mcg)) three times a week by subcutaneous injection for, e.g., 24 to 48 weeks. An exemplary recommended dosing schedule of INFERGEN for the treatment of chronic HCV is 9 mcg three times a week by subcutaneous injection for, e.g., 24 to 48 weeks. Depending on a number of factors (including but not limited to the activity and the pharmacokinetics of the polypeptide of the invention and the size and health of the patient), the polypeptide may be administered in lower amounts (such as, for example, about 2, 3, 4, 5, 6, 7, or 8 mcg) and/or less frequently (such as once per week or twice per week) than described above.

Likewise, a composition comprising a conjugate of the invention will generally be administered at a dose and frequency similar to what is employed in HCV therapeutic regimens using clinically-approved interferon-alpha conjugates, such as, e.g., PEGASYS® (Peginterferon alfa-2a; Hoffmann-La Roche, Inc.) or PEG-INTRON® (peginterferon alfa-2b; Schering Corporation). An exemplary recommended dosing schedule of PEGASYS for the treatment of chronic HCV is 180 mcg once weekly by subcutaneous injection for, e.g., 24 to 48 weeks. Depending on a number of factors (including but not limited to the molecular weight, activity, and pharmacokinetics of the conjugate of the invention and the size and health of the patient), the conjugate may be administered in lower amounts (such as, for example, about 25, 50, 75, 100, 125, or 150 mcg) and/or less frequently (such as once every 10 days, or once every 2 weeks) than described above.

In some instances the polypeptide or conjugate of the invention is administered in combination with one or more additional therapeutic agent(s). For example, the polypeptide or conjugate of the invention may be administered in combination with a small-molecule antiviral drug such as Ribavirin, which is sold under the names COPEGUS® (Hoffmann-La Roche, Inc) and REBETOL® (Schering Corporation). Alternatively, or in addition to a small-molecule antiviral drug, the polypeptide or conjugate of the invention may be administered in combination with one or more additional cytokine, such as, for example, IFN-gamma, which is sold under the name Actimmune® (interferon gamma-1b; InterMune, Inc.), IL-2, which is sold under the name PROLEUKIN® IL-2 (aldesleukin recombinant human interleukin-2 (rhIL-2); Chiron Corp.), or IL-12 (interleukin-12).

The precise amount and frequency of administration of the polypeptide or conjugate of the invention will depend on a number of factors such as the specific activity and the pharmacokinetic properties of the polypeptide or the conjugate, as well as the nature of the condition being treated (such as, the genotype of the Hepatitis C virus being treated), among other factors known to those of skill in the art. Normally, the dose should be capable of preventing or lessening the severity or spread of the indication being treated. Such a dose may be termed an "effective" or "therapeutically effective" amount. It will be apparent to those of skill in the art that an effective amount of a polypeptide, conjugate or composition of the invention depends, inter alia, upon the condition being treated, the dose, the administration schedule, whether the polypeptide or conjugate or composition is administered alone or in combination with other therapeutic agents, the serum half-life and other pharmacokinetic properties of the polypeptide, conjugate or composition, as well as the size, age, and general health of the patient. The dosage and frequency of administration is ascertainable by one skilled in the art using known techniques.

The effectiveness of treatment may be determined by measuring viral load, for example by determining the titer or level of virus in serum or plasma using methods known in the art, such as, e.g., by monitoring viral RNA levels using quantitative PCR-based tests, such as the COBAS AMPLICOR® HCV Test, v2.0 or the COBAS AMPLICOR HCV MONITOR® Test, v2.0 (both from Roche Diagnostics). In some instances, an effective amount of a composition of the invention is one that is sufficient to achieve a reduction in viral load by at least 2 log units, at least 3 log units, at least 4 log units, at least 5 log units, at least 6 log units or at least 7 log units over the course of treatment, compared to the viral load prior to treatment (which is generally in the range of $10^5$-$10^7$ copies of HCV RNA/ml for chronic HCV patients). In some instances an effective amount of a composition of the invention is an amount that is sufficient to reduce viral load to levels which are essentially undetectable, such as, for example, less than about 500 copies/ml serum or less than about 100 copies/ml serum. The invention includes a method of reducing the level of HCV RNA in serum of a patient infected with HCV, comprising administering to the patient a composition of the invention in an amount effective to reduce the level of HCV RNA compared to the HCV RNA level present prior to the start of treatment.

The effectiveness of treatment may alternatively or in addition be determined by measuring a parameter indicative of a condition associated with HCV infection, such as, e.g., liver damage. For example, the level of serum alanine aminotransferase (ALT) may be measured using a standard assay. In general, an ALT level of less than about 50 international units/ml (IU/ml) serum is considered normal. A higher ALT level may be indicative of ongoing liver damage. In some instances, an effective amount of a composition of the invention is an amount effective to reduce ALT level, in a patient with a higher than normal ALT level, to less than about 50 IU/ml of serum. Thus, the invention includes a method of reducing the serum ALT level of a patient infected with HCV exhibiting an initial ALT level greater than 50 IU/ml, comprising administering to the patient a composition of the invention in an amount effective to reduce the ALT level to less than about 50 IU/ml.

Human Immunodeficiency Virus

In another aspect the invention provides a method of treating a patient infected with Human Immunodeficiency Virus (HIV), such as HIV-1 or HIV-2, or a disease or condition associated with HIV infection, such as, for example, AIDS-related Kaposi's sarcoma, comprising administering to the patient an effective amount of a composition of the invention comprising one or more polypeptide or conjugate of the invention, optionally in association with other antiviral therapeutic agents as described below. The invention also provides a composition for use in treating a patient infected with HIV or a disease or condition associated with HIV infection, comprising one or more polypeptide or conjugate of the invention and a pharmaceutically acceptable carrier or excipient. A patient diagnosed as infected with HIV includes a patient exhibiting detectable levels of HIV RNA or proviral DNA in the blood, and/or exhibiting detectable levels of p24 antigen or anti-HIV antibody in serum.

A composition comprising a polypeptide of the invention will generally be administered at a dose and frequency similar to what is employed in HIV therapeutic regimens using interferon-alpha polypeptides such as, e.g. ROFERON®-A (Interferon alfa-2a, recombinant; Hoffmann-La Roche Inc.), INTRON® A (Interferon alfa-2b, recombinant; Schering Corporation), and INFERGEN® (interferon alfacon-1; InterMune, Inc.). As was noted above, exemplary recommended dosing schedules of ROFERON or INTRON A for the treatment of chronic HCV is 3 million IU (approximately 15 micrograms (mcg)) three times a week by subcutaneous injection for, e.g., 24 to 48 weeks, and a exemplary recommended dosing schedule of INFERGEN for the treatment of chronic HCV is 9 mcg three times a week by subcutaneous injection for, e.g., 24 to 48 weeks. An exemplary recommended dosing schedule of ROFERON for the treatment of AIDS-related Kaposi's sarcoma is 36 million units daily for 10 to 12 weeks, then 36 million units 3 times a week. An exemplary recommended dosing schedule of INTRON A for the treatment of AIDS-related Kaposi's sarcoma is 30 million IU/m2 three times a week administered subcutaneously. Such dosing schedules provide useful ranges for dosage of a polypeptide of the invention for the treatment of HIV or a disease or condition associated with HIV infection. Depending on a number of factors (including but not limited to the activity and the pharmacokinetics of the polypeptide of the invention and the size, age and health of the patient), the polypeptide of the invention may be administered in lower amounts and/or less frequently than described above.

Likewise, a composition comprising a conjugate of the invention will generally be administered at a dose and frequency similar to what is employed in HIV therapeutic regimens using interferon-alpha conjugates, such as, e.g., PEGASYS® (Peginterferon alfa-2a; Hoffmann-La Roche, Inc.) or PEG-INTRON® (peginterferon alfa-2b; Schering Corporation). An exemplary dosing schedule of PEG-INTRON for the treatment of HIV is between about 1.0 mcg/kg/week and 3.0 mcg/kg/week by subcutaneous injection for, e.g., 24 to 48 weeks. Such a dosing schedule provides a useful range for dosage of a conjugate of the invention for the treatment of HIV. Depending on a number of factors (including but not limited to the molecular weight, activity, and pharmacokinetics of the conjugate of the invention and the size, age and health of the patient), the conjugate may be administered in lower amounts (such as, for example, about 0.1, 0.25, 0.50, or 0.75 mcg/kg/week) and/or less frequently (such as once every 10 days, or once every 2 weeks) than described above.

In some instances the polypeptide or conjugate of the invention is administered in combination with one or more additional therapeutic agent(s). Current clinical treatments of HIV-1 infection in man include multi-drug combination therapies generally termed Highly Active Antiretroviral Therapy ("HAART"). The polypeptide or conjugate of the invention may thus be administered in combination with HAART or other antiviral therapeutic compounds. Typical components of HAART, which involve various combinations of nucleoside reverse transcriptase inhibitors ("NRTI"), non-nucleoside reverse transcriptase inhibitors ("NNRTI") and HIV protease inhibitors ("PI"), are described, for example, in A. M. Vandamme et al. (1998) Antiviral Chemistry & Chemotherapy, 9:187-203; "Drugs for HIV Infection" in The Medical Letter Vol. 39 (Issue 1015) Dec. 5, 1997, pages 111-116; and published United States Patent Application US 20020182179 A1; each of which is incorporated by reference herein. If the HIV-infected patient is also infected with HCV, the polypeptide or conjugate of the invention may be administered in combination with an antiviral drug such as Ribavirin, which is sold under the names COPEGUS® (Hoffmann-La Roche, Inc) and REBETOL® (Schering Corporation), along with HAART.

The precise amount and frequency of administration of the polypeptide or conjugate of the invention, and administration of additional therapeutic agents such as HAART and/or Ribavirin, will depend on a number of factors such as the specific activity and the pharmacokinetic properties of the polypeptide or the conjugate, as well as the nature of the condition being treated (such as, the presence of additional viral infections such as HCV), among other factors known to those of skill in the art. Normally, the dose should be capable of preventing or lessening the severity or spread of the indication being treated. Such a dose may be termed an "effective" or "therapeutically effective" amount. It will be apparent to those of skill in the art that an effective amount of a polypeptide, conjugate or composition of the invention depends, inter alia, upon the condition being treated, the dose, the administration schedule, whether the polypeptide or conjugate or composition is administered alone or in combination with other therapeutic agents, the serum half-life and other pharmacokinetic properties of the polypeptide, conjugate or composition, as well as the size, age, and general health of the patient. The dosage and frequency of administration is ascertainable by one skilled in the art using known techniques.

In addition to general uses described above, a polypeptide or conjugate of the invention may be administered to the following subsets of patients infected with HIV: as an adjuvant therapy, for example to HAART as described above; as monotherapy or combination therapy in early stage patients when the viral load is generally high; as a combined anti-viral and immunodulatory agent for patients undergoing structured treatment interruptions (STI) or "drug holidays"; as salvage therapy in patients whose HAART options are limited; as an antiviral method of treatment to keep viral load in check without initiating HAART therapy in order to delay the appearance of HAART resistant virus.

The effectiveness of treatment may be determined by measuring viral load, for example by determining the titer or level of virus in serum or plasma using methods known in the art, such as, e.g., by monitoring HIV-1 viral RNA levels using quantitative RT-PCR based tests, such as the AMPLICOR HIV-1 MONITOR® Test, v1.5 (Roche Diagnostics). In some instances, an effective amount of a composition of the invention is one that is sufficient to achieve a reduction in viral load by at least 0.5 log units, at least 1 log unit, at least 2 log units, at least 3 log units, at least 4 log units, at least 5 log units, at least 6 log units or at least 7 log units over the course of treatment, compared to the viral load prior to treatment. In some instances an effective amount of a composition of the invention is an amount that is sufficient to reduce viral load to levels which are essentially undetectable, such as, for example, less than about 50-100 copies HIV-1 RNA per ml serum. The invention includes a method of reducing the level of HIV RNA in serum of a patient infected with HIV, comprising administering to the patient a composition of the invention in an amount effective to reduce the level of HIV RNA compared to the HIV RNA level present prior to the start of treatment.

The effectiveness of treatment may alternatively or in addition be determined by a serum markers for HIV replication, such as the presence of HIV p24 antigen in the blood. In some instances an effective amount of a composition of the invention is an amount that is sufficient to reduce the level of p24 antigen in the blood to 50%, 25%, 10% or 5% of the level present prior to the start of treatment. In some instances an effective amount of a composition of the invention is an amount that is sufficient to reduce the level of p24 antigen to a level which is essentially undetectable. The invention includes a method of reducing the level of p24 antigen in serum of a patient infected with HIV, comprising administering to the patient a composition of the invention in an amount effective to reduce the level of p24 antigen compared to the p24 antigen level present prior to the start of treatment.

Hepatitis B Virus

In another aspect, the invention provides a method of treating a patient infected with Hepatitis B Virus (HBV), comprising administering to the patient an effective amount of a composition of the invention comprising one or more polypeptide or conjugate of the invention. The invention also provides a composition for use in treating a patient infected with HBV, comprising one or more polypeptide or conjugate of the invention and a pharmaceutically acceptable carrier or excipient.

A patient diagnosed as infected with HBV exhibits detectable hepatitis B surface antigen (HBsAg) in the serum. Chronic HBV infection is further categorized as either "replicative" or "non-replicative". In replicative infection, the patient usually has a relatively high serum concentration of viral DNA and detectable HBeAg, which is an alternatively processed protein of the HBV pre-core gene that is synthesized under conditions of high viral replication. However, in rare strains of HBV with mutations in the pre-core gene, replicative infection can occur in the absence of detectable serum HBeAg. Patients with chronic hepatitis B and replicative infection have a generally worse prognosis and a greater chance of developing cirrhosis and/or hepatocellular carcinoma than those without HBeAg. In non-replicative infection, the rate of viral replication in the liver is low, serum HBV DNA concentration is generally low and hepatitis Be antigen (HBeAg) is not detected.

A composition comprising a polypeptide of the invention will generally be administered at a dose and frequency similar to what is employed in HBV therapeutic regimens using clinically-approved interferon-alpha polypeptides, such as, e.g. INTRON® A (Interferon alfa-2b, recombinant; Schering Corporation). An exemplary recommended dosing schedule of INTRON A for the treatment of chronic HBV in adults is 30 to 35 million IU per week by subcutaneous or intramuscular injection, either as 5 million IU per day (qd) or as 10 million IU three times per week (tiw) for 16 weeks. Depending on a number of factors (including, but not limited to, the activity and the pharmacokinetics of the polypeptide of the invention, and the size and health of the patient), the polypeptide of the invention may be administered in lower amounts (such as, for example, about 5, 10, 15, 20, or 25 million IU per week) and/or less frequently (such as once per week or twice per week) than described above.

Likewise, a composition comprising a conjugate of the invention will generally be administered at a dose and frequency similar to what is employed in HBV therapeutic regimens using interferon-alpha conjugates currently undergoing clinical trials, such as, e.g., PEGASYS® (Peginterferon alfa-2a; Hoffmann-La Roche, Inc.). Exemplary dosing schedules of PEGASYS for the treatment of chronic HBV is between 90 mcg-270 mcg injected once per week for a total of 24 weeks. Depending on a number of factors (including but not limited to the molecular weight, activity, and pharmacokinetics of the conjugate of the invention and the size and health of the patient), the conjugate may be administered in lower amounts (such as, for example, about 25, 50, 75, 100, 125, 150, or 200 mcg) and/or less frequently (such as once every 10 days, or once every 2 weeks) than described above.

In some instances the polypeptide or conjugate of the invention is administered in combination with one or more additional therapeutic agent(s). For example, the polypeptide or conjugate of the invention may be administered in combination with antiviral drugs such as lamivudine (also known as 3TC), which is sold under the name Epivir-HBV® (GlaxoSmithKline), or adefovir dipivoxil, which is sold under the name Hepsera® (Gilead Sciences).

The precise amount and frequency of administration of the polypeptide or conjugate of the invention will depend on a number of factors such as the specific activity and the pharmacokinetic properties of the polypeptide or the conjugate, as well as the nature of the condition being treated (such as, e.g., in the case of chronic HBV infection, whether the infection is replicative or non-replicative), among other factors known to those of skill in the art. Normally, the dose should be capable of preventing or lessening the severity or spread of the indication being treated. Such a dose may be termed an "effective" or "therapeutically effective" amount. It will be apparent to those of skill in the art that an effective amount of a polypeptide, conjugate or composition of the invention depends, inter alia, upon the condition being treated, the dose, the administration schedule, whether the polypeptide or conjugate or composition is administered alone or in combination with other therapeutic agents, the serum half-life and other pharmacokinetic properties of the polypeptide, conjugate or composition, as well as the size, age, and general health of the patient. The dosage and frequency of administration is ascertainable by one skilled in the art using known techniques.

The effectiveness of treatment may be determined for example by measuring the viral load, e.g. the level of viral DNA in serum or plasma, using methods known in the art. Methods for monitoring HBV DNA levels include quantitative PCR-based tests, such as the COBAS AMPLICOR HBV MONITOR® Test, v2.0 or the AMPLICOR HBV MONITOR® Test, v2.0 (both from Roche Diagnostics). In some instances an effective amount of a composition of the invention is an amount that is sufficient to reduce viral DNA to, e.g., less than about 500,000 copies/ml serum or less than about 100,000 copies/ml serum or less than about 10,000 copies/ml serum, or to levels which are essentially undetectable (such as, for example, less than about 1000 copies/ml serum, less than about 500 copies/ml serum, or less than about 200 copies/ml serum). The invention includes a method of reducing the level of HBV DNA in serum of a patient infected with HBV, comprising administering to the patient a composition of the invention in an amount effective to reduce the level of HBV DNA compared to the HBV DNA level present prior to the start of treatment.

The effectiveness of treatment may alternatively or in addition be determined by measuring other serum markers for HBV replication, such as HBeAg. In some instances an effective amount of a composition of the invention is an amount that is sufficient to reduce the level of HBeAg in serum to 50%, 25%, 10% or 5% of the level present prior to the start of treatment. In some instances an effective amount of a composition of the invention is an amount that is sufficient to reduce the level of HBeAg to a level which is essentially undetectable. The invention includes a method of reducing the level of HBeAg in serum of a patient infected with HBV, comprising administering to the patient a composition of the invention in an amount effective to reduce the level of HBeAg compared to the HBeAg level present prior to the start of treatment.

As discussed above, another serum marker indicative of HBV infection is HBsAg. Thus, the effectiveness of treatment may alternatively or in addition be determined by measuring the level of HBsAg in the serum. In some instances an effective amount of a composition of the invention is an amount that is sufficient to reduce the level of HBsAg in serum to 50%, 25%, 10% or 5% of the level present prior to the start of treatment. In some instances an effective amount of a composition of the invention is an amount that is sufficient to reduce level of HBsAg to a level which is essentially undetectable. The invention includes a method of reducing the level of HBsAg in serum of a patient infected with HBV, comprising administering to the patient a composition of the invention in an amount effective to reduce the level of HBsAg compared to the HBsAg level present prior to the start of treatment.

The effectiveness of treatment may alternatively or in addition be determined by measuring a parameter indicative of a condition associated with HBV infection, such as, e.g., liver damage. For example, the level of serum alanine aminotransferase (ALT) may be measured using a standard assay. In general, an ALT level of less than about 50 international units/ml (IU/ml) serum is considered normal. A higher ALT level may be indicative of ongoing liver damage. In some instances, an effective amount of a composition of the invention is an amount effective to reduce ALT level, in a patient with a higher than normal ALT level, to less than about 50 IU/ml of serum. Thus, the invention includes a method of reducing the serum ALT level of a patient infected with HBV exhibiting an initial ALT level greater than 50 IU/ml, comprising administering to the patient a composition of the invention in an amount effective to reduce the ALT level to less than about 50 IU/ml.

Human T-Lymphotropic Virus

In another aspect the invention provides a method of treating a patient infected with a Human T-Lymphotropic Virus, such as Human T-Lymphotropic Virus type 1 (HTLV-1), or a disease or condition associated with HTLV-1 infection, such as, for example, adult T-cell leukemia/lymphoma (ATLL), HTLV-1-associated myelopathy (HAM), Tropical Spastic Paraparesis (TSP), uveitis, or arthropathy. The method comprises administering to the patient an effective amount of a composition of the invention comprising one or more polypeptide or conjugate of the invention. The invention also provides a composition for use in treating a patient infected with HTLV-1, or a disease or condition associated with HTLV-1 infection, the composition comprising one or more polypeptide or conjugate of the invention and a pharmaceutically acceptable carrier or excipient. A patient diagnosed with HTLV-1 infection includes a patient exhibiting HTLV-1 proviral DNA in the blood and/or antibody to an HTLV-1 antigen in the serum.

A composition comprising a polypeptide of the invention will generally be administered at a dose and frequency similar to what is employed in HCV or oncology therapeutic regimens using clinically-approved interferon-alpha polypeptides, such as, e.g. ROFERON®-A (Interferon alfa-2a, recombinant; Hoffmann-La Roche Inc.) and INTRON® A (Interferon alfa-2b, recombinant; Schering Corporation). Exemplary recommended dosing schedules of ROFERON or INTRON A for the treatment of chronic HCV is 3 million IU (approximately 15 micrograms (mcg)) three times a week by subcutaneous injection for, e.g., 24 to 48 weeks. An exemplary recommended dosing schedule of ROFERON for the treatment of hairy-cell leukemia is 3-5 million units daily by subcutaneous injection for 16 to 24 weeks, then 3 million units 3 times a week for maintenance. An exemplary recommended dosing schedule of INTRON A for the treatment of hairy-cell leukemia is 2 million IU/m2 (square meter of body surface) administered subcutaneously 3 times a week for 6 months. Such dosing schedules provide useful ranges for dosage of a polypeptide of the invention for the treatment of HTLV-1 infection, or a disease or condition associated with HTLV-1 infection such as adult T-cell leukemia/lymphoma (ATLL), HTLV-1-associated myelopathy (HAM), or Tropical Spastic Paraparesis (TSP). Depending on a number of factors (including but not limited to the activity and the pharmacokinetics of the polypeptide of the invention and the size, age and health of the patient), the polypeptide may be administered in lower amounts and/or less frequently than described above.

Likewise, a composition comprising a conjugate of the invention will generally be administered at a dose and frequency similar to what is employed in HCV therapeutic or oncology therapeutic regimens using clinically-approved interferon-alpha conjugates, such as, e.g., PEGASYS® (Peginterferon alfa-2a; Hoffmann-La Roche, Inc.) or PEG-INTRON® (peginterferon alfa-2b; Schering Corporation). An exemplary recommended dosing schedule of PEGASYS for the treatment of chronic HCV is 180 mcg once weekly by subcutaneous injection for, e.g., 24 to 48 weeks. An exemplary recommended dosing schedule of PEG-INTRON for the treatment of chronic myelogenous leukemia is 6 mcg/kg body weight once weekly by subcutaneous injection for, e.g., 52 weeks. Such dosing schedules provide useful ranges for dosage of a conjugate of the invention for the treatment of HTLV-1 infection, or a disease or condition associated with HTLV-1 infection such as adult T-cell leukemia/lymphoma (ATLL), HTLV-1-associated myelopathy (HAM), or Tropical Spastic Paraparesis (TSP). Depending on a number of factors (including but not limited to the molecular weight, activity, and pharmacokinetics of the conjugate of the invention and the size, age and health of the patient), the conjugate may be administered in lower amounts and/or less frequently than described above.

In some instances the polypeptide or conjugate of the invention is administered in combination with one or more additional therapeutic agent(s). For example, the polypeptide or conjugate of the invention may be administered in combination with an antiretroviral drug such as zidovudine (AZT) and/or lamivudine (3TC). It may also be administered in combination with peripheral blood stem cell transplantation, conventional chemotherapy, or high dose chemotherapy with autologous or allogeneic bone marrow transplantation. Alternatively, the polypeptide or conjugate of the invention may be combined with other immunotherapy, for example with anti-interleukin-2 receptor monoclonal antibodies or injection of cytotoxic T-cells directed against virus antigens.

The precise amount and frequency of administration of the polypeptide or conjugate of the invention will depend on a number of factors such as the specific activity and the pharmacokinetic properties of the polypeptide or the conjugate, as well as the nature of the condition being treated, among other factors known to those of skill in the art. Normally, the dose should be capable of preventing or lessening the severity or spread of the indication being treated. Such a dose may be termed an "effective" or "therapeutically effective" amount. It will be apparent to those of skill in the art that an effective amount of a polypeptide, conjugate or composition of the invention depends, inter alia, upon the condition being treated, the dose, the administration schedule, whether the polypeptide or conjugate or composition is administered alone or in combination with other therapeutic agents, the serum half-life and other pharmacokinetic properties of the polypeptide, conjugate or composition, as well as the size, age, and general health of the patient. The dosage and frequency of administration is ascertainable by one skilled in the art using known techniques.

The effectiveness of treatment may be determined by measuring the HTLV-1 viral load, such as, for example, measuring the level of HTLV-1 proviral DNA in the blood using methods known in the art, for example by quantitative PCR as described by Saito et al., (2004) J. Infect Dis. 189(1):29-40. In some instances, an effective amount of a composition of the invention is one that is sufficient to achieve a reduction in viral load by at least 0.5 log unit, such as at least 1 log unit, at least 2 log units, at least 3 log units, at least 4 log units, at least 5 log units, at least 6 log units, or at least 7 log units over the course of treatment, compared to the viral load prior to treatment. In some instances an effective amount of a composition of the invention is an amount that is sufficient to reduce viral load to levels which are essentially undetectable. The invention includes a method of reducing the level of HTLV-1 proviral DNA in blood of a patient infected with HTLV-1, comprising administering to the patient a composition of the invention in an amount effective to reduce the level of HTLV-1 proviral DNA compared to that present prior to the start of treatment.

The effectiveness of treatment may alternatively or in addition be determined by measuring titer of an anti-HTLV-1 antibody in the serum, using methods known in the art, such as, for example, by commercially-available tests such as INNO-LIA™ HTLV I/II (Innogenetics; Gent Belgium) and Abbott HTLV-I/HTLV-II EIA (Abbott Laboratories; Abbott Park, Ill.). In some instances an effective amount of a composition of the invention is an amount that is sufficient to reduce the titer of an anti-HTLV-1 antibody in the serum to 50%, 25%, 10% or 5% of the titer present prior to the start of treatment. In some instances an effective amount of a composition of the invention is an amount that is sufficient to reduce the titer of an anti-HTLV-1 antibody in the serum to a level which is essentially undetectable. The invention includes a method of reducing the titer of an anti-HTLV-1 antibody in the serum of a patient infected with HTLV-1, comprising administering to the patient a composition of the invention in an amount effective to reduce the titer of the anti-HTLV-1 antibody in the serum compared to that present prior to the start of treatment.

Human Papillomavirus

In another aspect the invention provides a method of treating a patient infected with a Human Papillomavirus (HPV), or a disease or condition associated with HPV infection, such as, for example, warts of the hands and feet, or lesions of the mucous membranes of the oral, anal and genital cavities. While some types of HPV are relatively harmless, other types are spread through sexual contact and give rise to genital or venereal warts (termed condylomata acuminata) which may give rise to cervical cancer and other genital cancers. The method comprises administering to the patient infected with HPV an effective amount of a composition of the invention comprising one or more polypeptide or conjugate of the invention. The invention also provides a composition for use in treating a patient infected with HPV, or a disease or condition associated with HPV infection, the composition comprising one or more polypeptide or conjugate of the invention and a pharmaceutically acceptable carrier or excipient. A patient diagnosed with HPV infection includes a patient exhibiting HPV viral DNA in biopsied tissue (such as genital tissue), and sometimes (but not always) exhibiting visible lesions, e.g. on genital tissues.

A composition comprising a polypeptide of the invention will generally be administered at a dose and frequency similar to what is employed in HPV therapeutic regimens using clinically-approved interferon-alpha polypeptides, such as, for example, INTRON® A (Interferon alfa-2b, recombinant; Schering Corporation). A recommended dose of INTRON A for the treatment of condylomata acuminata is 1.0 million IU injected into each lesion, for up to 5 lesions, using a tuberculin or similar syringe and a 25- to 30-gauge needle, three times per week on alternate days, for 3 weeks. Patients with 6 to 10 condylomata may receive a second (sequential) course of treatment at the above dosage schedule, to treat up to five additional condylomata per course of treatment. Patients with greater than 10 condylomata may receive additional sequences depending on how large a number of condylomata are present. The interferon may alternatively or in addition be applied topically, e.g. in a cream or ointment form (as described for example in Stentella et al. (1996) Clin. Exp. Obstet. Gynecol. 23(1):29-36). Such dosing schedules provide useful ranges for dosage of a polypeptide of the invention for the treatment of HPV infection, or a disease or condition associated with HPV infection such as condylomata acuminata. Depending on a number of factors (including but not limited to the activity and the pharmacokinetics of the polypeptide of the invention and the size, age and health of the patient), the polypeptide of the invention may be administered in lower amounts and/or less frequently than described above. Likewise, a composition comprising a conjugate of the invention will generally be administered, e.g. intralesionally or topically, at a dose effective to reduce the amount of HPV viral DNA in the effected tissues or to reduce the size/or number of genital lesions in the infected individual.

In some instances the polypeptide or conjugate of the invention is administered in combination with one or more additional therapeutic agent(s). For example, the polypeptide or conjugate of the invention may be administered in combination with an anti-HPV therapeutic such as Podofilox (Condylox) and/or Podophyllin (Pododerm, Podocon-25).

The precise amount and frequency of administration of the polypeptide or conjugate of the invention will depend on a number of factors such as the specific activity and the pharmacokinetic properties of the polypeptide or the conjugate, as well as the nature of the condition being treated, among other factors known to those of skill in the art. Normally, the dose should be capable of preventing or lessening the severity or spread of the indication being treated. Such a dose may be termed an "effective" or "therapeutically effective" amount. It will be apparent to those of skill in the art that an effective amount of a polypeptide, conjugate or composition of the invention depends, inter alia, upon the condition being treated, the dose, the administration schedule, whether the polypeptide or conjugate or composition is administered alone or in combination with other therapeutic agents, the serum half-life and other pharmacokinetic properties of the polypeptide, conjugate or composition, as well as the size, age, and general health of the patient. The dosage and frequency of administration is ascertainable by one skilled in the art using known techniques.

The effectiveness of treatment may be determined by measuring the HPV viral load, such as, for example, measuring the level of HPV viral DNA in biopsied tissue. In some instances, an effective amount of a composition of the invention is one that is sufficient to achieve a reduction in viral load by at least 0.5 log unit, such as at least 1 log unit, at least 2 log units, at least 3 log units, at least 4 log units, at least 5 log units, at least 6 log units, or at least 7 log units over the course of treatment, compared to the viral load prior to treatment. In some instances an effective amount of a composition of the invention is an amount that is sufficient to reduce viral load to levels which are essentially undetectable. The invention includes a method of reducing the level of HPV viral DNA in tissue of a patient infected with HPV, comprising administering to the patient a composition of the invention in an amount effective to reduce the level of HPV viral DNA compared to that present prior to the start of treatment.

The effectiveness of treatment may alternatively or in addition be determined by observing the size or number of genital lesions (condylomata) in the infected individual. In some instances an effective amount of a composition of the invention is an amount that is sufficient to reduce the size and/or number of condylomata in the infected individual. The invention includes a method of reducing reduce the size and/or number of condylomata in a patient infected with HPV, comprising administering to the patient a composition of the invention in an amount effective to reduce the size and/or number of condylomata in the patient compared to those present prior to the start of treatment.

Formulations and Routes of Administration

Therapeutic formulations of the polypeptide or conjugate of the invention are typically administered in a composition that includes one or more pharmaceutically acceptable carriers or excipients. Such pharmaceutical compositions may be prepared in a manner known per se in the art to result in a polypeptide pharmaceutical that is sufficiently storage-stable and is suitable for administration to humans or animals.

Drug Form

The polypeptide or conjugate of the invention can be used "as is" and/or in a salt form thereof. Suitable salts include, but are not limited to, salts with alkali metals or alkaline earth metals, such as sodium, potassium, calcium and magnesium, as well as e.g. zinc salts. These salts or complexes may by present as a crystalline and/or amorphous structure.

Excipients

"Pharmaceutically acceptable" means a carrier or excipient that at the dosages and concentrations employed does not cause any untoward effects in the patients to whom it is administered. Such pharmaceutically acceptable carriers and excipients are well known in the art (see Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)).

Mix of Drugs

The composition of the invention may be administered alone or in conjunction with other therapeutic agents. Ribavirin, for example, is often co-administered with IFN-alpha and has been shown to increase efficacy in antiviral treatments, such as HCV treatment. A variety of small molecules are being developed against both viral targets (viral proteases, viral polymerase, assembly of viral replication complexes) and host targets (host proteases required for viral processing, host kinases required for phosphorylation of viral targets such as NS5A and inhibitors of host factors required to efficiently utilize the viral IRES). Other cytokines may be co-administered, such as for example IL-2, IL-12, IL-23, IL-27, or IFN-gamma. These agents may be incorporated as part of the same pharmaceutical composition or may be administered separately from the polypeptide or conjugate of the invention, either concurrently or in accordance with another treatment schedule. In addition, the polypeptide, conjugate or composition of the invention may be used as an adjuvant to other therapies.

Patients

A "patient" for the purposes of the present invention includes both humans and other mammals. Thus the methods are applicable to both human therapy and veterinary applications.

Types of Composition and Administration Route

The pharmaceutical composition comprising the polypeptide or conjugate of the invention may be formulated in a variety of forms, e.g. as a liquid, gel, lyophilized, or as a compressed solid. The preferred form will depend upon the particular indication being treated and will be apparent to one skilled in the art.

The administration of the formulations of the present invention can be performed in a variety of ways, including, but not limited to, orally, subcutaneously, intravenously, intracerebrally, intranasally, transdermally, intraperitoneally, intramuscularly, intrapulmonary, vaginally, rectally, intraocularly, or in any other acceptable manner. The formulations can be administered continuously by infusion, although bolus injection is acceptable, using techniques well known in the art, such as pumps (e.g., subcutaneous osmotic pumps) or implantation. In some instances the formulations may be directly applied as a solution, cream, ointment, or spray.

Parenterals

An example of a pharmaceutical composition is a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

Parenterals may be prepared for storage as lyophilized formulations or aqueous solutions by mixing, as appropriate, the polypeptide having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives are added to retard microbial growth, and are typically added in amounts of about 0.2%-1% (w/v). Suitable preservatives for use with the present invention include phenol, benzyl alcohol, meta-cresol, methyl paraben, propyl paraben, octadecyldimethylbenzyl ammonium chloride, benzalkonium halides (e.g. benzalkonium chloride, bromide or iodide), hexamethonium chloride, alkyl parabens such as methyl or propyl paraben, catechol, resorcinol, cyclohexanol and 3-pentanol.

Isotonicifiers are added to ensure isotonicity of liquid compositions and include polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, α-monothioglycerol and sodium thiosulfate; low molecular weight polypeptides (i.e. <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active protein weight.

Non-ionic surfactants or detergents (also known as "wetting agents") may be present to help solubilize the therapeutic agent as well as to protect the therapeutic polypeptide against agitation-induced aggregation, which also permits the formulation to be exposed to shear surface stress without causing denaturation of the polypeptide. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.).

Additional miscellaneous excipients include bulking agents or fillers (e.g. starch), chelating agents (e.g. EDTA), antioxidants (e.g., ascorbic acid, methionine, vitamin E) and cosolvents.

The active ingredient may also be entrapped in microcapsules prepared, for example, by coacervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington's Pharmaceutical Sciences, supra.

In one aspect of the invention the composition is a liquid composition, such as an aqueous composition, and comprises a sulfoalkyl ether cyclodextrin derivative of the formula

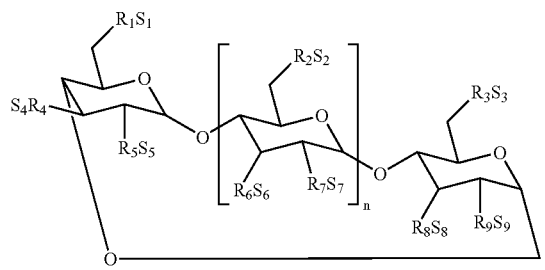

wherein n is 4, 5 or 6; $R_1$, $R_2$, $R_3$, $R_4$, $R_5$, $R_6$, $R_7$, $R_8$, and $R_9$ are each, independently, —O— or a —O—$(C_2$-$C_6$ alkyl)-$SO_3$— group, wherein at least one of $R_1$, $R_2$ or $R_3$ is independently a —O—$(C_2$-$C_6$ alkyl)-$SO_3$— group; and $S_1$, $S_2$, $S_3$, $S_4$, $S_5$, $S_6$, $S_7$, $S_8$, and $S_p$ are each, independently, a pharmaceutically acceptable cation, including $H^+$.

It should be noted that when n=4, the sulfoalkyl ether cyclodextrin may also be referred to as a α-sulfoalkyl ether cyclodextrin. In a similar way, when n=5, the term β-sulfoalkyl ether cyclodextrin may be employed and when n=6, the sulfoalkyl ether cyclodextrin may also be referred to as a γ-sulfoalkyl ether cyclodextrin.

In a further embodiment, n is 5 or 6. In a preferred embodiment n=6.

In a still further embodiment $R_1$, $R_2$ or $R_3$ is independently selected from the group consisting of —$OCH_2CH_2CH_2SO_3$—, —$OCH_2CH_2CH_2CH_2SO_3$— and —$OCH_2CH_2CH_2CH_2CH_2SO_3$—. Most preferably, $R_1$, $R_2$ or $R_3$ is independently —$OCH_2CH_2CH_2CH_2SO_3$—.

In a further embodiment $S_1$, $S_2$, $S_3$, $S_4$, $S_5$, $S_6$, $S_7$, $S_8$, and $S_9$ are each, independently, a pharmaceutically acceptable cation selected from $H^+$, alkali metals (e.g. $Li^+$, $Na^+$, $K^+$), alkaline earth metals (e.g., $Ca^{+2}$, $Mg^{+2}$), ammonium ions and amine cations such as the cations of ($C_1$-$C_6$) alkylamines, piperidine, pyrazine, ($C_1$-$C_6$) alkanolamine and ($C_4$-$C_8$)cycloalkanolamine. Most preferably, $S_1$, $S_2$, $S_3$, $S_4$, $S_5$, $S_6$, $S_7$, $S_8$, and $S_9$ are each, independently, a pharmaceutically acceptable cation selected from the group consisting of $H^+$, $Li^+$, $Na^+$, $K^+$, in particular $Na^+$.

The sulfoalkyl ether cyclodextrin may contain from 1 to 18 sulfoalkyl groups (when n=4), from 1-21 sulfoalkyl groups (when n=5) or from 1-21 (when n=6). In a preferred embodiment of the invention n=5 and the sulfoalkylether derivative comprises, on average, 2-20 sulfoalkyl groups (in particular sulfobutyl groups), such as 3-10 sulfoalkyl groups (in particular sulfobutyl groups), more preferably 4-9 sulfoalkyl groups (in particular sulfobutyl groups), even more preferably 5-9 sulfoalkyl groups (in particular sulfobutyl groups), such as 6-8 sulfoalkyl groups (in particular sulfobutyl groups), e.g. 7 sulfoalkyl groups (in particular sulfobutyl groups).

In some instances the sulfoalkyl ether cyclodextrin derivative is a salt, in particular a sodium salt, of β-cyclodextrin sulfobutyl ether (i.e. n=5), which on average contains 7 sulfobutyl groups. This sulfoalkyl ether cyclodextrin derivative is also termed SBE7-β-CD and is available as Captisol® (Cyclex, Overland Park, Kans.).

The term "$C_1$-$C_6$ alkyl" represents a branched or straight alkyl group having from one to six carbon atoms. Typical $C_1$-$C_6$ alkyl groups include, but are not limited to, methyl ethyl, n-propyl, iso-propyl, n-butyl, iso-butyl, sec-butyl, tert-butyl, n-pentyl, iso-pentyl, n-hexyl and iso-hexyl.

The term "$C_2$-$C_6$ alkyl" represents a branched or straight alkyl group having from two to six carbon atoms. Typical $C_2$-$C_6$ alkyl groups include, but are not limited to, ethyl, n-propyl, iso-propyl, n-butyl, iso-butyl, sec-butyl, tert-butyl, n-pentyl, iso-pentyl, n-hexyl and iso-hexyl.

Further details concerning compositions comprising the polypeptides disclosed herein and sulfoalkyl ether cyclodextrin derivatives can be found in WO 03/002152, particularly the section entitled "The sulfoalkyl ether cyclodextrin derivative" on pp. 37-49, incorporated herein by reference.

Parenteral formulations to be used for in vivo administration must be sterile. This is readily accomplished, for example, by filtration through sterile filtration membranes.

Sustained Release Preparations

Suitable examples of sustained-release preparations include semi-permeable matrices of solid hydrophobic polymers containing the polypeptide or conjugate, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the ProLease® technology or Lupron Depot® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for long periods such as up to or over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Oral Administration

For oral administration, the pharmaceutical composition may be in solid or liquid form, e.g. in the form of a capsule, tablet, suspension, emulsion or solution. The pharmaceutical composition is preferably made in the form of a dosage unit containing a given amount of the active ingredient. A suitable daily dose for a human or other mammal may vary widely depending on the condition of the patient and other factors, but can be determined by persons skilled in the art using routine methods.

Solid dosage forms for oral administration may include capsules, tablets, suppositories, powders and granules. In such solid dosage forms, the active compound may be admixed with at least one inert diluent such as sucrose, lactose, or starch. Such dosage forms may also comprise, as is normal practice, additional substances, e.g. lubricating agents such as magnesium stearate. In the case of capsules, tablets and pills, the dosage forms may also comprise buffering agents. Tablets and pills can additionally be prepared with enteric coatings.

The polypeptides or conjugates may be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, they may be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be subjected to conventional pharmaceutical operations such as sterilization and/or may contain conventional adjuvants such as preservatives, stabilizers, wetting agents, emulsifiers, buffers, fillers, etc., e.g. as disclosed elsewhere herein.

Liquid dosage forms for oral administration may include pharmaceutically acceptable emulsions, solutions, suspensions, syrups and elixirs containing inert diluents commonly used in the art, such as water. Such compositions may also comprise adjuvants such as wetting agents, sweeteners, flavoring agents and perfuming agents.

Pulmonary Delivery

Formulations suitable for use with a nebulizer, either jet or ultrasonic, will typically comprise the polypeptide or conjugate dissolved in water at a concentration of, e.g., about 0.01 to 25 mg of conjugate per mL of solution, preferably about 0.1 to 10 mg/mL. The formulation may also include a buffer and a simple sugar (e.g., for protein stabilization and regulation of osmotic pressure), and/or human serum albumin ranging in concentration from 0.1 to 10 mg/ml. Examples of buffers that may be used are sodium acetate, citrate and glycine. Preferably, the buffer will have a composition and molarity suitable to adjust the solution to a pH in the range of 3 to 9. Generally, buffer molarities of from 1 mM to 50 mM are suitable for this purpose. Examples of sugars which can be utilized are lactose, maltose, mannitol, sorbitol, trehalose, and xylose, usually in amounts ranging from 1% to 10% by weight of the formulation.

The nebulizer formulation may also contain a surfactant to reduce or prevent surface induced aggregation of the protein caused by atomization of the solution in forming the aerosol. Various conventional surfactants can be employed, such as polyoxyethylene fatty acid esters and alcohols, and polyoxyethylene sorbitan fatty acid esters. Amounts will generally range between 0.001% and 4% by weight of the formulation. An especially preferred surfactant for purposes of this invention is polyoxyethylene sorbitan monooleate.

Specific formulations and methods of generating suitable dispersions of liquid particles of the invention are described in WO 94/20069, U.S. Pat. No. 5,915,378, U.S. Pat. No. 5,960,792, U.S. Pat. No. 5,957,124, U.S. Pat. No. 5,934,272, U.S. Pat. No. 5,915,378, U.S. Pat. No. 5,855,564, U.S. Pat. No. 5,826,570 and U.S. Pat. No. 5,522,385 which are hereby incorporated by reference.

Formulations for use with a metered dose inhaler device will generally comprise a finely divided powder. This powder may be produced by lyophilizing and then milling a liquid conjugate formulation and may also contain a stabilizer such as human serum albumin (HSA). Typically, more than 0.5% (w/w) HSA is added. Additionally, one or more sugars or sugar alcohols may be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the conjugate present. Such formulations are then lyophilized and milled to the desired particle size.

The properly sized particles are then suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant. This mixture is then loaded into the delivery device. An example of a commercially available metered dose inhaler suitable for use in the present invention is the Ventolin metered dose inhaler, manufactured by Glaxo Inc., Research Triangle Park, N.C., USA.

Formulations for powder inhalers will comprise a finely divided dry powder containing conjugate and may also include a bulking agent, such as lactose, sorbitol, sucrose, or mannitol in amounts which facilitate dispersal of the powder from the device, e.g., 50% to 90% by weight of the formulation. The particles of the powder shall have aerodynamic properties in the lung corresponding to particles with a density of about 1 g/cm² having a median diameter less than 10 micrometers, preferably between 0.5 and 5 micrometers, most preferably of between 1.5 and 3.5 micrometers. An example of a powder inhaler suitable for use in accordance with the teachings herein is the Spinhaler powder inhaler, manufactured by Fisons Corp., Bedford, Mass., USA.

The powders for these devices may be generated and/or delivered by methods disclosed in U.S. Pat. No. 5,997,848, U.S. Pat. No. 5,993,783, U.S. Pat. No. 5,985,248, U.S. Pat. No. 5,976,574, U.S. Pat. No. 5,922,354, U.S. Pat. No. 5,785,049 and U.S. Pat. No. 5,654,007.

Mechanical devices designed for pulmonary delivery of therapeutic products, include but are not limited to nebulizers, metered dose inhalers, and powder inhalers, all of which are familiar to those of skill in the art. Specific examples of commercially available devices suitable for the practice of this invention are the Ultravent nebulizer, manufactured by Mallinckrodt, Inc., St. Louis, Mo., USA; the Acorn II nebulizer, manufactured by Marquest Medical Products, Englewood, Colo., USA; the Ventolin metered dose inhaler, manufactured by Glaxo Inc., Research Triangle Park, N.C., USA; the Spinhaler powder inhaler, manufactured by Fisons Corp., Bedford, Mass., USA the "standing cloud" device of Nektar Therapeutics, Inc., San Carlos, Calif., USA; the AIR inhaler manufactured by Alkermes, Cambridge, Mass., USA; and the AERx pulmonary drug delivery system manufactured by Aradigm Corporation, Hayward, Calif., USA.

Kits

The present invention also provides kits including the polypeptides, conjugates, polynucleotides, expression vectors, cells, methods, compositions, and systems, and apparatuses of the invention. Kits of the invention optionally comprise at least one of the following of the invention: (1) an apparatus, system, system component, or apparatus component as described herein; (2) at least one kit component comprising a polypeptide or conjugate or polynucleotide of the invention; a plasmid expression vector encoding a polypeptide of the invention; a cell expressing a polypeptide of the invention; or a composition comprising at least one of any such component; (3) instructions for practicing any method described herein, including a therapeutic or prophylactic method, instructions for using any component identified in (2) or any composition of any such component; and/or instructions for operating any apparatus, system or component described herein; (4) a container for holding said at least one such component or composition, and (5) packaging materials.

In a further aspect, the present invention provides for the use of any apparatus, component, composition, or kit described above and herein, for the practice of any method or assay described herein, and/or for the use of any apparatus, component, composition, or kit to practice any assay or method described herein.

EXAMPLES

The following examples are offered to illustrate the present invention, but not to limit the spirit or scope of the present invention in any way.

Materials and Methods

I. Determination of Surface-Accessible Residues

Accessible Surface Area (ASA)

The computer program Access (B. Lee and F. M. Richards, J. Mol. Biol. 55: 379-400 (1971)) version 2 (©1983 Yale University) was used to compute the accessible surface area (ASA) of the individual atoms in the structure. This method typically uses a probe-size of 1.4 Å and defines the Accessible Surface Area (ASA) as the area formed by the center of the probe. Prior to this calculation all water molecules and all hydrogen atoms should be removed from the coordinate set, as should other atoms not directly related to the protein.

Fractional ASA of Side Chain

The fractional ASA of the side chain atoms is computed by division of the sum of the ASA of the atoms in the side chain by a value representing the ASA of the side chain atoms of that residue type in an extended ALA-x-ALA tripeptide. See Hubbard, Campbell & Thornton (1991) *J. Mol. Biol.* 220, 507-530. For this example the CA atom is regarded as a part of the side chain of glycine residues but not for the remaining residues. The following values are used as standard 100% ASA for the side chain (Table 6):

| Ala | 69.23 | Å² |
| Arg | 200.35 | Å² |
| Asn | 106.25 | Å² |
| Asp | 102.06 | Å² |
| Cys | 96.69 | Å² |
| Gln | 140.58 | Å² |
| Glu | 134.61 | Å² |
| Gly | 32.28 | Å² |
| His | 147.00 | Å² |
| Ile | 137.91 | Å² |
| Leu | 140.76 | Å² |
| Lys | 162.50 | Å² |
| Met | 156.08 | Å² |
| Phe | 163.90 | Å² |
| Pro | 119.65 | Å² |
| Ser | 78.16 | Å² |
| Thr | 101.67 | Å² |
| Trp | 210.89 | Å² |
| Tyr | 176.61 | Å² |
| Val | 114.14 | Å² |

Residues not detected in the structure are defined as having 100% exposure as they are thought to reside in flexible regions. In the case where an ensemble of NMR structures is analyzed, the average ASA value of the ensemble is used.

Determination of Surface Exposed Residues when No Three-Dimensional Structure is Available:

When no three-dimensional structure is available or if the structure is not detailed enough to determine surface accessibility (e.g. if only the position of the CA atoms is known) the surface accessibility may be inferred from a sequence alignment created as follows:

A: If the structure is known but not detailed enough to determine surface accessibility:

The low detail structure is included in a structure-based sequence alignment to the known structures of the sequence family using the MODELER program available from Molecular Simulations, Inc.

B: If no structure is known:

The sequence is aligned to a predefined sequence alignment, including the sequences of the known structures of the sequence family, that may be prepared using the "profile/structure alignment" option of the program ClustalW (Thompson et al. (1994) *Nucleic Acids Research* 22:4673-4680).

From the sequence alignment obtained in A or B, residues in the sequence to be analyzed at positions equivalent to residues exposed in at least one of the other sequences having a known structure are defined as being exposed. The degree of exposure is taken to be the largest value for the equivalent residues in the other sequences. In cases where the sequence to be analyzed is at an insertion (i.e. there are no equivalent residues in the other sequences) this residue is defined as being fully exposed, as it most probably is located in a turn/loop region. In cases where a low detailed structure exists, those residues not observed in the structure are defined as being fully exposed, as they are thought to be in flexible regions.

Determining Distances Between Atoms:

The distance between atoms is readily determined using molecular graphics software, e.g. InsightII® 98.0 from Molecular Simulations, Inc.

II. Protein Expression and Purification

A. Expression and Purification from CHO Cells

Some polypeptides of the invention were produced in Chinese Hamster Ovary (CHO) K1 cells (ATCC: CCL-61) that were stably transfected and selected with G418 to establish clonal cell lines.

1. CHO Expression Construct:

Nucleic acids encoding polypeptides of the invention were cloned into a CHO expression vector, under control of the SV40 promoter and in-frame with a sequence which encodes an N-terminal leader sequence, and, optionally, one or two a C-terminal tag sequences. The leader sequence was either a generic leader sequence, IFN alpha 6 leader or a modified IFN alpha 6 leader sequence, and C-terminal tags included an E-tag (Amersham Biosciences) &/or a His-tag. Plasmid production was in XL1-Blue cells.

2. Selection of Stable Subclones Expressing IFN-Alpha Polypeptides:

Materials:

Culture medium: DMEM-F12 with G418, FBS and Penicillin, Streptomycin and Glutamine (PSG; Gibco/Invitrogen);

1×PBS (Gibco/Invitrogen);

Trypsin/EDTA

Anti E-Tag Antibody-HRP conjugate (Amersham BioSciences)

ECL Plus Western Blotting detection Reagents (Amersham BioSciences)

Procedure: Stable transfectants were generated under selection with G418 in DMEM/F-12 medium with FBS and penicillin. Cells were split into T175 flasks with 50 ml of selection medium and incubated in a 37° C. $CO_2$ incubator for ~24 hr. or until cells reached 80% confluence. Cells were harvested by washing with PBS followed by addition of 2.5 ml Trypsin/EDTA and incubation at 37° C. for 3-5 min. Cells were collected and recovered by centrifugation at 1000 g for 30 min in a Beckman Model bench top centrifuge. Cells were washed once in PBS and resuspended in 3 ml PBS with 1% FBS. The cell density was determined and adjusted to $1 \times 10^6$ cell/ml with PBS/FBS. For each IFN-alpha, polypeptide cells were sorted in a DakoCytomation MoFlo sorter into 2-5 96 well plates containing 200 ml of selection medium. The plates were incubated in a 37° C. incubator for 10-14 days to allow the sorted cells to grow. Two subclones were selected for each IFN-alpha polypeptide for high level expression first by dot blot analysis and subsequently confirmed by Western blot analysis using an anti-E tag antibody-HRP conjugate and chemiluminescent detection.

3. Protein Expression:

Materials:

DMEM-F12 medium (Gibco/Invitrogen)

Ultra CHO medium (BioWhittaker)

CHO III A medium (Gibco/Invitrogen)

Ex-Cyte Growth Enhancing Media supplement (Serologicals Proteins)

ITSA (Insulin, Transferrin, Selenium supplement for adherent culture; Gibco/Invitrogen)

Penicillin/Streptomycin (P/S)

FBS, PBS, Trypsin

Procedure:

Day 1: Cells from one T-175 flask were transferred to one roller bottle (1700 $cm^2$) in 300 ml DMEM-F12 with 10% FBS and 1× P/S and grown in a 37° C. $CO_2$ incubator.

Day 3: Medium was changed to 300 ml fresh DMEM-F12-FBS-P/S.

Day 5: The medium was changed to 300 ml Ultra CHO with $\frac{1}{1000}$ Ex-Cyte and P/S.

Day 7: The media was replaced with 300 ml CHO III A+P/S production medium.

Supernatants were harvested on Day 8, 9 and 10. The supernatants were centrifuged at 2000 g for 20 min in a Beckman Coulter Allegra 6R bench top centrifuge and filtered using a 0.2μ PES bottle top sterile filter and stored at 4° C. for purification.

4. Protein Purification:

Some polypeptides of the invention were expressed as fusion proteins containing a 13 amino acid E-tag sequence at the C-terminus. Such polypeptides were purified using an E-tag affinity column, as follows.

Materials: Recombinant Phage Antibody System Purification Module (Amersham BioSciences, Cat. No. 17-1362-01). Purification kit contains a 16 mm diameter×25 mm height (5 ml bed volume) anti E-Tag column and associated buffers.

Procedure: Supernatants collected from CHO-HK1 cells in roller bottles were clarified using a combination of centrifugation at 2800×g for 20 min and filtration using a 0.2μ PES bottle top filter module. Supernatants were loaded onto the E-tag column equilibrated in RPAS binding buffer at 150 cm/h (5 ml/min). The column was washed with 5 CV (column volume) of binding buffer and the protein was eluted at 75 cm/h (2.5 ml/min) with RPAS elution buffer. Elution fractions were neutralized with 0.05 volumes of 1M Tris-Cl pH 8.0, dialyzed into PBS, concentrated to 0.1-1.5 mg/ml and stored frozen in aliquots at –80° C. Samples for assays were formulated at 50 μg/ml in PBS with 0.5% BSA and stored frozen in aliquots at –80° C. Samples were routinely analyzed by SDS-PAGE followed by Coomassie staining using materials, reagents and protocols obtained from Invitrogen. Protein concentrations were routinely determined by the BCA assay using an IFN-alpha standard, the concentration of which had been verified by amino acid analysis.

B. Expression and Purification from *E. coli*

Some polypeptides of the invention were produced in *E. coli* as inclusion bodies, which were purified and refolded as follows.

1. *E. coli* Expression Construct

In some instances, nucleic acids encoding polypeptides of the invention were modified for improved expression in *E. coli*. Such modifications comprised replacing rare Arg-Arg codon pairs AGGAGG at nucleotide positions 34-39, and AGGAGA at nucleotide positions 64-69 (position numbering relative to SEQ ID NO:18), each with Arg-Arg codon pairs such as CGTCGC which are preferred in *E. coli*, and adding a methionine codon (ATG) to the 5' end of the coding sequence. The coding sequence was placed into the pET-42 expression vector (Novagen) under control of a T7 promoter with kanamycin selection marker, or into the pQE80-Kan expression vector (Qiagen) under the control of a T5 promoter with kanamycin selection marker.

2. Protein Expression pET-42 vectors containing interferon coding sequences were transformed into an *E. coli* strain such as BL21(DE3) using standard methods, and plated on to agar plates containing 50 µg/ml kanamycin and incubated at 37° C. After 18-24 h, three separate colonies were picked and transferred into tubes containing 5 ml of 2×YT with 50 µg/ml kanamycin and incubated overnight at 37° C. The overnight culture was used to inoculate 2 sets of flasks containing 100 ml of 2×YT with 50 µg/ml kanamycin. The growth of the culture at 37° C. was monitored at $OD_{600}$. The culture was induced at an $OD_{600}$ of 0.5-0.8 with 1 mM IPTG for 3 h at 37° C. IPTG induced cultures were analyzed for expression by SDS-PAGE by lysing pelleted cells in SDS sample buffer. The corresponding uninduced sets of cultures were used to prepare frozen stocks by addition of 25% glycerol and freezing cells in 1 ml aliquots at −80° C. pQE80-Kan vectors containing interferon coding sequences were transformed into *E. coli* strains W3110 or W3110-fhuA. Expression was verified as described above.

Larger scale shake flask expression was performed by inoculating 4×1 L 2×YT media+kanamycin with 25 ml of an overnight culture. Cultures were monitored at OD600 and induced with 1 mM IPTG at 0.5-0.8 OD units. After 3 h of induction cells are harvested by centrifugation at 5000 g and stored frozen at −80° C. Cells were disrupted using 2-3 passes through a French press or a APV 1000 homogenizer at 10,000 psi and processed as described under "Isolation of IB" and subsequent sections.

Fed-batch fermentation was conducted at 10 L scale in a B. Braun bioreactor in Terrific Broth (TB) medium supplemented with trace element solution and 40 mg/L kanamycin. Fermentation was initiated by inoculating the bioreactor with a 400 ml overnight culture in TB medium. During the initial growth phase the dissolved oxygen (DO) was maintained at 50% by varying the agitation rate. When the OD600 of the culture reached 5.0, the glycerol/amino acid feed was initiated at 0.5 ml/min and the agitation was set to 1000 rpm. The feed rate was adjusted to maintain the DO at 40% for the rest of the fermentation process. When the OD600 reached 25 the culture was induced by addition of IPTG to a final concentration of 1 mM. Three hours post induction the cells were harvested by centrifugation at 10000×g in a Beckman centrifuge and the cell paste was stored at −60° C. The OD600 at harvest was typically around 35-40.

3. Isolation, Solubilization, Sulfonation and Refolding of Inclusion Bodies (IB)

For isolating IB the thawed cell paste was resuspended in 1×PBS at 10 ml per gram of cell paste and mixed until a uniform slurry was obtained. The cells were disrupted by two passes through a microfluidizer at 17,000-19,000 psi. The cell lysate was adjusted to 1% Triton-X100, mixed for 10 min and the IB were recovered by centrifugation at 10,000 g for 60 min at 2-8° C. The IB pellet was washed once by resuspending in PBS with 1% Triton-X100 and recovered by centrifugation as above and stored frozen at −80° C.

For solubilizing IB, the IB pellet was resuspended in Urea buffer (50 mM Tris-Cl, 200 mM NaCl, 8 M urea, 2 mM DTT, 1 mM EDTA, pH 8.0) at 10 ml buffer per gram of cell paste. The suspension was mixed for 30 min and centrifuged at 10,000 g for 30 min at 2-8° C. The pellet was washed once by resuspending in the Urea buffer without DTT, centrifuged as above and washed twice with water. The washed pellet was solubilized in Guanidine buffer (50 mM Tris-Cl, 200 mM NaCl, 8 M guanidine-HCl, 1 mM EDTA, pH 8.0) at 10 ml buffer per gram pellet, mixed for 30-60 min and centrifuged at 10,000 g for 30 min at 2-8° C. The supernatant containing the solubilized IFN was adjusted to 10 mg/ml sodium sulfite and 5 mg/ml sodium tetrathionate to initiate the sulfonation process which was performed at 2-8° C. for 16 hours. Post-sulfonation the IFN solution was diluted 2-fold with water and the IFN pellet was recovered by centrifugation at 10,000 g at 2-8° C. The pellet was washed twice with water and resuspended in Guanidine buffer as above. The protein concentration of the sulfonated IFN was determined by absorbance at 280 nm.

The refolding process was initiated by diluting the sulfonated IFN in Guanidine buffer at 2-8° C. to a final concentration of 100 mg/ml in Refolding buffer (50 mM Tris-Cl, 20 mM NaCl, 2 mM reduced glutathione, 1 mM oxidized glutathione). Refolding was performed at 2-8° C. with slow mixing for 6-8 h, followed by addition of $CuSO_4$ to a final concentration of 2 mM followed by an additional refolding period of 16-20 h. The progress of the refolding reaction was monitored by SDS-PAGE and reverse phase HPLC.

4. Purification

The refolded IFN was purified using three chromatography steps. The refolding solution was adjusted to 80% ammonium sulfate (weight/volume), filtered through a 0.2 µM filter and loaded at 200 cm/h onto a 20 ml Butyl Sepharose Fast Flow Hydrophobic Interaction Chromatography (HIC) column (Amersham Biosciences) equilibrated in Equil buffer (50 mM Tris-Cl, 0.8 M ammonium sulfate, pH 8.0). The HIC column was washed with 8 column volumes (CV) of Equil buffer, followed by 8 CV of Wash buffer (50 mM Tris-Cl, 0.5 M ammonium sulfate, pH 8.0). IFN was eluted with 15% ammonium sulfate in 50 mM Tris-Cl, pH 8.0.

The HIC pool was adjusted to 50 mM sodium acetate using 0.5 M sodium acetate, pH 4.5 stock and diluted two fold. This adjusted pool was loaded at 90 cm/h on to a 5 ml HiTrap CM Sepharose Fast Flow column (Amersham Biosciences), equilibrated in 50 mM sodium acetate, 100 mM NaCl, pH 5.0. Post loading the column was washed with 5 CV under equilibration buffer conditions and IFN was eluted using a 20 CV gradient from 100-650 mM NaCl. Peak fractions containing IFN were pooled based on absorbance at 280 nm.

The CM Sepharose pool was adjusted to 20 mM 1,3 diaminopropane using a 2 M 1,3 diaminopropane stock to set pH at ~10. The sample was loaded at 200 cm/h on to a 5 ml HiTrap Q Sepharose Fast Flow column (Amersham Biosciences), equilibrated in 50 mM 1,3 diaminopropane, 100 mM NaCl, pH 10.0. Post loading the column was washed with 5 CV of buffer under equilibration conditions and IFN was eluted using a 20 CV gradient from 100-500 mM NaCl. The fractions containing IFN are pooled based on absorbance at 280 nm and immediately dialyzed against 250-500 volumes of 50 mM sodium acetate, 150 mM NaCl, pH 5.0 or 50 mM sodium borate, pH 9.0. Post-dialysis the IFN samples were sterile filtered using a 0.2 µM filter in a biosafety cabinet, the concentration was measured by absorbance at 280 nm and the samples are stored at 2-8° C. for periods up to a week or in aliquots at −80° C. for extended storage. For activity assays the sample was generally formulated in 0.5% BSA, PBS pH 7.4 at 5, 20 and 50 ug/ml, and stored frozen in aliquots at −80° C.

III. Activity Assays

A. EMCV-HuH7 Antiviral Assay

Provided below is an exemplary assay for antiviral activity of interferon-alpha polypeptides and conjugates of the invention. The assay is a cell-based dose-response assay used to assess the anti-viral potency of a drug, and is sometimes referred to as "protection from cytopathic effect" (or PCPE) assay. Briefly, cells are incubated with drug and exposed to virus. In the absense of drug, cells exposed to virus die. With increasing concentrations of drug, an increasing proportion of cells survive. The number of surviving cells can be measured directly (e.g., by visual counts) or indirectly by estimating metabolic rate. For example, metabolic dyes such as MTT or WST-1 may be used as an indirect measure of cell survival. Live cells metabolize such dyes to form metabolic products which can be quantified by spectrophotometry (optical density).

Materials:

Cells:

HuH7 Cells: Human hepatoma cell line (obtained from Dr. Michael Lai, USC-Surgery Department, Los Angeles, Calif.). The cell line may also be obtained from the Cell Bank of the Japanese Collection of Research Bioresources (JCRB)/Health Science Research Resources Bank (HSRRB), Osaka, Japan. The HuH7 cell line was originally established in the laboratory of Dr. J. Sato (Okayama University School of Medicine) from a 57-year old Japanese male with well-differentiated hepatocellular carcinoma (Nakabayashi, H., et al. (1982) Cancer Res. 42(9):3858-63). The cell line is negative for Hepatitis B surface antigen.

VERO Cells: African green monkey kidney cell line (ATCC # CCL-81)

L-929 Cells: Murine fibroblast cell line (ATCC # CCL-1)

Virus:

Encephalomyocarditis virus (EMCV): tissue culture adapted strain (ATCC # VR-129B). High titer viral stocks were produced in-house by passage in VERO cells Complete Media:

Dulbecco's Modified Eagle Medium (DMEM, Gibco Cat. No. 11965-092)

10% Fetal Bovine Serum (FBS, Hyclone Cat. No. SH30071.03)

1× Penicillin-streptomycin (PS, Gibco Cat. No. 15140-122)

Reduced Serum Media:

Dulbecco's Modified Eagle Medium (DMEM, Gibco Cat. No. 11965-092)

2% Fetal Bovine Serum (FBS, Hyclone Cat. No. SH30071.03)

1× Penicillin-streptomycin (PS, Gibco Cat. No. 15140-122)

Trypsin/EDTA (Gibco Cat. No. 25300-054)

WST-1 (Roche; Cat. No. 1 644 807)

HuH7 cells were maintained in Complete Media at 37° C. in a humidified 5% $CO_2$ incubator. The cells were harvested with trypsin and split twice weekly when confluent to a final density of 1-2×10$^6$ cells per 25 ml in a T175 flask. One day prior to the assay, the cells were trypsinized and seeded into new T175 flasks at a density of 4.5×10$^6$ cells per 25 ml to ensure that the cells were in log phase prior to the assay.

Procedure:

A high titer EMCV virus stock was amplified in VERO cells. The lethal concentration at which 95% of the cells were killed ($LC_{95}$) was determined by an EMCV viral killing curve on HuH7 cell monolayers. Briefly, HuH7 cells were plated on day one in 96-well microtiter plates at 6×10$^4$ cells per well. Virus was serial diluted 1:3 in DMEM+2% FBS with 10 dilution points and added to the cells on day two. Twenty-four hours post-infection, cell survival was determined by a tetrazolium salt metabolism assay, WST-1 (Roche). The $LC_{95}$ determined for the HuH7-EMCV assay corresponded to an MOI of 0.034 (PFU/cell). Titer of the virus stock was determined by a standard plaque assay on L929 cells.

On day one of the assay, log phase HuH7 cells were harvested with trypsin, resuspended in Reduced Serum Media and concentrated by centrifugation. The cell pellets, corresponding to 5 T175 flasks of cells, were resuspended in 10 ml of Reduced Serum Media, filtered through a 40 micron Nylon cell strainer and counted with a hemocytometer. Cell viability was determined by trypan blue exclusion. The cells were resuspended in Reduced Serum Media to a final density of 6×10$^5$ cells/ml. One hundred microliters of the diluted cells were added to each well of a 96-well assay plates (6×10$^4$ cells/well) and the plates were incubated at 37° C. in a humidified 5% $CO_2$ incubator for 4 hours.

The potencies of "reference" interferon alphas and interferon-alpha polypeptides of the invention (also called "test samples") were determined by dose-response analysis. There was generally one test sample and one reference IFN-alpha per plate, each with three replicate curves of IFN-alpha treated/EMCV challenged cells and two replicate curves of IFN-alpha treatment alone. The later was assayed to control for potential antiproliferative effects of IFN-alpha on HuH7 cells. The dose-response curves for the reference IFN-alphas generally consisted of 8 three-fold dilutions ranging from 100 ng/ml to 0.05 ng/ml. For the IFN-alpha test samples, the three-fold dilutions generally ranged from 5 ng/ml to 0.002 ng/ml. Eight wells each of cells treated with virus but no IFN-alpha and cells alone were also run as controls.

The IFN-alpha dilutions were prepared using Reduced Serum Media. One hundred microliters of the diluted IFN-alpha preparations were transferred to the assay plates. The assay plates were incubated at 37° C. in a humidified 5% $CO_2$ incubator for 16 hours.

On day two, the cells were challenged with EMC virus. Medium was aspirated from each well of the assay plate. The EMCV stock was diluted 1:5400 in DMEM+2% FBS. One hundred microliters of the diluted virus, corresponding to 0.034 viral particles per cell, was added to each well. The cells were incubated with virus at 37° C. in a humidified 5% $CO_2$ incubator for 24 hours.

On day three, the number of viable cells in each well was quantified by WST-1 assay. Medium was aspirated from each well of the assay plate. The WST-1 reagent was diluted 1:20 in Reduced Serum Media, 100 µl of the diluted WST-1 reagent was added to each well and the cells were incubated at 37° C. in a humidified 5% $CO_2$ incubator for 60 minutes. The number of viable cells in each well was quantified by measuring OD at 450 nm on a plate reader.

Analysis:

The antiviral potency of the IFN-alpha reference and test samples were calculated with the equation:

Antiviral potency=(Viable cells$_{C+I+V}$–Viable cells$_{C+V}$)/(Viable cells$_{C+I}$–Viable cells$_{C+V}$)*100% where C+V=HuH7 cells+EMCV, C+I=HuH7 cells+IFN-α, and C+I+V=HuH7 cells+IFN-α+EMCV Dose-response curves were analyzed by non-linear regression using GraphPad Prism 4 (GraphPad Software Inc.) The following equation was used for the curve fits:

$$Y = \text{Bottom} + \frac{(\text{Top} - \text{Bottom})}{1 + 10^{(LogEC50 - X) \cdot HillSlope}}$$

Bottom is the Y value at the bottom plateau; Top is the Y value at the top plateau, and Log EC50 is the X value when the response is halfway between Bottom and Top. The Levenberg-Marquardt method was used as optimization algorithm.

B. $T_H1$ Differentiation Assay

Provided below is an exemplary assay for $T_H1$ differentiation activity of interferon-alpha polypeptides and conjugates of the invention.

Assay Procedure:

Human buffy coats (25-30 ml) containing leukocytes and erythrocytes prepared from 500 ml blood were collected from Stanford Blood Bank the day of assay initiation and kept at room temperature. Each buffy coat was carefully transferred to a T75 flask and diluted to 100 ml with PBS. For each buffy coat, 13 ml of Histopaque/Ficoll (Sigma H8889) was pipetted into four 50 ml centrifuge tubes, and 25 ml of diluted blood sample was carefully overlaid on top of the Histopaque/Ficoll without disrupting the interface. The tubes were then centrifuged (20° C., 2500 rpm) for 20 minutes. Using 3 ml plastic transfer pipettes, the top plasma was removed to the mononuclear cell layer, followed by transfer of the PBMCs to two 50 ml conical tubes (cells from 2 Histopaque/Ficoll/buffy coat tubes to one tube). The PBMCs were then diluted to 50 ml/tube with PBS and centrifuged (20° C., 1000 rpm) for 10 minutes to remove platelets. After removal of PBS, the PBMCs and remaining RBCs were mixed to prevent aggregation. 5 ml of RBC lysis buffer (ammonium chloride buffer) was added and two tubes of cells were combined to one tube. Each tube, now containing the total PBMC and RBC isolate from one donor, was incubated at room temperature for 10 min. Potential clots of blood cells were removed by filtering the cells with a cell strainer (70 um, Falcon Cat. No. 2350). PBS was added to a total volume of 50 ml followed by centrifugation (20° C., 1000 rpm) for 10 min. The cell number was finally counted using a hemocytometer.

Next, a fraction of each PBMC preparation was prestained and analyzed by FACS to select PBMC preparations with a percentage of naïve Th0 cells above 15%. Two ml of PBMCs were stained with 20 µt FITC-conjugated anti-human CD45RA (Pharmigen, Cat. No. 555488), 20 µl Cy-chrome conjugated anti-human CD4 (Pharmigen, Cat. No. 555348), 10 µl PE-conjugated anti-human CD8 (Pharmigen, Cat. No. 555367), 10 µl PE-conjugated anti-human CD14 (Pharmigen, Cat. No. 555398), and 10 µl PE-conjugated anti-human CD20 (Pharmigen, Cat. No. 555623), and incubated on ice for 45 minutes. The cells were washed with PBS, resuspended in 1 ml PBS, and filtered with a 40 µm cell strainer (Falcon, Cat. No. 2340). The percentage of naïve $T_H0$ cells (positive to CD4 and CD45RA and negative to CD8, CD14, CD20) were quantified by FACS, and PBMC preparations with more than 15% naïve $T_H0$ cells were selected for the assay.

The selected PBMC preparations were stained with 800 µl FITC-conjugated anti-human CD45RA, 800 µl Cy-chrome conjugated anti-human CD4, 500 µl PE-conjugated anti-human CD8, 200 µl PE-conjugated anti-human CD14, and 200 µl PE-conjugated anti-human CD20, and incubated on ice for 60 minutes. The cells were washed with PBS, PI was added, and the cells were diluted with 20 ml/ml PBS followed by filtering with a 40 µm cell strainer. The cells were FACS sorted, and $1\times10^4$ naïve $T_H0$ cells (positive to CD4 and CD45RA and negative to CD8, CD14, CD20) were transferred by MOFLO into each well of 96 well round bottom plates, containing 160l DMEM plus Penicillin-streptomycin plus 2 mM Glutamine and 10% Fetal Bovine Serum (Hyclone Cat. No. SH30071.03).

Twenty µl Dynabeads CD3/CD28 T cell expander (Dynal, Cat. No. 111.32) were added to each well. The stimulatory effect of the Dynabeads was calibrated prior to the experiment to avoid lot-to-lot variance. Next, 20 µl/well of protein samples were added to the assay plates. Generally, concentration ranges for IL-4 and IL-12 standards (obtained from R&D Systems) were from 0.04 pg/ml to 10 ng/ml, and concentration ranges for IFN-alpha test samples and IFN-alpha reference sample were from 0.76 pg/ml to 200 ng/ml.

The cells were incubated at 37° C. in a humidified 5% $CO_2$ incubator for 7 days. Supernatants from each well were harvested to determine the degree of $T_H1$ expansion through quantification of the IFN-γ content, using a standard ELISA.

Analysis:

Response=IFN-γ concentrations in pg/ml.

The following equation was used for curve fitting:

$$Y = \text{Bottom} + \frac{(\text{Top} - \text{Bottom})}{1 + 10^{(LogEC50-X) \cdot HillSlope}}$$

The variable Bottom is the Y value at the bottom plateau; Top is the Y value at the top plateau, and Log EC50 is the X value when the response is halfway between Bottom and Top. The Levenberg-Marquardt method was used as optimization algorithm.

C. Daudi Antiproliferation Assay

Provided below is an exemplary assay for antiproliferative activity of interferon-alpha polypeptides and conjugates of the invention.

Cell Line Maintenance:

Daudi Burkitt's lymphoma cells grown in suspension were maintained in T175 tissue culture flasks, containing 50 ml culture medium (RPMI+10% Fetal Bovine Serum (FBS, Hyclone Cat. No. SH30071.03)+1× Penicillin-streptomycin (PS, Gibco Cat. No. 15140-122)+2 mM Glutamine), at 37° C. in a humidified 5% $CO_2$ incubator. The cells were split 1:10 when confluent.

Assay Procedure:

Daudi cells were spun down and washed with 1×PBS. The cell number was adjusted to $10^5$ cells/ml. 80 µl culture medium was added to each well in 96 well round bottom assay plates followed by transfer of 100 µl cells ($10^4$ cells/well) to each well.

Eleven dilutions of the IFN-alpha reference material and IFN-alpha test samples, ranging from 200 ng/ml to 0.2 pg/ml (4-fold dilutions), were prepared in dilution plates using culture medium. Twenty µl of the diluted IFN-alpha preparations were then transferred to the assay plates.

The cells were incubated at 37° C. in a humidified 5% $CO_2$ incubator. After 48 hours, 1 µCi of methyl-$^3$H thymidine (Amersham Pharmacia, Cat. No. TRK758) was added to each well followed by incubation for 24 hours at 37° C. in a humidified 5% $CO_2$ incubator. The cells were harvested on the following day and incorporation of thymidine was determined.

Analysis:

The $EC_{50}$ of the IFN-alpha reference and samples were calculated using the equation:

$$Y = \text{Bottom} + \frac{(\text{Top} - \text{Bottom})}{1 + 10^{(LogEC50-X) \cdot HillSlope}}$$

where Bottom is the Y value at the bottom plateau; Top is the Y value at the top plateau, and Log EC50 is the X value when the response is halfway between Bottom and Top. The Levenberg-Marquardt method was used as optimization algorithm.

Example 1

Determination of Surface-Accessible Residues of Interferon-Alphas

Surface Exposure of Human Interferon-α2a Residues:

Based on the 24 NMR structures of human interferon-alpha 2a reported by Klaus et al., *J. Mol. Biol.*, 274: 661-675 (1997), the fractional ASA of side chains was calculated. The sequence numbering used below is based on the mature sequence of the human interferon-alpha 2a protein (identified herein as SEQ ID NO:32+R23K). It is noted that this structure contains two disulphide bridges involving Cys1-Cys98 and Cys29-Cys138, respectively. By computing the ASA and the fractional ASA and taking the average of the 24 structures, focusing on the ASA of the side chains, it was determined that the following residues have more than 25% fractional ASA: D2, L3, P4, Q5, T6, H7, S8, L9, G10, R12, R13, M16, A19, Q20, R22, K23, I24, S25, L26, F27, S28, L30, K31, R33, H34, D35, G37, Q40, E41, E42, G44, N45, Q46, Q48, K49, A50, E51, E58, Q61, Q62, N65, S68, T69, K70, D71, S73, A74, D77, E78, T79, L80, D82, K83, T86, Y89, Q90, N93, D94, E96, A97, V99, I100, Q101, G102, V103, G104, T106, E107, T108, P109, L110, M111, K112, E113, D114, L117, R120, K121, Q124, R125, T127, L128, K131, E132, K133, K134, Y135, S136, P137, C138, A145, M148, R149, S152, L153, N156, Q158, E159, S160, L161, R162, S163, K164 and E165, with position numbering relative to that of the interferon-alpha 2a sequence identified herein as SEQ ID NO:32+R23K.

The following residues were determined to have on average more than 50% fractional ASA of their side chain: D2, L3, P4, Q5, T6, H7, S8, L9, R12, R13, M16, A19, S25, F27, S28, K31, R33, H34, D35, G37, E41, G44, N45, Q46, Q48, K49, N65, K70, A74, D77, E78, T79, D82, K83, T86, Y89, Q90, N93, D94, I100, Q101, G102, G104, T106, E107, T108, P109, L110, E113, D114, L117, R120, K121, Q124, R125, L128, K131, E132, K134, P137, R149, E159, L161, R162, S163, K164 and E165, with position numbering relative to that of the interferon-alpha 2a sequence identified herein as SEQ ID NO:32+R23K.

Surface Exposure of Residues Corresponding to SEQ ID NO:1:

Owing to an insertion of an amino acid after position 44 of the human interferon-alpha 2 subtypes—such as, for example, interferon-alpha 2b (SEQ ID NO:32) and interferon-alpha 2a (SEQ ID NO:32+R23K)—in many interferon alpha sequences, including all of the known human interferon alpha sequences (apart from the IFN-alpha 2 subtypes) and certain polypeptides of the invention, the position numbering of the surface-exposed residues will be shifted by one residue past position number 44 in, for example, the sequences shown in the alignment FIG. 2, relative to the numbering of the sequence denoted hIFNalpha 2b (SEQ ID NO:32).

Based on the above analysis, the following positions, numbered relative to SEQ ID NO:1, are considered to contain amino acid residues having more than 25% fractional ASA: positions 2, 3, 4, 5, 6, 7, 8, 9, 10, 12, 13, 16, 19, 20, 22, 23, 24, 25, 26, 27, 28, 30, 31, 33, 34, 35, 37, 40, 41, 42, 44, 46, 47, 49, 50, 51, 52, 59, 62, 63, 66, 69, 70, 71, 72, 74, 75, 78, 79, 80, 81, 83, 84, 87, 90, 91, 94, 95, 97, 98, 100, 101, 102, 103, 104, 105, 107, 108, 109, 110, 111, 112, 113, 114, 115, 118, 121, 122, 125, 126, 128, 129, 132, 133, 134, 135, 136, 137, 138, 139, 146, 149, 150, 153, 154, 157, 159, 160, 161, 162, 163, 164, 165, and 166.

Likewise, the following positions, again numbered relative to SEQ ID NO:1, are considered contain amino acid residues having on average more than 50% fractional ASA of their side chain: 2, 3, 4, 5, 6, 7, 8, 9, 12, 13, 16, 19, 25, 27, 28, 31, 33, 34, 35, 37, 41, 44, 46, 47, 49, 50, 66, 71, 75, 78, 79, 80, 83, 84, 87, 90, 91, 94, 95, 101, 102, 103, 105, 107, 108, 109, 110, 111, 114, 115, 118, 121, 122, 125, 126, 129, 132, 133, 135, 138, 150, 160, 162, 163, 164, 165, and 166.

Example 2

Antiviral Activities of Interferon-Alpha Polypeptides

Patients with chronic HCV infection have initial viral loads in the range of $10^4$-$10^7$ copies of HCV RNA/ml. Upon treatment with IFN-alpha, the viral load characteristically undergoes two distinct log-linear phases of decline reflecting two distinct mechanisms (FIG. 1B). The initial drop in viral load occurs in about the first two days and is believed to be due to the reduction in rate of virus production by infected liver cells in the face of the IFN-alpha therapy.

The major technical challenge with HCV is that the virus cannot be grown in vitro and has only recently been cultured in tractable animal models. There are, however, viruses that replicate in vitro which are considered to be useful surrogates for HCV viral replication. In vitro surrogate assays believed to be predictive of in vivo HCV antiviral activity include the assay described above, which measures the ability of test molecules to protect cells from the cytopathic effect of viral infection, using EMC RNA virus (EMCV) in the human liver-derived cell line HuH7.

Antiviral activities of some IFN-alpha polypeptides of the invention were assayed in the EMCV/HuH7 antiviral assay described in the Materials and Methods section above. Some such polypeptides exhibited antiviral activities about equal to or greater than that of a reference molecule, e.g., huIFN-alpha 2b (SEQ ID NO:32) or huIFN-alpha 2a (SEQ ID NO:32+R23K), as evidenced by the $EC_{50}$ (the concentration of sample which yields half-maximal protective response in the assay) of the polypeptide of the invention being about equal to or less than the $EC_{50}$ of the reference molecule. Some such polypeptides of the invention exhibited at least about a 1.5-fold higher, at least about a two-fold higher, at least about a four-fold higher, at least about a five-fold higher, or at least about a ten-fold higher antiviral activity than the reference molecule (as evidenced by the $EC_{50}$ of the polypeptide being about 0.66× or lower, about 0.5× or lower, about 0.25× or lower, about 0.2× or lower, or about 0.1× or lower than the $EC_{50}$ of the reference molecule, respectively).

Table 7 below shows relative antiviral activities of exemplary IFN-alpha polypeptides of the invention, in comparison to IFN-alpha Con1 and human IFN-alpha 2b assayed under the same conditions, expressed as antiviral activity relative to huIFN-alpha 2b ($EC_{50}$ huIFN-alpha 2b/$EC_{50}$ sample).

TABLE 7

| Sample name | Sequence | Antiviral activity relative to huIFNα-2b |
|---|---|---|
| B9x14 | SEQ ID NO:3 | ≧10 |
| B9x25 | SEQ ID NO:12 | ≧10 |
| B9x16 | SEQ ID NO:3 + H47Q | ≧10 |
| B9x28 | SEQ ID NO:12 + E133K, A140S | ≧10 |

TABLE 7-continued

| Sample name | Sequence | Antiviral activity relative to huIFNα-2b |
|---|---|---|
| B9x23 | SEQ ID NO.12 + H47Q | ≧10 |
| B9x18 | SEQ ID NO:3 + H47Q, V51T, F55S, L56V, Y58H | ≧10 |
| B9x22 | SEQ ID NO.12 + V51T, F55S, L56V, Y58H | ≧10 |
| B9x11 | SEQ ID NO:3 + E133K, A140S | ≧10 |
| B9x17 | SEQ ID NO:3 + V51T, F55S, L56V, Y58H | ≧10 |
| B9x27 | SEQ ID NO.12 + H47Q, E133K, A140S | ≧10 |
| B9x12 | SEQ ID NO:3 + H47Q, E133K, A140S | ≧10 |
| B9x21 | SEQ ID NO:12 + H47Q, V51T, F55S, L56V, Y58H | ≧10 |
| B9x26 | SEQ ID NO:12 + V51T, F55S, L56V, Y58H, E133K, A140S | ≧5 |
| B9x24 | SEQ ID NO:12 + H47Q, V51T, F55S, L56V, Y58H, E133K, A140S | ≧5 |
| B9x15 | SEQ ID NO:3 + H47Q, V51T, F55S, L56V, Y58H, E133K, A140S | ≧5 |
| 25Ep05 | SEQ ID NO:12 + H47Q, V51T, F55S, L56V, Y58H, N72D, N95D, F154L, K160E, R161S, R164S | ≧2.5 |
| IFNα-Con1 | SEQ ID NO:43 | ~2 |
| huIFNα-2b | SEQ ID NO:32 | 1 |

Example 3

$T_H1$ Differentiation Activities of Interferon-Alpha Polypeptides

Patients with chronic HCV infection have initial viral loads in the range of $10^4$-$10^7$ copies of HCV RNA/ml. Upon treatment with IFN-alpha, the viral load characteristically undergoes two distinct log-linear phases of decline reflecting two distinct mechanisms (FIG. 1). The initial drop in viral load occurs in about the first two days and is believed to be due to the reduction in rate of virus production by infected liver cells in response to IFN-alpha therapy. This reaches a new steady state after about two days at which time a second, less rapid, log linear phase of viral clearance is observed. This second phase is believed to be due to killing of infected liver cells by antigen specific T cells. IFN-alpha therapy is believed to play a key role in this biological response through the stimulation of antigen specific T cells to differentiate into $T_H1$ cells.

Without being limited to a particular theory, it is proposed that an interferon-alpha with an improved ability to stimulate differentiation of $T_H0$ cells to $T_H1$ cells may exhibit a more robust second phase of viral clearance, and may therefore have improved efficacy in viral clearance. Based on this working hypothesis, an assay was developed to measure $T_H1$ differentiation activity of interferon-alphas on naïve $T_H0$ cells isolated from blood donors.

$T_H1$ differentiation activities of some IFN-alpha polypeptides of the invention were assayed as described in the Materials and Methods section above. Some such polypeptides of the invention exhibit $T_H1$ differentiation activities about equal to that of a reference molecule, e.g., huIFN-alpha 2b (SEQ ID NO:32) or huIFN-alpha 2a (SEQ ID NO:32+R23K), as evidenced by the $EC_{50}$ (the concentration of sample which yields half-maximal production of interferon-gamma in the assay) of the polypeptide being about equal to the $EC_{50}$ of the reference molecule. Some polypeptides of the invention exhibited $T_H1$ differentiation activities greater than that of the reference molecule, as evidenced by the $EC_{50}$ of the polypeptide being lower than the $EC_{50}$ of the reference molecule.

Example 4

Antiproliferative Activities of Interferon-Alpha Polypeptides

IFN-alpha inhibits proliferation of many cell types, although the antiproliferative effects often occur at higher doses than are required for the antiviral response. Daudi cells are a human derived EVB-transformed B cell line that is IFN-alpha sensitive. This IFN-alpha responsive cell line serves as a useful probe of the antiproliferative effects of the IFN-alpha polypeptides of the invention. Furthermore, antiproliferative activity of IFN-alpha on megakaryocytes and neutrophils at high dose is believed to contribute to thrombocytopenia and neutropenia, respectively. The Daudi antiproliferation assay may serve as a useful surrogate assay for antiproliferative effects on these other lymphoid cell types.

Antiproliferative activities of some IFN-alpha polypeptides of the invention were assayed as described in the Materials and Methods section above. Some polypeptides of the invention exhibit antiproliferative activities about equal to that of a reference molecule, such as huIFN-alpha 2b (SEQ ID NO:32) or huIFN-alpha 2a (SEQ ID NO:32+R23K), as evidenced by the $EC_{50}$ (the concentration which yields half-maximal thymidine incorporation in the assay) of the polypeptide being about equal to the $EC_{50}$ of the reference molecule. Some polypeptides of the invention exhibit antiproliferative activities about equal to or greater than that of the reference molecule, as evidenced by the $EC_{50}$ of the polypeptide being about equal to or less than (e.g., about 0.75-fold, about 0.5-fold, or about 0.25-fold) the $EC_{50}$ of the reference molecule. Some polypeptides of the invention exhibit antiproliferative activities which are about equal to or less than that of the reference molecule, as evidenced by the $EC_{50}$ of the polypeptide being about equal to or greater than the $EC_{50}$ of the reference molecule. Some such polypeptides of the invention exhibit about a 0.75-fold or lower, about a 0.66-fold or lower, about a 0.5-fold or lower, about a 0.25-fold or lower, about a 0.2-fold or lower, or about a 0.1-fold or lower antiproliferative activity than that of the reference molecule (as evidenced by the $EC_{50}$ of the polypeptide being at least about 1.3-fold greater, at least about 1.5-fold greater, at least about 2-fold greater, at least about 4-fold greater, at least about 5-fold greater, or at least about 10-fold greater than the $EC_{50}$ of the reference molecule, respectively); such polypeptides of the invention nevertheless exhibit a measurable antiproliferative activity.

Table 8 below shows relative antiproliferative activities of several exemplary polypeptides of the invention, in comparison to human IFN-alpha 2b and IFN-alpha Con1 assayed under the same conditions, expressed as antiproliferative activity relative to huIFN-alpha 2b ($EC_{50}$ huIFN-alpha 2b/$EC_{50}$ sample).

TABLE 8

| Sample name | Sequence | Anti-proliferative activity relative to huIFNα-2b |
|---|---|---|
| B9x14 | SEQ ID NO:3 | ≧0.5 |
| B9x25 | SEQ ID NO:12 | ≧0.5 |
| B9x16 | SEQ ID NO:3 + H47Q | ≧0.25 |
| B9x23 | SEQ ID NO:12 + H47Q | ≧0.5 |
| B9x18 | SEQ ID NO:3 + H47Q, V51T, F55S, L56V, Y58H | ≧0.25 |
| B9x22 | SEQ ID NO:12 + V51T, F55S, L56V, Y58H | ≧0.5 |
| B9x17 | SEQ ID NO:3 + V51T, F55S, L56V, Y58H | ≧0.5 |
| B9x27 | SEQ ID NO:12 + H47Q, E133K, A140S | ≧0.25 |
| B9x21 | SEQ ID NO:12 + H47Q, V51T, F55S, L56V, Y58H | ≧0.5 |
| B9x26 | SEQ ID NO:12 + V51T, F55S, L56V, Y58H, E133K, A140S | ≧0.25 |
| B9x24 | SEQ ID NO:12 + H47Q, V51T, F55S, L56V, Y58H, E133K, A140S | ≧0.25 |
| B9x15 | SEQ ID NO:3 + H47Q, V51T, F55S, L56V, Y58H, E133K, A140S | ≧0.25 |
| IFNα-Con1 | SEQ ID NO:43 | ~1.5 |
| huIFNα-2b | SEQ ID NO:32 | 1 |

Example 5

Pegylation of Interferon-Alpha Polypeptides

Cys-PEGylation

A polypeptide of the invention which contains a free cysteine, (such as, for example, B9x14CHO6 (SEQ ID NO:49), which contains a cysteine at position 164), may be cysteine-PEGylated as follows. The polypeptide is first partially reduced with an equimolar concentration of TCEP (Triscarboxyethylphosphine) at 4° C. for 30 min in 50 mM MES, 100 mM NaCl, pH 6.0. The reduced polypeptide is then reacted with a 4 fold molar excess of mPEG-MAL reagent (with a PEG moiety such as a 20 kDa or 30 kDa linear mPEG, or a 40 kDa branched mPEG2) for 1 h at 4° C. under the same conditions. The PEGylated reaction mixture is loaded on to a SP-Sepharose HP column equilibrated with 50 mM MES, pH 6.0, 100 mM NaCl. After a 10 CV (column volume) wash step a gradient from 0-600 mM NaCl is applied to fractionate the PEGylated and unPEGylated fractions. Fractions are collected and aliquots are analyzed by SDS-PAGE. Fractions containing monoPEGylated species are pooled and formulated for assays for interferon-alpha activity as described above.

Lys-PEGylation

A polypeptide of the invention comprising the sequence SEQ ID NO:47 was buffer-exchanged into 50 mM sodium borate pH 9 by dialysis or gel filtration, and was concentrated to between 1 and 5 mg/ml. The solution was cooled to 2-8° C. A 3- to 4-times molar excess of dry powdered NHS-mPEG2 40 kDa (Nektar; Huntsville, Ala.) over protein was added to the protein solution and stirred using a stir bar. The stir speed was kept as high as possible without frothing. The reaction was complete after about 1 h, after which the reaction was diluted 8-10 fold with 50 mm sodium acetate, 100 mM NaCl pH 5 (optionally including 0.05% TWEEN80). The sample was filtered and loaded onto a HiTrap SPFF column equilibrated with 50 mm sodium acetate, 100 mm NaCl pH 5. The column was washed extensively with 10-15 column volumes of starting buffer. A 100 mm to 1 M NaCl gradient in the same buffer was used to separate PEGylated proteins from non-PEGylated protein. Fractions containing PEGylated proteins were pooled and formulated for interferon-alpha activity assays, and in some instances were further characterized by amino acid analysis and/or MALDI-TOF mass spectrometry. Preliminary experiments indicate that a polypeptide of the invention comprising the sequence SEQ ID NO:47, when lysine-PEGylated as described above, exhibits over 10-fold higher antiviral activity than a lysine-PEGylated huIFN-alpha 2a conjugate.

N-Terminal PEGylation

A polypeptide of the invention comprising the sequence SEQ ID NO:47 was initially buffer exchanged into 50 mM sodium borate pH 9 by dialysis or gel filtration, and concentrated to between 1 and 5 mg/ml, after which the polypeptide was buffer exchanged into 100 mM sodium phosphate pH 4 by dialysis. A precipitate that on occasion formed during dialysis redissolved readily. The protein solution was cooled to 4° C. A 4 to 10 times molar excess of dry powdered mPEG2-butylALD 40 kDa (Nektar; Huntsville, Ala.) over protein was added to the protein solution and stirred using a stir bar. The stir speed was kept as high as possible without frothing. Subsequently a $\frac{1}{10}$ vol of 200 mM NaCNBH$_3$ in 100 mM potassium phosphate pH 4 was added. The reaction was complete after several hours but could be left overnight. The solution was diluted 5-10 fold with 50 mM sodium acetate, 100 mM NaCl pH 4 (optionally including 0.05% TWEEN80). The sample was filtered and loaded onto a HiTrap SPFF column equilibrated with 50 mM sodium acetate, 100 mM NaCl pH 4. The column was washed extensively with 10-15 column volumes of starting buffer. A 100 mm to 1 M NaCl gradient in the same buffer was used to separate PEGylated proteins from non-PEGylated protein. Fractions containing PEGylated protein were pooled and formulated for interferon-alpha activity assays, and in some instances were further characterized by amino acid analysis and/or MALDI-TOF mass spectrometry. Preliminary experiments indicate that a polypeptide of the invention comprising the sequence SEQ ID NO:47, when N-terminally PEGylated as described above, exhibits over 10-fold higher antiviral activity than a lysine-PEGylated huIFN-alpha 2a conjugate.

Example 6

In Vivo Assays

Measurement of Half-Life of a Polypeptide or Conjugate of the Invention

Measurement of biological or serum half-life may be carried out in a number of ways described in the literature. For example, biological half-life may be determined using an ELISA method to detect serum levels of interferon-alpha after e.g. subcutaneous or intramuscular administration. Use of an ELISA method to determine the pharmacokinetics of interferon-alpha administered subcutaneously is e.g. described by Rostaing et al. (1998), J. Am. Soc. Nephrol. 9(12): 2344-48. Merimsky et al. (1991), Cancer Chemother. Pharmacol. 27(5); 406-8, describe the determination of the serum level of an interferon-alpha administered intramuscularly.

Determining In Vitro Immunogenicity

Reduced immunogenicity of a polypeptide or conjugate of the invention can be determined by use of an ELISA method measuring the immunoreactivity of the molecule relative to a reference molecule or preparation, typically a known interferon-alpha protein. The ELISA method is based on antibodies from patients treated with the reference protein. The immunogenicity is considered to be reduced when the polypeptide or conjugate of the invention has a statistically significant lower response in the assay than the reference molecule or preparation.

While the foregoing invention has been described in some detail for purposes of clarity and understanding, it will be clear to one skilled in the art from a reading of this disclosure that various changes in form and detail can be made without departing from the true scope of the invention. It is understood that the examples and embodiments described herein are for illustrative purposes only and that various modifications or changes in light thereof will be suggested to persons skilled in the art and are to be included within the spirit and purview of this application and scope of the appended claims. For example, all the techniques and apparatus described above may be used in various combinations. All publications, patents, patent applications, and/or other documents cited in this application are incorporated herein by reference in their entirety for all purposes to the same extent as if each individual publication, patent, patent application, and/or other document were individually indicated to be incorporated herein by reference in its entirety for all purposes.

What is claimed is:

1. An isolated or recombinant nucleic acid comprising a polynucleotide sequence which encodes a polypeptide comprising a sequence which differs in 0 to 8 amino acid positions from the sequence of SEQ ID NO:3, which polypeptide exhibits antiviral activity.

2. An isolated host cell comprising the nucleic acid of claim 1.

3. A vector comprising the nucleic acid of claim 1.

4. The vector of claim 3, wherein the vector comprises a plasmid, a cosmid, a phage, or a virus.

5. The vector of claim 3, which is an expression vector comprising the nucleic acid operably linked to a promoter.

6. An isolated host cell comprising the vector of claim 5.

7. The host cell of claim 6, wherein the host cell is a eukaryotic host cell.

8. The host cell of claim 6, wherein the host cell is a bacterial host cell.

9. The host cell of claim 8, wherein the bacterial host cell is *E. coli*.

10. The nucleic acid of claim 1, wherein the antiviral activity of the encoded polypeptide is equal to or greater than the antiviral activity of huIFN-alpha 2b or huIFN-alpha 2a.

11. The nucleic acid of claim 10, wherein the antiviral activity of the encoded polypeptide is at least two-fold greater than the antiviral activity of huIFN-alpha 2b or huIFN-alpha 2a.

12. The nucleic acid of claim 1, wherein the encoded polypeptide further exhibits antiproliferative activity and wherein the polypeptide exhibits a ratio of antiviral activity/antiproliferative activity at least two-fold greater than the ratio of antiviral activity/antiproliferative activity exhibited by huIFN-alpha 2b or huIFN-alpha 2a.

13. The nucleic acid of claim 12, wherein the encoded polypeptide exhibits a ratio of antiviral/antiproliferative activity at least four-fold greater than the ratio of antiviral activity/antiproliferative activity exhibited by huIFN-alpha 2b or huIFN-alpha 2a.

14. A method for preparing a recombinant polypeptide, wherein the polypeptide comprises a sequence which differs in 0 to 8 amino acid positions from the sequence of SEQ ID NO:3, which polypeptide exhibits antiviral activity, the method comprising:
providing a culture comprising a host cell, the host cell comprising an expression vector comprising a promoter operably linked to a nucleic acid, the nucleic acid comprising a polynucleotide sequence which encodes the polypeptide,
culturing the culture under conditions which permit expression of the polypeptide, and
recovering the polypeptide.

15. The method of claim 14, wherein the host cell is a eukaryotic host cell.

16. The method of claim 14, wherein the host cell is a bacterial host cell.

17. The method of claim 16, wherein the bacterial host cell is *E. coli*.

18. The method of claim 14, wherein the antiviral activity of the polypeptide is equal to or greater than the antiviral activity of huIFN-alpha 2b or huIFN-alpha 2a.

19. The method of claim 18, wherein the antiviral activity of the polypeptide is at least two-fold greater than the antiviral activity of huIFN-alpha 2b or huIFN-alpha 2a.

20. The method of claim 14, wherein the polypeptide further exhibits antiproliferative activity and wherein the polypeptide exhibits a ratio of antiviral activity/antiproliferative activity at least two-fold greater than the ratio of antiviral activity/antiproliferative activity exhibited by huIFN-alpha 2b or huIFN-alpha 2a.

21. The method of claim 20, wherein the polypeptide exhibits a ratio of antiviral/antiproliferative activity at least four-fold greater than the ratio of antiviral activity/antiproliferative activity exhibited by huIFN-alpha 2b or huIFN-alpha 2a.

* * * * *